US008232380B2

(12) United States Patent
Kwok et al.

(10) Patent No.: US 8,232,380 B2
(45) Date of Patent: Jul. 31, 2012

(54) SHADE REGULATORY REGIONS

(75) Inventors: Shing Kwok, Woodland Hills, CA (US); Amy Jo Miyamoto, Belleville, WI (US); Kenneth Bounds, Tarzana, CA (US)

(73) Assignee: Ceres, Inc., Thousand Oaks, CA (US)

( * ) Notice: Subject to any disclaimer, the term of this patent is extended or adjusted under 35 U.S.C. 154(b) by 585 days.

(21) Appl. No.: 12/197,886

(22) Filed: Aug. 25, 2008

(65) Prior Publication Data

US 2009/0199312 A1 Aug. 6, 2009

Related U.S. Application Data

(63) Continuation-in-part of application No. PCT/US2007/062762, filed on Feb. 23, 2007.

(60) Provisional application No. 60/776,307, filed on Feb. 24, 2006.

(51) Int. Cl.
*C12N 15/63* (2006.01)
*C12N 15/82* (2006.01)
*C12N 15/87* (2006.01)
*A01H 1/00* (2006.01)

(52) U.S. Cl. ........ 536/24.1; 800/278; 800/285; 800/287

(58) Field of Classification Search .................. None
See application file for complete search history.

(56) References Cited

U.S. PATENT DOCUMENTS

| | | | |
|---|---|---|---|
| 4,987,071 A | 1/1991 | Cech et al. | |
| 5,034,323 A | 7/1991 | Jorgensen et al. | |
| 5,204,253 A | 4/1993 | Sanford et al. | |
| 5,231,020 A | 7/1993 | Jorgensen et al. | |
| 5,254,678 A | 10/1993 | Haseloff et al. | |
| 5,362,865 A | 11/1994 | Austin | |
| 5,538,880 A | 7/1996 | Lundquist et al. | |
| 5,591,616 A | 1/1997 | Hiei et al. | |
| 5,659,122 A | 8/1997 | Austin | |
| 6,011,198 A | 1/2000 | Ko et al. | |
| 6,326,527 B1 | 12/2001 | Kirihara et al. | |
| 6,329,571 B1 | 12/2001 | Hiei | |
| 6,423,885 B1 | 7/2002 | Waterhouse et al. | |
| 6,452,067 B1 | 9/2002 | Bedbrook et al. | |
| 6,573,099 B2 | 6/2003 | Graham | |
| 6,747,189 B1 | 6/2004 | McElroy et al. | |
| 6,753,139 B1 | 6/2004 | Baulcombe et al. | |
| 6,777,588 B2 | 8/2004 | Waterhouse et al. | |
| 6,858,429 B2 | 2/2005 | Quail et al. | |
| 2003/0101479 A1* | 5/2003 | Cheikh et al. ................. | 800/278 |
| 2003/0175783 A1 | 9/2003 | Waterhouse et al. | |
| 2003/0175965 A1 | 9/2003 | Lowe et al. | |
| 2003/0180945 A1 | 9/2003 | Wang et al. | |
| 2004/0214330 A1 | 10/2004 | Waterhouse et al. | |
| 2005/0132432 A1 | 6/2005 | Haseloff et al. | |
| 2005/0266559 A1 | 12/2005 | Kwok | |

FOREIGN PATENT DOCUMENTS

| | | |
|---|---|---|
| WO | 97/01952 | 1/1997 |
| WO | 98/36083 | 8/1998 |
| WO | 98/53083 | 11/1998 |
| WO | 99/32619 | 7/1999 |

OTHER PUBLICATIONS

Carabelli et al. 1996, PNAS 93:3530-3535.*
Bevan et al. 1998, Genbank Accession No. AL021811.*
Baud, et al., "The AtSUC5 sucrose transporter specifically expressed in the endosperm is involved in early seed development in *Arabidopsis*," *Plant Journal*, 2005, 43(6):824-836.
Bechtold et al., "In planta Agrobacterium mediated gene transfer by infiltration of adult *Arabidopsis thaliana* plants," *C.R. Acad. Sci. Paris*, 1993, 316: 1194-1199.
Breitholtz, et al., "LHC II protein phosphorylation in leaves of *Arabidopsis thaliana* mutants deficient in non-photochemical quenching," *Photosynth Research*, 2005, 84 (1-3): 217-223.
Carabelli, et al., "Twilight-zone and canopy shade induction of the *Athb-2* homeobox gene in green plants ," *Proc. Natl. Acad. Sci. USA*, 1996, 93: 3530-3535.
Chenna et al., "Multiple sequence alignment with the Clustal series of programs," *Nucleic Acids Res.*, 2003, 31(13):3497-500.
de Feyter and Gaudron, "Expressing Ribozymes in Plants," *Method in Molecular Biology*, vol. 74, Chatper 43, Edited by Turner, P.C, Humana Press Inc., Totowa, NJ, 1997, pp. 403-415.
Degenhardt and Tobin, "A DNA binding activity for one of two closely defined phytochrome regulatory elements in an Lhcb promoter is more abundant in etiolated than in green plants," *Plant Cell*, 1996, 8: 31-41.
GenBank Accession No. AAL38260, Dec. 10, 2001.
GenBank Accession No. AAN72153, Nov. 19, 2002.
GenBank Accession No. AAO41893, Feb. 14, 2003.
GenBank Accession No. AAY02244, Apr. 20, 2005.
GenBank Accession No. ABB36796, Nov. 2, 2005.
GenBank Accession No. AJ306827, Apr. 19, 2002.
GenBank Accession No. AL161580, Mar. 20, 2000.
GenBank Accession No. BAC42303, Feb. 14, 2004.
GenBank Accession No. CAD58040, Apr. 15, 2005.
GenBank Accession No. NP_173109, Nov. 4, 2005.
GenBank Accession No. NP_174546, Nov. 4, 2005.
GenBank Accession No. NP_195024, Nov. 4, 2005.
GenBank Accession No. NP_200658, Nov. 4, 2005.
GenBank Accession No. NP_565292, Nov. 4, 2005.
GenBank Accession No. NP_568579, Nov. 4, 2005.
GenBank Accession No. Q5HZ36, Sep. 13, 2005.
Giuliano et al., "An evolutionarily conserved protein binding sequence upstream of a plant light-regulated gene," *Proc. Natl. Acad. Sci. USA*, 1988, 85: 7089-7093.

(Continued)

*Primary Examiner* — Li Zheng

(74) *Attorney, Agent, or Firm* — Fish & Richardson P.C.

(57) ABSTRACT

Regulatory regions suitable for directing the expression of a heterologous polynucleotide under light conditions in which the red/far red ratio is less than 1 are described, as well as nucleic acid constructs that include these regulatory regions. Also disclosed are transgenic plants that contain such constructs and methods of producing such transgenic plants.

15 Claims, 2 Drawing Sheets

OTHER PUBLICATIONS

Green et al., "Binding site requirements for pea nuclear protein factor GT-1 correlate with sequences required for light-dependent transcriptional activation of the *rbcS-3A* gene," *EMBO J.*, 1988, 7 (13):4035-4044.

Guatelli et al., "Isothermal, in vitro amplification of nucleic acids by a multienzyme reaction modeled after retroviral replication," *Proc. Natl. Acad. Sci.* USA, 1990, 87: 1874-1878.

Higo et al., "Plant cis-acting regulatory DNA elements (PLACE) database: Research, 1999," *Nucleic Acids Research*, 27(1): 297-300.

Hudson and Quail, "Identification of promoter motifs involved in the network of phytochrome A-regulated gene expression by combined analysis of genomic sequence and microarray data," *Plant Physiol.*, 2003, 133: 1605-1616.

Lewis, "PCR's competitors are alive and well and moving rapidly towards commercialization," *Genetic Engineering News*, 1992, 12(9): 1.

Ngai et al., "Light-induced transcriptional repression of the pea AS1 gene: identification of *cis*-elements and transfactors," *Plant Journal*, 1997, 12:1021-1234.

Perriman et al., "Effective ribozyme delivery in plant cells," *Proc. Natl. Acad. Sci.*, USA, 1995, 92(13): 6175-6179.

'A Database of Plant Cis-acting Regulatory DNA Elements' [online]. PLACE, 1991-2006 [retrieved on Oct. 8, 2008]. Retrieved from the Internet: <URL: www.dna.affrc.go.jp/PLACE/>, 3 pages.

'A Database of Plant Cis-acting Regulatory DNA Elements' [online]. PLACE, [retrieved on Oct. 8, 2008]. Retrieved from the Internet: <URL: www.dna.affrc.go.jp/PLACE/signalscan.html>, 2 pages.

Prestridge, "SIGNAL SCAN: a computer program that scans DNA sequences for eukaryotic transcriptional elements," *Comput Appl Biosci.*, 1991, 7(2):203-206.

Riechmann, et al., "*Arabidopsis* transcription factors: Genome-wide comparative analysis among eukaryotes," *Science*, 2000, 290: 2105-2110.

Terzaghi and Cashmore, "Light-Regulated Transcription," *Annual Review of Plant Physiology and Plant Molecular Biology*, 1995, vol. 46: 445-474.

Thum et al., "Analysis of barley chloroplast *psbD* light-responsive promoter elements in transplastomic tobacco," *Plant. Mol. Biol.*, 2001, 47:353-366.

Weiss, "Hot prospect for new gene amplifier," *Science*, 1991, 254: 1292-1293.

Yang et al., "*Arabidopsis* membrane steroid binding protein 1 is involved in inhibition of cell elongation," *Plant Cell*, 2005, 17:116-131.

Yang et al., "Overexpression of a mutant basic helix-loop-helix protein HFR1, HFR1-deltaN105, activates a branch pathway of light signaling in *Arabidopsis*," *Plant Physiol.*, 2003, 133(4):1630-1642.

\* cited by examiner

SHADE REGULATORY REGIONS

CROSS-REFERENCE TO RELATED APPLICATIONS

This application is a continuation-in-part and claims the benefit of 35 U.S.C. §119(a) of International Application No. PCT/US2007/062762, having an International Filing Date of Feb. 23, 2007, which claims the benefit of priority under 35 U.S.C. §119(e) to U.S. Provisional Application No. 60/776,307, filed Feb. 24, 2006, all of which are incorporated herein by reference in their entirety.

BACKGROUND

1. Technical Field

This document relates to methods and materials involved in regulating gene expression in eukaryotic organisms (e.g., plants).

2. Incorporation-By-Reference & Text

The material in the accompanying sequence listing is hereby incorporated by reference into this application. The accompanying file containing the sequence listing, was created on Feb. 23, 2007 and is 287 KB. The file can be accessed using Microsoft Word on a computer that uses Windows OS.

3. Background Information

An essential element for genetic engineering of plants is the ability to express genes using various regulatory regions. The expression pattern of a transgene, conferred by a regulatory region is critical for the timing, location, and conditions under which a transgene is expressed, as well as the intensity with which the transgene is expressed in a transgenic plant. Plants grown under dense canopies or at high density perceive a decrease in the ratio of red to far-red incoming light, and respond to it by growing faster and taller (Cerdan and Chory, 2003). Densely planted crops tend to place energy into stem and petiole elongation to lift the leaves into the sunlight rather than putting energy into storage or reproductive structures. This negatively affects yields by reducing the amount of harvestable products such as seeds, fruits and tubers. In addition, tall spindly plants tend to be less wind resistant and lodge more easily, further reducing crop yield. There is continuing need for suitable regulatory regions that can improve agricultural and forest plant growth potential.

SUMMARY

This document provides material and methods involving regulatory regions having the ability to direct transcription in eukaryotic organisms (e.g., plants). For example, this document provides regulatory regions having the ability to direct transcription in vascular cells of plant roots. Also provided herein are nucleic acid constructs, plant cells, and plants containing such regulatory regions, and methods of using such regulatory regions to express polynucleotides in plants and to alter the phenotype of plant cells. Regulatory regions that direct transcription in plant roots can be used, for example, to modulate (e.g., increase or decrease) uptake of nutrients and water.

In one aspect, the invention features an isolated nucleic acid comprising a regulatory region having 90 percent or greater sequence identity to the polynucleotide sequence set forth in SEQ ID NO:1 or SEQ ID NO:125. The regulatory region directs transcription of an operably linked heterologous polynucleotide under far red light conditions. The nucleic acid can have a sequence identity of 95 percent or greater, or 98 percent or greater to SEQ ID NO: 1. In another aspect, a nucleic acid construct can comprise the regulatory region operably linked to a heterologous polynucleotide. The heterologous polynucleotide can have a nucleotide sequence encoding a polypeptide. The polypeptide can be a zinc finger (B-box type) polypeptide. The polypeptide can comprise an amino acid sequence having 80% or greater sequence identity to an amino acid sequence selected from the group consisting of SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, and SEQ ID NO:119. The heterologous polynucleotide can be in antisense orientation relative to the regulatory region. The heterologous polynucleotide can be transcribed into an interfering RNA.

An isolated nucleic acid comprising a regulatory region comprising a 5' segment having 90 percent or greater sequence identity to residues 1-1000 of the polynucleotide sequence set forth in SEQ ID NO: 1 or SEQ ID NO: 125, and a 3' segment comprising a TATA box. The regulatory region directs transcription of an operably linked heterologous polynucleotide under light conditions in which the red/far red ratio is less than 1. In another aspect, a nucleic acid construct can comprise the regulatory region operably linked to a heterologous polynucleotide. The heterologous polynucleotide can have a nucleotide sequence encoding a polypeptide. The polypeptide can be a zinc finger (B-box type) polypeptide. The polypeptide can comprise an amino acid sequence having 80% or greater sequence identity to an amino acid sequence selected from the group consisting of SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, and SEQ ID NO:119. The heterologous polynucleotide can be in antisense orientation relative to the regulatory region. The heterologous polynucleotide can be transcribed into an interfering RNA.

The invention also features a transgenic plant or plant cell transformed with a nucleic acid construct comprising a regulatory region having 90 percent or greater sequence identity to the polynucleotide sequence set forth in SEQ ID NO:1 or SEQ ID NO:125, operably linked to a heterologous polynucleotide.

The invention also features a method of producing a transgenic plant. The method comprises introducing into a plant cell an isolated polynucleotide comprising a nucleic acid construct comprising a regulatory region having 90 percent or greater sequence identity to the polynucleotide sequence set forth in SEQ ID NO:1 or SEQ ID NO:125, operably linked to a heterologous polynucleotide; and growing a plant from the plant cell.

In another aspect, an isolated nucleic acid is featured. The isolated nucleic acid can comprise a nucleotide sequence having 95% or greater sequence identity to a nucleotide sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, and SEQ ID NO:78, or a nucleotide sequence encoding a polypeptide having 80% or greater sequence identity to an amino acid sequence selected from the group consisting of SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, and SEQ ID NO:79.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 1 is an ethidium bromide stained gel showing the amount of reverse transcriptase-mediated polymerase chain reaction (RT-PCR) product from genes in *Arabidopsis thaliana* $T_2$ seedlings at 1 hr, 24 hrs, 48 hrs and 72 hrs after transfer to far red and white light conditions. AUX/IAA29=endogenous AUX/IAA29 gene; HAP1=PR0924::HAP1-VP16 construct; ATHB-2=endogenous ATHB-2 gene; Tubulin=endogenous tubulin gene. T2#1=$T_2$ seedlings of PR0924 event -01; T2#3=$T_2$ seedlings of PR0924 event -03; T2#5=$T_2$ seedlings of PR0924 event -05; Col=untransformed Col-0 seedlings. W=white light conditions; FR=far red light conditions.

DETAILED DESCRIPTION

Figure 2:
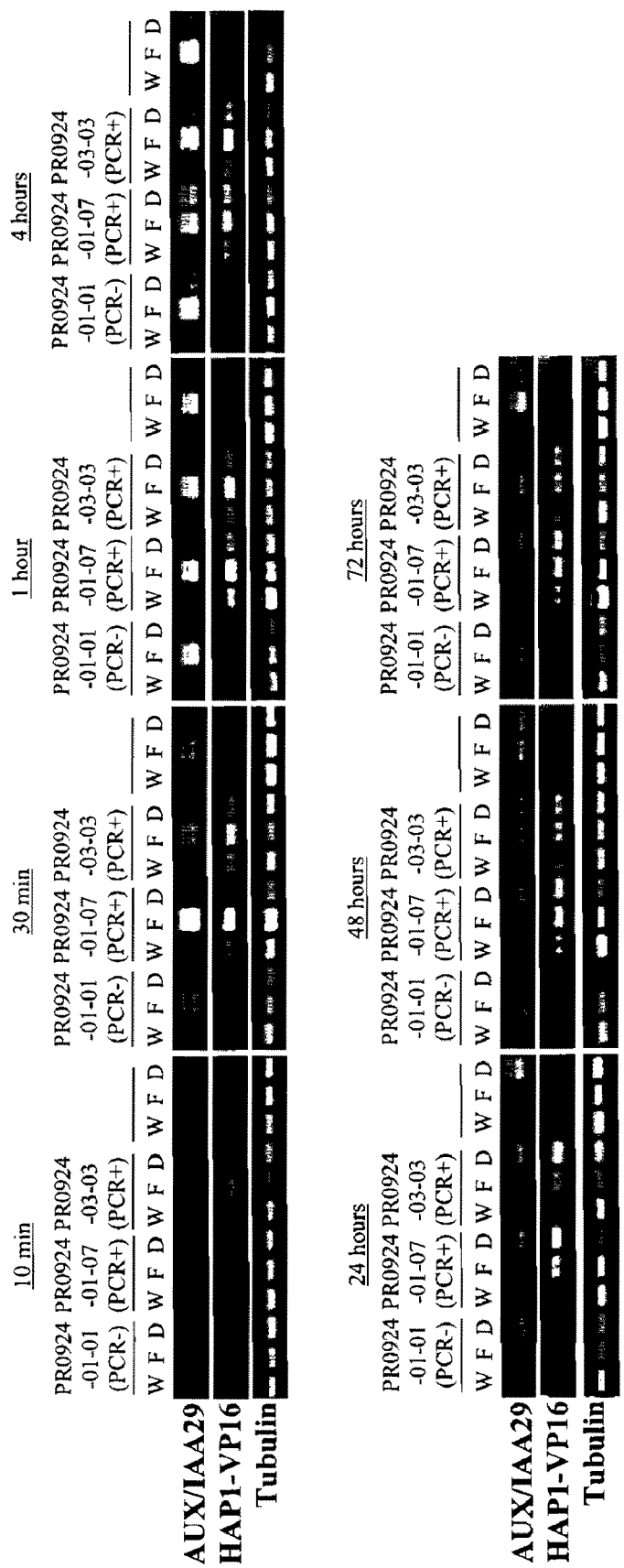
FIG. 2 is an ethidium bromide stained gel showing the amount of reverse transcriptase-mediated polymerase chain reaction (RT-PCR) product from genes in *Arabidopsis thaliana* $T_3$ seedlings at 10 min, 30 min, 1 hr, 4 hrs, 24 hrs, 48 hrs and 72 hrs after transfer to far red and white light conditions. AUX/IAA29=endogenous AUX/IAA29 gene; HAP1=PR0924::HAP1-VP16 construct; ATHB-2=endogenous ATHB-2 gene; Tubulin=endogenous tubulin gene. T3#1=$T_3$ seedlings of PR0924 event -01-01; T3#3=$T_3$ seedlings of PR0924 event -03-03; Col=untransformed Col-0 seedlings. W=white light conditions; FR=far red light conditions.

The invention features isolated nucleic acids comprising regulatory regions. The terms "nucleic acid" and "polynucleotide" are used interchangeably herein, and refer to both RNA and DNA, including cDNA, genomic DNA, synthetic DNA, and DNA or RNA containing nucleic acid analogs. Polynucleotides can have any three-dimensional structure. A nucleic acid can be double-stranded or single-stranded, i.e., a sense strand or an antisense strand. Non-limiting examples of polynucleotides include genes, gene fragments, exons, introns, messenger RNA (mRNA), transfer RNA, ribosomal RNA, siRNA, micro-RNA, ribozymes, cDNA, recombinant polynucleotides, branched polynucleotides, plasmids, vectors, isolated DNA of any sequence, isolated RNA of any sequence, nucleic acid probes, and primers, as well as nucleic acid analogs.

An isolated nucleic acid can be, for example, a naturally-occurring DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule, independent of other sequences, e.g., a chemically synthesized nucleic acid, or a cDNA or genomic DNA fragment produced by the polymerase chain reaction (PCR) or restriction endonuclease treatment. An isolated nucleic acid also refers to a DNA molecule that is incorporated into a vector, an autonomously replicating plasmid, or a virus, or transformed into the genome of a prokaryote or eukaryote. In addition, an isolated nucleic acid can include an engineered nucleic acid such as a DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not to be considered an isolated nucleic acid.

Regulatory Regions

A regulatory region described herein is a nucleic acid that can direct transcription when the regulatory region is operably linked 5' to a heterologous nucleic acid. As used herein, "heterologous nucleic acid" refers to a nucleic acid other than the naturally occurring sequence to which the regulatory region was operably linked. With regard to one regulatory region provided herein, PR0924 (SEQ ID NO: 1), a heterologous nucleic acid is a nucleic acid other than the AUX/IAA29 coding sequence from *Arabidopsis*. With regard to another regulatory region provided herein, SEQ ID NO:125, a heterologous nucleic acid is a nucleic acid other than the AUX/IAA29 coding sequence from *Populus balsamifera* subsp. *trichocarpa*. The term "operably linked" refers to positioning of a regulatory region and a transcribable sequence in a nucleic acid so as to allow or facilitate transcription of the transcribable sequence. For example, a regulatory region is operably linked to a coding sequence when RNA polymerase is able to transcribe the coding sequence into mRNA, which then can be translated into a protein encoded by the coding sequence.

Regulatory regions can include, without limitation, promoter sequences, enhancer sequences, response elements, protein recognition sites, inducible elements, promoter control elements, protein binding sequences, 5' and 3' untranslated regions (UTRs), transcriptional start sites, termination sequences, polyadenylation sequences, and introns.

A 5' untranslated region (5' UTR) of a gene is generally defined as a polynucleotide segment between the transcription start site (TSS) and the coding sequence start site (ATG codon) of a messenger RNA or cDNA. Alternately, 5' UTR can be synthetically produced or manipulated DNA elements. A "plant 5'UTR" can be a native or non-native 5'UTR that is functional in plant cells. A 5' UTR can be used as a 5' regulatory element for modulating expression of an operably linked transcribable polynucleotide molecule. For example, 5' UTRs derived from heat shock protein genes have been demonstrated to enhance gene expression in plants (see for example, U.S. Pat. No. 5,659,122 and U.S. Pat. No. 5,362,865, all of which are incorporated herein by reference). Examples of 5'UTRs include those shown in SEQ ID NO: 1, SEQ ID NO:120, SEQ ID NO:121, and SEQ ID NO:125.

The nucleic acid sequence set forth in SEQ ID NO:1 and SEQ ID NO:125 are examples of regulatory regions provided herein. However, a regulatory region can have a nucleotide sequence that deviates from that set forth in SEQ ID NO:1 or SEQ ID NO:125, while retaining the ability to direct expression of an operably linked nucleic acid. For example, a regulatory region having 90% or greater (e.g., 91% or greater, 92% or greater, 93% or greater, 94% or greater, 95% or greater, 96% or greater, 97% or greater, 98% or greater, or 99% or greater) sequence identity to the nucleotide sequence set forth in SEQ ID NO:1 or SEQ ID NO:125 can direct expression of an operably linked nucleic acid.

A regulatory region can also be a fragment (e.g., 500, 600, 700, 800, 900, 1000, 1100, 1200, 1300, 1400, 1500, 1600, 1700, 1800, 1900, 2000, 2100, 2200, 2500, or 2700 nucleotides) of SEQ ID NO:1 or SEQ ID NO:125, while retaining the ability to direct expression of an operably linked nucleic acid. The nucleic acid sequences set forth in SEQ ID NOs: 122-124 are additional examples of regulatory regions provided herein.

As used herein, the term "percent sequence identity" refers to the degree of identity between any given query sequence, e.g., SEQ ID NO:1 or SEQ ID NO:125, and a subject sequence. A subject sequence typically has a length that is from 80 percent to 200 percent of the length of the query sequence, e.g., 82, 85, 87, 89, 90, 93, 95, 97, 99, 100, 105, 110, 115, 120, 130, 140, 150, 160, 170, 180, 190, or 200 percent of the length of the query sequence. A percent identity for any subject nucleic acid or polypeptide relative to a query nucleic acid or polypeptide can be determined as follows. A query sequence (e.g., a nucleic acid sequence or an amino acid sequence) is aligned to one or more subject sequences using the computer program ClustalW (version 1.83, default parameters), which allows alignments of nucleic acid or polypeptide sequences to be carried out across their entire length (global alignment). Chenna et al, *Nucleic Acids Res.*, 31(13):3497-500 (2003).

ClustalW calculates the best match between a query and one or more subject sequences, and aligns them so that identities, similarities and differences can be determined. Gaps of one or more residues can be inserted into a query sequence, a subject sequence, or both, to maximize sequence alignments.

For fast pairwise alignment of nucleic acid sequences, the following default parameters are used: word size: 2; window size: 4; scoring method: percentage; number of top diagonals: 4; and gap penalty: 5. For alignments of multiple nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method: percentage; number of top diagonals: 5; gap penalty: 3. For alignments of multiple protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The ClustalW output is a sequence alignment that reflects the relationship between sequences. ClustalW can be run, for example, at the Baylor College of Medicine Search Launcher site (searchlauncher.bcm.tmc.edu/multi-align/multi-align.html) and at the European Bioinformatics Institute site on the World Wide Web (ebi.ac.uk/clustalw).

To determine percent identity of a subject nucleic acid or amino acid sequence to a query sequence, the sequences are aligned using ClustalW, the number of identical matches in the alignment is divided by the length of the query sequence, and the result is multiplied by 100. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

A regulatory region can contain conserved regulatory motifs. Such a regulatory region can be SEQ ID NO:1 or SEQ ID NO:125, or a regulatory region having a nucleotide sequence that deviates from that set forth in SEQ ID NO:1 or SEQ ID NO:125, while retaining the ability to direct expression of an operably linked nucleic acid. For example, a regulatory region can contain a CAAT box or a TATA box. A CAAT box is a conserved nucleotide sequence involved in initiation of transcription. A CAAT box functions as a recognition and binding site for regulatory proteins called transcription factors. A TATA box is another conserved nucleotide sequence involved in transcription initiation. A TATA box seems to be important in determining accurately the position at which transcription is initiated.

Other conserved regulatory motifs can be identified using methods known in the art. For example, a regulatory region can be analyzed using the PLACE (PLAnt Cis-acting regulatory DNA Elements) Web Signal Scan program on the world wide web at dna.affrc.go.jp/PLACE/signalscan.html. See, Higo et al., *Nucleic Acids Research*, 27(1):297-300 (1999); and Prestridge, *CABIOS*, 7:203-206 (1991). Examples of conserved regulatory motifs can be found in the PLACE database on the world wide web at dna.affrc.go.jp/PLACE/. See, Higo et al., supra.

A regulatory region such as SEQ ID NO:1 or SEQ ID NO:125, or a regulatory region having a nucleotide sequence that deviates from that set forth in SEQ ID NO:1 or SEQ ID NO:125, while retaining the ability to direct expression of an operably linked nucleic acid, can contain one or more conserved regulatory motifs, which can be found in the PLACE database. For example, such a regulatory region can contain a -10PEHVPSBD motif having the consensus sequence TATTCT. See, Thum et al., *Plant. Mol. Biol.*, 47:353-366 (2001). Such a regulatory region can also contain an ASF1 MOTIF-CAMV motif having the consensus sequence TGACG. See Terzaghi and Cashmore, *Annu. Rev. Plant. Physiol. Plant. Mol. Biol.*, 46:445-474 (1995). Such a regulatory region can also contain a BOXCPSAS1 motif having the consensus sequence CTCCCAC. See, Ngai et al, *Plant J.,* 12:1021-1234 (1997). Such a regulatory region can also contain an IBOX motif having the consensus sequence GATAAG) and an IBOXCORE motif having the consensus sequence GATAA. See, Giuliano et al, *Proc. Natl. Acad. Sci. USA,* 85:7089-7093 (1988); and Terzaghi and Cashmore, supra. Such a regulatory region can also contain a CACGTGMOTIF motif having the consensus sequence CACGTG. See, Hudson and Quail, *Plant Physiol.,* 133: 1605-1616 (2003); and Terzaghi and Cashmore, supra. Such a regulatory region can also contain a GT1CORE motif having the consensus sequence GGTTAA. See, Green et al., EMBO J., 7, 4035-4044 (1988); and Terzaghi and Cashmore, supra. Such a regulatory region can also contain a REALPHALGLHCB21 motif having the consensus sequence AACCAA. See, Degenhardt and Tobin, *Plant Cell,* 8: 31-41 (1996).

A regulatory region featured herein can be made by cloning 5' flanking sequences of an *Arabidopsis* or a *Populus* AUX/IAA29 gene. Alternatively, a regulatory region can be made by chemical synthesis and/or PCR technology. PCR refers to a technique in which target nucleic acids are amplified. Generally, sequence information from the ends of the region of interest or beyond is employed to design oligonucleotide primers that are identical or similar in sequence to opposite strands of the template to be amplified. PCR can be used to amplify specific sequences from DNA as well as RNA, including sequences from total genomic DNA or total cellular RNA. Primers are typically 14 to 40 nucleotides in length, but can range from 10 nucleotides to hundreds of nucleotides in length. PCR is described, for example, in PCR Primer. *A Laboratory Manual, Ed. by Dieffenbach and Dveksler, Cold Spring Harbor Laboratory Press,* 1995. Nucleic acids also can be amplified by ligase chain reaction, strand displacement amplification, self-sustained sequence replication, or nucleic acid sequence-based amplification. See, for example, Lewis, *Genetic Engineering News,* 12(9): 1 (1992); Guatelli et al., *Proc. Natl. Acad. Sci. USA,* 87:1874-1878 (1990); and Weiss, *Science,* 254:1292 (1991). Various lengths of a regulatory region described herein can be made by similar techniques. A regulatory region also can be made by ligating together fragments of various regulatory regions. Methods for ligation of nucleic acid fragments, including PCR fragments, are known to those of ordinary skill in the art. PCR strategies also are available by which site-specific nucleotide sequence modifications can be introduced into a template nucleic acid.

In some embodiments, a regulatory region comprises a 5' segment having 90% or greater sequence identity to a 5' fragment of SEQ ID NO:1 or SEQ ID NO:125 operably linked to a 3' segment comprising a TATA box. Such a regulatory region can comprise at least nucleotides 1-1000 (e.g., 1-1050, 1-1100, 1-1150, 1-1200, 1-1300, 1-1500, 1-1800, 1-2000, 1-2500, or 1-2800) of SEQ ID NO:1 or SEQ ID NO:125. The TATA box segment can be from SEQ ID NO:1, SEQ ID NO:125, or can be a TATA box segment heterologous to those in SEQ ID NO:1 or SEQ ID NO:125. For example, such a regulatory region can comprise at least nucleotides 1-1000 of SEQ ID NO:1 operably linked to a 3' segment of SEQ ID NO:1 that includes the TATA box. In some cases, such a regulatory region can also include a 5'UTR. The 5' UTR can be from SEQ ID NO:1, SEQ ID NO:125, or can be a heterologous UTR.

The ability of a regulatory region to direct expression of an operably linked nucleic acid can be assayed using methods known to one having ordinary skill in the art. In particular, regulatory regions of varying lengths and regulatory regions comprising combinations of various regulatory regions ligated together can be operably linked to a reporter nucleic acid and used to transiently or stably transform a cell, e.g., a plant cell. Suitable reporter nucleic acids include β-glucuronidase (GUS), green fluorescent protein (GFP), yellow fluorescent protein (YFP), and luciferase (LUC). Expression of the gene product encoded by the reporter nucleic acid can be monitored in such transformed cells using standard techniques.

When a heterologous nucleic acid is operably linked to an environment-responsive regulatory region and transformed into a plant, transcription occurs only or predominantly those environmental conditions to which the regulatory region is responsive. A regulatory region disclosed herein drives expression preferentially under far red light conditions at 22° C. Far red light conditions refers to a ratio of the fluence at 633 nm to the fluence at 740 nm (red/far red) of less than 1, e.g., less than 0.9, less than 0.8, less than 0.7, less than 0.6, less than 0.5, less than 0.4, less than 0.3, less than 0.2, less than 0.1, or less than 0.05. The expression profile of a regulatory region can be determined by continuous exposure to light at an intensity of about 8 lux with the following fluence rates: $Blue_{450}$=0.005 µmol/m$^2$/s, $Red_{633}$=7 µmol/m$^2$/s, Far $Red_{740}$=69 µmol/m$^2$/s. The photon flux from 400 to 700 nm, defined as Photosynthetic Photon Flux Density (PPFD), is about 5 µmol/m$^2$/s. The ratio of the fluence at 633 nm to the fluence at 740 nm (red/far red) under these conditions is about 0.1.

Far red light conditions are a useful system for simulating shade. The ratio of red:far-red light perceived by plant phytochromes is important in determining whether plants display shade avoidance phenotypes. Typically, a red/far-red ratio of <1 results in shade avoidance responses. Phytochrome responses can further be subdivided into different classes based on the radiation energy of light that is required to obtain the response. These include the low fluence responses (LFRs), the very low fluence responses (VLFRs), and the high irradiance response (HIRs). LFRs are the classic phytochrome responses such as seed germination, that are red/far-red (R/FR) reversible. VLFRs are not reversible and are sensitive to a broad spectrum of light between 300 and 780 nm. HIRs require prolonged or high frequency intermittent illumination and usually are dependent on fluence rate of light. The physiological results of far-red HIR are a reduction in hypocotyl elongation and open and expanded cotyledons with a reduced ability to green.

Nucleic Acid Constructs

Nucleic acid constructs containing nucleic acids such as those described herein also are provided. A nucleic acid construct can be a vector. A vector is a replicon, such as a plasmid, phage, or cosmid, into which another DNA segment may be inserted so as to bring about the replication of the inserted segment. Generally, a vector is capable of replication when associated with the proper control elements. Suitable vector backbones include, for example, those routinely used in the art such as plasmids, viruses, artificial chromosomes, BACs, YACs, or PACs. The term "vector" includes cloning, transformation, and expression vectors, as well as viral vectors and integrating vectors. An expression vector is a vector that includes one or more regulatory regions. Suitable expression vectors include, without limitation, plasmids and viral vectors derived from, for example, bacteriophage, baculoviruses, and retroviruses. Numerous vectors and expression systems are commercially available from such corporations as Novagen (Madison, Wis.), Clontech (Palo Alto, Calif.), Stratagene (La Jolla, Calif.), and Invitrogen/Life Technologies (Carlsbad, Calif.).

A nucleic acid construct includes a regulatory region as disclosed herein. A construct also includes a heterologous nucleic acid operably linked to the regulatory region, in which case the construct can be introduced into an organism and used to direct expression of the operably linked nucleic acid. If a heterologous nucleic acid includes a polypeptide coding sequence, the coding sequence can be operably linked to the regulatory region in the sense or antisense orientation. The regulatory region can be operably linked from approximately 1 to 150 nucleotides upstream of the ATG translation start codon of a heterologous nucleic acid in the sense orientation. For example, the regulatory region can be operably linked 1 nucleotide, 2 nucleotides, 3 nucleotides, 4 nucleotides, 5 nucleotides, 6 nucleotides, 7 nucleotides, 8 nucleotides, 9 nucleotides, 10 nucleotides, 11 nucleotides, 12 nucleotides, 13 nucleotides, 14 nucleotides, 15 nucleotides, 16 nucleotides, 17 nucleotides, 18 nucleotides, 19 nucleotides, 20 nucleotides, 25 nucleotides, 30 nucleotides, 35 nucleotides, 40 nucleotides, 45 nucleotides, 50 nucleotides, 55 nucleotides, 60 nucleotides, 65 nucleotides, 70 nucleotides, 75 nucleotides, 80 nucleotides, 85 nucleotides, 90 nucleotides, 95 nucleotides, 100 nucleotides, 110 nucleotides, 120 nucleotides, 130 nucleotides, 140 nucleotides, or 150 nucleotides upstream of the ATG translation start codon of a heterologous nucleic acid in the sense orientation. In some cases, the regulatory region can be operably linked from approximately 151 to 500 nucleotides upstream of the ATG translation start codon of a heterologous nucleic acid in the sense orientation. In some cases, the regulatory region can be operably linked from approximately 501 to 1125 nucleotides upstream of the ATG translation start codon of a heterologous nucleic acid in the sense orientation.

In some embodiments, a heterologous nucleic acid is transcribed and translated into a polypeptide. Suitable polypeptides include, without limitation, screenable and selectable markers such as green fluorescent protein, yellow fluorescent protein, luciferase, β-glucuronidase, or neomycin phosphotransferase II. Suitable polypeptides also include polypeptides that affect response to shade conditions in plants. In some embodiments, a heterologous nucleic acid encodes a polypeptide involved in inhibition of cell elongation, e.g., an MSBP1 polypeptide (At5g52240) or an HFR1 polypeptide (At1g02340). See, e.g., Yang et al., Plant Cell 17:116-131 (2005), and Yang et al, Plant Physiol. 133:1630-1642 (2003). Suitable polypeptides also include polypeptides whose expression is induced by exposure to light, such as those set forth in SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:117, and SEQ ID NO:119. Examples of nucleic acids that encode suitable polypeptides include those sequences set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:112, SEQ ID NO:114, SEQ ID NO:116, and SEQ ID NO:118.

A nucleic acid construct may include a heterologous nucleic acid that is transcribed into an RNA useful for inhibiting expression of a gene. Suitable constructs from which such an RNA can be transcribed include antisense constructs. Antisense nucleic acid constructs can include a regulatory region of the invention operably linked, in antisense orientation, to a nucleic acid molecule that is heterologous to the regulatory element. Thus, for example, a transcription product can anneal to the sense coding sequence of an endogenous polypeptide. A transcription product can also be unpolyadenylated, lack a 5' cap structure, or contain an unsplicable intron. Constructs containing operably linked nucleic acid molecules in sense orientation also can be used to inhibit the expression of a gene. Methods of co-suppression using a full-length cDNA sequence as well as a partial cDNA sequence are known in the art. See, e.g., U.S. Pat. No. 5,231,020.

Alternatively, a heterologous nucleic acid can be transcribed into a ribozyme. See, U.S. Pat. No. 6,423,885. Heterologous nucleic acid molecules can encode ribozymes designed to cleave particular mRNA transcripts, thus preventing expression of a polypeptide. Hammerhead ribozymes are useful for destroying particular mRNAs, although various ribozymes that cleave mRNA at site-specific recognition sequences can be used. Hammerhead ribozymes cleave mRNAs at locations dictated by flanking regions that form complementary base pairs with the target mRNA. The sole requirement is that the target RNA contain a 5'-UG-3' nucleotide sequence. The construction and production of hammerhead ribozymes is known in the art. See, for example, U.S. Pat. No. 5,254,678. Hammerhead ribozyme sequences can be embedded in a stable RNA such as a transfer RNA (tRNA) to increase cleavage efficiency in vivo. Perriman et al., *Proc. Natl. Acad. Sci. USA,* 92(13):6175-6179 (1995); de Feyter and Gaudron, *Methods in Molecular Biology, Vol.* 74, Chapter 43, "Expressing Ribozymes in Plants," Edited by Turner, P. C, Humana Press Inc., Totowa, N.J. RNA endoribonucleases which have been described, such as the one that occurs naturally in *Tetrahymena thermophila*, can be useful. See, for example, U.S. Pat. Nos. 4,987,071 and 6,423,885.

PTGS, e.g., RNAi, can also be used to inhibit the expression of a gene. For example, a construct can be prepared that includes a sequence that is transcribed into an RNA that can anneal to itself, e.g., a double stranded RNA having a stem-loop structure. In some embodiments, one strand of the stem portion of a double stranded RNA comprises a sequence that is similar or identical to the sense coding sequence of a polypeptide, and that is from about 10 nucleotides to about 2,500 nucleotides in length. The length of the sequence that is similar or identical to the sense coding sequence can be from 10 nucleotides to 500 nucleotides, from 15 nucleotides to 300 nucleotides, from 20 nucleotides to 100 nucleotides, or from 25 nucleotides to 100 nucleotides. The other strand of the stem portion of a double stranded RNA comprises a sequence that is similar or identical to the antisense strand of the coding sequence of the polypeptide, and can have a length that is shorter, the same as, or longer than the corresponding length of the sense sequence. In some cases, one strand of the stem portion of a double stranded RNA comprises a sequence that is similar or identical to the 3' or 5' untranslated region of an mRNA encoding a polypeptide, and the other strand of the stem portion of the double stranded RNA comprises a sequence that is similar or identical to the sequence that is complementary to the 3' or 5' untranslated region, respectively, of the mRNA encoding the polypeptide. In other embodiments, one strand of the stem portion of a double stranded RNA comprises a sequence that is similar or identical to the sequence of an intron in the pre-mRNA encoding a polypeptide, and the other strand of the stem portion comprises a sequence that is similar or identical to the sequence that is complementary to the sequence of the intron in the pre-mRNA. The loop portion of a double stranded RNA can be from 3 nucleotides to 5,000 nucleotides, e.g., from 3 nucleotides to 25 nucleotides, from 15 nucleotides to 1,000 nucleotides, from 20 nucleotides to 500 nucleotides, or from 25 nucleotides to 200 nucleotides. The loop portion of the RNA can include an intron. A double stranded RNA can have zero, one, two, three, four, five, six, seven, eight, nine, ten, or more stem-loop structures. A construct including a sequence that is operably linked to a regulatory region and a transcription termination sequence, and that is transcribed into an RNA that can form a double stranded RNA, is transformed into plants as described herein. Methods for using RNAi to inhibit the expression of a gene are known to those of skill in the art. See, e.g., U.S. Pat. Nos. 5,034,323; 6,326,527; 6,452,067; 6,573,099; 6,753,139; and 6,777,588. See also WO 97/01952; WO 98/53083; WO 99/32619; WO 98/36083; and U.S. Patent Publications 20030175965, 20030175783, 20040214330, and 20030180945.

If desired, a nucleic acid construct further can include a 3' untranslated region (3' UTR), which can increase stability of a transcribed sequence by providing for the addition of multiple adenylate ribonucleotides at the 3' end of the transcribed mRNA sequence. A 3' UTR can be, for example, the nopaline synthase (NOS) 3' UTR. A nucleic acid construct also can contain inducible elements, intron sequences, enhancer sequences, insulator sequences, or targeting sequences other than those present in a regulatory region described herein. Regulatory regions and other nucleic acids can be incorporated into a nucleic acid construct using methods known in the art.

A nucleic acid construct may contain more than one regulatory region. In some embodiments, each regulatory region is operably linked to a heterologous nucleic acid. For example, a nucleic acid construct may contain two regulatory regions, each operably linked to a different heterologous nucleic acid. The two regulatory regions can be the same or different, and one or both of the regulatory regions in such a construct can be a regulatory region described herein.

Transgenic Plants and Cells

Nucleic acids provided herein can be used to transform plant cells and generate transgenic plants. Thus, transgenic plants and plant cells containing the nucleic acids described herein also are provided, as are methods for making such transgenic plants and plant cells. A plant or plant cell can be transformed by having the construct integrated into its genome, i.e., can be stably transformed. Stably transformed cells typically retain the introduced nucleic acid sequence with each cell division. A plant or plant cell also can be transiently transformed such that the construct is not integrated into its genome. Transiently transformed cells typically lose some or all of the introduced nucleic acid construct with each cell division, such that the introduced nucleic acid cannot be detected in daughter cells after sufficient number of cell divisions. Both transiently transformed and stably transformed transgenic plants and plant cells can be useful in the methods described herein.

Transgenic plant cells used in the methods described herein can constitute part or all of a whole plant. Such plants can be grown in a manner suitable for the species under consideration, either in a growth chamber, a greenhouse, or in a field. Transgenic plants can be bred as desired for a particular purpose, e.g., to introduce a recombinant nucleic acid into other lines, to transfer a recombinant nucleic acid to other species, or for further selection of other desirable traits. Alternatively, transgenic plants can be propagated vegetatively for those species amenable to such techniques.

As used herein, a transgenic plant also refers to progeny of an initial transgenic plant. Progeny include descendants of a particular plant or plant line. Progeny of an instant plant include seeds formed on $F_1$, $F_2$, $F_3$, $F_4$, $F_5$, $F_6$, and subsequent generation plants, or seeds formed on $BC_1$, $BC_2$, $BC_3$, and subsequent generation plants, or seeds formed on $F_1BC_1$, $F_1BC_2$, $F_1BC_3$, and subsequent generation plants. The designation $F_1$ refers to the progeny of a cross between two parents that are genetically distinct. The designations $F_2$, $F_3$, $F_4$, $F_5$, and $F_6$ refer to subsequent generations of self- or sib-pollinated progeny of an $F_1$ plant. Seeds produced by a transgenic plant can be grown and then selfed (or outcrossed and selfed) to obtain plants and seeds homozygous for the nucleic acid construct.

Transgenic plant cells can be grown in suspension culture, or tissue or organ culture. Solid and/or liquid tissue culture techniques can be used. When using solid medium, transgenic plant cells can be placed directly onto the medium or can be placed onto a filter film that is then placed in contact with the medium. When using liquid medium, transgenic plant cells can be placed onto a floatation device, e.g., a porous membrane that contacts the liquid medium. Solid medium typically is made from liquid medium by adding agar. For example, a solid medium can be Murashige and Skoog (MS) medium containing agar and a suitable concentration of an auxin, e.g., 2,4-dichlorophenoxyacetic acid (2,4-D), and a suitable concentration of a cytokinin, e.g., kinetin.

Techniques for transforming a wide variety of higher plant species are known in the art. The polynucleotides and/or recombinant vectors described herein can be introduced into the genome of a plant host using any of a number of known methods, including electroporation, microinjection, and biolistic methods. Alternatively, polynucleotides or vectors can be combined with suitable T-DNA flanking regions and introduced into a conventional *Agrobacterium tumefaciens* host vector. Such *Agrobacterium tumefaciens*-mediated transformation techniques, including disarming and use of binary vectors, are well known in the art. Other gene transfer and transformation techniques include protoplast transformation through calcium or PEG, electroporation-mediated uptake of naked DNA, electroporation of plant tissues, viral vector-mediated transformation, and microprojectile bombardment (see, e.g., U.S. Pat. Nos. 5,538,880; 5,204,253; 5,591,616; and 6,329,571). If a cell or tissue culture is used as the recipient tissue for transformation, plants can be regenerated from transformed cultures using techniques known to those skilled in the art.

The polynucleotides and vectors described herein can be used to transform a number of monocotyledonous and dicotyledonous plants and plant cell systems, including dicots such as alfalfa, amaranth, apple, beans (including kidney beans, lima beans, green beans), broccoli, cabbage, carrot, castor bean, cherry, chick peas, chicory, clover, cocoa, coffee, cotton, cottonseed, crambe, eucalyptus, flax, grape, grapefruit, lemon, lentils, lettuce, linseed, mango, melon (e.g., watermelon, cantaloupe), mustard, orange, peach, peanut, pear, peas, pepper, plum, poplar, potato, rapeseed (high erucic acid and canola), safflower, sesame, soybean, spinach, strawberry, sugarbeet, sunflower, tea, tomato, as well as monocots such as banana, barley, date palm, field corn, garlic, millet, oat, oil palm, onion, pineapple, popcorn, rice, rye, sorghum, sudangrass, sugarcane, sweet corn, switchgrass, turf grasses, and wheat. Gymnosperms such as fir, pine and spruce can also be suitable.

Thus, the methods and compositions described herein can be used with dicotyledonous plants belonging, for example, to the orders *Apiales, Arecales, Aristochiales, Asterales, Batales, Campanulales, Capparales, Caryophyllales, Casuarinales, Celastrales, Cornales, Curcubitales, Diapensales, Dilleniales, Dipsacales, Ebenales, Ericales, Eucomiales, Euphorbiales, Fabales, Fagales, Gentianales, Geraniales, Haloragales, Hamamelidales, Illiciales, Juglandales, Lamiales, Laurales, Lecythidales, Leitneriales, Linales, Magniolales, Malvales, Myricales, Myrtales, Nymphaeales, Papaverales, Piperales, Plantaginales, Plumbaginales, Podostemales, Polemoniales, Polygalales, Polygonales, Primulales, Proteales, Rafflesiales, Ranunculales, Rhamnales, Rosales, Rubiales, Salicales, Santales, Sapindales, Sarraceniaceae, Scrophulariales, Solanales, Trochodendrales, Theales, Umbellales, Urticales,* and *Violales*. The methods and compositions described herein also can be utilized with monocotyledonous plants such as those belonging to the orders *Alismatales, Arales, Arecales, Bromeliales, Commelinales, Cyclanthales, Cyperales, Eriocaulales, Hydrocharitales, Juncales, Liliales, Najadales, Orchidales, Pandanales, Poales, Restionales, Triuridales, Typhales, Zingiberales,* and with plants belonging to *Gymnospermae*, e.g., *Cycadales, Ginkgoales, Gnetales*, and *Pinales*.

The methods and compositions can be used over a broad range of plant species, including species from the dicot genera *Alseodaphne, Amaranthus, Anacardium, Angophora, Apium, Arabidopsis, Arachis, Atropa, Azadirachta, Beilschmiedia, Beta, Bixa, Brassica, Calendula, Camellia, Canarium, Cannabis, Capsicum, Carthamus, Catharanthus, Cicer, Cichorium, Cinnamomum, Citrus, Citrullus, Coccolus, Cocos, Coffea, Corylus, Corymbia, Crambe, Croton, Cucumis, Cucurbita, Cuphea, Daucus, Dianthus, Dioscorea, Duguetia, Eschscholzia, Eucalyptus, Euphoria, Ficus, Fragaria, Glaucium, Glycine, Glycyrrhiza, Gossypium, Helianthus, Hevea, Hyoscyamus, Jatropha, Juglans, Lactuca, Landolphia, Lens, Linum, Litsea, Lupinus, Lycopersicon, Majorana, Malus, Mangifera, Manihot, Medicago, Mentha, Micropus, Nicotiana, Ocimum, Olea, Papaver, Parthenium, Persea, Petunia, Phaseolus, Pistacia, Pisum, Populus, Prunus, Pyrus, Raphanus, Ricinus, Rosa, Rosmarinus, Rubus, Salix, Salvia, Senecio, Sesamum, Sinapis, Sinomenium, Simmondsia, Solanum, Spinacia, Stephania, Tagetes, Theobroma, Thymus, Trifolium, Trigonella, Vaccinium, Vicia, Vigna, Vinca, Vitis*; and the monocot genera *Agrostis, Allium, Ananas, Andropogon, Asparagus, Avena, Cocos, Curcuma, Cynodon, Elaeis, Eragrostis, Festuca, Festulolium, Heterocallis, Hordeum, Lemna, Lolium, Musa, Oryza, Panicum, Pennisetum, Phleum, Phoenix, Poa, Saccharum, Secale, Sorghum, Triticosecale, Triticum, Zoysia* and *Zea*; and the gymnosperm genera *Abies, Cunninghamia, Picea, Pinus* and *Pseudotsuga*.

A particularly suitable group of species with which to practice the invention include plants from the genera *Brassica, Triticum, Glycine, Zea, Oryza*, and *Populus*.

A transformed cell, callus, tissue, or plant can be identified and isolated by selecting or screening the engineered plant material for particular traits or activities, e.g., those encoded by marker genes or antibiotic resistance genes. Such screening and selection methodologies are well known to those having ordinary skill in the art. In addition, physical and biochemical methods can be used to identify transformants. These include Southern analysis or PCR amplification for detection of a polynucleotide; Northern blots, S1 RNase protection, primer-extension, quantitative PCR, or reverse transcriptase PCR (RT-PCR) amplification for detecting RNA transcripts; enzymatic assays for detecting enzyme or ribozyme activity of polypeptides and polynucleotides; and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are well known.

A regulatory region disclosed herein can be used to express any of a number of heterologous nucleic acids of interest in a plant. For example, a regulatory region disclosed herein can be used to express a polypeptide or an interfering RNA. In some cases, a regulatory region disclosed herein can be used to express a zinc finger (B-box type) polypeptide, such as that encoded by locus At3g21890, under shade conditions in a plant. In some cases, a regulatory region disclosed herein can be used to express under shade conditions in a plant an interfering RNA that inhibits expression of an AXR1 polypeptide (At2g32410) or a C22-αhydroxylase P450 polypeptide such as that encoded by locus At3g50660. Expression of such a polypeptide or interfering RNA can affect the phenotype of a plant, e.g., a transgenic plant, when expressed in the plant, e.g., at the appropriate time(s), in the appropriate tissue(s), or at the appropriate expression levels. Thus, transgenic plants (or plant cells) can have an altered phenotype as compared to a corresponding control plant (or plant cell) that either lacks the transgene or does not express the transgene. A corresponding control plant can be a corresponding wild-type plant, a corresponding plant that is not transgenic but otherwise is of the same genetic background as the transgenic plant of interest, or a corresponding plant of the same genetic background in which expression of the transgene is suppressed, inhibited, or not induced, e.g., where expression is under the control of an inducible promoter. A plant can be said "not to express" a transgene when the plant exhibits less than 10%, e.g., less than 9%, 8%, 7%, 6%, 5%, 4%, 3%, 2%, 1%, 0.5%, 0.1%, 0.01%, or 0.001%, of the amount of the polypeptide, mRNA encoding the polypeptide, or transcript of the transgene exhibited by the plant of interest. Expression can be evaluated using methods including, for example, quantitative PCR, RT-PCR, Northern blots, S1 RNase protection, primer extensions, Western blots, protein gel electrophoresis, immunoprecipitation, enzyme-linked immunoassays, microarray technology, and mass spectrometry. It should be noted that if a transgene is expressed under the control of a tissue-preferential or broadly expressing promoter, expression can be evaluated in a selected tissue or in the entire plant. Similarly, if a transgene is expressed at a particular time, e.g., at a particular time during development or upon induction, expression can be evaluated selectively during a desired time period.

Use of a regulatory region provided herein to regulate transcription of a sucrose transporter polypeptide such as SUC5 (At1g71890) in a plant can maintain development and maturation of fruit under shade conditions, compared to a corresponding control plant. See, Baud, et al, Plant J. 43:824-836 (2005). Such a trait can increase plant survival and seedling establishment of high density plant populations in crops even when plants are near mature growth stages. In some embodiments, use of the methods and compositions described herein to express a light harvesting complex, e.g., a CAB (At3g54890); a CAB2 (At1g29920); an LHCA5 (At1 g45474); an LHCB2 (At2g05100); or an LHCB5 (At4g10340) polypeptide under shade conditions in a plant can preserve plastid ultrastructure present at the onset of darkness, compared to a corresponding control plant. See, Breitholtz, et al., Photosynth Res. 84:217-223 (2005).

Seeds of transgenic plants describe herein can be conditioned and bagged in packaging material by means known in the art to form an article of manufacture. Packaging material such as paper and cloth are well known in the art. Such a bag of seed preferably has a package label accompanying the bag, e.g., a tag or label secured to the packaging material, a label printed on the packaging material, or a label inserted within the bag. The package label may indicate the seed contained therein incorporates transgenes that provide improved response to shade conditions.

The invention will be further described in the following examples, which do not limit the scope of the invention described in the claims.

EXAMPLES

The following symbols are used in the Examples: for *Arabidopsis*—$T_1$: first generation transformant; $T_2$: second generation, progeny of self-pollinated $T_1$ plants; $T_3$: third generation, progeny of self-pollinated $T_2$ plants; for rice—$T_0$: first generation; $T_1$: second generation, progeny of self-pollinated $T_0$ plants; $T_2$: third generation, progeny of self-pollinated $T_1$ plants. Independent transformations are referred to as events.

Example 1

PR0924::HAP1-VP16 Two Component Expression Vector

A 5' region from the AUX/IAA29 gene of *Arabidopsis thaliana* ecotype Columbia was amplified using PCR. The AUX/IAA29 gene (locus tag—At4g32280) is reported to encode a transcription factor. See, Riechmann, et al., *Science* 290:2105 (2000). The resulting 3000 base pair fragment was designated PR0924 (SEQ ID NO:1).

PR0924 was cloned into a binary vector, pNewBin4-HAP1-GFP, such that it was operably linked to a synthetic HAP1-VP16 coding sequence. See, U.S. Patent Publication No. 20050223422. The HAP1-VP16 coding sequence comprised a DNA binding domain of a yeast HAP1 zinc finger transcription factor polypeptide fused to a transcriptional activation domain of a herpes simplex virus VP16 polypeptide. The pNewBin4-HAP1-GFP binary vector construct also contained a HAP1 upstream activation sequence operably linked to a GFP coding sequence optimized for expression in plants. See, e.g., U.S. Patent Publication 20050132432. GFP is expressed in response to expression of the HAP1-VP16 polypeptide. The binary vector construct also contained a phosphinothricin acetyltransferase gene that confers Finale™ resistance to transformed plants.

Wild-type *Arabidopsis thaliana* ecotype Columbia (Col-0) plants were transformed with the binary vector containing the PR0924::HAP1-VP16 construct essentially as described in Bechtold et al., *C. R. Acad. Sci. Paris,* 316:1194-1199 (1993) and transformation events were identified based on Finale™ resistance. Plants from six independent events, designated PR0924-01 through PR0924-06, were chosen for further study. $T_1$ plants from the six independent events were grown, allowed to self-pollinate, and the resulting $T_2$ seeds harvested. Untransformed wild-type *Arabidopsis thaliana* ecotype Columbia (Col-0) plants were used as controls. The in planta nucleotide sequence of PR0924 in mature $T_3$ plants was confirmed by DNA sequencing in both directions.

Example 2

Analysis of GFP Fluorescence in PR0924 Plants $T_2$ seeds from each event described in Example 1 were plated on sterile 0.5% sucrose, 1× MS agar media and stratified at 4° C. for 3-4 days in the dark. Stratified seeds were then placed into Conviron® growth chambers and grown for 7 days under the following conditions: 22° C., 16 hr white light, 8 hr dark cycle at a PPFD of 70 µmol/m²/s and a ratio of red/far red light of 10.66.

Half of the plates were then transferred to a growth chamber and grown at 22° C. under continuous white light as described above. The remaining plates were transferred to a growth chamber grown at 22° C. under SNAP-LITE™ far red light boxes (Quantum Devices, SL1515-670-735) for continuous exposure to far red light at 8 lux with the following fluence rates: Blue$_{450}$=0.005 µmol/m²/s, Red$_{633}$=7 µmol/m²/s, Far Red$_{740}$=69 µmol/m²/s. The PAR$_{400-700}$ was 5 µmol/m²/s and the ratio of red/far red light was 0.1. Plates containing control seedlings were transferred and grown under the same conditions (continuous white or far red light). Plants from the PR0924 and control populations were removed from the chambers at 1 hr, 4 hr, 24, 48, or 72 hr, and GFP expression was measured by confocal microscopy and fluorescence scanning using a Typhoon® imaging system. The images were then visually examined to evaluate GFP fluorescence under far red conditions relative to GFP fluorescence under white light conditions. If fluorescence under far red conditions was greater than that observed under white light conditions, it was concluded that GFP expression had been induced.

The results are shown in Table 1. These results indicated that, at 24, 48 and 72 hours after transfer, plants from the PR0924-01 and -03 events showed increased GFP fluorescence under far red light conditions when compared to the GFP fluorescence of PR0924 events under white light conditions. At 72 hours after transfer, GFP fluorescence in cotyledons, hypocotyls, petioles, and developing true leaves could be readily observed in PR0924-01 and -03 seedlings.

Plants from events -05 and -06 also showed an increase in GFP fluorescence under far red light conditions relative to the corresponding -05 and -06 plants under white light conditions, although to a lesser extent than the increase observed with plants of the -01 and -03 events.

Seedlings from the PR0924-02 and -04 events showed a low level of GFP fluorescence in both white and far red light conditions. Seedlings from PR0924-02 and -04 events also showed greater GFP fluorescence at 72 hours under far red light relative to white light, but the increase was less than that observed for PR0924-01 and -03 seedlings.

No GFP fluorescence was observed in untransformed Col-0 plants at any time point under either white or far red light conditions.

GFP fluorescence was also analyzed as described above in $T_3$ seedlings of events-01 and -03. The results are shown in Table 2. The results showed that there was increased GFP expression under far red light conditions at 24, 48, and 72 hours after transfer, compared to expression under white light conditions. GFP fluorescence was observed in the cotyledons, hypocotyls, petioles and developing true leaves of $T_3$ seedlings at 24, 48, and 72 hours after transfer. No GFP fluorescence was observed in untransformed Col-0 plants or in seedlings from a $T_3$ segregant that lacked the PR0924::HAP1-VP16 construct.

TABLE 1

| PR0924 | Induction of GFP Fluorescence | | | | |
|---|---|---|---|---|---|
| Event | 1 hr | 4 hr | 24 hr | 48 hr | 72 hr |
| -01 | - | - | ++ | +++++ | ++++++ |
| -02 | - | - | - | - | + |
| -03 | - | - | ++ | +++++ | ++++++ |
| -04 | - | - | - | - | + |
| -05 | - | - | + | +++ | ++++ |
| -06 | - | - | - | - | ++ |

TABLE 2

| PR0924 | Induction of GFP Fluorescence | | | | |
|---|---|---|---|---|---|
| Event | 1 hr | 4 hr | 24 hr | 48 hr | 72 hr |
| -01-07 | - | - | ++ | +++++ | ++++++ |
| -03-03 | - | - | ++ | +++++ | ++++++ |
| -01-01* | - | - | - | - | - |

*Denotes segregant lacking the PR0924::HAP1-VP16 construct

Example 3

Analysis of PR0924::HAP1-VP16 Transcription

RT-PCR analysis was carried out to evaluate the amount of HAP1-VP16 transcript and the amount of endogenous AUX/IAA29 transcript present after transfer to far-red or to white light conditions. PR0924-01, -03 and -05 seedlings were analysed at 1, 24, 48 and 72 hours after transfer as described in Example 2. Untransformed Col-0 seedlings were used as control seedlings. The amount of endogenous ATHB-2 and tubulin transcripts was also measured. Expression of ATHB-2 is known to be induced by far red light. Carabelli, et al., *Proc. Natl. Acad. Sci. USA*, 93: 3530-3535 (1996). Expression of tubulin is not affected by differences in light spectrum.

Figure 1:
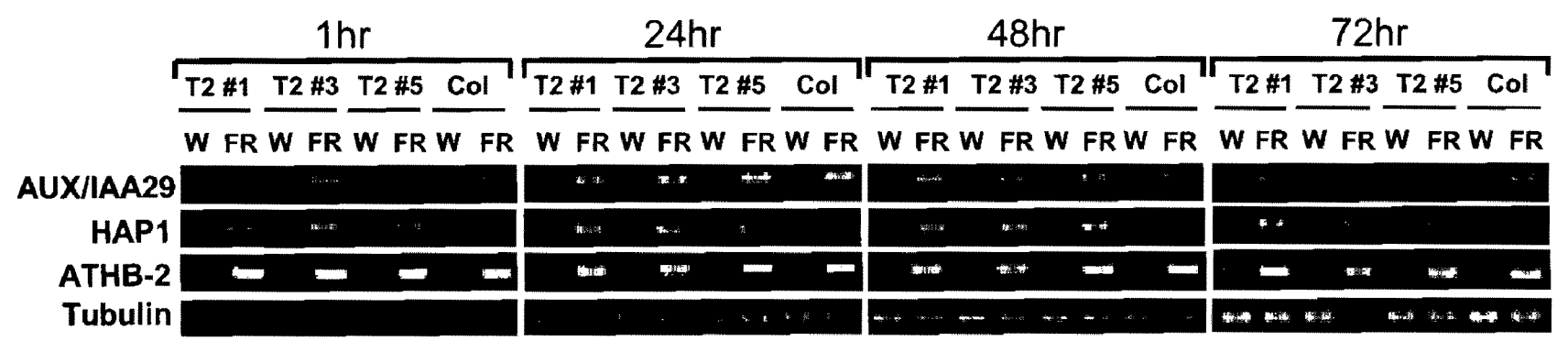

The results, shown in FIG. 1, indicate that HAP1-VP16, AUX/IAA29 and ATHB-2 transcripts can be detected as early as 1 hour after transfer to far red light conditions. These results suggest that transcription driven by the PR0924 regulatory region is induced within one hour after exposure to far red light conditions.

Transcription of the PR0924::HAP-VP16 transgene was also analyzed in $T_3$ seedlings of PR0924-01-07 and PR0924-03-03 lines as described above. As shown in FIG. 2, HAP1-VP16, AUX/IAA29, and ATHB-2 transcripts were detected as early as 30 minutes after transfer to far red light conditions. These results suggest that transcription driven by the PR0924 regulatory region is induced within 30 minutes after exposure to far red light conditions.

In a second set of experiments, transcription of the PR0924::HAP-VP16 transgene was analyzed in $T_3$ seedlings of PR0924-01-07 and PR0924-03-03 lines under 8 hours of far red light conditions or low light conditions followed by 2 hours of white light exposure. The results shown in Table 3, confirm that transcription driven by the PR0924 regulatory region is induced by far red light conditions, and indicate that transcription driven by the PR0924 regulatory region returns to basal levels by 2 hours after white light exposure. Table 4 shows that transcription driven by the PR0924 regulatory region is also induced by exposure to low light conditions. These results suggest that transcription driven by the PR0924 regulatory region is induced by far red light conditions and low light conditions, and return to basal levels within 2 hours upon exposure to white light conditions.

TABLE 3

| Line | Far Red Exposure Time | | | | | | White Light Exposure Time | | | |
|---|---|---|---|---|---|---|---|---|---|---|
| | 10 min. | 30 min. | 1 hr | 2 hr | 4 hr | 8 hr | 10 min. | 30 min. | 1 hr | 2 hr |
| HAP-VP16 Expression | | | | | | | | | | |
| PR0924-01-07 | 1.02 | 21.11 | 16.37 | 2765.52 | 601.88 | 76.99 | 26.6 | 80.63 | 29.86 | 0.89 |
| PR0924-03-03 | 1.1 | 7.64 | 794.19 | 1136.2 | 1260.69 | 182.07 | 41.74 | 103.97 | 14.59 | 1.74 |
| PR0924-01-01** | 0 | 0 | 0 | 0 | 0 | 0 | 0.62* | 1.62* | 5.79* | 0.28* |
| Endogenous AUX/IAA29 Expression | | | | | | | | | | |
| PR0924-01-07 | 9.62 | 217.77 | 45.25 | 0.11 | 82.52 | 238.86 | 10.93 | 4.44 | 0.38 | 0.69 |
| PR0924-03-03 | 8.38 | 161.27 | 99.27 | 203.19 | 132.51 | 144.51 | 6.35 | 5.34 | 0.31 | 0.91 |
| PR0924-01-01** | 2.43 | 3.07 | 488.88 | 397.09 | 2325.51 | 128 | 17.55 | 13 | 0.26 | 0.15 |

*HAP-VP16 detected in non-transgenic control plants is an artifact of qRT-PCR, and results after >33 cycles of qRT-PCR.
**Denotes segregant lacking the PR0924::HAP1-VP16 construct

TABLE 4

| Line | Low Light Exposure Time | | | | | | White Light Exposure Time | | | |
|---|---|---|---|---|---|---|---|---|---|---|
| | 10 min. | 30 min. | 1 hr | 2 hr | 4 hr | 8 hr | 10 min. | 30 min. | 1 hr | 2 hr |
| HAP-VP16 Expression | | | | | | | | | | |
| PR0924-01-07 | 0.37 | 3.36 | 0.15 | 49.64 | 16.19 | 1.38 | 0.39 | 1.26 | 1.91 | 0.2 |
| PR0924-03-03 | 0.64 | 0.64 | 9.62 | 21.61 | 47.67 | 0.76 | 0.66 | 0.64 | 1.15 | 1.12 |
| PR0924-01-01** | 0 | 0 | 0 | 0 | 0 | 0 | 0.2* | 0.6* | 6.96* | 2.41* |
| Endogenous AUX/IAA29 | | | | | | | | | | |
| PR0924-01-07 | 1.74 | 3.95 | 0.13 | 0 | 2.38 | 0.41 | 0.37 | 0.49 | 1.4 | 4.49 |
| PR0924-03-03 | 1.48 | 2.09 | 0.84 | 3.69 | 13.22 | 3.82 | 2.09 | 0.05 | 0.12 | 0.39 |
| PR0924-01-0** | 1.27 | 0.65 | 1.32 | 4.76 | 23.43 | 8 | 0.81 | 2.52 | 0.03 | 0.91 |

*HAP-VP16 detected in non-transgenic control plants is an artifact of qRT-PCR, and results after >33 cycles of qRT-PCR.
**Denotes segregant lacking the PR0924::HAP1-VP16 construct

Example 4

Analysis of PR0924::HAP1-VP16 Transcription Under Tobacco Natural Shade Canopy Transcription of the PR0924::HAP-VP16 transgene was analyzed in $T_3$ seedlings of PR0924-01-07 and PR0924-03-03 lines under 8 hours of natural shade canopy created by leaves of tobacco plants, followed by 2 hours of non-canopy exposure under standard greenhouse lighting conditions. Seedlings were planted as in Example 3 but were grown in standard greenhouse conditions where the non-canopy lighting is PAR ~250 μmol/m²/s, R:FR=4.2, under a 16 hour light/8 hour dark cycle. For the tobacco natural canopy induction conditions, the lighting conditions were PAR=2.1-5.6 μmol/m²/s, R:FR<0.3. The results shown in Table 5, confirm that transcription driven by the PR0924 regulatory region is induced by natural canopy conditions between 30 minutes and 4 hours, that transcription levels are still elevated at 8 hours. The results also indicate that transcription driven by the PR0924 regulatory region returns to basal levels by 1-2 hours after non canopy exposure. A similar trend is seen for the endogenous gene, AUXIAA29, or At4g32280, with recovery to basal levels occurring after 30 minutes.

TABLE 5

| Natural Shade Canopy HAP-VP16 Expression | | | | | | | | | | |
|---|---|---|---|---|---|---|---|---|---|---|
| | Time Under Natural Shade Canopy | | | | | | White Light Exposure Time | | | |
| Line | 10 min. | 30 min. | 1 hr | 2 hr | 4 hr | 8 hr | 10 min. | 30 min. | 1 hr | 2 hr |
| PR0924-01-07 | 0.93 | 2.05 | 11.58 | 84.45 | 228.07 | 30.55 | 4.39 | 27.86 | 2.52 | 0.4 |
| PR0924-03-03 | 0.83 | 1.74 | 40.32 | 140.39 | 0.98 | 3.91 | 0.84 | 13.3 | 0.98 | 1.55 |
| PR0924-01-01** | 2 | 0 | 1.66 | 0 | 0 | 0 | 0 | 0 | 0 | 0 |

| Natural Shade Canopy AUX/IAA29 Expression | | | | | | | | | | |
|---|---|---|---|---|---|---|---|---|---|---|
| | Far Red Exposure Time | | | | | | White Light Exposure Time | | | |
| Line | 10 min. | 30 min. | 1 hr | 2 hr | 4 hr | 8 hr | 10 min. | 30 min. | 1 hr | 2 hr |
| PR0924-01-07 | 0.27 | 1.18 | 4.09 | 114.04 | 99.27 | 49.64 | 4 | 2.35 | 2.19 | 0.87 |
| PR0924-03-03 | 0 | 8.57 | 1.91 | 51.98 | 1.87 | 8.57 | 1.76 | 1.2 | 0.43 | 1.62 |
| PR0924-01-01** | 0.17 | 0.76 | 21.86 | 741 | 217.77 | 103.97 | 61.11 | 2.52 | 2.52 | 2.76 |

**Denotes segregant lacking the PR0924::HAP1-VP16 construct

Example 5

Analysis of GFP Fluorescence in PT0672 Plants

A portion of SEQ ID NO:1, designated PT0672, was cloned into the pNewBin4-HAP1-GFP binary vector, such that it was operably linked to the HAP1-VP16 coding sequence. The PT0672 fragment consisted of nucleotides 2001 to 3000 of SEQ ID NO:1. The vector was transformed into *Arabidopsis thaliana* ecotype WS-2 as described in Example 1. $T_2$ seedlings were grown, transferred to far red or white light conditions, and analysed for GFP fluorescence as described in Example 2. High GFP expression was observed throughout the root vasculature and hypocotyl. However, no induction of GFP expression under far red light conditions was observed. See, U.S. Publication No. US2005/0266559.

Example 6

Analysis of GFP Fluorescence and PR0924::HAP1-VP16 Transcription in Rice Plants Wild-type *Oryza sativa* subspecies *japonica* (Kitaake cultivar) calli were transformed with the binary vector containing the PR0924::HAP1-VP16 construct described in Example 1 using techniques similar to those described in U.S. Pat. No. 6,329,571. Transformation events were selected based on Finale™ resistance. Plants were regenerated from Finale™-resistant calli. Plants from two events were chosen for further study. To plants were grown, allowed to self-pollinate, and the resulting $T_1$ seeds harvested. Non-transgenic segregate plants were used as controls. The in planta nucleotide sequence of PR0924 in mature $T_2$ plants was confirmed by DNA sequencing in both directions, and is shown in SEQ ID NO 1.

Ten to twenty $T_2$ seeds for each condition (continuous white and far red light) were sown in tubes of sterile 0.15% sucrose, 0.5×MS agar media and grown for 2, 6, or 12 days in Conviron® growth chambers under the following conditions: 22° C., 16 hr white light, 8 hr dark cycle at a PPFD of 70 $\mu mol/m^2/s$ and a ratio of red/far red light of 10.66.

Half of the plants were allowed continued growth at 22° C. under continuous white light as described above. The remaining plates were transferred to a growth chamber grown at 22° C. under SNAP-LITE™ far red light boxes for continuous exposure to far red light at ~8 lux with the following fluence rates: $Blue_{450}=0$ $\mu W/cm^2$, $Red_{660}=65$ $\mu W/cm^2$, Far $Red_{730}=525$ $\mu W/cm^2$. The $PAR_{400-700}$ was 1.2 $\mu mol/m^2/s$ and the ratio of red/far red light was 0.12. Tubes containing control seedlings were transferred and grown under the same conditions (continuous white or far red light). Plants from the PR0924 and control populations were removed from the chambers at 12 or 14 days, and GFP expression was analyzed as described in Example 2.

The results are shown in Table 6. These results indicate that plants from rice PR0924 events showed GFP fluorescence induction under far red light conditions. GFP fluorescence was primarily observed in the collar region between the leaf sheath and leaf blade, as well as the leaf vasculature. Some GFP fluorescence was also observed in the leaf blade. Non-transgenic segregant controls did not express GFP when grown in either white light or far red conditions.

TABLE 6

| Days in white light | Days in far red light | GFP expression |
|---|---|---|
| 2 | 12 | ++ |
| 2 | 10 | ++ |
| 6 | 8 | ++ |
| 12 | 2 | + |

RT-PCR analysis was carried out in $T_2$ plants from one event to evaluate the amount of HAP1-VP16 transcript present after transfer to far-red or to white light conditions as described in Example 3. Expression of HAP was 24.82-fold higher in homozygous transgenic PR0924 plants exposed to 12 days of continuous far red light than in control plants exposed to continuous white light.

Example 7

Mutagenized Derivatives of PR0924

Derivatives of PR0924 (SEQ ID NO:1) are generated by introducing mutations into the nucleotide sequence of the native *Arabidopsis* promoter as disclosed in U.S. Pat. No. 6,747,189, incorporated herein by reference. A plurality of mutagenized DNA segments derived from PR0924 including derivatives with nucleotides deletions and modifications are generated and inserted into a plant transformation vector operably linked to a GFP marker gene. Each of the plant transformation vectors are prepared essentially as described in Example 1, except that the full length PR0924 is replaced by a mutagenized derivative of PR0924. Rice plants are transformed with each of the plant transformation vectors and analyzed for expression of the GFP marker to identify those mutagenized derivatives having promoter activity.

Example 8

PR0924 Fragments

Fragments of PR0924 (SEQ ID NO:1) are isolated by designing primers to clone fragments of the full length PR0924. A plurality of cloned fragments of PR0924 ranging in size from 50 nucleotide up to the full length of PR0924 are obtained using PCR. A fragment from the 5' end of PR0924 comprising nucleotides 1-1000 of SEQ ID NO:1, and fragments of about 50, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600 and 1650 nucleotides in length from various parts of PR0924 comprising the TATA box are obtained and inserted into a plant transformation vector operably linked to a GFP marker gene. Each of the plant transformation vectors are prepared essentially as described in Example 1 except that the full length PR0924 is replaced by a fragment of PR0924 or a combination of the 5' end fragment and one of the other fragments that has the TATA box. *Arabidopsis* plants are transformed with each of the plant transformation vectors and analyzed for expression of the GFP marker to identify those fragments having promoter activity.

Example 9

YP2622 and YP2623

Two fragments of PR0924 (SEQ ID NO:1) were generated using PCR. A 1.5 kb fragment was generated and designated YP2622 (SEQ ID NO:120) and a 2 kb fragment was generated and designated YP2623 (SEQ ID NO:121). YP2622 and YP2623 were each inserted into a plant transformation vector operably linked to a GFP marker gene as described in Example 1. *Arabidopsis thaliana* ecotype Columbia plants were transformed with each of the plant transformation vectors and analyzed for expression of the GFP marker to measure promoter induction in response to far-red light using methods described in Example 1. No T2 seedlings from YP2622 or YP2623 transgenic promoter::GFP lines showed induction after 8 hr and 24 hr of far-red light induction. The positive control, PR0924-01-07 shows induction at 8 and 24 hours after far-red light exposure.

Example 10

Identification and Isolation of PR0924 Sequences from Organisms Other than *Arabidopsis thaliana*

The AUX/IAA29 coding sequence from *Arabidopsis* was used to query public genomic sequences. Other AUX/IAA29 sequences were identified, including a 3000 base pair fragment from the 5' region of the AUX/IAA29 gene of *Populus balsamifera* subsp. *trichocarpa*. The nucleotide sequence of this region is shown in the sequence listing as SEQ ID NO: 125. The 5' region of the *Populus balsamifera* subsp. *trichocarpa* AUX/IAA29 gene can be amplified using PCR and inserted into a plant transformation vector operably linked to a GFP marker gene. Plants can transformed with the plant transformation vector and analyzed for expression of the GFP marker.

This region can be used as a regulatory region alone or methods to clone and sequence larger genomic fragments, such as genome walking, can be used to identify sequences further upstream. Functional fragments can also be identified by using deletional analysis. These fragments can be parts of BAC sequences or from further genome sequencing efforts.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A nucleic acid construct comprising a regulatory region operably linked to a heterologous polynucleotide, said regulatory region having at least 98 percent sequence identity to the polynucleotide sequence set forth in SEQ ID NO: 1, wherein said regulatory region contains a BOXCPSAS1 motif, and wherein said regulatory region directs transcription of said operably linked heterologous polynucleotide under light conditions in which the red/far red ratio is less than 1.

2. The nucleic acid construct of claim 1, wherein said regulatory region contains a -10PEHVPSBD motif, an ASF1MOTIFCAMV motif, an IBOX motif and an IBOXCORE motif, a CACGTGMOTIF motif, GT1CORE motif, or a REALPHALGLHCB21 motif.

3. The nucleic acid construct of claim 1, wherein said heterologous polynucleotide comprises a nucleotide sequence encoding a polypeptide.

4. The nucleic acid construct of claim 3, wherein said polypeptide is a zinc finger (B-box type) polypeptide.

5. The nucleic acid construct of claim 1, wherein said heterologous polynucleotide is in an antisense orientation relative to said regulatory region.

6. The nucleic acid construct of claim 1, wherein said heterologous polynucleotide is transcribed into an interfering RNA.

7. A transgenic plant or plant cell transformed with the nucleic acid of claim 1.

8. A method of producing a transgenic plant, said method comprising (a) introducing into a plant cell an isolated polynucleotide comprising the nucleic acid construct of claim 1; and (b) growing a plant from said plant cell.

9. A nucleic acid construct comprising a regulatory region operably linked to a heterologous polynucleotide, said regulatory region comprising a 5' segment having at least 98 percent sequence identity to the polynucleotide sequence set forth in nucleotides 1-1000 of SEQ ID NO: 1, and a 3' segment comprising a TATA box, wherein said regulatory region contains a BOXCPSAS1 motif, and wherein said regulatory region directs transcription of said operably linked heterologous polynucleotide under light conditions in which the red/far red ratio is less than 1.

10. The nucleic acid construct of claim 9, wherein said heterologous polynucleotide comprises a nucleotide sequence encoding a polypeptide.

11. The nucleic acid construct of claim 10, wherein said polypeptide is a zinc finger (B-box type) polypeptide.

12. The nucleic acid construct of claim 9, wherein said heterologous polynucleotide is transcribed into an interfering RNA.

13. A transgenic plant or plant cell transformed with the nucleic acid of claim 9.

14. A method of producing a transgenic plant, said method comprising (a) introducing into a plant cell an isolated polynucleotide comprising the nucleic acid construct of claim 9; and (b) growing a plant from said plant cell.

15. A nucleic acid construct comprising a regulatory region operably linked to a heterologous polynucleotide, said regulatory region comprising the polynucleotide sequence set forth in SEQ ID NO: 1, wherein said regulatory region directs transcription of said operably linked heterologous polynucleotide under light conditions in which the red/far red ratio is less than 1.

* * * * *

UNITED STATES PATENT AND TRADEMARK OFFICE
CERTIFICATE OF CORRECTION

PATENT NO. : 8,232,380 B2
APPLICATION NO. : 12/197886
DATED : July 31, 2012
INVENTOR(S) : Shing Kwok It is certified that error appears in the above-identified patent and that said Letters Patent is hereby corrected as shown below:

Column 243 (Claim 2), line 15, delete "GT1CORE" and insert --a GT1CORE--, therefor.

Column 243 (Claim 7), line 29, after "nucleic acid", insert --construct--.

Column 244 (Claim 13), line 20, after "nucleic acid", insert --construct--.

Signed and Sealed this
Ninth Day of October, 2012

David J. Kappos
*Director of the United States Patent and Trademark Office*

```
                         SEQUENCE LISTING

<160> NUMBER OF SEQ ID NOS: 125

<210> SEQ ID NO 1
<211> LENGTH: 3000
<212> TYPE: DNA
<213> ORGANISM: Arabidopsis thaliana
<220> FEATURE:
<221> NAME/KEY: misc_feature
<223> OTHER INFORMATION: in planta sequence for Promoter Construct
      PR0924
<220> FEATURE:
<221> NAME/KEY: misc_feature
<222> LOCATION: (995)..(1000)
<223> OTHER INFORMATION: Motif Name: -10PEHVPSBD
<220> FEATURE:
<221> NAME/KEY: misc_feature
<222> LOCATION: (2686)..(2691)
<223> OTHER INFORMATION: Motif Name: -10PEHVPSBD
<220> FEATURE:
<221> NAME/KEY: misc_feature
<222> LOCATION: (141)..(145)
<223> OTHER INFORMATION: Motif Name: ASF1MOTIFCAMV
<220> FEATURE:
<221> NAME/KEY: misc_feature
<222> LOCATION: (1858)..(1862)
<223> OTHER INFORMATION: Motif Name: ASF1MOTIFCAMV
<220> FEATURE:
<221> NAME/KEY: misc_feature
<222> LOCATION: (117)..(122)
<223> OTHER INFORMATION: Motif Name: IBOX
<220> FEATURE:
<221> NAME/KEY: misc_feature
<222> LOCATION: (525)..(530)
<223> OTHER INFORMATION: Motif Name: IBOX
<220> FEATURE:
<221> NAME/KEY: misc_feature
<222> LOCATION: (2146)..(2151)
<223> OTHER INFORMATION: Motif Name: IBOX
<220> FEATURE:
<221> NAME/KEY: misc_feature
<222> LOCATION: (2518)..(2523)
<223> OTHER INFORMATION: Motif Name: IBOX
<220> FEATURE:
<221> NAME/KEY: misc_feature
<222> LOCATION: (290)..(296)
<223> OTHER INFORMATION: Motif Name: BOXCPSAS1
<220> FEATURE:
<221> NAME/KEY: misc_feature
<222> LOCATION: (294)..(299)
<223> OTHER INFORMATION: Motif Name: CACGTGMOTIF
<220> FEATURE:
<221> NAME/KEY: misc_feature
<222> LOCATION: (756)..(761)
<223> OTHER INFORMATION: Motif Name: CACGTGMOTIF
<220> FEATURE:
```

```
<221> NAME/KEY: misc_feature
<222> LOCATION: (1589)..(1594)
<223> OTHER INFORMATION: Motif Name: GT1CORE
<220> FEATURE:
<221> NAME/KEY: misc_feature
<222> LOCATION: (2743)..(2748)
<223> OTHER INFORMATION: Motif Name: GT1CORE
<220> FEATURE:
<221> NAME/KEY: misc_feature
<222> LOCATION: (260)..(265)
<223> OTHER INFORMATION: Motif Name: REALPHALGLHCB21
<220> FEATURE:
<221> NAME/KEY: misc_feature
<222> LOCATION: (1717)..(1722)
<223> OTHER INFORMATION: Motif Name: REALPHALGLHCB21
<220> FEATURE:
<221> NAME/KEY: misc_feature
<222> LOCATION: (1783)..(1788)
<223> OTHER INFORMATION: Motif Name: REALPHALGLHCB21
<220> FEATURE:
<221> NAME/KEY: misc_feature
<222> LOCATION: (2877)..(2883)
<223> OTHER INFORMATION: Motif Name: TATA-box
<220> FEATURE:
<221> NAME/KEY: misc_feature
<222> LOCATION: (2909)..(2909)
<223> OTHER INFORMATION: transcription start site
<220> FEATURE:
<221> NAME/KEY: misc_feature
<222> LOCATION: (2909)..(3000)
<223> OTHER INFORMATION: 5' untranslated region

<400> SEQUENCE: 1
atctataacg agttaacatg ttgccagttt gaatcaagaa gcttggatga tgaatgaatg      60
gatcggtttg tggtacaatt cttaaaattg tagtagagga gacagagaaa aaacatgata     120
agactttggt atttcaaact tgacggagac aagacagtaa gccaaatctg tcacaaaaac     180
actcaaactc ttttctcagt gttttgagtt taaagagaga cttattcact tcccctttcg     240
taacacttat ttgtctccca accaaacagt ttctgtcctt tcccttgtcc tcccacgtgc     300
atctttatat ctcatgactt ttcgtttcta gatcttgaat aatgtcttag tggattaggt     360
ttgttgtcgg taaattaggt gaccgttttt ttcttatatt tggaagatcg cgggatgaag     420
cagatactga gtttcagggc atacacacct aatttgaaaa tcattgttag tccaatttca     480
ctttaatctt gtttacaaaa aaattgatct gaaaatgttg atgggataag taaaaatgta     540
agttttgcta gtagtcatga tataataata gcaaaaccag atcaattttg agcaaaagga     600
agaaacaaaa aacagatcga tcccacgagc aagactaagt gtaaagtggt tcccacaaga     660
gccatatgga tatggtcctt caactttaa agcccattac ttcagtggtc gacccgacat     720
tacgccacga gtagtcacgc acgcacgact ccgttcacgt gacattcacg ttgatatttc     780
cccctctact ctcttctgct tggttgatct aaaaaacatg aagagaccaa cctaatttca     840
tattaatata tgatatagac ttcatactca acagtcactt tcgtaatcca aatccatatc     900
ttacgaaatt agttcttaat aaaggttgtg gattaagtta atatattgtg ttaagagtta     960
agacacagca tataaccttg taccaacagt gctttattct taaatggaaa caaaacatat    1020
gtcaatgtca agcatacagc taaaatatca ttatctaata ttaagagtaa aacaagataa    1080
ttaaaaattg aaacaacacc atatttttat agctttactt atcgtatttt tctagtcttc    1140
atggtaattg tgttgcttta ttttgtttat aaatgaattt ggttcgacca gatagtctaa    1200
tatcagtttt taaacactgg ttttaataaa atcatatgtc ggcaattcaa cctgttacgt    1260
tgtatgattg tatcctagtc aaatagggga ggaggtacta gtcgtttcaa ttagtttacg    1320
taatcaatcc aaagaaacta taagctataa agatcctcaa tttgttggtt acaataaaaa    1380
```

```
caacagttgt caaaatttat gtttataaaa agtaataact atgttccttc ccatatagag    1440
caaagtacct caggataggc aaaccgtact taatagccct tattcataat ttgatccaac    1500
tcttccccac aaaattgcaa ctgatgaagt caatacttgt atagtgagtc aagctataaa    1560
tgtctagtga tagttttgtc tcttaaaagg ttaacaaaag ttatgacaag ctgaaaaatc    1620
agagtttgct aggagtatta cttacagtta tcagtttaag tatcacattt atagtattgt    1680
atacaatgat tcttaaattc caccttttcc gtgcgaaacc aaattttcta ttggaaacat    1740
agaatgtaaa caaaaatatg ggacgttgtc cgttccaaca ttaaccaaac ttgtctatta    1800
ctaatattcg tgttggtttg atgttggatg tctaaattcg ttgaatcatg tgtctcttga    1860
cgaaatatgc atcttcttat ttcttagtat agatgcactt tatcattctt ttagtacatg    1920
cttaattttt tttttaaaa tatgttgatt gtcatattgc caaagtatg aattaaagac    1980
gcacatctaa cacaagttag cagccgtaaa tccttccata aatttatttt gcaagttttg    2040
ctcattatat aatgagcgga atttatgata taatcgtttg taataatgtt atgttttgat    2100
caaaatttga aattaaaagt aggtgagaac ttgttataca gtgtagataa ggtggatctt    2160
gaatataaaa ataaaattta taagatgtat ttaaagcaga aaagcataaa acttagata    2220
aaataatgta aaaatgtgtt agcatcaatg ttgggatatt ggccgacccg aacttaatca    2280
atgtcggaag ccattacttc tctcccaaaa gaccttttc cttcggagaa ctaggaactt    2340
cctcactacc tttcgcttaa cgtgaaagcc ataaatttca tatattcata aaaatcagaa    2400
aatctaaaac tgtttagtat cacctgtttt tggtatagac tattggtttt gtgttacttc    2460
ctaaactata tgatttcgta cttcattgga tcttatagag atgaatattc gtaaaaagat    2520
aagttatctg gtgaaacgtt acttcagtca tgttgggtct agatttacat actactatga    2580
aacattttaa gataataatt atcctagcca actatatgtt ctatattatg ggccaagaag    2640
atatagaact aaaagttcag aatttaacga tataaattac tagtatattc taatacttga    2700
atgattactg ttttagttgt ttagaataaa tagtagcgtg ttggttaaga taccatctat    2760
ccacatctat atttgtgtgg gttacataaa atgtacataa tattatatac atatatatgt    2820
atattttga taaagccata tattactcct tgacctctgc ccccatttcc ttttactata    2880
aataggaata ctcatgatcc tctaattcag caatcaacac caacgaacac aacctttcc    2940
aaagccaata ataaaagaac aaaagctttt agtttcatca aagacgaagc tgccttagaa    3000
```

<210> SEQ ID NO 2
<211> LENGTH: 495
<212> TYPE: DNA
<213> ORGANISM: Populus balsamifera subsp. trichocarpa
<220> FEATURE:
<221> NAME/KEY: misc_feature
<222> LOCATION: (1)..(495)
<223> OTHER INFORMATION: Ceres ANNOT ID no.1443290
<220> FEATURE:
<221> NAME/KEY: misc_feature
<222> LOCATION: (1)..(495)
<223> OTHER INFORMATION: Encodes the peptide sequence at SEQ ID NO:3

<400> SEQUENCE: 2

```
atggaaaaat ctaaggttgg caagggagct tacctcaacg ggaatcccca tcattccttc      60
tcttcttcct ctgcttctca agacatgtc agctacagct gcggtatttg cgggtatgaa     120
ttgaacttga gctcctccaa tcggaacacc tcatctattg gctctaaata tgggaaatcc     180
ataaagagag ggatcatctc attcttcttc atcgatgaga gcagatttac ccaggttgat     240
gaattccaat gcattccctt cttttcaaga aactcctggg gtttgttcca ccggagaaca     300
```

```
gcacttcttt gccgcaagtg tggtaataat attggaattg cttatgatga taaagcctca    360
gcttatccac ttgtagcaga cggatctgac tcttcctcag tcagtgaagt ttccaaacat    420
cgaaaatatg atgttaaaat ccgtgccttg cagccttctt ctgttgacca gtttagcact    480
ccaattcaca cctga                                                     495
```

<210> SEQ ID NO 3
<211> LENGTH: 164
<212> TYPE: PRT
<213> ORGANISM: Populus balsamifera subsp. trichocarpa
<220> FEATURE:
<221> NAME/KEY: misc_feature
<222> LOCATION: (1)..(164)
<223> OTHER INFORMATION: Ceres ANNOT ID no. 1443290

<400> SEQUENCE: 3

```
Met Glu Lys Ser Lys Val Gly Lys Gly Ala Tyr Leu Asn Gly Asn Pro
1               5                   10                  15

His His Ser Phe Ser Ser Ser Ala Ser Gln Arg His Val Ser Tyr
            20                  25                  30

Ser Cys Gly Ile Cys Gly Tyr Glu Leu Asn Leu Ser Ser Ser Asn Arg
        35                  40                  45

Asn Thr Ser Ser Ile Gly Ser Lys Tyr Gly Lys Ser Ile Lys Arg Gly
    50                  55                  60

Ile Ile Ser Phe Phe Phe Ile Asp Glu Ser Arg Phe Thr Gln Val Asp
65                  70                  75                  80

Glu Phe Gln Cys Ile Pro Phe Phe Ser Arg Asn Ser Trp Gly Leu Phe
                85                  90                  95

His Arg Arg Thr Ala Leu Leu Cys Arg Lys Cys Gly Asn Asn Ile Gly
            100                 105                 110

Ile Ala Tyr Asp Asp Lys Ala Ser Ala Tyr Pro Leu Val Ala Asp Gly
        115                 120                 125

Ser Asp Ser Ser Ser Val Ser Glu Val Ser Lys His Arg Lys Tyr Asp
    130                 135                 140

Val Lys Ile Arg Ala Leu Gln Pro Ser Ser Val Asp Gln Phe Ser Thr
145                 150                 155                 160

Pro Ile His Thr
```

<210> SEQ ID NO 4
<211> LENGTH: 1197
<212> TYPE: DNA
<213> ORGANISM: Populus balsamifera subsp. trichocarpa
<220> FEATURE:
<221> NAME/KEY: misc_feature
<222> LOCATION: (1)..(1197)
<223> OTHER INFORMATION: Ceres ANNOT ID no.1448905
<220> FEATURE:
<221> NAME/KEY: misc_feature
<222> LOCATION: (1)..(1197)
<223> OTHER INFORMATION: Encodes the peptide sequence at SEQ ID NO:5

<400> SEQUENCE: 4

```
atgagctctc ttcgagcaga tccgccgacc tccaaaattc acccagaagc agaagcagaa    60
gcaactacta gttgtttttg ttcttcttca aaaatcgacc atttcgaccg ccttcctgac    120
tctcttctgt tattcgtttt caacaaaatc ggcgatgtca agctcttgg tcgttgctgt    180 gttgtttctc gccgcttcca ctctctcgtc cctcaggtcg ataacgttgt tgtccgtgta    240
gactgtgtca tctccgatga cgacacctcc tcttcttcct cctccatcaa gtcacactct    300
tcttcttctt ctggcttctc ctccatcttt cgtttagtct tcggtggcat ttccaaaccc    360
```

```
ttccaagctc tgagtcagat gtttggaacc aaggtcaatt cgcgaaatgg aaatgggcct    420 tcccttttctg tcgccgccga tgatgatatg gagctggatc aagctggtgt cacccatcat   480
tctccaactc aggttcttaa gaattttaat gagattcgct ttctaagaat cgagttaccc    540
agtggggaat tggaattga tgatgggggtt ctttttaaaat ggagggctga tttcggatct    600 accccttgata attgtgttat tcttggtgct gcttctgtca ttaccaataa taagatttct    660
tctgctatgc aacaagaaaa tgctgctgct gctgctgctg ccgatgatga tgataatgga    720
agcataccgg agtcatttta caccaatggg ggattgaagt tgagagttgt gtggactatt    780
agctctttaa ttgctgcatc tgccaggcat tatttgcttc aaccaattat tgctgagcat    840
aagactcttg atagtttggt cttggctgat gctgatgggc agggagtgtt gtgtatgaat    900
agggagcaat tggaagagtt gagggtcaag ccgttatcgg cttcttctgc ttccaagagg    960
actcttgtgc ctgcacttaa tatgcgcctt tggtatgctc ctcacttgga attgctgat    1020 ggggttgtgt tgaaaggtgc aacattggtt gctattaggc ctagtgaaca ggctgctact   1080
aagaaggatg tgtctgatgt ctcctgggtc tctaccacgt ttgaggagcc ttatggtaca   1140
gcagctaaga tgctggtgaa gagaaggact tactgcttgg agatgaactc attctga      1197
```

```
<210> SEQ ID NO 5
<211> LENGTH: 398
<212> TYPE: PRT
<213> ORGANISM: Populus balsamifera subsp. trichocarpa
<220> FEATURE:
<221> NAME/KEY: misc_feature
<222> LOCATION: (1)..(398)
<223> OTHER INFORMATION: Ceres ANNOT ID no. 1448905
<220> FEATURE:
<221> NAME/KEY: misc_feature
<222> LOCATION: (35)..(81)
<223> OTHER INFORMATION: Pfam Name: F-box
      Pfam Description: F-box domain

<400> SEQUENCE: 5

Met Ser Ser Leu Arg Ala Asp Pro Pro Thr Ser Lys Ile His Pro Glu
1               5                   10                  15

Ala Glu Ala Glu Ala Thr Thr Ser Cys Phe Cys Ser Ser Ser Lys Ile
                20                  25                  30

Asp His Phe Asp Arg Leu Pro Asp Ser Leu Leu Leu Phe Val Phe Asn
            35                  40                  45

Lys Ile Gly Asp Val Lys Ala Leu Gly Arg Cys Cys Val Val Ser Arg
        50                  55                  60

Arg Phe His Ser Leu Val Pro Gln Val Asp Asn Val Val Val Arg Val
65                  70                  75                  80

Asp Cys Val Ile Ser Asp Asp Thr Ser Ser Ser Ser Ser Ser Ser Ile
                85                  90                  95

Lys Ser His Ser Ser Ser Ser Gly Phe Ser Ser Ile Phe Arg Leu
            100                 105                 110

Val Phe Gly Gly Ile Ser Lys Pro Phe Gln Ala Leu Ser Gln Met Phe
        115                 120                 125

Gly Thr Lys Val Asn Ser Arg Asn Gly Asn Gly Pro Ser Leu Ser Val
    130                 135                 140

Ala Ala Asp Asp Asp Met Glu Leu Asp Gln Ala Gly Val Thr His His
145                 150                 155                 160

Ser Pro Thr Gln Val Leu Lys Asn Phe Asn Glu Ile Arg Phe Leu Arg
                165                 170                 175

Ile Glu Leu Pro Ser Gly Glu Leu Gly Ile Asp Asp Gly Val Leu Leu
            180                 185                 190
```

```
Lys Trp Arg Ala Asp Phe Gly Ser Thr Leu Asp Asn Cys Val Ile Leu
        195                 200                 205
Gly Ala Ala Ser Val Ile Thr Asn Asn Lys Ile Ser Ser Ala Met Gln
210                 215                 220
Gln Glu Asn Ala Ala Ala Ala Ala Ala Asp Asp Asp Asn Gly
225                 230                 235                 240
Ser Ile Pro Glu Ser Phe Tyr Thr Asn Gly Gly Leu Lys Leu Arg Val
        245                 250                 255
Val Trp Thr Ile Ser Ser Leu Ile Ala Ala Ser Ala Arg His Tyr Leu
        260                 265                 270
Leu Gln Pro Ile Ile Ala Glu His Lys Thr Leu Asp Ser Leu Val Leu
        275                 280                 285
Ala Asp Ala Asp Gly Gln Gly Val Leu Cys Met Asn Arg Glu Gln Leu
        290                 295                 300
Glu Glu Leu Arg Val Lys Pro Leu Ser Ala Ser Ser Ala Ser Lys Arg
305                 310                 315                 320
Thr Leu Val Pro Ala Leu Asn Met Arg Leu Trp Tyr Ala Pro His Leu
        325                 330                 335
Glu Leu Pro Asp Gly Val Val Leu Lys Gly Ala Thr Leu Val Ala Ile
        340                 345                 350
Arg Pro Ser Glu Gln Ala Ala Thr Lys Lys Asp Val Ser Asp Val Ser
        355                 360                 365
Trp Val Ser Thr Thr Phe Glu Glu Pro Tyr Gly Thr Ala Ala Lys Met
        370                 375                 380
Leu Val Lys Arg Arg Thr Tyr Cys Leu Glu Met Asn Ser Phe
385                 390                 395

<210> SEQ ID NO 6
<211> LENGTH: 2037
<212> TYPE: DNA
<213> ORGANISM: Populus balsamifera subsp. trichocarpa
<220> FEATURE:
<221> NAME/KEY: misc_feature
<222> LOCATION: (1)..(2037)
<223> OTHER INFORMATION: Ceres ANNOT ID no.1454522
<220> FEATURE:
<221> NAME/KEY: misc_feature
<222> LOCATION: (1)..(2037)
<223> OTHER INFORMATION: Encodes the peptide sequence at SEQ ID NO:7

<400> SEQUENCE: 6
atggcgacat actttcatgg gaatcctgaa atccaagcag ctgctgcatc agcggaaggt      60
cttcaaactc ttgtgcttat gaaccctact tatgtccaat actctgaaac ccctccacca     120
ccacaatcca caaccttgt attccttaac gccgctgctt ctgctgctgc aacagcctc     180
tctcctccgc cgcacctctc gggccacgcg ccatcgaaca cccaacaatt cgtcggtatc     240
cctttggacc ctaactccca tgaggcttct actttgcatg gacttattcc ccgtgtccat     300
tacaattttt ataatccaat tgactctaca tcgactgcgc gtgaaacacc acgcgcccaa     360
caaggcctgt ctttgagcct ctcctcacaa cagcaaggcg ttttggatc acaggctcaa     420
gctgtgtctg gtgaagatat aagggtgtct ggtgggttgg tgtcaccagg ttcgggtgtg     480
acaaatgggg taccgggtat gcaaggggtc ttgttgagct caaagtactt gaaggccact     540
gaagagctac ttgatgaggt tgttaatgtg aatagtaatg gaatcaagag tgaattgtca     600
aagaagagta acgggattag tagtaataat agcaataagg tgattggaga gtcatcaacc     660
ggagaaggt ctggcgaagg agaagcaagt gggaagcgcg gaccgagct ttccactgca     720
```

```
gagaggcagg aaattcatat gaagaaggct aagcttatga gcatgctcga tgaggtggag    780
cagaggtaca ggcagtatca tcaccagatg cagatagtga tttcctcgtt tgagcaagca    840
gcaggaattg gttcagcaaa gacatacaca gcccttgcat tgaaaacaat ctccaagcag    900
tttaggtgct tgaaagatgc aataacaggt caaattaaag ctgcaaacaa aagcttaggt    960
gaagaggatt gcttaggagg aaagattgaa ggttcaaggc tcaaatttgt cgatcatcac   1020
cttcgacaac agcgtgcact tcagcagttg ggaatgatcc agcacaatgc ttggagaccc   1080
cagagaggat tgcctgaaag atcagtttca gttctccgtg cttggctctt cgaacacttt   1140
ctccacccct atcccaagga ttcagacaaa cacatgctcg caaacaaac agggctcacg    1200
aggagccagg tgtctaattg gttcataaat gctcgagttc gactttggaa gccaatggta   1260
gaagaaatgt acatggagga aattaaggaa caagaacaga atggatcaga ggacaaaaca   1320
agcaagagcg aacacaatga agatgctgct tcaaggtcag ttctgcaaga gaaaggttca   1380
gttaacggaa atctaactag aagcttcaag tccttggaca attcaccgga tgctcctct    1440
gcaatctcaa tacccacatc ttcaacatct cctgttgggg gaaatctccg aaaccagtct   1500
ggatttcct ttatgggtc atcagaatta gacgggatca cacaagggag cccaaagaaa    1560
ccaagaagcc atgatttgat acaatccca actagtgtgc catccattaa catggatatc   1620
aagcctggcg aggcaaacaa tgagcaggtt tctatgaaat cggcgatga gaggcagagt    1680
agggatggct actcattcat aggaggccaa accaacttca ttggaggttt tgggcaatat   1740
ccaatggggg aaattgggag gtttgatgga gagcagttca cgccaaggtt ttctggcaat   1800
ggtgtctctc tcactcttgg gctacctcat tgtgaaaacc tctccttatc aggtactcat   1860
caaacttttc ttccaaacca aacattcaa ctgggaagaa gagtagagat cggcgaacca    1920
aatgagtatg gagcccttaa cacatccacg cctcactctt caactgcata tgagagcatt   1980
gacattcaga accgaaagag gttatagca caactgttgc cagactttgt ggcctga      2037
```

<210> SEQ ID NO 7
<211> LENGTH: 678
<212> TYPE: PRT
<213> ORGANISM: Populus balsamifera subsp. trichocarpa
<220> FEATURE:
<221> NAME/KEY: misc_feature
<222> LOCATION: (1)..(678)
<223> OTHER INFORMATION: Ceres ANNOT ID no. 1454522
<220> FEATURE:
<221> NAME/KEY: misc_feature
<222> LOCATION: (169)..(310)
<223> OTHER INFORMATION: Pfam Name: POX
    Pfam Description: Associated with HOX
<220> FEATURE:
<221> NAME/KEY: misc_feature
<222> LOCATION: (359)..(417)
<223> OTHER INFORMATION: Pfam Name: Homeobox
    Pfam Description: Homeobox domain

<400> SEQUENCE: 7

Met Ala Thr Tyr Phe His Gly Asn Pro Glu Ile Gln Ala Ala Ala Ala
1               5                   10                  15

Ser Ala Glu Gly Leu Gln Thr Leu Val Leu Met Asn Pro Thr Tyr Val
            20                  25                  30

Gln Tyr Ser Glu Thr Pro Pro Pro Gln Ser Asn Asn Leu Val Phe
        35                  40                  45

Leu Asn Ala Ala Ala Ser Ala Ala Ala Asn Ser Leu Ser Pro Pro Pro
    50                  55                  60

His Leu Ser Gly His Ala Pro Ser Asn Thr Gln Gln Phe Val Gly Ile
65                  70                  75                  80

```
Pro Leu Asp Pro Asn Ser His Glu Ala Ser Thr Leu His Gly Leu Ile
                85                  90                  95
Pro Arg Val His Tyr Asn Phe Tyr Asn Pro Ile Asp Ser Thr Ser Thr
            100                 105                 110
Ala Arg Glu Thr Pro Arg Ala Gln Gln Gly Leu Ser Leu Ser Leu Ser
            115                 120                 125
Ser Gln Gln Gln Gly Gly Phe Gly Ser Gln Ala Gln Ala Val Ser Gly
        130                 135                 140
Glu Asp Ile Arg Val Ser Gly Leu Val Ser Pro Gly Ser Gly Val
145                 150                 155                 160
Thr Asn Gly Val Pro Gly Met Gln Gly Val Leu Ser Ser Lys Tyr
                165                 170                 175
Leu Lys Ala Thr Glu Glu Leu Leu Asp Glu Val Val Asn Val Asn Ser
            180                 185                 190
Asn Gly Ile Lys Ser Glu Leu Ser Lys Lys Ser Asn Gly Ile Ser Ser
            195                 200                 205
Asn Asn Ser Asn Lys Val Ile Gly Glu Ser Ser Thr Gly Glu Gly Ser
        210                 215                 220
Gly Glu Gly Glu Ala Ser Gly Lys Arg Gly Pro Glu Leu Ser Thr Ala
225                 230                 235                 240
Glu Arg Gln Glu Ile His Met Lys Lys Ala Lys Leu Met Ser Met Leu
                245                 250                 255
Asp Glu Val Glu Gln Arg Tyr Arg Gln Tyr His His Gln Met Gln Ile
            260                 265                 270
Val Ile Ser Ser Phe Glu Gln Ala Ala Gly Ile Gly Ser Ala Lys Thr
        275                 280                 285
Tyr Thr Ala Leu Ala Leu Lys Thr Ile Ser Lys Gln Phe Arg Cys Leu
    290                 295                 300
Lys Asp Ala Ile Thr Gly Gln Ile Lys Ala Ala Asn Lys Ser Leu Gly
305                 310                 315                 320
Glu Glu Asp Cys Leu Gly Gly Lys Ile Glu Gly Ser Arg Leu Lys Phe
                325                 330                 335
Val Asp His His Leu Arg Gln Gln Arg Ala Leu Gln Gln Leu Gly Met
            340                 345                 350
Ile Gln His Asn Ala Trp Arg Pro Gln Arg Gly Leu Pro Glu Arg Ser
        355                 360                 365
Val Ser Val Leu Arg Ala Trp Leu Phe Glu His Phe Leu His Pro Tyr
    370                 375                 380
Pro Lys Asp Ser Asp Lys His Met Leu Ala Lys Gln Thr Gly Leu Thr
385                 390                 395                 400
Arg Ser Gln Val Ser Asn Trp Phe Ile Asn Ala Arg Val Arg Leu Trp
                405                 410                 415
Lys Pro Met Val Glu Glu Met Tyr Met Glu Glu Ile Lys Glu Gln Glu
            420                 425                 430
Gln Asn Gly Ser Glu Asp Lys Thr Ser Lys Ser Glu His Asn Glu Asp
        435                 440                 445
Ala Ala Ser Arg Ser Val Leu Gln Glu Lys Gly Ser Val Asn Gly Asn
    450                 455                 460
Leu Thr Arg Ser Phe Lys Ser Leu Asp Asn Ser Pro Asp Ala Pro Ser
465                 470                 475                 480
Ala Ile Ser Ile Pro Thr Ser Ser Thr Ser Pro Val Gly Gly Asn Leu
                485                 490                 495
Arg Asn Gln Ser Gly Phe Ser Phe Met Gly Ser Ser Glu Leu Asp Gly
```

```
            500             505             510
Ile Thr Gln Gly Ser Pro Lys Lys Pro Arg Ser His Asp Leu Ile Gln
        515             520             525

Ser Pro Thr Ser Val Pro Ser Ile Asn Met Asp Ile Lys Pro Gly Glu
        530             535             540

Ala Asn Asn Glu Gln Val Ser Met Lys Phe Gly Asp Glu Arg Gln Ser
545             550             555             560

Arg Asp Gly Tyr Ser Phe Ile Gly Gly Gln Thr Asn Phe Ile Gly Gly
                565             570             575

Phe Gly Gln Tyr Pro Met Gly Glu Ile Gly Arg Phe Asp Gly Glu Gln
            580             585             590

Phe Thr Pro Arg Phe Ser Gly Asn Gly Val Ser Leu Thr Leu Gly Leu
        595             600             605

Pro His Cys Glu Asn Leu Ser Leu Ser Gly Thr His Gln Thr Phe Leu
        610             615             620

Pro Asn Gln Asn Ile Gln Leu Gly Arg Arg Val Glu Ile Gly Glu Pro
625             630             635             640

Asn Glu Tyr Gly Ala Leu Asn Thr Ser Thr Pro His Ser Ser Thr Ala
                645             650             655

Tyr Glu Ser Ile Asp Ile Gln Asn Arg Lys Arg Phe Ile Ala Gln Leu
            660             665             670

Leu Pro Asp Phe Val Ala
        675

<210> SEQ ID NO 8
<211> LENGTH: 2226
<212> TYPE: DNA
<213> ORGANISM: Populus balsamifera subsp. trichocarpa
<220> FEATURE:
<221> NAME/KEY: misc_feature
<222> LOCATION: (1)..(2226)
<223> OTHER INFORMATION: Ceres ANNOT ID no.1455110
<220> FEATURE:
<221> NAME/KEY: misc_feature
<222> LOCATION: (1)..(2226)
<223> OTHER INFORMATION: Encodes the peptide sequence at SEQ ID NO:9

<400> SEQUENCE: 8
atgtcctcaa aattcaattc gtcccaattt tcctccctcg acgacgacga cgacgacttc      60
caaatccctc tctcccaaac accaaaacag actctttcta tccgcaacaa accgctgac     120 aatcctcgcc gtccgtcaaa aaagccaaag aaacccccca atcccggcaa agaaaatata     180
gatcccaact ctctactcct atatcagaaa actgagtccg gtgccaatga cttcaattta     240
gacgagaatt gcagtttgga ttttatagag tcaagcatcg attgtactgt ttcttctaaa     300
gttggaaacg agaaatttga tagcgggagc ggtaaaaaag aaaaattgga agtgagtgga     360
ggatatttgt gtaattcgat tgaggctagg ttaatgaaat caagagtgga ttatagtgga     420
gttaatgttg gtaatgaaga ggatttcgaa gaaaatagtg agcttgatgc cttaattaag     480
ttatgtaccg aggaagaaga aagtgaagct agagagaaaa ttaaggttgt tcttggtggt     540
gatgacggca gacctgaggt tgtgccacga ggcgtggagg gtcctgtttg tggtccgaag     600
aaagttgttg tgtcacctgt tgttaaatgg ctaaggaatc tgggtttaga gagatatgaa     660
gaggattttg ttcgagaaga gattgattgg gagactttac agtggctgac agaagaggga     720
atgctagttg gggccttaac cagtgcttgc cacacctgga agaactcttt aaggcccac     780 aacataaaaa atgcaggatt tggttcaaga actgaagtag taggattagg aatgtcagga     840
ggacgagcag cacaggacct ctttggcatt ggtgtcactg cacttggtcc taggaagaag     900
```

```
attgtgcatg ctcttagtga gcttagaaaa gggtctaatc acgcaatcga ggcacatgga    960
gatgcacacg cctttggtga agttggttca cggagaagcc atggagcaga aatgcaagta   1020
gaggcttcta aaattattgg cgatgacact agtaaaccaa ctgcaaacaa attgattacg   1080
gattattttc ctggatctgt acctatcaag aaaaaaacta gtgtcatctc taaagaacaa   1140
cggggagcag aaaaaagtca gccaggctat gttcgtaaac aagggggtgaa aaactatact   1200
aaaaaaggaa agttcaaaga tattcctttg tggtgtagca taccagggac accatttaga   1260
gtggatgctt tcaaatatct tagaggagat tgttcccatt ggtttcttac tcacttccac   1320
atggaccatt atcaaggatt aacaaggtct ttctgtcatg ggaagattta ctgctccttg   1380
atcacagcaa agcttgtaaa tttaaagatt gggatcccct gggatagttt acatgtttta   1440
cctctcaacc aaaagatctg tattgctggt gttgatgtga catgcttgga tgcaaaccac   1500
tgtccaggct ccattataat tctcttcgaa cctcccaatg gtaaggctgt gctacacacg   1560
ggagattttc gttttctga aagatggtt acaatgcctg ttttgcaaat gtcttctatc   1620
catactctca tccttgatac tacatattgt aatgcccagt atgactttcc gaagcaggag   1680
gctgtaatac aatttgtcat tgaggccatt caagctgaag ctttcaaccc caaaacactt   1740
tttttgatcg gaagctatac aattggaaag gaaaggttgt ttttggaggt tgctcgtgtg   1800
ctccataaga aggtttatgt caacatggca aaattccgtc ttttagaatg cttgggggttc   1860
cctgaagaag atatgaggtg gattacatta aatgaacaag aaagccacat tcatgttgtg   1920
cctatgtgga cgcttgcaag cttcaaaaga ttgaaacatt tatcgagtca atatgcaggt   1980
cgattcactc tcatagttgc tttctccccc actggctgga catttggtaa agggaagaag   2040
aaatctccag ggagaaggtg tcagcaggga actattataa gatacgaagt accatacagt   2100
gagcattgca gttttacaga actcagagag tttgtgaagt tgtgtctcc tgaaaacata   2160
ataccaagtg taaataatga tggaccagat tctgccaatg atatggtttc cctcctgctg   2220
tcttga                                                              2226
```

<210> SEQ ID NO 9
<211> LENGTH: 741
<212> TYPE: PRT
<213> ORGANISM: Populus balsamifera subsp. trichocarpa
<220> FEATURE:
<221> NAME/KEY: misc_feature
<222> LOCATION: (1)..(741)
<223> OTHER INFORMATION: Ceres ANNOT ID no. 1455110
<220> FEATURE:
<221> NAME/KEY: misc_feature
<222> LOCATION: (207)..(229)
<223> OTHER INFORMATION: Pfam Name: SAM_2
      Pfam Description: SAM domain (Sterile alpha motif)
<220> FEATURE:
<221> NAME/KEY: misc_feature
<222> LOCATION: (284)..(309)
<223> OTHER INFORMATION: Pfam Name: SAM_1
      Pfam Description: SAM domain (Sterile alpha motif)
<220> FEATURE:
<221> NAME/KEY: misc_feature
<222> LOCATION: (627)..(725)
<223> OTHER INFORMATION: Pfam Name: DRMBL
      Pfam Description: DNA repair metallo-beta-lactamase

<400> SEQUENCE: 9

Met Ser Ser Lys Phe Asn Ser Ser Gln Phe Ser Ser Leu Asp Asp Asp
1               5                   10                  15

Asp Asp Asp Phe Gln Ile Pro Leu Ser Gln Thr Pro Lys Gln Thr Leu
            20                  25                  30

```
Ser Ile Arg Asn Lys Pro Ala Asp Asn Pro Arg Arg Pro Ser Lys Lys
         35                  40                  45

Pro Lys Lys Pro Pro Asn Pro Gly Lys Glu Asn Ile Asp Pro Asn Ser
 50                  55                  60

Leu Leu Leu Tyr Gln Lys Thr Glu Ser Gly Ala Asn Asp Phe Asn Leu
 65                  70                  75                  80

Asp Glu Asn Cys Ser Leu Asp Phe Ile Glu Ser Ser Ile Asp Cys Thr
                 85                  90                  95

Val Ser Ser Lys Val Gly Asn Glu Lys Phe Asp Ser Gly Ser Gly Lys
                100                 105                 110

Lys Glu Lys Leu Glu Val Ser Gly Gly Tyr Leu Cys Asn Ser Ile Glu
            115                 120                 125

Ala Arg Leu Met Lys Ser Arg Val Asp Tyr Ser Gly Val Asn Val Gly
        130                 135                 140

Asn Glu Glu Asp Phe Glu Glu Asn Ser Glu Leu Asp Ala Leu Ile Lys
145                 150                 155                 160

Leu Cys Thr Glu Glu Glu Glu Ser Glu Ala Arg Glu Lys Ile Lys Val
                165                 170                 175

Val Leu Gly Gly Asp Asp Gly Arg Pro Glu Val Val Pro Arg Gly Val
                180                 185                 190

Glu Gly Pro Val Cys Gly Pro Lys Lys Val Val Ser Pro Val Val
            195                 200                 205

Lys Trp Leu Arg Asn Leu Gly Leu Glu Arg Tyr Glu Glu Asp Phe Val
210                 215                 220

Arg Glu Glu Ile Asp Trp Glu Thr Leu Gln Trp Leu Thr Glu Glu Gly
225                 230                 235                 240

Met Leu Val Gly Ala Leu Thr Ser Ala Cys His Thr Trp Lys Glu Leu
                245                 250                 255

Phe Lys Ala His Asn Ile Lys Asn Ala Gly Phe Gly Ser Arg Thr Glu
            260                 265                 270

Val Val Gly Leu Gly Met Ser Gly Gly Arg Ala Ala Gln Asp Leu Phe
        275                 280                 285

Gly Ile Gly Val Thr Ala Leu Gly Pro Arg Lys Lys Ile Val His Ala
        290                 295                 300

Leu Ser Glu Leu Arg Lys Gly Ser Asn His Ala Ile Glu Ala His Gly
305                 310                 315                 320

Asp Ala His Ala Phe Gly Glu Val Gly Ser Arg Arg Ser His Gly Ala
                325                 330                 335

Glu Met Gln Val Glu Ala Ser Lys Ile Ile Gly Asp Thr Ser Lys
            340                 345                 350

Pro Thr Ala Asn Lys Leu Ile Thr Asp Tyr Phe Pro Gly Ser Val Pro
        355                 360                 365

Ile Lys Lys Lys Thr Ser Val Ile Ser Lys Glu Gln Arg Gly Ala Glu
    370                 375                 380

Lys Ser Gln Pro Gly Tyr Val Arg Lys Gln Gly Val Lys Asn Tyr Thr
385                 390                 395                 400

Lys Lys Gly Lys Phe Lys Asp Ile Pro Leu Trp Cys Ser Ile Pro Gly
                405                 410                 415

Thr Pro Phe Arg Val Asp Ala Phe Lys Tyr Leu Arg Gly Asp Cys Ser
                420                 425                 430

His Trp Phe Leu Thr His Phe His Met Asp His Tyr Gln Gly Leu Thr
            435                 440                 445

Arg Ser Phe Cys His Gly Lys Ile Tyr Cys Ser Leu Ile Thr Ala Lys
450                 455                 460
```

-continued

```
Leu Val Asn Leu Lys Ile Gly Ile Pro Trp Asp Ser Leu His Val Leu
465                 470                 475                 480

Pro Leu Asn Gln Lys Ile Cys Ile Ala Gly Val Asp Val Thr Cys Leu
                485                 490                 495

Asp Ala Asn His Cys Pro Gly Ser Ile Ile Ile Leu Phe Glu Pro Pro
            500                 505                 510

Asn Gly Lys Ala Val Leu His Thr Gly Asp Phe Arg Phe Ser Glu Lys
        515                 520                 525

Met Val Thr Met Pro Val Leu Gln Met Ser Ile His Thr Leu Ile
    530                 535                 540

Leu Asp Thr Thr Tyr Cys Asn Ala Gln Tyr Asp Phe Pro Lys Gln Glu
545                 550                 555                 560

Ala Val Ile Gln Phe Val Ile Glu Ala Ile Gln Ala Glu Ala Phe Asn
                565                 570                 575

Pro Lys Thr Leu Phe Leu Ile Gly Ser Tyr Thr Ile Gly Lys Glu Arg
            580                 585                 590

Leu Phe Leu Glu Val Ala Arg Val Leu His Lys Lys Val Tyr Val Asn
        595                 600                 605

Met Ala Lys Phe Arg Leu Leu Glu Cys Leu Gly Phe Pro Glu Glu Asp
    610                 615                 620

Met Arg Trp Ile Thr Leu Asn Glu Gln Glu Ser His Ile His Val Val
625                 630                 635                 640

Pro Met Trp Thr Leu Ala Ser Phe Lys Arg Leu Lys His Leu Ser Ser
                645                 650                 655

Gln Tyr Ala Gly Arg Phe Thr Leu Ile Val Ala Phe Ser Pro Thr Gly
            660                 665                 670

Trp Thr Phe Gly Lys Gly Lys Lys Ser Pro Gly Arg Arg Cys Gln
        675                 680                 685

Gln Gly Thr Ile Ile Arg Tyr Glu Val Pro Tyr Ser Glu His Cys Ser
    690                 695                 700

Phe Thr Glu Leu Arg Glu Phe Val Lys Phe Val Ser Pro Glu Asn Ile
705                 710                 715                 720

Ile Pro Ser Val Asn Asn Asp Gly Pro Asp Ser Ala Asn Asp Met Val
                725                 730                 735

Ser Leu Leu Leu Ser
            740

<210> SEQ ID NO 10
<211> LENGTH: 1398
<212> TYPE: DNA
<213> ORGANISM: Populus balsamifera subsp. trichocarpa
<220> FEATURE:
<221> NAME/KEY: misc_feature
<222> LOCATION: (1)..(1398)
<223> OTHER INFORMATION: Ceres ANNOT ID no.1455953
<220> FEATURE:
<221> NAME/KEY: misc_feature
<222> LOCATION: (1)..(1398)
<223> OTHER INFORMATION: Encodes the peptide sequence at SEQ ID NO:11

<400> SEQUENCE: 10
atggggctgg aatcagtggg agatctagct ctgaacataa tcttaacaaa acttggtcca      60
aaagagacag tacaagtact atgtgtcagc aaaaagttca aggatttagc ttcagaggaa    120
tctctctggt cattattttg ccgtcaagat cttgatcttt ctgctcctct tgaccatcat    180
ggaaatcatc tgccttcttt taaggcaact tataagttat ggagagaagc ctttcatatg    240
tatccttggc cccttgtaaa gcgagttaaa agttgttggg acagactcac gagctggttg    300
```

```
accgcgaact tcctgaagt taaggctacc ctaggaaagg gtgcatcaga aggtgagatt      360
caaaagttgg aaagaatttt gaaagttaag ttgcctcttc ccacaagact tctctaccgc      420
tttcatgatg gtcaacattt ctcagacaaa aatctgtcag gtggcatggc tggttgtcca      480
ttgggcctga taggtggcta ctgtttttat aatcactcgg ttaatgtcta cttattatca      540
ctacatgagg taatctctaa aacgcaggaa atagtgcggc acctgaactt acccgataca      600
tccgagtata ttgttgtggc tgcttcatcc tcatacgttg gaaagttttt cttcctgaac      660
tgttctgatg ccaactcta tgttgggacc cagaattttc aacagatgc agaaatgatg        720 ccatgtgtac ctcaggcatt gattagtcca gtccgtgatt caacagtga ccaacaacag       780 gatgctatgt tgttatggtt agaagaacat ggccgtcgct tgcacaatgg catgatcaaa      840
attctcggca aggaaatat aaaagcatc tctcagtttc agaagaatc tcctctctgt         900 tcaactgctg taaccagtgg tgtaaaggtt cgtgcttctg ctgttttgt gccagaggct       960 gctgatctgg aagatatttc tacaaaatac gtgttcgctt attcaatccg catgtccctt     1020
ctaccagaag gatgcatcat caacggaatg cacttcagct cttgccaact gcacctgagg     1080
cactgggtta tcagtgctaa tgatactgct gtatctaatg tcaatgcaga ggctgtgata     1140
ggcaagggtc ctcctgtgtg gccttctaga tgcaacaatt gggagcttct aaaagtgcct     1200
actggtgaca aattcccact cttgtttcca ggcgagaaaa aatttgttta tgagagttgt     1260
acacctctgc caacttctac tggctctgtt gaaggttctt tcacatttgt ccctggcaga     1320
ttggcagatc caaaaggaat tccatttgaa gttgaagtcg gtcggtttcc gctccaactg     1380
ccagactaca ttttctga                                                   1398
```

<210> SEQ ID NO 11
<211> LENGTH: 465
<212> TYPE: PRT
<213> ORGANISM: Populus balsamifera subsp. trichocarpa
<220> FEATURE:
<221> NAME/KEY: misc_feature
<222> LOCATION: (1)..(465)
<223> OTHER INFORMATION: Ceres ANNOT ID no. 1455953
<220> FEATURE:
<221> NAME/KEY: misc_feature
<222> LOCATION: (3)..(48)
<223> OTHER INFORMATION: Pfam Name: F-box
    Pfam Description: F-box domain
<220> FEATURE:
<221> NAME/KEY: misc_feature
<222> LOCATION: (404)..(461)
<223> OTHER INFORMATION: Pfam Name: DUF525
    Pfam Description: Protein of unknown function (DUF525)

<400> SEQUENCE: 11

Met Gly Leu Glu Ser Val Gly Asp Leu Ala Leu Asn Ile Ile Leu Thr
1               5                   10                  15

Lys Leu Gly Pro Lys Glu Thr Val Gln Val Leu Cys Val Ser Lys Lys
            20                  25                  30

Phe Lys Asp Leu Ala Ser Glu Glu Ser Leu Trp Ser Leu Phe Cys Arg
        35                  40                  45

Gln Asp Leu Asp Leu Ser Ala Pro Leu Asp His His Gly Asn His Leu
    50                  55                  60

Pro Ser Phe Lys Ala Thr Tyr Lys Leu Trp Arg Glu Ala Phe His Met
65                  70                  75                  80

Tyr Pro Trp Pro Leu Val Lys Arg Val Lys Ser Cys Trp Asp Arg Leu
                85                  90                  95

Thr Ser Trp Leu Thr Ala Asn Phe Pro Glu Val Lys Ala Thr Leu Gly

```
                          100                 105                 110
Lys Gly Ala Ser Glu Gly Glu Ile Gln Lys Leu Glu Arg Ile Leu Lys
            115                 120                 125

Val Lys Leu Pro Leu Pro Thr Arg Leu Leu Tyr Arg Phe His Asp Gly
130                 135                 140

Gln His Phe Ser Asp Lys Asn Leu Ser Gly Gly Met Ala Gly Cys Pro
145                 150                 155                 160

Leu Gly Leu Ile Gly Gly Tyr Cys Phe Tyr Asn His Ser Val Asn Val
            165                 170                 175

Tyr Leu Leu Ser Leu His Glu Val Ile Ser Lys Thr Gln Glu Ile Val
            180                 185                 190

Arg His Leu Asn Leu Pro Asp Thr Ser Glu Tyr Ile Val Val Ala Ala
            195                 200                 205

Ser Ser Ser Tyr Val Gly Lys Phe Phe Leu Asn Cys Ser Asp Gly
            210                 215                 220

Gln Leu Tyr Val Gly Thr Gln Asn Phe Pro Thr Asp Ala Glu Met Met
225                 230                 235                 240

Pro Cys Val Pro Gln Ala Leu Ile Ser Pro Val Arg Asp Phe Asn Ser
            245                 250                 255

Asp Gln Gln Gln Asp Ala Met Leu Leu Trp Leu Glu Glu His Gly Arg
            260                 265                 270

Arg Leu His Asn Gly Met Ile Lys Ile Leu Gly Lys Gly Asn Ile Lys
            275                 280                 285

Ser Ile Ser Gln Phe Pro Glu Glu Ser Pro Leu Cys Ser Thr Ala Val
            290                 295                 300

Thr Ser Gly Val Lys Val Arg Ala Ser Ala Val Phe Val Pro Glu Ala
305                 310                 315                 320

Ala Asp Leu Glu Asp Ile Ser Thr Lys Tyr Val Phe Ala Tyr Ser Ile
            325                 330                 335

Arg Met Ser Leu Leu Pro Glu Gly Cys Ile Ile Asn Gly Met His Phe
            340                 345                 350

Ser Ser Cys Gln Leu His Leu Arg His Trp Val Ile Ser Ala Asn Asp
            355                 360                 365

Thr Ala Val Ser Asn Val Asn Ala Glu Ala Val Ile Gly Lys Gly Pro
370                 375                 380

Pro Val Trp Pro Ser Arg Cys Asn Asn Trp Glu Leu Leu Lys Val Pro
385                 390                 395                 400

Thr Gly Asp Lys Phe Pro Leu Leu Phe Pro Gly Glu Lys Glu Phe Val
            405                 410                 415

Tyr Glu Ser Cys Thr Pro Leu Pro Thr Ser Thr Gly Ser Val Glu Gly
            420                 425                 430

Ser Phe Thr Phe Val Pro Gly Arg Leu Ala Asp Pro Lys Gly Ile Pro
            435                 440                 445

Phe Glu Val Glu Val Gly Arg Phe Pro Leu Gln Leu Pro Asp Tyr Ile
            450                 455                 460

Phe
465

<210> SEQ ID NO 12
<211> LENGTH: 672
<212> TYPE: DNA
<213> ORGANISM: Populus balsamifera subsp. trichocarpa
<220> FEATURE:
<221> NAME/KEY: misc_feature
<222> LOCATION: (1)..(672)
<223> OTHER INFORMATION: Ceres ANNOT ID no.1461298
```

```
<220> FEATURE:
<221> NAME/KEY: misc_feature
<222> LOCATION: (1)..(672)
<223> OTHER INFORMATION: Encodes the peptide sequence at SEQ ID NO:13

<400> SEQUENCE: 12
atggactcaa catctggagt agcttctgcg cccgacccga atagtggaga accgggtcca      60
tcagcgggat catcttcagc atcagcatca ctgccacaac aacagcaacc agagggatca     120
tcaccgccag caccaccaag tagatacgag tcgcagaaga ggagagactg gaacactttc     180
ttacagtact taaagaacca caagccacca ttaactctag ctcgttgcag tggtgcacat     240
gtgatcgagt tcttgaaata cttggatcaa tttggtaaga ccaaagtcca cataacgggc     300
tgtccttatt ttgggcaccc gaacccgcca gcaccttgct cttgtccact taagcaggcc     360
tggggtagtc ttgatgcgct aatcggacgg cttagagctg cttatgaaga aaacggtgga     420
cggccagaat cgaacccttt tggggctaga gctgtcagga tttacttgag ggaagttcga     480
gaaggtcaag ctaaagctag agggattccc tacgagaaga agaagcgaaa aaggtctaat     540
gttgctgttg ctacggtgaa tgtgtcggtg gaggcagctg gtggtggctc tactagtggt     600
ggcggagggg ggagtggtga tgctgatagt agtgctgctg cagcagctgc tgctgctaca     660
acaaccgtat ag                                                        672

<210> SEQ ID NO 13
<211> LENGTH: 223
<212> TYPE: PRT
<213> ORGANISM: Populus balsamifera subsp. trichocarpa
<220> FEATURE:
<221> NAME/KEY: misc_feature
<222> LOCATION: (1)..(223)
<223> OTHER INFORMATION: Ceres ANNOT ID no. 1461298
<220> FEATURE:
<221> NAME/KEY: misc_feature
<222> LOCATION: (30)..(162)
<223> OTHER INFORMATION: Pfam Name: DUF640
     Pfam Description: Protein of unknown function (DUF640)

<400> SEQUENCE: 13

Met Asp Ser Thr Ser Gly Val Ala Ser Ala Pro Asp Pro Asn Ser Gly
1               5                   10                  15

Glu Pro Gly Pro Ser Ala Gly Ser Ser Ala Ser Ala Ser Leu Pro
            20                  25                  30

Gln Gln Gln Gln Pro Glu Gly Ser Ser Pro Ala Pro Pro Ser Arg
        35                  40                  45

Tyr Glu Ser Gln Lys Arg Arg Asp Trp Asn Thr Phe Leu Gln Tyr Leu
    50                  55                  60

Lys Asn His Lys Pro Pro Leu Thr Leu Ala Arg Cys Ser Gly Ala His
65                  70                  75                  80

Val Ile Glu Phe Leu Lys Tyr Leu Asp Gln Phe Gly Lys Thr Lys Val
                85                  90                  95

His Ile Thr Gly Cys Pro Tyr Phe Gly His Pro Asn Pro Pro Ala Pro
            100                 105                 110

Cys Ser Cys Pro Leu Lys Gln Ala Trp Gly Ser Leu Asp Ala Leu Ile
        115                 120                 125

Gly Arg Leu Arg Ala Ala Tyr Glu Glu Asn Gly Gly Arg Pro Glu Ser
    130                 135                 140

Asn Pro Phe Gly Ala Arg Ala Val Arg Ile Tyr Leu Arg Glu Val Arg
145                 150                 155                 160

Glu Gly Gln Ala Lys Ala Arg Gly Ile Pro Tyr Glu Lys Lys Lys Arg
                165                 170                 175
```

```
Lys Arg Ser Asn Val Ala Val Ala Thr Val Asn Val Ser Val Glu Ala
        180                 185                 190

Ala Gly Gly Gly Ser Thr Ser Gly Gly Gly Gly Ser Gly Asp Ala
        195                 200                 205

Asp Ser Ser Ala Ala Ala Ala Ala Ala Ala Thr Thr Thr Val
        210                 215                 220

<210> SEQ ID NO 14
<211> LENGTH: 570
<212> TYPE: DNA
<213> ORGANISM: Populus balsamifera subsp. trichocarpa
<220> FEATURE:
<221> NAME/KEY: misc_feature
<222> LOCATION: (1)..(570)
<223> OTHER INFORMATION: Ceres ANNOT ID no.1463997
<220> FEATURE:
<221> NAME/KEY: misc_feature
<222> LOCATION: (1)..(570)
<223> OTHER INFORMATION: Encodes the peptide sequence at SEQ ID NO:15

<400> SEQUENCE: 14
atggaagagc tgcaaaacaa taaaaaacga gtcagggatg actcgttcga gctggagttg      60
gatttgccgg aggtgaagaa atcagagag gatttattgg gcatcatcga tgattccgac      120
cctgactcgc tgggtcagga tcttgactcc gtcatgaaga gttttgagca agagatatcc      180
gcgtattcat catctccggt gcccgtcgtc gacctgacgt ccgaatccgg cgagtcccgg      240
ccggatctag ggtaccttct agaagcttct gatgatgagc tcggcttgcc cccgtccatg      300
aattcctcga ggggggaggt caagggtgaa gaagagaccg agttggtccg agttgactcg      360
gcggagtcat ccggaatcgg tggagagata tggggttg aggaccagat tccgacttat        420
gactcgttcg ggctgggagc aggggacgtt gattataata gcaggtatgt ggcgttcgat      480
gatgggttgt tcgagtactc taatgcttgc ttcgactcga ccgagtttgt ggatttgtcg      540
tggcggttcg gcggcatgcc ggccgagtaa                                       570

<210> SEQ ID NO 15
<211> LENGTH: 189
<212> TYPE: PRT
<213> ORGANISM: Populus balsamifera subsp. trichocarpa
<220> FEATURE:
<221> NAME/KEY: misc_feature
<222> LOCATION: (1)..(189)
<223> OTHER INFORMATION: Ceres ANNOT ID no. 1463997

<400> SEQUENCE: 15

Met Glu Glu Leu Gln Asn Asn Lys Lys Arg Val Arg Asp Asp Ser Phe
1               5                   10                  15

Glu Leu Glu Leu Asp Leu Pro Glu Val Lys Lys Ile Arg Glu Asp Leu
            20                  25                  30

Leu Gly Ile Ile Asp Asp Ser Asp Pro Asp Ser Leu Gly Gln Asp Leu
        35                  40                  45

Asp Ser Val Met Lys Ser Phe Glu Gln Glu Ile Ser Ala Tyr Ser Ser
    50                  55                  60

Ser Pro Val Pro Val Val Asp Leu Thr Ser Glu Ser Gly Glu Ser Arg
65                  70                  75                  80

Pro Asp Leu Gly Tyr Leu Leu Glu Ala Ser Asp Glu Leu Gly Leu
                85                  90                  95

Pro Pro Ser Met Asn Ser Ser Arg Gly Glu Val Lys Gly Glu Glu
            100                 105                 110

Thr Glu Leu Val Arg Val Asp Ser Ala Glu Ser Ser Gly Ile Gly Gly
```

```
                115                 120                 125
Glu Ile Trp Gly Phe Glu Asp Gln Ile Pro Thr Tyr Asp Ser Phe Gly
        130                 135                 140

Leu Gly Ala Gly Asp Val Asp Tyr Asn Ser Arg Tyr Val Ala Phe Asp
145                 150                 155                 160

Asp Gly Leu Phe Glu Tyr Ser Asn Ala Cys Phe Asp Ser Thr Glu Phe
                165                 170                 175

Val Asp Leu Ser Trp Arg Phe Gly Gly Met Pro Ala Glu
            180                 185

<210> SEQ ID NO 16
<211> LENGTH: 981
<212> TYPE: DNA
<213> ORGANISM: Populus balsamifera subsp. trichocarpa
<220> FEATURE:
<221> NAME/KEY: misc_feature
<222> LOCATION: (1)..(981)
<223> OTHER INFORMATION: Ceres ANNOT ID no.1474088
<220> FEATURE:
<221> NAME/KEY: misc_feature
<222> LOCATION: (1)..(981)
<223> OTHER INFORMATION: Encodes the peptide sequence at SEQ ID NO:17

<400> SEQUENCE: 16
atggcagttg aaactcctca tatgagcctc aatttcccct tcacaactta tcacaaacagg      60 gatcttgtga agcaaatca cgcaaacatg aatttataca atacccagat ggattctggc      120
cttgttttca atgaaccagt gcctgaaaca ctcatgtcgt tctatcagtc ttctcttggt      180
tgtgacccaa tttctgctgc taaggcttct aataaagatg atagtagtct cacctacaat      240
gttcctgctg ttgctgctcc aagaaagagg gctagagact cgatcaatga tgacaacttt      300
gatgcttttc atgcctctca aaagaccaaa gtctctcctt tatcttcttt cattgatcac      360
gatatcctct ttcagatcca acaacagcaa tctgaaaatcg accgtttcat tgatgatcat      420
aatcagaaag ttagaatgga acttgaagag aggaaaaaga ggcaatcaag aatgttggta      480
tcagcaatac aagaaggaat gattaagaaa gtgaaagaga agacgaaga gattcaaaga      540 atgggaaaaa taaactggtt tcttcaagaa aaagcgaaga gtttatacgt agagaatcaa      600
atttggaggg attagcaca agccaatgag gccacagcaa attcattacg gagcaattta      660
gaacaagtct tggcgcacgc aagtggtggc gctgccactc tggcagatga tgcagaatcc      720
agttgctgtg gaagtagtga tcatgggagg tgcacgttag ctggtggaga gagggtgcg      780 gtgaaggata gatggtagt ggttaaggat aatcttaacc acaacaggat gtgtaaaaag      840
tgtggggaga gggagtcaag tgtgctgctg ctgccgtgca ggcatctttg cctgtgtaca      900
ttatgtgggt ccaatctgat tggttcttgc ccagtatgtg attctgtcat gactgctagt      960
gtccatgtta acatgtcttg a                                                981

<210> SEQ ID NO 17
<211> LENGTH: 326
<212> TYPE: PRT
<213> ORGANISM: Populus balsamifera subsp. trichocarpa
<220> FEATURE:
<221> NAME/KEY: misc_feature
<222> LOCATION: (1)..(326)
<223> OTHER INFORMATION: Ceres ANNOT ID no. 1474088

<400> SEQUENCE: 17

Met Ala Val Glu Thr Pro His Met Ser Leu Asn Phe Pro Ser Gln Leu
1               5                   10                  15

Ile Thr Asn Arg Asp Leu Val Lys Ala Asn His Ala Asn Met Asn Leu
```

```
                    20                  25                  30
Tyr Asn Thr Gln Met Asp Ser Gly Leu Val Phe Asn Glu Pro Val Pro
                35                  40                  45

Glu Thr Leu Met Ser Phe Tyr Gln Ser Ser Leu Gly Cys Asp Pro Ile
 50                  55                  60

Ser Ala Ala Lys Ala Ser Asn Lys Asp Asp Ser Ser Leu Thr Tyr Asn
 65                  70                  75                  80

Val Pro Ala Val Ala Ala Pro Arg Lys Arg Ala Arg Asp Ser Ile Asn
                85                  90                  95

Asp Asp Asn Phe Asp Ala Phe His Ala Ser Gln Lys Thr Lys Val Ser
                100                 105                 110

Pro Leu Ser Ser Phe Ile Asp His Asp Ile Leu Phe Gln Ile Gln Gln
            115                 120                 125

Gln Gln Ser Glu Ile Asp Arg Phe Ile Asp Asp His Asn Gln Lys Val
        130                 135                 140

Arg Met Glu Leu Glu Arg Lys Lys Arg Gln Ser Arg Met Leu Val
145                 150                 155                 160

Ser Ala Ile Gln Glu Gly Met Ile Lys Lys Val Lys Glu Lys Asp Glu
                165                 170                 175

Glu Ile Gln Arg Met Gly Lys Ile Asn Trp Phe Leu Gln Glu Lys Ala
                180                 185                 190

Lys Ser Leu Tyr Val Glu Asn Gln Ile Trp Arg Asp Leu Ala Gln Ala
            195                 200                 205

Asn Glu Ala Thr Ala Asn Ser Leu Arg Ser Asn Leu Glu Gln Val Leu
        210                 215                 220

Ala His Ala Ser Gly Gly Ala Ala Thr Leu Ala Asp Asp Ala Glu Ser
225                 230                 235                 240

Ser Cys Cys Gly Ser Ser Asp His Gly Arg Cys Thr Leu Ala Gly Gly
                245                 250                 255

Glu Glu Gly Ala Val Lys Asp Lys Met Val Val Lys Asp Asn Leu
                260                 265                 270

Asn His Asn Arg Met Cys Lys Lys Cys Gly Glu Arg Glu Ser Ser Val
            275                 280                 285

Leu Leu Leu Pro Cys Arg His Leu Cys Leu Cys Thr Leu Cys Gly Ser
        290                 295                 300

Asn Leu Ile Gly Ser Cys Pro Val Cys Asp Ser Val Met Thr Ala Ser
305                 310                 315                 320

Val His Val Asn Met Ser
            325

<210> SEQ ID NO 18
<211> LENGTH: 831
<212> TYPE: DNA
<213> ORGANISM: Populus balsamifera subsp. trichocarpa
<220> FEATURE:
<221> NAME/KEY: misc_feature
<222> LOCATION: (1)..(831)
<223> OTHER INFORMATION: Ceres ANNOT ID no.1485507
<220> FEATURE:
<221> NAME/KEY: misc_feature
<222> LOCATION: (1)..(831)
<223> OTHER INFORMATION: Encodes the peptide sequence at SEQ ID NO:19

<400> SEQUENCE: 18
atggttaaca tgtgtagtca tattataaaa cctgagagcc aaatagagaa gtcagaacag    60
gatagcattt ttccagagag agagagagga aaaggcaaaa aggaaagaag aaattctttg   120
ttagagggag gggatctaca caggaaact tacaacaaaa tggctcttta tgttgatgaa   180
```

```
gaagagatat ggaaatgttt aaagcaccct tccaagcgtc gccgaacagg aatctgccac        240
gtgtgcctcc gcgaacgtct ctcctctctt tgccctgact gcgctagcgc gcgcccctgc        300
acttgctacg ccaccaccgc gtcctcctct tctggcacca cttcatcctc ctcctcccac        360
tgcttctcct ccgcttccgg aatcggaagc gtcggtcgag tctccaattt aatcgagagc        420
gaacccgctt ttcgtcgctc tcgatcccta gctgttccgt ttctccggtc aaagccatcg        480
gctgaccata gttataacaa ccacaaagcg tcctcgtcgt tctggtcatt gttcaaggga        540
gggcatggta acaggagcat gagagaggag gtcgaaagac gacacgtggt gattttgaag        600
gaggaggagc tggaggaatc atcgaggaag gtaaatgaag atgaggagag gaggaggatg        660
atgaggaagt caagatcggt ggcggtgact tcagagtcaa gaggaagtga cgtgaggaga        720
tcgtcaaagg gagggaaggg atggtatttc cctagtccga tcaaggtttt caagcaatcg        780
atctcgagag ggattttggc gcatgaaagg tcgcctttgt atagaggttg a                 831
```

<210> SEQ ID NO 19
<211> LENGTH: 223
<212> TYPE: PRT
<213> ORGANISM: Populus balsamifera subsp. trichocarpa
<220> FEATURE:
<221> NAME/KEY: misc_feature
<222> LOCATION: (1)..(223)
<223> OTHER INFORMATION: Ceres ANNOT ID no. 1485507

<400> SEQUENCE: 19

```
Met Ala Leu Tyr Val Asp Glu Glu Ile Trp Lys Cys Leu Lys His
 1               5                  10                  15

Pro Ser Lys Arg Arg Thr Gly Ile Cys His Val Cys Leu Arg Glu
                20                  25                  30

Arg Leu Ser Ser Leu Cys Pro Asp Cys Ala Ser Ala Arg Pro Cys Thr
         35                  40                  45

Cys Tyr Ala Thr Thr Ala Ser Ser Ser Gly Thr Thr Ser Ser Ser
     50                  55                  60

Ser Ser His Cys Phe Ser Ser Ala Ser Gly Ile Gly Ser Val Gly Arg
 65                  70                  75                  80

Val Ser Asn Leu Ile Glu Ser Glu Pro Ala Phe Arg Arg Ser Arg Ser
                 85                  90                  95

Leu Ala Val Pro Phe Leu Arg Ser Lys Pro Ser Ala Asp His Ser Tyr
            100                 105                 110

Asn Asn His Lys Ala Ser Ser Ser Phe Trp Ser Leu Phe Lys Gly Gly
        115                 120                 125

His Gly Asn Arg Ser Met Arg Glu Glu Val Glu Arg His Val Val
    130                 135                 140

Ile Leu Lys Glu Glu Glu Leu Glu Glu Ser Ser Arg Lys Val Asn Glu
145                 150                 155                 160

Asp Glu Glu Arg Arg Arg Met Met Arg Lys Ser Arg Ser Val Ala Val
                165                 170                 175

Thr Ser Glu Ser Arg Gly Ser Asp Val Arg Arg Ser Ser Lys Gly Gly
            180                 185                 190

Lys Gly Trp Tyr Phe Pro Ser Pro Ile Lys Val Phe Lys Gln Ser Ile
        195                 200                 205

Ser Arg Gly Ile Leu Ala His Glu Arg Ser Pro Leu Tyr Arg Gly
    210                 215                 220
```

<210> SEQ ID NO 20
<211> LENGTH: 726

-continued

```
<212> TYPE: DNA
<213> ORGANISM: Populus balsamifera subsp. trichocarpa
<220> FEATURE:
<221> NAME/KEY: misc_feature
<222> LOCATION: (1)..(726)
<223> OTHER INFORMATION: Ceres ANNOT ID no.1493443
<220> FEATURE:
<221> NAME/KEY: misc_feature
<222> LOCATION: (1)..(726)
<223> OTHER INFORMATION: Encodes the peptide sequence at SEQ ID NO:21

<400> SEQUENCE: 20
atggtgtctg ctgaagctgc tcgtaacgtt gttgggatta tcgggaatgt catctccttt      60
ggcctatttt tatctccagt tccaacattt tatcgcattt gtaagaagaa agatgtggaa     120
gagtttcaac cttatcctta tgctgcgacg gtgttgaact gcttgttctg gattctctat     180
gggctgccga tagttaaacc agacagcact cttgttgtga ccattaacag tgttggtctt     240
gtattggagc tgatctactt gagcatattt tgcattttg acacgcagaa taaggggcgg      300
aagaaggttt tcttgtgct tttggcgaa gtaatcttta tggccgctat tgttgtaacc       360 actttctag cttccacac tcatgagaaa agaactcttt tgtgggagt tttctgtgac        420 atcttcaaca ttttgatgta cgcttcacct cttactataa aaaggttgt gaccacaaag      480 agtgtggaat acatgccatt gtcccttca ttggccaact tccttaatgg ctgtgtctgg      540
acagcttatg ctctcatcag atttgatatc ttcatactgg tcagcaatgg tcttggagct    600
ttctttggtt ttctccagct cgtccttac gccttctact acaaatctac tcctaaacgc     660
ggtagtcaag atgtgaagcc atctgagatc cagctttccg cttcagatgc agcctccaga    720
gcatga                                                                726

<210> SEQ ID NO 21
<211> LENGTH: 241
<212> TYPE: PRT
<213> ORGANISM: Populus balsamifera subsp. trichocarpa
<220> FEATURE:
<221> NAME/KEY: misc_feature
<222> LOCATION: (1)..(241)
<223> OTHER INFORMATION: Ceres ANNOT ID no. 1493443
<220> FEATURE:
<221> NAME/KEY: misc_feature
<222> LOCATION: (9)..(98)
<223> OTHER INFORMATION: Pfam Name: MtN3_slv
      Pfam Description: MtN3/saliva family

<400> SEQUENCE: 21

Met Val Ser Ala Glu Ala Ala Arg Asn Val Val Gly Ile Ile Gly Asn
1               5                   10                  15

Val Ile Ser Phe Gly Leu Phe Leu Ser Pro Val Pro Thr Phe Tyr Arg
            20                  25                  30

Ile Cys Lys Lys Lys Asp Val Glu Glu Phe Gln Pro Tyr Pro Tyr Ala
        35                  40                  45

Ala Thr Val Leu Asn Cys Leu Phe Trp Ile Leu Tyr Gly Leu Pro Ile
    50                  55                  60

Val Lys Pro Asp Ser Thr Leu Val Val Thr Ile Asn Ser Val Gly Leu
65                  70                  75                  80

Val Leu Glu Leu Ile Tyr Leu Ser Ile Phe Cys Ile Phe Asp Thr Gln
                85                  90                  95

Asn Lys Gly Arg Lys Lys Val Phe Leu Val Leu Phe Gly Glu Val Ile
            100                 105                 110

Phe Met Ala Ala Ile Val Val Thr Thr Phe Leu Ala Phe His Thr His
        115                 120                 125
```

```
Glu Lys Arg Thr Leu Phe Val Gly Val Phe Cys Asp Ile Phe Asn Ile
130                 135                 140

Leu Met Tyr Ala Ser Pro Leu Thr Ile Lys Lys Val Val Thr Thr Lys
145                 150                 155                 160

Ser Val Glu Tyr Met Pro Leu Ser Leu Ser Leu Ala Asn Phe Leu Asn
                165                 170                 175

Gly Cys Val Trp Thr Ala Tyr Ala Leu Ile Arg Phe Asp Ile Phe Ile
            180                 185                 190

Leu Val Ser Asn Gly Leu Gly Ala Phe Phe Gly Phe Leu Gln Leu Val
        195                 200                 205

Leu Tyr Ala Phe Tyr Tyr Lys Ser Thr Pro Lys Arg Gly Ser Gln Asp
    210                 215                 220

Val Lys Pro Ser Glu Ile Gln Leu Ser Ala Ser Asp Ala Ala Ser Arg
225                 230                 235                 240

Ala

<210> SEQ ID NO 22
<211> LENGTH: 2043
<212> TYPE: DNA
<213> ORGANISM: Populus balsamifera subsp. trichocarpa
<220> FEATURE:
<221> NAME/KEY: misc_feature
<222> LOCATION: (1)..(2043)
<223> OTHER INFORMATION: Ceres ANNOT ID no.1504954
<220> FEATURE:
<221> NAME/KEY: misc_feature
<222> LOCATION: (1)..(2043)
<223> OTHER INFORMATION: Encodes the peptide sequence at SEQ ID NO:23

<400> SEQUENCE: 22
atgtcaggag gtgggtgtag tatagtttgg ttcagaagag atctaaggt agaagataac      60 ccggcacttg cagctggtgt aagagcaggt gctgttgttg ctgtgtttgt atgggcaccc    120
gaggaggaag gccattatta tcccggtagg gtctcaaggt ggtggcttaa acaaagtttg    180
gctcatcttg actcttcttt aaggagtctt ggtacttctc ttgttactaa gagatcaact    240
gatagtgttt cttctcttct tgaggttgtc aaatctaccg gtgctactca gcttttattc    300
aaccacttat atgaccccctt gtcactggtt agggatcacc gggcaaagga gattttgact   360
gctcaaggta ttactgtaag atcttttaac gcggacttgc tttatgaacc atgggatgtt    420
aatgatgccc agggccgtcc gttcacaacc tttgacactt tctgggaaag atgcctcagc    480 atgcctttg atccagaggc tccacttctc ccgcctaaga ggattatttc gggtgatgta    540
tccagatgcc cttcagtcac gctggtattt gaagatgaat cagagaaagg aagcaatgca    600
cttcttgcaa gagcatggtc acctggatgg agcaatgctg atagggcttt gaccactttc    660
attaacggac cactaattga gtactctatg aatcgtagaa aggctgatag cgccacaacc    720
tcatttctct caccacactt gcattttggg gaggtgagtg tgagaaaagt cttccatctt    780
gttcgcatca agcaggttct gtgggcaaat gaagggaaca gggccggcga agagagtgta    840
aacttgttta tcaagtcaat tggtcttagg gaatattcaa gatacttgag tttcaaccat    900
ccttgcactc atgaaaggcc tcttcttggg caccttaagt ttttcccttg ggttgtggac    960
gaaggctatt ttaaggcatg gagacaaggt agaacaggtt atccattagt tgacgctgga   1020
atgagagaat gtgggctgc tggttggctg catgatcgta tacgtgtggt agttgctagt    1080
ttctttgtga aggttctaca acttccatgg agatggggaa tgaagtatt tttgggatacc   1140 ctattggatg cagatttaga gagcgatgct cttgggtggc aatacataac cggcactctc   1200
ccagacagcc gtgagtttga tcgcatagat aatccacagt ttgagggtta caaatttgac   1260
```

```
ccgaatggag aatatgtacg ccggtggctt cctgaacttg ctaggctacc aactgaatgg    1320
atacaccacc catggaatgc acctgaatct gtactccaag ctgccggaat tgagctggga    1380
tcaaattacc ctctccctat tgtagggata gatgcagcaa aggtcaggtt ggaagaagca    1440 cttttcagaaa tgtggcagca agaagctgct tcaagagctg caattgagaa tggaacagag    1500
gaagggcttg gagactcctc tgaatcagcc ccatttgcct tccccgaaga catacatatg    1560
gaggaaaacc atgagcctgt gagaaacaat cctcctgcta caaatcgtcg ctatgaggat    1620
cagatggtcc caagcatgac atcttccttt ctgagaattg aagacgaaga aacttctgat    1680
gtacgcaatt ctacaggaga tggcagagca gaggtgccaa gagatgtaaa tgtgaatcaa    1740
gaaccaagaa gagacgcttt gaaccagggg tttgttcaaa ctgttcgtaa taacactgct    1800
ttgtcaccat ttaatatttc gagaggtctg acaaatgttg aagactcgac cgcagagtct    1860
tcaagtagtg gtaggagaga gagggatgga ggtatagttc agtttggtc ccctccaact    1920 tctagttact cagagcagtt tgttggtgat gacaatggaa ttggagcaac ttcttcttac    1980
ttgcagaggc atccacagtc tcaccagata atcaattgga ggcggctatc tcaaactggg    2040
taa                                                                 2043
```

<210> SEQ ID NO 23
<211> LENGTH: 680
<212> TYPE: PRT
<213> ORGANISM: Populus balsamifera subsp. trichocarpa
<220> FEATURE:
<221> NAME/KEY: misc_feature
<222> LOCATION: (1)..(680)
<223> OTHER INFORMATION: Ceres ANNOT ID no. 1504954
<220> FEATURE:
<221> NAME/KEY: misc_feature
<222> LOCATION: (207)..(485)
<223> OTHER INFORMATION: Pfam Name: FAD_binding_7
    Pfam Description: FAD binding domain of DNA photolyase
<220> FEATURE:
<221> NAME/KEY: misc_feature
<222> LOCATION: (5)..(176)
<223> OTHER INFORMATION: Pfam Name: DNA_photolyase
    Pfam Description: DNA photolyase

<400> SEQUENCE: 23

Met Ser Gly Gly Gly Cys Ser Ile Val Trp Phe Arg Arg Asp Leu Arg
1               5                   10                  15

Val Glu Asp Asn Pro Ala Leu Ala Ala Gly Val Arg Ala Gly Ala Val
                20                  25                  30

Val Ala Val Phe Val Trp Ala Pro Glu Glu Gly His Tyr Tyr Pro
            35                  40                  45

Gly Arg Val Ser Arg Trp Trp Leu Lys Gln Ser Leu Ala His Leu Asp
        50                  55                  60

Ser Ser Leu Arg Ser Leu Gly Thr Ser Leu Val Thr Lys Arg Ser Thr
65                  70                  75                  80

Asp Ser Val Ser Ser Leu Leu Glu Val Val Lys Ser Thr Gly Ala Thr
                85                  90                  95

Gln Leu Leu Phe Asn His Leu Tyr Asp Pro Leu Ser Leu Val Arg Asp
            100                 105                 110

His Arg Ala Lys Glu Ile Leu Thr Ala Gln Gly Ile Thr Val Arg Ser
        115                 120                 125

Phe Asn Ala Asp Leu Leu Tyr Glu Pro Trp Asp Val Asn Asp Ala Gln
    130                 135                 140

Gly Arg Pro Phe Thr Thr Phe Asp Thr Phe Trp Glu Arg Cys Leu Ser
145                 150                 155                 160

```
Met Pro Phe Asp Pro Glu Ala Pro Leu Leu Pro Pro Lys Arg Ile Ile
            165                 170                 175
Ser Gly Asp Val Ser Arg Cys Pro Ser Val Thr Leu Val Phe Glu Asp
            180                 185                 190
Glu Ser Glu Lys Gly Ser Asn Ala Leu Leu Ala Arg Ala Trp Ser Pro
            195                 200                 205
Gly Trp Ser Asn Ala Asp Arg Ala Leu Thr Thr Phe Ile Asn Gly Pro
210                 215                 220
Leu Ile Glu Tyr Ser Met Asn Arg Arg Lys Ala Asp Ser Ala Thr Thr
225                 230                 235                 240
Ser Phe Leu Ser Pro His Leu His Phe Gly Glu Val Ser Val Arg Lys
                245                 250                 255
Val Phe His Leu Val Arg Ile Lys Gln Val Leu Trp Ala Asn Glu Gly
            260                 265                 270
Asn Arg Ala Gly Glu Glu Ser Val Asn Leu Phe Ile Lys Ser Ile Gly
            275                 280                 285
Leu Arg Glu Tyr Ser Arg Tyr Leu Ser Phe Asn His Pro Cys Thr His
            290                 295                 300
Glu Arg Pro Leu Leu Gly His Leu Lys Phe Phe Pro Trp Val Val Asp
305                 310                 315                 320
Glu Gly Tyr Phe Lys Ala Trp Arg Gln Gly Arg Thr Gly Tyr Pro Leu
                325                 330                 335
Val Asp Ala Gly Met Arg Glu Leu Trp Ala Ala Gly Trp Leu His Asp
            340                 345                 350
Arg Ile Arg Val Val Val Ala Ser Phe Phe Val Lys Val Leu Gln Leu
            355                 360                 365
Pro Trp Arg Trp Gly Met Lys Tyr Phe Trp Asp Thr Leu Leu Asp Ala
            370                 375                 380
Asp Leu Glu Ser Asp Ala Leu Gly Trp Gln Tyr Ile Thr Gly Thr Leu
385                 390                 395                 400
Pro Asp Ser Arg Glu Phe Asp Arg Ile Asp Asn Pro Gln Phe Glu Gly
                405                 410                 415
Tyr Lys Phe Asp Pro Asn Gly Glu Tyr Val Arg Arg Trp Leu Pro Glu
            420                 425                 430
Leu Ala Arg Leu Pro Thr Glu Trp Ile His His Pro Trp Asn Ala Pro
            435                 440                 445
Glu Ser Val Leu Gln Ala Ala Gly Ile Glu Leu Gly Ser Asn Tyr Pro
            450                 455                 460
Leu Pro Ile Val Gly Ile Asp Ala Ala Lys Val Arg Leu Glu Glu Ala
465                 470                 475                 480
Leu Ser Glu Met Trp Gln Gln Glu Ala Ala Ser Arg Ala Ala Ile Glu
                485                 490                 495
Asn Gly Thr Glu Glu Gly Leu Gly Asp Ser Ser Glu Ser Ala Pro Phe
            500                 505                 510
Ala Phe Pro Glu Asp Ile His Met Glu Glu Asn His Glu Pro Val Arg
            515                 520                 525
Asn Asn Pro Pro Ala Thr Asn Arg Arg Tyr Glu Asp Gln Met Val Pro
            530                 535                 540
Ser Met Thr Ser Ser Phe Leu Arg Ile Glu Asp Glu Glu Thr Ser Asp
545                 550                 555                 560
Val Arg Asn Ser Thr Gly Asp Gly Arg Ala Glu Val Pro Arg Asp Val
                565                 570                 575
Asn Val Asn Gln Glu Pro Arg Arg Asp Ala Leu Asn Gln Gly Phe Val
```

```
                    580              585              590
Gln Thr Val Arg Asn Asn Thr Ala Leu Ser Pro Phe Asn Ile Ser Arg
                595              600              605

Gly Leu Thr Asn Val Glu Asp Ser Thr Ala Glu Ser Ser Ser Ser Gly
            610              615              620

Arg Arg Glu Arg Asp Gly Gly Ile Val Pro Val Trp Ser Pro Pro Thr
625              630              635              640

Ser Ser Tyr Ser Glu Gln Phe Val Gly Asp Asn Gly Ile Gly Ala
                645              650              655

Thr Ser Ser Tyr Leu Gln Arg His Pro Gln Ser His Gln Ile Ile Asn
            660              665              670

Trp Arg Arg Leu Ser Gln Thr Gly
        675              680
```

<210> SEQ ID NO 24
<211> LENGTH: 528
<212> TYPE: DNA
<213> ORGANISM: Populus balsamifera subsp. trichocarpa
<220> FEATURE:
<221> NAME/KEY: misc_feature
<222> LOCATION: (1)..(528)
<223> OTHER INFORMATION: Ceres ANNOT ID no.1524883
<220> FEATURE:
<221> NAME/KEY: misc_feature
<222> LOCATION: (1)..(528)
<223> OTHER INFORMATION: Encodes the peptide sequence at SEQ ID NO:25

<400> SEQUENCE: 24

```
atgggcagag gagctaccct ctagttcttca tcttcttttg aaagcagcaa ctacccatct     60
gtatcaagca agtcttctct ctctcagcta agaaagacc taagcacaga tctcaggctt     120
ggacttagca tctcaacctc tcaacaggag aaccctccta caccaagtga tcagcaactt     180
tcggactggc caccaatcaa gccatttcta aggaaggcat tagcgtcaga agaaaatgag     240
tgcagtagtg ccaccttctt cgtcaaggtt tacatggaag cattccgat tggaaggaag      300
ctcaacctct tagcccatga tggttaccat gacttaatac agactcttga ccaaatgttc     360
aacactagca ttctctggcc tgaaatggat attgaacatt ctgggcaatg tcatgtgttg     420
acatatgaag acaaagaggg ggattggttg attgttgggg atgttccctg ggagatgttc     480
ttaccttctg tgcggagatt gaagatcact agggcagaca gcctatga                 528
```

<210> SEQ ID NO 25
<211> LENGTH: 175
<212> TYPE: PRT
<213> ORGANISM: Populus balsamifera subsp. trichocarpa
<220> FEATURE:
<221> NAME/KEY: misc_feature
<222> LOCATION: (1)..(175)
<223> OTHER INFORMATION: Ceres ANNOT ID no. 1524883
<220> FEATURE:
<221> NAME/KEY: misc_feature
<222> LOCATION: (63)..(125)
<223> OTHER INFORMATION: Pfam Name: AUX_IAA
     Pfam Description: AUX/IAA family

<400> SEQUENCE: 25

```
Met Gly Arg Gly Ala Thr Ser Ser Ser Ser Ser Phe Glu Ser Ser
1               5                   10                  15

Asn Tyr Pro Ser Val Ser Ser Lys Ser Ser Leu Ser Gln Leu Lys Lys
                20                  25                  30

Asp Leu Ser Thr Asp Leu Arg Leu Gly Leu Ser Ile Ser Thr Ser Gln
            35                  40                  45
```

Gln Glu Asn Pro Ser Thr Pro Ser Asp Gln Gln Leu Ser Asp Trp Pro
            50                  55                  60

Pro Ile Lys Pro Phe Leu Arg Lys Ala Leu Ala Ser Glu Glu Asn Glu
 65                  70                  75                  80

Cys Ser Ser Ala Thr Phe Phe Val Lys Val Tyr Met Glu Gly Ile Pro
                85                  90                  95

Ile Gly Arg Lys Leu Asn Leu Leu Ala His Asp Gly Tyr His Asp Leu
            100                 105                 110

Ile Gln Thr Leu Asp Gln Met Phe Asn Thr Ser Ile Leu Trp Pro Glu
        115                 120                 125

Met Asp Ile Glu His Ser Gly Gln Cys His Val Leu Thr Tyr Glu Asp
    130                 135                 140

Lys Glu Gly Asp Trp Leu Ile Val Gly Asp Val Pro Trp Glu Met Phe
145                 150                 155                 160

Leu Pro Ser Val Arg Arg Leu Lys Ile Thr Arg Ala Asp Ser Leu
                165                 170                 175

<210> SEQ ID NO 26
<211> LENGTH: 462
<212> TYPE: DNA
<213> ORGANISM: Populus balsamifera subsp. trichocarpa
<220> FEATURE:
<221> NAME/KEY: misc_feature
<222> LOCATION: (1)..(462)
<223> OTHER INFORMATION: Ceres ANNOT ID no.1525600
<220> FEATURE:
<221> NAME/KEY: misc_feature
<222> LOCATION: (1)..(462)
<223> OTHER INFORMATION: Encodes the peptide sequence at SEQ ID NO:27

<400> SEQUENCE: 26
atgggtctat caagtctgcc agctccatct gaaggagtat tatgtgtgct tttagtaaac    60
actgccttgt caatttccat tgtcaaagga atagtccgtt caatccttca tattgttggc   120
atccgtttgt caccatctgc atcactccca tcgtcagata atgctgaaga caccagagag   180
tcgcttgaat tcgtttaag tcccccagag aattacattg aggagttccg aagcaggatg   240
ccatcaatcc gattcaacac ggtgtgcagc tgtgaacagc ctgaacatga ctgctcggtt   300
tgcctgaccc aatttgagcc agaatcggag ataaatagcc tgtcatgtgg ccatatcttt   360
cataaaatgt gcttggagaa gtggttggac tattggaaca ttacatgccc tctttgcagg   420
actcctttgc tgcctgaaga ggatgcatct tgcttttggt ga                      462

<210> SEQ ID NO 27
<211> LENGTH: 153
<212> TYPE: PRT
<213> ORGANISM: Populus balsamifera subsp. trichocarpa
<220> FEATURE:
<221> NAME/KEY: misc_feature
<222> LOCATION: (1)..(153)
<223> OTHER INFORMATION: Ceres ANNOT ID no. 1525600
<220> FEATURE:
<221> NAME/KEY: misc_feature
<222> LOCATION: (98)..(139)
<223> OTHER INFORMATION: Pfam Name: zf-C3HC4
      Pfam Description: Zinc finger, C3HC4 type (RING finger)

<400> SEQUENCE: 27

Met Gly Leu Ser Ser Leu Pro Ala Pro Ser Glu Gly Val Leu Cys Val
  1               5                  10                  15

Leu Leu Val Asn Thr Ala Leu Ser Ile Ser Ile Val Lys Gly Ile Val
                20                  25                  30

Arg Ser Ile Leu His Ile Val Gly Ile Arg Leu Ser Pro Ser Ala Ser

|  | 35 |  |  |  | 40 |  |  |  |  | 45 |  |  |
|---|---|---|---|---|---|---|---|---|---|---|---|---|

Leu Pro Ser Ser Asp Asn Ala Glu Asp Thr Arg Glu Ser Leu Glu Phe
   50                            55                        60

Arg Leu Ser Pro Pro Glu Asn Tyr Ile Glu Glu Phe Arg Ser Arg Met
65                      70                         75                       80

Pro Ser Ile Arg Phe Asn Thr Val Cys Ser Cys Glu Gln Pro Glu His
                         85                         90                       95

Asp Cys Ser Val Cys Leu Thr Gln Phe Glu Pro Glu Ser Glu Ile Asn
             100                      105                      110

Ser Leu Ser Cys Gly His Ile Phe His Lys Met Cys Leu Glu Lys Trp
         115                      120                     125

Leu Asp Tyr Trp Asn Ile Thr Cys Pro Leu Cys Arg Thr Pro Leu Leu
   130                       135                        140

Pro Glu Glu Asp Ala Ser Cys Phe Trp
145                 150

<210> SEQ ID NO 28
<211> LENGTH: 1509
<212> TYPE: DNA
<213> ORGANISM: Populus balsamifera subsp. trichocarpa
<220> FEATURE:
<221> NAME/KEY: misc_feature
<222> LOCATION: (1)..(1509)
<223> OTHER INFORMATION: Ceres ANNOT ID no.1536088
<220> FEATURE:
<221> NAME/KEY: misc_feature
<222> LOCATION: (1)..(1509)
<223> OTHER INFORMATION: Encodes the peptide sequence at SEQ ID NO:29

<400> SEQUENCE: 28

| | | | | |
|---|---|---|---|---|
| atggaattca cttgtttaca caacaaatgc atttcacctt ctcttactgt tctctctagg | 60 |
| gtttcaattt cattttccaa tcttcctaaa cgcgccgttt catttcaccg gcggcggaga | 120 |
| aatttgtgct ttgcaacatt agtcgatggg aaacgtacta gtgaagttgt gagcaaaaga | 180 |
| ggaggagaag aagaagacga atttggggat ttgaagtctt ggatgcataa aaatggattg | 240 |
| cctccttgca aagttgtgct taaagaaaga ccttctcatg acaagaaact tcgacctatt | 300 |
| cattatgttg ctgctagcga ggatcttcag gccagtgatg tggcggtttc ggtgcccaat | 360 |
| tcgcttgttg ttacactcga gagggttttg ggaaatgaga ctcttgcgga actcttaacc | 420 |
| acaaacaaat tatcggaatt ggcatgcttg gccttatacc tgatgtatga aagaagcaa | 480 |
| ggaaagaagt cattctggta tccatatata agggagcttg atcgtcagcg aggtaggggt | 540 |
| cagctggctg tggaatctcc acttttatgg tctgaggctg aattggctta cctgactggt | 600 |
| agcccaacta aggctgaagt tcttgacagg gcagatggaa ttaaaagaga atatgaggag | 660 |
| ctagacactg tttggttcat ggctggttct ctgtttcagc aatatccata tgatatacct | 720 |
| actgaagcct ttccctttga gatttttaaa caagcttttg tagccattca atcctgtgtg | 780 |
| gtgcatttac agaaagtcag tttggctcga agatttgctt tggttcctct tggaccacct | 840 |
| ttgctagcat acagtagcaa ctgcaaggca atgttaactg ctgttgatgg tgctgttgaa | 900 |
| ttagtggttg atcgaccata caaggctggg agcccattgt tgtatggtg tgggccacag | 960 |
| ccaaattcaa aattgctttt aaactatggc tttgttgatg aagataatcc ttatgaccga | 1020 |
| atagcagttg aggcagcact gaacactgag gaccctcagt atcaggacaa agaaatggtt | 1080 |
| gctcaaagaa atgggaaatt gtcagtgcaa gttttcaag tatacgctgg aaaggaaaaa | 1140 |
| gaagccgtgt cagatattct tccttatttg cgattgggat atgtatcaga tccttctgaa | 1200 |
| atgcaatctg taatttcttc tcaaggtcca gtttgtccag taagcccttg tatggaacaa | 1260 |

-continued

```
gcagtgttag atcagcttac tgtttatttt agaacgcgcc ttgctggcta ttgtaccagc   1320
ataagtgaag atgagttgat gttggcagat cctaacttga accccaagaa gcgagtggct   1380
actcagcttg ttagattgga aaagaaaatg ctgaaggcat gcttgcaggc tacagttgat   1440
ttgataaacc agttacctga tcacaccatg cctccatgcc agctcctta tgcccctta    1500 ttgaaatga                                                          1509
```

<210> SEQ ID NO 29
<211> LENGTH: 502
<212> TYPE: PRT
<213> ORGANISM: Populus balsamifera subsp. trichocarpa
<220> FEATURE:
<221> NAME/KEY: misc_feature
<222> LOCATION: (1)..(502)
<223> OTHER INFORMATION: Ceres ANNOT ID no. 1536088
<220> FEATURE:
<221> NAME/KEY: misc_feature
<222> LOCATION: (103)..(324)
<223> OTHER INFORMATION: Pfam Name: SET
      Pfam Description: SET domain

<400> SEQUENCE: 29

```
Met Glu Phe Thr Cys Leu His Asn Lys Cys Ile Ser Pro Ser Leu Thr
1               5                   10                  15

Val Leu Ser Arg Val Ser Ile Ser Phe Ser Asn Leu Pro Lys Arg Ala
            20                  25                  30

Val Ser Phe His Arg Arg Arg Asn Leu Cys Phe Ala Thr Leu Val
        35                  40                  45

Asp Gly Lys Arg Thr Ser Glu Val Val Ser Lys Arg Gly Gly Glu Glu
    50                  55                  60

Glu Asp Glu Phe Gly Asp Leu Lys Ser Trp Met His Lys Asn Gly Leu
65                  70                  75                  80

Pro Pro Cys Lys Val Val Leu Lys Glu Arg Pro Ser His Asp Lys Lys
                85                  90                  95

Leu Arg Pro Ile His Tyr Val Ala Ala Ser Glu Asp Leu Gln Ala Ser
            100                 105                 110

Asp Val Ala Val Ser Val Pro Asn Ser Leu Val Val Thr Leu Glu Arg
        115                 120                 125

Val Leu Gly Asn Glu Thr Leu Ala Glu Leu Leu Thr Thr Asn Lys Leu
    130                 135                 140

Ser Glu Leu Ala Cys Leu Ala Leu Tyr Leu Met Tyr Glu Lys Lys Gln
145                 150                 155                 160

Gly Lys Lys Ser Phe Trp Tyr Pro Tyr Ile Arg Glu Leu Asp Arg Gln
                165                 170                 175

Arg Gly Arg Gly Gln Leu Ala Val Glu Ser Pro Leu Leu Trp Ser Glu
            180                 185                 190

Ala Glu Leu Ala Tyr Leu Thr Gly Ser Pro Thr Lys Ala Glu Val Leu
        195                 200                 205

Asp Arg Ala Asp Gly Ile Lys Arg Glu Tyr Glu Glu Leu Asp Thr Val
    210                 215                 220

Trp Phe Met Ala Gly Ser Leu Phe Gln Gln Tyr Pro Tyr Asp Ile Pro
225                 230                 235                 240

Thr Glu Ala Phe Pro Phe Glu Ile Phe Lys Gln Ala Phe Val Ala Ile
                245                 250                 255

Gln Ser Cys Val Val His Leu Gln Lys Val Ser Leu Ala Arg Arg Phe
            260                 265                 270

Ala Leu Val Pro Leu Gly Pro Pro Leu Leu Ala Tyr Ser Ser Asn Cys
```

```
                    275                 280                 285
Lys Ala Met Leu Thr Ala Val Asp Gly Ala Val Glu Leu Val Val Asp
    290                 295                 300

Arg Pro Tyr Lys Ala Gly Glu Pro Ile Val Val Trp Cys Gly Pro Gln
305                 310                 315                 320

Pro Asn Ser Lys Leu Leu Asn Tyr Gly Phe Val Asp Glu Asp Asn
                325                 330                 335

Pro Tyr Asp Arg Ile Ala Val Glu Ala Ala Leu Asn Thr Glu Asp Pro
            340                 345                 350

Gln Tyr Gln Asp Lys Arg Met Val Ala Gln Arg Asn Gly Lys Leu Ser
        355                 360                 365

Val Gln Val Phe Gln Val Tyr Ala Gly Lys Glu Lys Glu Ala Val Ser
    370                 375                 380

Asp Ile Leu Pro Tyr Leu Arg Leu Gly Tyr Val Ser Asp Pro Ser Glu
385                 390                 395                 400

Met Gln Ser Val Ile Ser Ser Gln Gly Pro Val Cys Pro Val Ser Pro
                405                 410                 415

Cys Met Glu Gln Ala Val Leu Asp Gln Leu Thr Val Tyr Phe Arg Thr
            420                 425                 430

Arg Leu Ala Gly Tyr Cys Thr Ser Ile Ser Glu Asp Glu Leu Met Leu
        435                 440                 445

Ala Asp Pro Asn Leu Asn Pro Lys Lys Arg Val Ala Thr Gln Leu Val
    450                 455                 460

Arg Leu Glu Lys Lys Met Leu Lys Ala Cys Leu Gln Ala Thr Val Asp
465                 470                 475                 480

Leu Ile Asn Gln Leu Pro Asp His Thr Met Pro Pro Cys Pro Ala Pro
                485                 490                 495

Tyr Ala Pro Leu Leu Lys
            500
```

<210> SEQ ID NO 30
<211> LENGTH: 624
<212> TYPE: DNA
<213> ORGANISM: Populus balsamifera subsp. trichocarpa
<220> FEATURE:
<221> NAME/KEY: misc_feature
<222> LOCATION: (1)..(624)
<223> OTHER INFORMATION: Ceres ANNOT ID no.1538900
<220> FEATURE:
<221> NAME/KEY: misc_feature
<222> LOCATION: (1)..(624)
<223> OTHER INFORMATION: Encodes the peptide sequence at SEQ ID NO:31

<400> SEQUENCE: 30

```
atgtggaacc ctaagcaaac tcaagaagag gatgattcat gggaggttag agccttcgca    60
gaggataccg gcaacatcaa cggcaccact tggccaccga ggtcttatac ttgcaccttt   120
tgtagaaggg aattccgctc agctcaagcc ctaggggggtc acatgaatgt tcaccgccgt   180
gaccgtgcta ggcttcacca aacacagcct ggttcaatca ccccaactc atcaacttcc    240 agttcttcct cgtctacttt tataatccca actcaagaat ttcccccaaa tgctgggtta   300
tgcttacttt accaactacc aaaccctaat ggagtcttca ctcccgcaac tatgaatgca   360
tgtgctactg attcaccttc tactcttctc tctatcacac catatcccca taacaacttg   420
atagagaaat ctcttaattt tctagtagct ccacctgaga taaatacttc tcattgttac   480
tcaatcaaag ccgagccctc ggcatccatt gataatagca ataatatcaa cagcgacaac   540
aactttaagg agttggcaca cgaagaactt gatctagagc tccggctagg gcacagatcg   600
```
acaacaccac caccatcatc ataa 624

<210> SEQ ID NO 31
<211> LENGTH: 207
<212> TYPE: PRT
<213> ORGANISM: Populus balsamifera subsp. trichocarpa
<220> FEATURE:
<221> NAME/KEY: misc_feature
<222> LOCATION: (1)..(207)
<223> OTHER INFORMATION: Ceres ANNOT ID no. 1538900

<400> SEQUENCE: 31

Met Trp Asn Pro Lys Gln Thr Gln Glu Glu Asp Asp Ser Trp Glu Val
1               5                   10                  15

Arg Ala Phe Ala Glu Asp Thr Gly Asn Ile Asn Gly Thr Thr Trp Pro
            20                  25                  30

Pro Arg Ser Tyr Thr Cys Thr Phe Cys Arg Arg Glu Phe Arg Ser Ala
        35                  40                  45

Gln Ala Leu Gly Gly His Met Asn Val His Arg Asp Arg Ala Arg
    50                  55                  60

Leu His Gln Thr Gln Pro Gly Ser Ile Asn Pro Asn Ser Ser Thr Ser
65                  70                  75                  80

Ser Ser Ser Ser Ser Thr Phe Ile Ile Pro Thr Gln Glu Phe Pro Pro
                85                  90                  95

Asn Ala Gly Leu Cys Leu Leu Tyr Gln Leu Pro Asn Pro Asn Gly Val
            100                 105                 110

Phe Thr Pro Ala Thr Met Asn Ala Cys Ala Thr Asp Ser Pro Ser Thr
        115                 120                 125

Leu Leu Ser Ile Thr Pro Tyr Pro His Asn Asn Leu Ile Glu Lys Ser
    130                 135                 140

Leu Asn Phe Leu Val Ala Pro Pro Glu Ile Asn Thr Ser His Cys Tyr
145                 150                 155                 160

Ser Ile Lys Ala Glu Pro Ser Ala Ser Ile Asp Asn Ser Asn Asn Ile
                165                 170                 175

Asn Ser Asp Asn Asn Phe Lys Glu Leu Ala His Glu Glu Leu Asp Leu
            180                 185                 190

Glu Leu Arg Leu Gly His Arg Ser Thr Thr Pro Pro Pro Ser Ser
        195                 200                 205

<210> SEQ ID NO 32
<211> LENGTH: 936
<212> TYPE: DNA
<213> ORGANISM: Glycine max
<220> FEATURE:
<221> NAME/KEY: misc_feature
<222> LOCATION: (1)..(936)
<223> OTHER INFORMATION: Ceres CLONE ID no.1042157
<220> FEATURE:
<221> NAME/KEY: misc_feature
<222> LOCATION: (1)..(936)
<223> OTHER INFORMATION: Encodes the peptide sequence at SEQ ID NO:33

<400> SEQUENCE: 32
attatcttct tcttctctac ctttcgatcc tttcactttg gcgtgaccga accattccac      60
tccctcgcaa acggtgtcg tgccgatcgc gttcgttcgg ttaaactcgc gcgttcagaa     120
tcctccggaa caacgctctt cgcccaattc cctataattc actcctctct ctctctcgct     180
ttctctggta acctcctcgc gacggtggct cttccgcatt ccgccgccgc cactgccatc     240
gccgttgccg ccgccggaaa acactaatca atagatggat gattctgcgt tcaaacgagg     300
cggtcacttt aatcgaactt actcgtgctc ttctcagaga gatgtctgtt acagctgtgg     360

-continued

```
cacttgtggt tatgagctga acctatcctc ctcaaaccgg gacactgcat ccattggatc    420
taaatacggg aagtccataa agcgaggtat tatatcattc ttcagcattg atcttagcag    480
atttactcag gttgatgaaa ttcagtgtgt gccccatttt gataagcact catggggttt    540
gtttcsccga agaaccaagc ttytttgtyg caagtgtggc amccatattg gaaatgcata    600
caatggttac acttcgtcct ttcctcttgt gtcagacgga gcagaatcat ytcctagttc    660
caaagtggtc agtcatacaa aatatgacat tygcatttgt gccttacaac cttcatyttt    720
tgaagaatyt ggaatccccg tgtttgcttg aactacctgg taaaaatagt aattcctacm    780
cagccaaatc cggtgacagg gtggttagaa gttcattaat atatgcagat ggtttggctt    840
gttttttgtg cttttcctaa tgaaaatgtg amtaatagtc gtgtgaaaga gttgtaagaa    900
ttaaattaaa aattattrca ggtgtgggat tttatg                              936
```

<210> SEQ ID NO 33
<211> LENGTH: 158
<212> TYPE: PRT
<213> ORGANISM: Glycine max
<220> FEATURE:
<221> NAME/KEY: misc_feature
<222> LOCATION: (1)..(158)
<223> OTHER INFORMATION: Ceres CLONE ID no. 1042157
<220> FEATURE:
<221> NAME/KEY: misc_feature
<222> LOCATION: (43)..(43)
<223> OTHER INFORMATION: Xaa is any aa or unknown
<220> FEATURE:
<221> NAME/KEY: misc_feature
<222> LOCATION: (91)..(91)
<223> OTHER INFORMATION: Xaa is any aa or unknown
<220> FEATURE:
<221> NAME/KEY: misc_feature
<222> LOCATION: (97)..(97)
<223> OTHER INFORMATION: Xaa is any aa or unknown
<220> FEATURE:
<221> NAME/KEY: misc_feature
<222> LOCATION: (99)..(99)
<223> OTHER INFORMATION: Xaa is any aa or unknown
<220> FEATURE:
<221> NAME/KEY: misc_feature
<222> LOCATION: (103)..(103)
<223> OTHER INFORMATION: Xaa is any aa or unknown
<220> FEATURE:
<221> NAME/KEY: misc_feature
<222> LOCATION: (126)..(126)
<223> OTHER INFORMATION: Xaa is any aa or unknown
<220> FEATURE:
<221> NAME/KEY: misc_feature
<222> LOCATION: (140)..(140)
<223> OTHER INFORMATION: Xaa is any aa or unknown
<220> FEATURE:
<221> NAME/KEY: misc_feature
<222> LOCATION: (148)..(148)
<223> OTHER INFORMATION: Xaa is any aa or unknown
<220> FEATURE:
<221> NAME/KEY: misc_feature
<222> LOCATION: (152)..(152)
<223> OTHER INFORMATION: Xaa is any aa or unknown

<400> SEQUENCE: 33

```
Met Asp Asp Ser Ala Phe Lys Arg Gly Gly His Phe Asn Arg Thr Tyr
 1               5                  10                  15

Ser Cys Ser Ser Gln Arg Asp Val Cys Tyr Ser Cys Gly Thr Cys Gly
            20                  25                  30

Tyr Glu Leu Asn Leu Ser Ser Ser Asn Arg Xaa Thr Ala Ser Ile Gly
        35                  40                  45

Ser Lys Tyr Gly Lys Ser Ile Lys Arg Gly Ile Ile Ser Phe Phe Ser
    50                  55                  60
```

```
Ile Asp Leu Ser Arg Phe Thr Gln Val Asp Glu Ile Gln Cys Val Pro
 65                  70                  75                  80

His Phe Asp Lys His Ser Trp Gly Leu Phe Xaa Arg Arg Thr Lys Leu
                 85                  90                  95

Xaa Cys Xaa Lys Cys Gly Xaa His Ile Gly Asn Ala Tyr Asn Gly Tyr
            100                 105                 110

Thr Ser Ser Phe Pro Leu Val Ser Asp Gly Ala Glu Ser Xaa Pro Ser
        115                 120                 125

Ser Lys Val Val Ser His Thr Lys Tyr Asp Ile Xaa Ile Cys Ala Leu
    130                 135                 140

Gln Pro Ser Xaa Phe Glu Glu Xaa Gly Ile Pro Val Phe Ala
145             150                 155
```

```
<210> SEQ ID NO 34
<211> LENGTH: 434
<212> TYPE: DNA
<213> ORGANISM: Brassica napus
<220> FEATURE:
<221> NAME/KEY: misc_feature
<222> LOCATION: (1)..(434)
<223> OTHER INFORMATION: Ceres CLONE ID no.1090611
<220> FEATURE:
<221> NAME/KEY: misc_feature
<222> LOCATION: (1)..(434)
<223> OTHER INFORMATION: Encodes the peptide sequence at SEQ ID NO:35

<400> SEQUENCE: 34 agatttgat  cgtagctaca  ttactctttc  ccatggctgc  ccctgatgag  gaccaacggt     60
ttattaagcc  tttcatctca  cataagtcag  ctaaatcatt  ggcgattccg  ctggccttca   120
acgaatactt  yccggatcca  ttgccaaata  cagtggagct  cctagactac  tatgggagat   180
cctggacgat  taggatgaag  aagagaggag  agacggtgtt  tttaactgtt  ggttgggaaa   240
actttgtaaa  ggataacgag  cttgaagacg  gtaagatgat  ggaattcatc  tatgactgcg   300
accggacctt  ttatgttgtc  atattcggtc  atggcggggt  tagcgagctt  agagtctttc   360
ctcaagccgt  agtagatgtt  ggtgactatg  cvacaggcga  agaagaagga  gaggaagagg   420
aagaggaaga  gaag                                                        434

<210> SEQ ID NO 35
<211> LENGTH: 134
<212> TYPE: PRT
<213> ORGANISM: Brassica napus
<220> FEATURE:
<221> NAME/KEY: misc_feature
<222> LOCATION: (1)..(134)
<223> OTHER INFORMATION: Ceres CLONE ID no. 1090611
<220> FEATURE:
<221> NAME/KEY: misc_feature
<222> LOCATION: (9)..(103)
<223> OTHER INFORMATION: Pfam Name: B3
      Pfam Description: B3 DNA binding domain
<220> FEATURE:
<221> NAME/KEY: misc_feature
<222> LOCATION: (33)..(33)
<223> OTHER INFORMATION: Xaa is any aa or unknown
<220> FEATURE:
<221> NAME/KEY: misc_feature
<222> LOCATION: (120)..(120)
<223> OTHER INFORMATION: Xaa is any aa or unknown

<400> SEQUENCE: 35

Met Ala Ala Pro Asp Glu Asp Gln Arg Phe Ile Lys Pro Phe Ile Ser
1               5                   10                  15

His Lys Ser Ala Lys Ser Leu Ala Ile Pro Leu Ala Phe Asn Glu Tyr
```

```
                    20                  25                  30
Xaa Pro Asp Pro Leu Pro Asn Thr Val Glu Leu Leu Asp Tyr Tyr Gly
         35                   40                  45

Arg Ser Trp Thr Ile Arg Met Lys Lys Arg Gly Glu Thr Val Phe Leu
 50                  55                  60

Thr Val Gly Trp Glu Asn Phe Val Lys Asp Asn Glu Leu Glu Asp Gly
 65                  70                  75                  80

Lys Met Met Glu Phe Ile Tyr Asp Cys Asp Arg Thr Phe Tyr Val Val
                 85                  90                  95

Ile Phe Gly His Gly Val Ser Glu Leu Arg Val Phe Pro Gln Ala
                100                 105                 110

Val Val Asp Val Gly Asp Tyr Xaa Thr Gly Glu Glu Glu Gly Glu Glu
        115                 120                 125

Glu Glu Glu Glu Glu Lys
    130

<210> SEQ ID NO 36
<211> LENGTH: 949
<212> TYPE: DNA
<213> ORGANISM: Brassica napus
<220> FEATURE:
<221> NAME/KEY: misc_feature
<222> LOCATION: (1)..(949)
<223> OTHER INFORMATION: Ceres CLONE ID no.1110032
<220> FEATURE:
<221> NAME/KEY: misc_feature
<222> LOCATION: (1)..(949)
<223> OTHER INFORMATION: Encodes the peptide sequence at SEQ ID NO:37

<400> SEQUENCE: 36
atccctcact aatttcaata ctgccactga taaaataaaa aagtttcacc gaacaaaaca      60
aagaaagaac cgaaagagta tggcggagga gttgttggct aacgaagaga ggctaactcg     120
gactgactca gctgagaaaa agcgagtcag gacgagtct gacgacacgg ttattgactc     180
ccccgaggtg aagaggctca gagacgattt attcgatgtt ctcgatgact cggatcctga     240
accggtgagt caagatctcg actcggtcat gaagagtttc gaggacgagc tatcttccac     300
ggttaccacg gcgcaaggat ccggcgaaac ccagccggat ctcggctacc ttctcgaggc     360
ttccgatgac gagcttggtc tgccgccggt ttctccggtt ccgtcgcga aggaggtgga     420
aacgacggag acgttaacgg atctggtgcg agcgtcgtcg gattcgtcag gagtcgacga     480
gctatggggg ttcgaggatc atttgtcgaa ttacggctcg ttagatttcg gttccggcgt     540
cggagatggt ggagattacc tcgccgtaga ggggctcttt gaattttccg attatggttt     600
cgatgccggc gagctatttt cgtggcggtc ggagtcttta ccggcggaat aaaaactttt     660
cggagttttt tatctgacgt gaaaaatgat aaaacgatgc cgttttgtaa agcgtgtggc     720
tgctatgtcg ttttttttac ccctatcat tttatggtag attgttaatt ttctattgat     780
taattattag gattaggaaa gtatgttttt ttattaggaa agttaaatac tttgttagtg     840
ggggtaattt tctagattaa tataatcgaa ttcgtttgtt tgttcttccc agatctttaa     900
tagttttgt tgatgtggaa aattatatta atatgaaata caccctgcc                  949

<210> SEQ ID NO 37
<211> LENGTH: 190
<212> TYPE: PRT
<213> ORGANISM: Brassica napus
<220> FEATURE:
<221> NAME/KEY: misc_feature
<222> LOCATION: (1)..(190)
<223> OTHER INFORMATION: Ceres CLONE ID no. 1110032
```

<400> SEQUENCE: 37

```
Met Ala Glu Glu Leu Ala Asn Glu Glu Arg Leu Thr Arg Thr Asp
1               5                   10                  15

Ser Ala Glu Lys Lys Arg Val Arg Asp Glu Ser Asp Asp Thr Val Ile
            20                  25                  30

Asp Ser Pro Glu Val Lys Arg Leu Arg Asp Asp Leu Phe Asp Val Leu
        35                  40                  45

Asp Asp Ser Asp Pro Glu Pro Val Ser Gln Asp Leu Asp Ser Val Met
    50                  55                  60

Lys Ser Phe Glu Asp Glu Leu Ser Ser Thr Val Thr Thr Ala Gln Gly
65                  70                  75                  80

Ser Gly Glu Thr Gln Pro Asp Leu Gly Tyr Leu Leu Glu Ala Ser Asp
                85                  90                  95

Asp Glu Leu Gly Leu Pro Pro Val Ser Pro Val Pro Val Ala Lys Glu
            100                 105                 110

Val Glu Thr Thr Glu Thr Leu Thr Asp Leu Val Arg Ala Ser Ser Asp
        115                 120                 125

Ser Ser Gly Val Asp Glu Leu Trp Gly Phe Glu Asp His Leu Ser Asn
    130                 135                 140

Tyr Gly Ser Leu Asp Phe Gly Ser Gly Val Gly Asp Gly Gly Asp Tyr
145                 150                 155                 160

Leu Ala Val Glu Gly Leu Phe Glu Phe Ser Asp Tyr Gly Phe Asp Ala
                165                 170                 175

Gly Glu Leu Phe Ser Trp Arg Ser Glu Ser Leu Pro Ala Glu
            180                 185                 190

<210> SEQ ID NO 38
<211> LENGTH: 814
<212> TYPE: DNA
<213> ORGANISM: Brassica napus
<220> FEATURE:
<221> NAME/KEY: misc_feature
<222> LOCATION: (1)..(814)
<223> OTHER INFORMATION: Ceres CLONE ID no.1118987
<220> FEATURE:
<221> NAME/KEY: misc_feature
<222> LOCATION: (1)..(814)
<223> OTHER INFORMATION: Encodes the peptide sequence at SEQ ID NO:39

<400> SEQUENCE: 38
aaattctcga ttcgcttata ttctcaaaac caacgctaaa taaaaacact ctcaaagaaa    60
aacaaaaaaa aaaccctagt tttgatggaa tcgactgatt cggggtcaca caacatgga   120 ggtgacccag gtccgtcctc cgtaacgccc tcttcacctc cggcgacgcc gcctagcagg   180
tacgagtcgc aaaaacgacg tgactggaac acgttcttgc agtacctcaa gaaccacaag   240
ccgcctctcg cgttatcacg atgtagcgga gcgcacgtga tcgagttcct caagtaccta   300
gatcagttcg gtaagaccaa agtccacgtg gcgacctgcc cttacttcgg acatcagcag   360
cctccctctc cttgcgcttg tcctctcaag caagcctggg gatctctcga tgctctgatc   420
ggacggttga gagctgcgta cgaggagcac ggtgggaggc ctgattccaa ccctttcgcc   480
gcacgtgcgg tcaggattta cttgagagaa tcagagaaa gtcaagccaa ggcacgtggg   540
attccatacg agaagaagaa acggaaacgg gcaccaactg tcactaccgc tagaattgac   600
gttgctccgt cgagacaaag tgaaggaggt ggtggttgta cgacagtga tccgtctgtc   660 gccgaagctg taccgcctta aattaaatta ttatatcata ttaattagtt ttcttgttat   720
attaagcatg gaactcacac ctttcgtact ataatgtatt ttatttttct atatgaacta   780
```
ttaagagttt tcttttgcca aaaaaaaaaa aaaa                                814

<210> SEQ ID NO 39
<211> LENGTH: 198
<212> TYPE: PRT
<213> ORGANISM: Brassica napus
<220> FEATURE:
<221> NAME/KEY: misc_feature
<222> LOCATION: (1)..(198)
<223> OTHER INFORMATION: Ceres CLONE ID no. 1118987
<220> FEATURE:
<221> NAME/KEY: misc_feature
<222> LOCATION: (13)..(146)
<223> OTHER INFORMATION: Pfam Name: DUF640
    Pfam Description: Protein of unknown function (DUF640)

<400> SEQUENCE: 39

Met Glu Ser Thr Asp Ser Gly Ser Gln Gln His Gly Gly Asp Pro Gly
1               5                   10                  15

Pro Ser Ser Val Thr Pro Ser Ser Pro Pro Ala Thr Pro Pro Ser Arg
            20                  25                  30

Tyr Glu Ser Gln Lys Arg Arg Asp Trp Asn Thr Phe Leu Gln Tyr Leu
        35                  40                  45

Lys Asn His Lys Pro Pro Leu Ala Leu Ser Arg Cys Ser Gly Ala His
    50                  55                  60

Val Ile Glu Phe Leu Lys Tyr Leu Asp Gln Phe Gly Lys Thr Lys Val
65                  70                  75                  80

His Val Ala Thr Cys Pro Tyr Phe Gly His Gln Gln Pro Pro Ser Pro
                85                  90                  95

Cys Ala Cys Pro Leu Lys Gln Ala Trp Gly Ser Leu Asp Ala Leu Ile
            100                 105                 110

Gly Arg Leu Arg Ala Ala Tyr Glu Glu His Gly Gly Arg Pro Asp Ser
        115                 120                 125

Asn Pro Phe Ala Ala Arg Ala Val Arg Ile Tyr Leu Arg Glu Val Arg
    130                 135                 140

Glu Ser Gln Ala Lys Ala Arg Gly Ile Pro Tyr Glu Lys Lys Lys Arg
145                 150                 155                 160

Lys Arg Ala Pro Thr Val Thr Thr Ala Arg Ile Asp Val Ala Pro Ser
                165                 170                 175

Arg Gln Ser Glu Gly Gly Gly Gly Cys Asn Asp Ser Asp Pro Ser Val
            180                 185                 190

Ala Glu Ala Val Pro Pro
        195

<210> SEQ ID NO 40
<211> LENGTH: 623
<212> TYPE: DNA
<213> ORGANISM: Glycine max
<220> FEATURE:
<221> NAME/KEY: misc_feature
<222> LOCATION: (1)..(623)
<223> OTHER INFORMATION: Ceres CLONE ID no.1238706
<220> FEATURE:
<221> NAME/KEY: misc_feature
<222> LOCATION: (1)..(623)
<223> OTHER INFORMATION: Encodes the peptide sequence at SEQ ID NO:41

<400> SEQUENCE: 40
atcacaaccc tttgaagtgt tgtcattact cattacacaa agaggcaatg gaggagtcaa     60
agaaatacga gaggatggtg aagcagacaa tggacaagaa caagaagaag ataacaaaa    120 ggggtcatgg ctctgggtca ggatccgggt tgcttggggt gaaggtgagg aagctccaaa   180

```
tactgatacc gggtggaaag agatgcaacc acccggatct gcttttatct aaaaccgtgg      240
attatattgt ccacttgaag ttgaagatta ggttccttaa agcactctca gatatgtact      300
ctctctgaaa atcctagcac tattcttctg cttcttcctc tcttcgttgt catataagct      360
atggtaagga ttttatttct atgtatatca attgtcattt ggagtttgct ttatgtcgta      420
ttttcatttg ttaaattggt tatctatatt catgtttatc cgacaatgtg taagaaattg      480
agtagtttga aattctaaaa tatgcttttt gaacttcttg gttttcccat tgcaaggcct      540
tcgtatactg atggctaata tttgatgtta taaattcata ttatcttata tttgaagagt      600
taagtttaaa aaaaaaaaaa aaa                                              623
```

<210> SEQ ID NO 41
<211> LENGTH: 86
<212> TYPE: PRT
<213> ORGANISM: Glycine max
<220> FEATURE:
<221> NAME/KEY: misc_feature
<222> LOCATION: (1)..(86)
<223> OTHER INFORMATION: Ceres CLONE ID no. 1238706

<400> SEQUENCE: 41

```
Met Glu Glu Ser Lys Lys Tyr Glu Arg Met Val Lys Gln Thr Met Asp
1               5                   10                  15

Lys Asn Lys Lys Lys Asn Asn Lys Arg Gly His Gly Ser Gly Ser Gly
            20                  25                  30

Ser Gly Leu Leu Gly Val Lys Val Arg Lys Leu Gln Ile Leu Ile Pro
        35                  40                  45

Gly Gly Lys Arg Cys Asn His Pro Asp Leu Leu Leu Ser Lys Thr Val
    50                  55                  60

Asp Tyr Ile Val His Leu Lys Leu Lys Ile Arg Phe Leu Lys Ala Leu
65                  70                  75                  80

Ser Asp Met Tyr Ser Leu
                85
```

<210> SEQ ID NO 42
<211> LENGTH: 1145
<212> TYPE: DNA
<213> ORGANISM: Triticum aestivum
<220> FEATURE:
<221> NAME/KEY: misc_feature
<222> LOCATION: (1)..(1145)
<223> OTHER INFORMATION: Ceres CLONE ID no.1324341
<220> FEATURE:
<221> NAME/KEY: misc_feature
<222> LOCATION: (1)..(1145)
<223> OTHER INFORMATION: Encodes the peptide sequence at SEQ ID NO:43

<400> SEQUENCE: 42

```
atcattcact catcaaacgc aacgcacaga gacagaggga gagggtccgt tgtacttgca      60
tccttccctg cccccctgccc ctcccctccc aagtccagaa atccgttcca ctctccccct     120
ccctctcgtc tgtgcacccg agacgctcct ctagatcagt tcctcggtgc ggttacctct     180
cgccggaagc cacgccacca tggtgtcgcc ggacgctatc cgcaccgtca tcggcgtcat     240
aggcaatgga accgccttgg tgctcttcct atcccagtg ccgacgttca tccaaatctg      300
gaagaagaag acggtggagc agtactcggg ggtgccgtac ctggcgacgc tgctgaattg     360
catgatgtgg gtgctctacg ggctcccgct ggtgcacccg cacagcatgc tcgtcatcac     420
catcaacggc accggcatgc tcatcgagct cacctacgtc gcgctcttcc tcaccttctc     480
cgtcggcgcc gcccgccgcc gagtcctcct cctgctggtc gccgaggtcg ccttcgtcgg     540
```

```
cggggttgcc gcgctcgtcc tctccctcgc ccacacccac gaccgcaggt ccatggtcgt      600
cggcatcctc tgcgtcctct tcggcaccgg catgtacgcc gcgccgctct ccgtcatgaa      660
aatggtgatc cagaccaaga gcgtggagta catgccgctg ttcctgtccg tggcctcgct      720
cgtcaatggc atctgctgga ctgcctacgc cctcatcaag ttcgacctct acatcaccat      780
ccccaacggg ctgggcgtga tgttcgctgt ggggcagata atcctgtacg ccatctacta      840
caagtcgacg cagcagatcc tggaggcccg caagcgcaag gccgaccagg tgcccatgac      900
cgaggtcgtc gtcgacggca agagcggcag cgccaccaac tcgggcgccg ccaacggcca      960
ctactagaag caataccact attaactccc ccgattgaag cgccttcata aatcgtcacc     1020
ttagctaatt ctcccatgaa tcatgtacgt acgctgtgcg cccagggctc ctcctgtgca     1080
ctgtcgcgtc ttcttgtgcg ctctactacc cttgaaagac ctgttttaca aaaaaaaaa     1140 aaaaa                                                                 1145
```

<210> SEQ ID NO 43
<211> LENGTH: 255
<212> TYPE: PRT
<213> ORGANISM: Triticum aestivum
<220> FEATURE:
<221> NAME/KEY: misc_feature
<222> LOCATION: (1)..(255)
<223> OTHER INFORMATION: Ceres CLONE ID no. 1324341
<220> FEATURE:
<221> NAME/KEY: misc_feature
<222> LOCATION: (9)..(98)
<223> OTHER INFORMATION: Pfam Name: MtN3_slv
      Pfam Description: MtN3/saliva family

<400> SEQUENCE: 43

```
Met Val Ser Pro Asp Ala Ile Arg Thr Val Ile Gly Val Ile Gly Asn
  1               5                  10                  15

Gly Thr Ala Leu Val Leu Phe Leu Ser Pro Val Pro Thr Phe Ile Gln
             20                  25                  30

Ile Trp Lys Lys Lys Thr Val Glu Gln Tyr Ser Ala Val Pro Tyr Leu
         35                  40                  45

Ala Thr Leu Leu Asn Cys Met Met Trp Val Leu Tyr Gly Leu Pro Leu
     50                  55                  60

Val His Pro His Ser Met Leu Val Ile Thr Ile Asn Gly Thr Gly Met
 65                  70                  75                  80

Leu Ile Glu Leu Thr Tyr Val Ala Leu Phe Leu Thr Phe Ser Val Gly
                 85                  90                  95

Ala Ala Arg Arg Arg Val Leu Leu Leu Val Ala Glu Val Ala Phe
            100                 105                 110

Val Gly Gly Val Ala Ala Leu Val Leu Ser Leu Ala His Thr His Asp
        115                 120                 125

Arg Arg Ser Met Val Val Gly Ile Leu Cys Val Leu Phe Gly Thr Gly
    130                 135                 140

Met Tyr Ala Ala Pro Leu Ser Val Met Lys Met Val Ile Gln Thr Lys
145                 150                 155                 160

Ser Val Glu Tyr Met Pro Leu Phe Leu Ser Val Ala Ser Leu Val Asn
                165                 170                 175

Gly Ile Cys Trp Thr Ala Tyr Ala Leu Ile Lys Phe Asp Leu Tyr Ile
            180                 185                 190

Thr Ile Pro Asn Gly Leu Gly Val Met Phe Ala Val Gly Gln Ile Ile
        195                 200                 205

Leu Tyr Ala Ile Tyr Tyr Lys Ser Thr Gln Gln Ile Leu Glu Ala Arg
```

```
                210                 215                 220
Lys Arg Lys Ala Asp Gln Val Pro Met Thr Glu Val Val Asp Gly
225                 230                 235                 240

Lys Ser Gly Ser Ala Thr Asn Ser Gly Ala Ala Asn Gly His Tyr
                245                 250                 255

<210> SEQ ID NO 44
<211> LENGTH: 981
<212> TYPE: DNA
<213> ORGANISM: Zea mays
<220> FEATURE:
<221> NAME/KEY: misc_feature
<222> LOCATION: (1)..(981)
<223> OTHER INFORMATION: Ceres CLONE ID no.1376391
<220> FEATURE:
<221> NAME/KEY: misc_feature
<222> LOCATION: (1)..(981)
<223> OTHER INFORMATION: Encodes the peptide sequence at SEQ ID NO:45

<400> SEQUENCE: 44
atcttccttt gttatcgtag ccacaaccct ctctcaacta catctcttaa catgaacaac      60
caaatcatcg ccgacgattt tccggtgaca ctgggagacc ggcagttaca atacatgcag     120
tctcgcgcca tagatctgat tcaaaccgca ccaagcttca ataaatatca tttcaaccaa     180
tctcccgtga tgttaaaacg acagagagat tatgcgtttg actccgaagc tctaatgaca     240
gctcggaaac gtaggtccgt tgcgtttgtc ccgccgcagt ctctaattga ggcacaactc     300
gtttctcaaa tccagcagca acaaacagat atcgatctgt tcgtcgctca gcaaacgcaa     360
acgctcagat tggagttaga agcgaggcag agaacgcaaa cgttgtcctt agtgtcagcg     420
gttcagtccg tgattgtcaa aaagcttaaa cagagagacg acgagattgt ccgaatgggt     480
aaactaaact atgtcttgca agagcgagtg aagagtctct acgtcgagaa tcagatcttg     540
cgtgacctcg ctcataccaa tgaagctaca gctaaaactc tccggtcaaa tcttgaacat     600
gttctcgctc aggtcgacga gttaccggcg accgcagcaa ccggcggaga tgttttcat     660 cctccggtag aagaggatgc tgtatcgagc tgcggaagct gcgacggtgc tgatggtaat     720
gatttcacgg cggggacagg aggatgtaaa cggtgcggtg aaaggacggc tagtgtgttg     780
gtgctgcctt gccgtcactt gtgtttgtgt acagtttgtg gatcggctct gttacaggcg     840
tgccctgtat gcgatacggt catgaatgct agtgttcatg ttaacatgtg atgagactca     900
tgacccattt ttaattttt agttttcttt ttagtgaagg atttaatagc atagtaaaag     960
taatactatt ataattttg g                                                981

<210> SEQ ID NO 45
<211> LENGTH: 279
<212> TYPE: PRT
<213> ORGANISM: Zea mays
<220> FEATURE:
<221> NAME/KEY: misc_feature
<222> LOCATION: (1)..(279)
<223> OTHER INFORMATION: Ceres CLONE ID no. 1376391

<400> SEQUENCE: 45

Met Asn Asn Gln Ile Ile Ala Asp Asp Phe Pro Val Thr Leu Gly Asp
1               5                   10                  15

Arg Gln Leu Gln Tyr Met Gln Ser Arg Ala Ile Asp Leu Ile Gln Thr
                20                  25                  30

Ala Pro Ser Phe Asn Lys Tyr His Phe Asn Gln Ser Pro Val Met Leu
            35                  40                  45

Lys Arg Gln Arg Asp Tyr Ala Phe Asp Ser Glu Ala Leu Met Thr Ala
```

```
                50                      55                      60
Arg Lys Arg Arg Ser Val Ala Phe Val Pro Pro Gln Ser Leu Ile Glu
 65                      70                      75                      80

Ala Gln Leu Val Ser Gln Ile Gln Gln Gln Gln Thr Asp Ile Asp Leu
                         85                      90                      95

Phe Val Ala Gln Gln Thr Gln Thr Leu Arg Leu Glu Leu Glu Ala Arg
                    100                     105                     110

Gln Arg Thr Gln Thr Leu Ser Leu Val Ser Ala Val Gln Ser Val Ile
                115                     120                     125

Val Lys Lys Leu Lys Gln Arg Asp Asp Glu Ile Val Arg Met Gly Lys
            130                     135                     140

Leu Asn Tyr Val Leu Gln Glu Arg Val Lys Ser Leu Tyr Val Glu Asn
145                     150                     155                     160

Gln Ile Leu Arg Asp Leu Ala His Thr Asn Glu Ala Thr Ala Lys Thr
                    165                     170                     175

Leu Arg Ser Asn Leu Glu His Val Leu Ala Gln Val Asp Glu Leu Pro
                180                     185                     190

Ala Thr Ala Ala Thr Gly Gly Asp Val Phe His Pro Pro Val Glu Glu
            195                     200                     205

Asp Ala Val Ser Ser Cys Gly Ser Cys Asp Gly Ala Asp Gly Asn Asp
210                     215                     220

Phe Thr Ala Gly Thr Gly Gly Cys Lys Arg Cys Gly Glu Arg Thr Ala
225                     230                     235                     240

Ser Val Leu Val Leu Pro Cys Arg His Leu Cys Leu Cys Thr Val Cys
                    245                     250                     255

Gly Ser Ala Leu Leu Gln Ala Cys Pro Val Cys Asp Thr Val Met Asn
                260                     265                     270

Ala Ser Val His Val Asn Met
            275

<210> SEQ ID NO 46
<211> LENGTH: 874
<212> TYPE: DNA
<213> ORGANISM: Zea mays
<220> FEATURE:
<221> NAME/KEY: misc_feature
<222> LOCATION: (1)..(874)
<223> OTHER INFORMATION: Ceres CLONE ID no.1384304
<220> FEATURE:
<221> NAME/KEY: misc_feature
<222> LOCATION: (1)..(874)
<223> OTHER INFORMATION: Encodes the peptide sequence at SEQ ID NO:47

<400> SEQUENCE: 46
cttactgctt caattcgatc gttgctagaa agttgaaacc acgacatcgg aggcgtgaaa      60
aagttttaag tcacaccgaa tcaatcaagt gggagggaca cgttcttcaa cctattaatc     120
aaaccccact cttctcggtc acgaaagtct tggaagcttt gcctgatttc gagcgacgat     180
ggacagatcg gcgtcggtgg gtatcaagga cggcggattt ggtggcaacc acttgtattc     240
tccatcattt tcttcttcat cttccatgag acatgtcaat tacagttgtg gatcttgtgg     300
gtacgagctg aacttgagct ccaccaatcg aattacatca tcaattggat cgaagtatgg     360
gaaatccatg aagactggaa tcatatcctt cttcaacatt gacgagggga gattcagcca     420
ggttgatgag ttccaatgca tgcctcactt ctccagatac tcttggggtt tgttcagacg     480
caagactaag cttctctgtc gccaatgtaa taactacata ggcaatgctt cttatgacaa     540
ggcccctcct gagtacgcac tcgtaacaca aaactcatcg cccaggaagg gtgtcactga     600
```

```
cactgttacc aagtatgata tcagaattcg tgcgcttcaa ccttcttccg gtgttgcttc    660
tctgtgactg agtgtgtttc ttctacaact gtatattgta gaaaattctt caaagtatca    720
gtactgtttt cataaggtgg gttcggcttt ttctttcttt ctcaaattgt acagtaattt    780
aacaatttgc cttttttttt ttttttttgtt tctgagaata ttgaggttaa atatgaattt    840
cacttgctca tgttcatcaa aaaaaaaaaa aaaa                                874
```

```
<210> SEQ ID NO 47
<211> LENGTH: 162
<212> TYPE: PRT
<213> ORGANISM: Zea mays
<220> FEATURE:
<221> NAME/KEY: misc_feature
<222> LOCATION: (1)..(162)
<223> OTHER INFORMATION: Ceres CLONE ID no. 1384304

<400> SEQUENCE: 47
```

```
Met Asp Arg Ser Ala Ser Val Gly Ile Lys Asp Gly Gly Phe Gly Gly
 1               5                  10                  15

Asn His Leu Tyr Ser Pro Ser Phe Ser Ser Ser Ser Met Arg His
             20                  25                  30

Val Asn Tyr Ser Cys Gly Ser Cys Gly Tyr Glu Leu Asn Leu Ser Ser
         35                  40                  45

Thr Asn Arg Ile Thr Ser Ser Ile Gly Ser Lys Tyr Gly Lys Ser Met
     50                  55                  60

Lys Thr Gly Ile Ile Ser Phe Phe Asn Ile Asp Glu Gly Arg Phe Ser
 65                  70                  75                  80

Gln Val Asp Glu Phe Gln Cys Met Pro His Phe Ser Arg Tyr Ser Trp
                 85                  90                  95

Gly Leu Phe Arg Arg Lys Thr Lys Leu Leu Cys Arg Gln Cys Asn Asn
            100                 105                 110

Tyr Ile Gly Asn Ala Ser Tyr Asp Lys Ala Pro Pro Glu Tyr Ala Leu
        115                 120                 125

Val Thr Gln Asn Ser Ser Pro Arg Lys Gly Val Thr Asp Thr Val Thr
    130                 135                 140

Lys Tyr Asp Ile Arg Ile Arg Ala Leu Gln Pro Ser Ser Gly Val Ala
145                 150                 155                 160

Ser Leu
```

```
<210> SEQ ID NO 48
<211> LENGTH: 818
<212> TYPE: DNA
<213> ORGANISM: Zea mays
<220> FEATURE:
<221> NAME/KEY: misc_feature
<222> LOCATION: (1)..(818)
<223> OTHER INFORMATION: Ceres CLONE ID no.1464359
<220> FEATURE:
<221> NAME/KEY: misc_feature
<222> LOCATION: (1)..(818)
<223> OTHER INFORMATION: Encodes the peptide sequence at SEQ ID NO:49

<400> SEQUENCE: 48
```

```
agacacacga cccacacaca cacacacaga gattcacaag caaaatcaag aaccctaaaa    60
tctaaagaac gtcctgacat aatcacacga tcaaaaatgg agggagaaac cgcagtgaag   120
gcagcggcaa gttcctcatc atcaccaagc cgctatgagt cgcaaaagag acgagactgg   180
aacactttcc tacagtatct aaaaaaccac aagccaccctt taaccctgtc tcgttgcagt   240
ggcgcacacg tcatcgagtt ccttaagtac ctcgaccagt ttggtaagac caaagtccac   300
```

-continued

```
gtcgcggctt gtcccttctt cggagtaccg tacccaccgg ctcagtgcac ttgccctctc    360
aggcaggctt ggggaagcct cgactctctc atcggccgtc taagggctgc gttcgaggaa    420
atcggcggtg gtcttccaga gtcaaaccct ttagctgcca aagcgattag gatctatctt    480
aaagaagtac gtgaaactca ggctaaggct cgagggattc catacgacaa gaagaaacgg    540
aaacgacctc gtacagctaa ggaaactcag aagcccgatg atggagaagg tgccggtgga    600
agtggaagtg gtgattctgc tttggttatt tctgcaactg tggtatagtc caaatataag    660
atgctaaaac taaatataag aaaactttgg catagtaatt ctctccgtgt tctttacttt    720
ataaatttta tatgttgtgt agtcgtttat ttgagttgta gaatgcaatt ataaatggaa    780
aagacggatc atagattatt ataaaaaaaa aaaaaaaa                            818
```

<210> SEQ ID NO 49
<211> LENGTH: 183
<212> TYPE: PRT
<213> ORGANISM: Zea mays
<220> FEATURE:
<221> NAME/KEY: misc_feature
<222> LOCATION: (1)..(183)
<223> OTHER INFORMATION: Ceres CLONE ID no. 1464359
<220> FEATURE:
<221> NAME/KEY: misc_feature
<222> LOCATION: (1)..(134)
<223> OTHER INFORMATION: Pfam Name: DUF640
      Pfam Description: Protein of unknown function (DUF640)

<400> SEQUENCE: 49

Met Glu Gly Glu Thr Ala Val Lys Ala Ala Ala Ser Ser Ser Ser Ser
1               5                   10                  15

Pro Ser Arg Tyr Glu Ser Gln Lys Arg Arg Asp Trp Asn Thr Phe Leu
            20                  25                  30

Gln Tyr Leu Lys Asn His Lys Pro Pro Leu Thr Leu Ser Arg Cys Ser
        35                  40                  45

Gly Ala His Val Ile Glu Phe Leu Lys Tyr Leu Asp Gln Phe Gly Lys
    50                  55                  60

Thr Lys Val His Val Ala Ala Cys Pro Phe Phe Gly Val Pro Tyr Pro
65                  70                  75                  80

Pro Ala Gln Cys Thr Cys Pro Leu Arg Gln Ala Trp Gly Ser Leu Asp
                85                  90                  95

Ser Leu Ile Gly Arg Leu Arg Ala Ala Phe Glu Glu Ile Gly Gly Gly
            100                 105                 110

Leu Pro Glu Ser Asn Pro Leu Ala Ala Lys Ala Ile Arg Ile Tyr Leu
        115                 120                 125

Lys Glu Val Arg Glu Thr Gln Ala Lys Ala Arg Gly Ile Pro Tyr Asp
    130                 135                 140

Lys Lys Lys Arg Lys Arg Pro Arg Thr Ala Lys Glu Thr Gln Lys Pro
145                 150                 155                 160

Asp Asp Gly Glu Gly Ala Gly Gly Ser Gly Ser Gly Asp Ser Ala Leu
                165                 170                 175

Val Ile Ser Ala Thr Val Val
            180

<210> SEQ ID NO 50
<211> LENGTH: 1139
<212> TYPE: DNA
<213> ORGANISM: Musa acuminata
<220> FEATURE:
<221> NAME/KEY: misc_feature
<222> LOCATION: (1)..(1139)
<223> OTHER INFORMATION: Ceres CLONE ID no.1726939

```
<220> FEATURE:
<221> NAME/KEY: misc_feature
<222> LOCATION: (1)..(1139)
<223> OTHER INFORMATION: Encodes the peptide sequence at SEQ ID NO:51

<400> SEQUENCE: 50
ctgtttgctc ccgtgctgtt taacttcgtc tgtccatatg gggatttggc gttgctggtg      60
ctttccaggg catagggctg gtgaagccca tggaggagtt tgcttcttcc accataacca     120
ccacctcaag cagcacctgc accaccacca ggccacaagc gacggagagg aggccgaggc     180
cacaaaagga gcaggcactc aactgcccta ggtgcaactc taccaacacc aagttctgct     240
actacaacaa ctacagcctc acccaaccca ggtacttctg caagacgtgc aggaggtatt     300
ggaccgaggg tggatccctc aggaacgtcc cagttggtgg tggctcaaga aagagcaaga     360
gggcctccat ctcctcggcc gccaccacca actcttcctc catcacagca gctatagcta     420
ctgcctcagc tcccaagaag attcatgctg acctcatccc tccgtatatc tcgctctcca     480
ccacctccga agctctaaag ttccatgagg ggcaggacct caacctggcc ttccgccaac     540
agagcctccg tcagtacagt gactaccccg acatagaaag tagcactgcc aacaacagca     600
gcaatgcata tgctgctgct ggttctctct cggccacgga gttgctaaag agtgggatga     660
ccgcaagagg cctcgggcct ttcatgccaa tgctgatgcc aatgccggaa taccccactg     720
ggttcggact gcaagaattc aggccaccca ctcttaactt tcctcttcat ggaatcggtg     780
aaggaggtag tagtgctggg tacgggagct tgccaggggt tggggagaac actggtacca     840
agctgccgtt tcccctcgag gatctgaagc cggtagtccc ttcaaacaac gttgcgagcc     900
aatttgagca gaacaggggg caaggtggtg atcctcaagg gttctggaat ggtatcattg     960
gaggaggctc atggtagaac aaaaagatct caaggagaac agccttccaa gattactaga    1020
acacaagaat gcatcttctt ttccatttca attcttgatg gcattgccgg gtcactttgt    1080
ttgcagttac tcaggcctca cataagacag atgatacata agttgcgtct ctttagctt     1139

<210> SEQ ID NO 51
<211> LENGTH: 295
<212> TYPE: PRT
<213> ORGANISM: Musa acuminata
<220> FEATURE:
<221> NAME/KEY: misc_feature
<222> LOCATION: (1)..(295)
<223> OTHER INFORMATION: Ceres CLONE ID no. 1726939
<220> FEATURE:
<221> NAME/KEY: misc_feature
<222> LOCATION: (32)..(94)
<223> OTHER INFORMATION: Pfam Name: zf-Dof
      Pfam Description: Dof domain, zinc finger

<400> SEQUENCE: 51

Met Glu Glu Phe Ala Ser Ser Thr Ile Thr Thr Thr Ser Ser Ser Thr
 1               5                   10                  15

Cys Thr Thr Thr Arg Pro Gln Ala Thr Glu Arg Arg Pro Arg Pro Gln
                20                  25                  30

Lys Glu Gln Ala Leu Asn Cys Pro Arg Cys Asn Ser Thr Asn Thr Lys
            35                  40                  45

Phe Cys Tyr Tyr Asn Asn Tyr Ser Leu Thr Gln Pro Arg Tyr Phe Cys
        50                  55                  60

Lys Thr Cys Arg Arg Tyr Trp Thr Glu Gly Gly Ser Leu Arg Asn Val
65                  70                  75                  80

Pro Val Gly Gly Gly Ser Arg Lys Ser Lys Arg Ala Ser Ile Ser Ser
                85                  90                  95
```

```
Ala Ala Thr Thr Asn Ser Ser Ile Thr Ala Ala Ile Ala Thr Ala
            100                 105                 110

Ser Ala Pro Lys Lys Ile His Ala Asp Leu Ile Pro Tyr Ile Ser
        115                 120                 125

Leu Ser Thr Thr Ser Glu Ala Leu Lys Phe His Glu Gly Gln Asp Leu
130                 135                 140

Asn Leu Ala Phe Arg Gln Gln Ser Leu Arg Gln Tyr Ser Asp Tyr Pro
145                 150                 155                 160

Asp Ile Glu Ser Ser Thr Ala Asn Asn Ser Ser Asn Ala Tyr Ala Ala
                165                 170                 175

Ala Gly Ser Leu Ser Ala Thr Glu Leu Leu Lys Ser Gly Met Thr Ala
            180                 185                 190

Arg Gly Leu Gly Pro Phe Met Pro Met Leu Met Pro Met Pro Glu Tyr
        195                 200                 205

Pro Thr Gly Phe Gly Leu Gln Glu Phe Arg Pro Pro Thr Leu Asn Phe
210                 215                 220

Pro Leu His Gly Ile Gly Gly Gly Ser Ser Ala Gly Tyr Gly Ser
225                 230                 235                 240

Leu Pro Gly Val Gly Glu Asn Thr Gly Thr Lys Leu Pro Phe Pro Leu
                245                 250                 255

Glu Asp Leu Lys Pro Val Val Pro Ser Asn Asn Val Ala Ser Gln Phe
            260                 265                 270

Glu Gln Asn Arg Gly Gln Gly Gly Asp Pro Gln Gly Phe Trp Asn Gly
        275                 280                 285

Ile Ile Gly Gly Gly Ser Trp
290                 295

<210> SEQ ID NO 52
<211> LENGTH: 1642
<212> TYPE: DNA
<213> ORGANISM: Panicum virgatum
<220> FEATURE:
<221> NAME/KEY: misc_feature
<222> LOCATION: (1)..(1642)
<223> OTHER INFORMATION: Ceres CLONE ID no.1796643
<220> FEATURE:
<221> NAME/KEY: misc_feature
<222> LOCATION: (1)..(1642)
<223> OTHER INFORMATION: Encodes the peptide sequence at SEQ ID NO:53

<400> SEQUENCE: 52
attctctccc tccttccggc tcacaccccc ctgattcccc catcagcctc acctcccctc      60
cactacctcc gagcagcagc caagagagag ggagctccgc aagccgcggc acaagaggag     120
gcaaacccta gcacaaagac tcactttctc cggagcaagc caggccggat agcatagcat     180
ccgcatcgcc gccgcatcac ccaccaccat gatcttcccc cctgccttcc tggattcctc     240
gagctggaac gataaccagc agcagcagca gcagcagcaa gctcaccacc accagcaggt     300
tgccgccagc ggaggtggcg gcgagggcaa tcatgacctt ctccagccat caatcatggg     360
gggagcgctt cccgaaggtg gtgctgctgg cggcggcggc ggcggcagg tggggccggc     420 gaagccgata tccatggccg agcgcgcgcg gctggcgagg atcccggtgc cggagccggg     480
gctcaagtgc ccccgctgcg agtccaccaa caccaagttc tgctacttca acaactactc     540
gctgtcgcag ccgcgccact tctgccgcgc ctgccgccgc tactgacgc gcggcggcgc     600 gctccgcaac gtgcccgtcg gcggggggcta ccgccgccac gccaagcgcg ccaagcccaa     660
gcaggcggcg gccgccggga cgacgtcatc ggcaccgcc accgccgcgc tggctcccgc     720
cgggtccgcc acgtcgtcag ccgcctgcac caccacgacc aacgtgcccg cgctcccgg     780
```

```
cggccccgcc atgctcggcg gcaaccactt gtccatgctg ccaccgctgc tgcgcctcgc    840
cgacttcgac gccatgagcc tcggctcgag cttctccggg atggggaagc cgcccctcga    900
cgccgcggga ggctactcgg tgggtggcgg cagctgtccc ggactggagc agtggagggt    960
gcagcagatg caaagcttcc cgttcctgca tgcgatggac cagggcccgc tgtggccacc   1020
tctggccatg acaatggcgc ccgggatgtt ccagctaggt ctagacagtg gcgatggccg   1080
tggcgccggt ggagaagacg ggtcgggaga gctccacgtg atgcaagcca agagggaagg   1140
cggcggcggc tacccagcaa gaggcatcta tggcgatcac cacctcgccg ctgccggtta   1200
cgcttcctat tccaacaatg ctgctacagg taaccatctc ttgtaatggt cagggccatc   1260
tacaatgatc gttaagacgt tagttgttcc tacaactagc tagagacgga gtgtgtgatg   1320
gtattgtgat atagaaaagg ctagcatgca tttgcaatgt tttcttcttc aagaactggt   1380
gaagagggag aggggagag agagagacaa tggtgctcga tttggacatg gacgagccgt   1440
atgctggatc atgcatgcac aagtattatc tatagctgca cgttagctcg catgatcact   1500
agcttggttt tatgtatctt ctttctttct ttctttcttt cttttccct atgatgatcg   1560 ggtccattta ggtttcactg tcgagcattt ggggtgaagt aatgtgtact gctgttgatc   1620
agaaaaaaaa aaaaaaaaaa aa                                            1642

<210> SEQ ID NO 53
<211> LENGTH: 270
<212> TYPE: PRT
<213> ORGANISM: Panicum virgatum
<220> FEATURE:
<221> NAME/KEY: misc_feature
<222> LOCATION: (1)..(270)
<223> OTHER INFORMATION: Ceres CLONE ID no. 1796643
<220> FEATURE:
<221> NAME/KEY: misc_feature
<222> LOCATION: (12)..(74)
<223> OTHER INFORMATION: Pfam Name: zf-Dof
      Pfam Description: Dof domain, zinc finger

<400> SEQUENCE: 53

Met Ala Glu Arg Ala Arg Leu Ala Arg Ile Pro Val Pro Glu Pro Gly
1               5                   10                  15

Leu Lys Cys Pro Arg Cys Glu Ser Thr Asn Thr Lys Phe Cys Tyr Phe
            20                  25                  30

Asn Asn Tyr Ser Leu Ser Gln Pro Arg His Phe Cys Arg Ala Cys Arg
        35                  40                  45

Arg Tyr Trp Thr Arg Gly Gly Ala Leu Arg Asn Val Pro Val Gly Gly
    50                  55                  60

Gly Tyr Arg Arg His Ala Lys Arg Ala Lys Pro Lys Gln Ala Ala Ala
65                  70                  75                  80

Ala Gly Thr Thr Ser Ser Ala Thr Ala Thr Ala Ala Leu Ala Pro Ala
                85                  90                  95

Gly Ser Ala Thr Ser Ser Ala Ala Cys Thr Thr Thr Asn Val Pro
            100                 105                 110

Ala Leu Pro Gly Gly Pro Ala Met Leu Gly Gly Asn His Leu Ser Met
        115                 120                 125

Leu Pro Pro Leu Leu Arg Leu Ala Asp Phe Asp Ala Met Ser Leu Gly
    130                 135                 140

Ser Ser Phe Ser Gly Met Gly Lys Pro Pro Leu Asp Ala Ala Gly Gly
145                 150                 155                 160

Tyr Ser Val Gly Gly Gly Ser Cys Pro Gly Leu Glu Gln Trp Arg Val
                165                 170                 175
```

```
Gln Gln Met Gln Ser Phe Pro Phe Leu His Ala Met Asp Gln Gly Pro
            180                 185                 190
Leu Trp Pro Pro Leu Ala Met Thr Met Ala Pro Gly Met Phe Gln Leu
        195                 200                 205
Gly Leu Asp Ser Gly Asp Gly Arg Gly Ala Gly Gly Glu Asp Gly Ser
    210                 215                 220
Gly Glu Leu His Val Met Gln Ala Lys Arg Glu Gly Gly Gly Tyr
225                 230                 235                 240
Pro Ala Arg Gly Ile Tyr Gly Asp His His Leu Ala Ala Ala Gly Tyr
                245                 250                 255
Ala Ser Tyr Ser Asn Asn Ala Ala Thr Gly Asn His Leu Leu
            260                 265                 270
```

<210> SEQ ID NO 54
<211> LENGTH: 1686
<212> TYPE: DNA
<213> ORGANISM: Panicum virgatum
<220> FEATURE:
<221> NAME/KEY: misc_feature
<222> LOCATION: (1)..(1686)
<223> OTHER INFORMATION: Ceres CLONE ID no.1797005
<220> FEATURE:
<221> NAME/KEY: misc_feature
<222> LOCATION: (1)..(1686)
<223> OTHER INFORMATION: Encodes the peptide sequence at SEQ ID NO:55

<400> SEQUENCE: 54

```
actcctccgt ctgtctcctc cccattccgc caccgcaaca acaaacccct cccggaatcc      60
agcccagtcc accggagcgc gccgccccgc cgatggcgtc accgcctccg ccggatccag     120
cgccgcctcc ctcggcgggg ttggaaagca tggaggggct cgtcatcgac acggtcattt     180
ccaaggccgg ggcgcgcccc gccgcggtgc tcgcgtgcgc cagcacccgc ctccgcgccg     240
ccgtcgccga cgaatccctt tggcgccgct tctgcgcaga ggacctgggg ctcgacgcgc     300
ccgtggaccc cgacggccag ccgctcccgt cgttccaggt tgcatataaa gtgtggttgg     360
agtcttttgg tatgtacccct ttacctctgg taaagagagt gaaagaattc tggagttcaa     420
tgaaaacatg gttgtctgaa acttccctg aggcagccaa acattgtgt aaaggtgtta      480
ctgaagctca actaaaatca gcagaggatg accttggttt caagcttcct atgcccacaa     540
agctgttgta tcgcttttgc aatgctcaac tgccttttag tgaaaaccat gaagctaata     600
aacgcatttc cactcatgga ataattgggg gctatgcgtt ttatgatcat gggtaaatg      660
tgcatttatc accacttgag caaatagttg aagagacaac agagttttgt cgcgagttcc     720
cggatgtctt cagtgggcgc aagctcatta gtggcgac ttcttggttt catccaaaaa       780
catttctcct gaattgctca aatggtgaac tatatgttgg cacaaacaac ttaccattag     840
gtgaaatgct gccttgtgtg cctaaagcgt tgataaagcc aactgataat gatcttcccc     900
aagatggatt acttctatgg ttagaagagc atctcagacg tttacagaac ggcatgatca     960
aaacccgtat gctgacgaag ttgaggtata tcagcttata tccagaagca cctccatcat    1020
gtacttcagc cgtgacaaat ggtgttaagg tacgcggatc tgctgtcttt gtaccagaac    1080
atcctgggga ccctcagcga agttgtatgt acacttactc aattcgcctg tcagttccag    1140
aggcttgcat gctaggtggc gtgtactatt cttcctgcca gcttaattca cgccactgga    1200
ccattcgatc aagggacagg gttgtttctg atgtgagggg agaaggtgtt attggacagt    1260
atcctgtgct gtcacctggt caggatgagt ttgtctacga gagctgcaca ccactggcca    1320
aagggcctgg agctgtggag ggctctttt tgtttgtgcc tggcaagttg agccggcctg     1380
```

-continued

```
aagggaagcc gttcgaggtc atagtggctc cgttccctct ggaggtgcct gagtacatct    1440
tctaatgact gttgagagaa ataatgtatc tatgtggtag atggttctcc caggtactta    1500
ttaacttggt ggagcaaagt ttctttactt gtgatgatct tgttggagta atgtaaaata    1560
tggaaccgtg tgcactttac ttgatgtagc agtcgatact aaacaaccac ctcagggact    1620
gcagcctagt aatctacaga tgggcctcag tctctatcct ggcaacaaaa aaaaaaaaa    1680 aaaaaa                                                               1686
```

<210> SEQ ID NO 55
<211> LENGTH: 450
<212> TYPE: PRT
<213> ORGANISM: Panicum virgatum
<220> FEATURE:
<221> NAME/KEY: misc_feature
<222> LOCATION: (1)..(450)
<223> OTHER INFORMATION: Ceres CLONE ID no. 1797005
<220> FEATURE:
<221> NAME/KEY: misc_feature
<222> LOCATION: (312)..(446)
<223> OTHER INFORMATION: Pfam Name: DUF525
      Pfam Description: Protein of unknown function (DUF525)

<400> SEQUENCE: 55

```
Met Ala Ser Pro Pro Pro Asp Pro Ala Pro Pro Pro Ser Ala Gly
1               5                   10                  15

Leu Glu Ser Met Glu Gly Leu Val Ile Asp Thr Val Ile Ser Lys Ala
                20                  25                  30

Gly Ala Arg Pro Ala Ala Val Leu Ala Cys Ala Ser Thr Arg Leu Arg
            35                  40                  45

Ala Ala Val Ala Asp Glu Ser Leu Trp Arg Arg Phe Cys Ala Glu Asp
        50                  55                  60

Leu Gly Leu Asp Ala Pro Val Asp Pro Asp Gly Gln Pro Leu Pro Ser
65                  70                  75                  80

Phe Gln Val Ala Tyr Lys Val Trp Leu Glu Ser Phe Gly Met Tyr Pro
                85                  90                  95

Leu Pro Leu Val Lys Arg Val Lys Glu Phe Trp Ser Ser Met Lys Thr
            100                 105                 110

Trp Leu Ser Glu Asn Phe Pro Glu Ala Ala Lys Thr Leu Cys Lys Gly
        115                 120                 125

Val Thr Glu Ala Gln Leu Lys Ser Ala Glu Asp Asp Leu Gly Phe Lys
130                 135                 140

Leu Pro Met Pro Thr Lys Leu Leu Tyr Arg Phe Cys Asn Ala Gln Leu
145                 150                 155                 160

Pro Phe Ser Glu Asn His Glu Ala Asn Lys Arg Ile Ser Thr His Gly
                165                 170                 175

Ile Ile Gly Gly Tyr Ala Phe Tyr Asp His Trp Val Asn Val His Leu
            180                 185                 190

Ser Pro Leu Glu Gln Ile Val Glu Glu Thr Thr Glu Phe Cys Arg Glu
        195                 200                 205

Phe Pro Asp Val Phe Ser Gly Arg Lys Leu Ile Ile Val Ala Thr Ser
    210                 215                 220

Trp Phe His Pro Lys Thr Phe Leu Leu Asn Cys Ser Asn Gly Glu Leu
225                 230                 235                 240

Tyr Val Gly Thr Asn Asn Leu Pro Leu Gly Glu Met Leu Pro Cys Val
                245                 250                 255

Pro Lys Ala Leu Ile Lys Pro Thr Asp Asn Asp Leu Pro Gln Asp Gly
            260                 265                 270
```

Leu Leu Leu Trp Leu Glu Glu His Leu Arg Arg Leu Gln Asn Gly Met
            275                 280                 285

Ile Lys Thr Arg Met Leu Thr Lys Leu Arg Tyr Ile Ser Leu Tyr Pro
290                 295                 300

Glu Ala Pro Pro Ser Cys Thr Ser Ala Val Thr Asn Gly Val Lys Val
305                 310                 315                 320

Arg Gly Ser Ala Val Phe Val Pro Glu His Pro Gly Asp Pro Gln Arg
                325                 330                 335

Ser Cys Met Tyr Thr Tyr Ser Ile Arg Leu Ser Val Pro Glu Ala Cys
            340                 345                 350

Met Leu Gly Gly Val Tyr Tyr Ser Ser Cys Gln Leu Asn Ser Arg His
            355                 360                 365

Trp Thr Ile Arg Ser Arg Asp Arg Val Val Ser Asp Val Arg Gly Glu
370                 375                 380

Gly Val Ile Gly Gln Tyr Pro Val Leu Ser Pro Gly Gln Asp Glu Phe
385                 390                 395                 400

Val Tyr Glu Ser Cys Thr Pro Leu Ala Lys Gly Pro Gly Ala Val Glu
                405                 410                 415

Gly Ser Phe Leu Phe Val Pro Gly Lys Leu Ser Arg Pro Glu Gly Lys
            420                 425                 430

Pro Phe Glu Val Ile Val Ala Pro Phe Pro Leu Glu Val Pro Glu Tyr
            435                 440                 445

Ile Phe
    450

<210> SEQ ID NO 56
<211> LENGTH: 679
<212> TYPE: DNA
<213> ORGANISM: Gossypium hirsutum
<220> FEATURE:
<221> NAME/KEY: misc_feature
<222> LOCATION: (1)..(679)
<223> OTHER INFORMATION: Ceres CLONE ID no.1798705
<220> FEATURE:
<221> NAME/KEY: misc_feature
<222> LOCATION: (1)..(679)
<223> OTHER INFORMATION: Encodes the peptide sequence at SEQ ID NO:57

<400> SEQUENCE: 56
acctcaatct ccctccttcg cgtttcttta ttcctaactc tctttaccac ctaaacctcc      60
ttccattcat ttttacgttt taatggatga gttaaacagc aagaagcggg ctagggacga     120
ctccaatgag tcgggtctgg actcgcccga cgtgaagaga ctcagagatg atttatttct     180
tgatgattca gattccttgc ctcttaatca agaccttgca tccgtaatga agagttttga     240
agaggagata tcagccgtcc catcgacttc gacggaatct atgccggttg tggatctcac     300
ttcggattct ggtgactcac aaccggatct tggttacctt ctcgaggctt ccgatgatga     360
acttggtctg cctcccccta cggcttccac aactgatgct gagggaaggt ccgaagcgac     420
tgatttggtg cgagctgact caaactcctc gggaatccat gatttgtggg ggttcgagga     480
acaaaacccc aactacgatt ctttcgagtt tggattcgtt gataatttca atgatggcac     540
cgttgcatat gatggactgt tcgagtattc cgatgtctat tacgattcct ccgatatttc     600
tggtcagcta tggcggccgg aaactttgtc ggcgaagtaa aaatccaaac ttaaaatcca     660
aaaaaaaaaa aaaaaaaa                                                   679

<210> SEQ ID NO 57
<211> LENGTH: 185

-continued

<212> TYPE: PRT
<213> ORGANISM: Gossypium hirsutum
<220> FEATURE:
<221> NAME/KEY: misc_feature
<222> LOCATION: (1)..(185)
<223> OTHER INFORMATION: Ceres CLONE ID no. 1798705

<400> SEQUENCE: 57

Met Asp Glu Leu Asn Ser Lys Lys Arg Ala Arg Asp Asp Ser Asn Glu
1               5                   10                  15

Ser Gly Leu Asp Ser Pro Asp Val Lys Arg Leu Arg Asp Asp Leu Phe
            20                  25                  30

Leu Asp Asp Ser Asp Ser Leu Pro Leu Asn Gln Asp Leu Ala Ser Val
        35                  40                  45

Met Lys Ser Phe Glu Glu Ile Ser Ala Val Pro Ser Thr Ser Thr
    50                  55                  60

Glu Ser Met Pro Val Val Asp Leu Thr Ser Asp Ser Gly Asp Ser Gln
65                  70                  75                  80

Pro Asp Leu Gly Tyr Leu Leu Glu Ala Ser Asp Glu Leu Gly Leu
                85                  90                  95

Pro Pro Pro Thr Ala Ser Thr Thr Asp Ala Glu Gly Arg Ser Glu Ala
            100                 105                 110

Thr Asp Leu Val Arg Ala Asp Ser Asn Ser Ser Gly Ile His Asp Leu
        115                 120                 125

Trp Gly Phe Glu Glu Gln Asn Pro Asn Tyr Asp Ser Phe Glu Phe Gly
    130                 135                 140

Phe Val Asp Asn Phe Asn Asp Gly Thr Val Ala Tyr Asp Gly Leu Phe
145                 150                 155                 160

Glu Tyr Ser Asp Val Tyr Tyr Asp Ser Ser Asp Ile Ser Gly Gln Leu
                165                 170                 175

Trp Arg Pro Glu Thr Leu Ser Ala Lys
            180                 185

<210> SEQ ID NO 58
<211> LENGTH: 1239
<212> TYPE: DNA
<213> ORGANISM: Panicum virgatum
<220> FEATURE:
<221> NAME/KEY: misc_feature
<222> LOCATION: (1)..(1239)
<223> OTHER INFORMATION: Ceres CLONE ID no.1805548
<220> FEATURE:
<221> NAME/KEY: misc_feature
<222> LOCATION: (1)..(1239)
<223> OTHER INFORMATION: Encodes the peptide sequence at SEQ ID NO:59

<400> SEQUENCE: 58
actcattcac tcaccaagaa gttgagcacc tagagcttca gctcagctca ttcgtttctt      60
ccggcttccc atccgggctt atcactagtg atcgctagct agcgaacaat tctctgaagt     120
tgtcgagctg agcactagct agcggccatg atctccccgg acaccatccg cacggccatt     180
ggcgtcatcg gcaatgggac tgctctggtg ctcttcctct ccccagttcc gacgttcatc     240
cgcatctgga agaaggggtc ggtggagcag tactcgccgg tgccgtacgt ggcaacgctc     300
ctcaactgca tgatgtgggt gctgtacggc ctaccgcttg tccaccccca gcatgctc      360 gtcatcacca tcaacggcac cggcatggcc atcgagctca cctacgtcac gctcttcctt     420
ctctactcca cgggacccgc tcgccgcaag gtcgtcctcc tctcgccgc cgaggtcgcc     480 ttcgtctgcg ccgtcgccgt tctagtgctc agcctggcgc acacgcacga gcgcaggtcc     540
atgatcgtcg gcatcctctg cgtcctcttc ggcaccggca tgtacgcggc cccgctctcc     600

```
gtcatgaaaa tggtgatcca gacgaagagc gtggagtaca tgccccctatt cctgtccta      660 gcttctctgg tgaacggcat ctgctggact gcctacgccc tcatcaaatt cgacctctac      720
atcacaatcc ccaacgggct gggcgttctg ttcgcggtgg cgcaggtggt cctctacgcc      780
atctactaca agtccaccca ggagatcatc gaggcgcgca ggcgcaaggc aaaccaggtc      840
gccatgaccg aggtcgtcgt cgacgacggc aagaccaaca acagccacgc cggcgccggc      900
ctctactgac gaagtcatcg atgatatata ccaagattaa ggaagcgctc ggcacaatat      960
aatcaagtat caagtcgccg ctggatgcct gtattgtgtg attgtgttct cccacaaga     1020 gatggaggcc acatcatgtt gtttcctaac tgcttgcgca cgctggacg gagtcaccgg     1080 gcctcttatt aggtgggagt gatgggacga ctgaggtggg ggattttagc taattccacc     1140
ttgccgatag ggtttagctt aatctcgatg tgtagcggca cttattaatg gtctcttgtc     1200
tcaaatttgt attgatcaga aaaaaaaaaa aaaaaaaa                             1239
```

<210> SEQ ID NO 59
<211> LENGTH: 253
<212> TYPE: PRT
<213> ORGANISM: Panicum virgatum
<220> FEATURE:
<221> NAME/KEY: misc_feature
<222> LOCATION: (1)..(253)
<223> OTHER INFORMATION: Ceres CLONE ID no. 1805548
<220> FEATURE:
<221> NAME/KEY: misc_feature
<222> LOCATION: (9)..(98)
<223> OTHER INFORMATION: Pfam Name: MtN3_slv
    Pfam Description: MtN3/saliva family

<400> SEQUENCE: 59

```
Met Ile Ser Pro Asp Thr Ile Arg Thr Ala Ile Gly Val Ile Gly Asn
1               5                   10                  15

Gly Thr Ala Leu Val Leu Phe Leu Ser Pro Val Pro Thr Phe Ile Arg
            20                  25                  30

Ile Trp Lys Lys Gly Ser Val Glu Gln Tyr Ser Pro Val Pro Tyr Val
        35                  40                  45

Ala Thr Leu Leu Asn Cys Met Met Trp Val Leu Tyr Gly Leu Pro Leu
    50                  55                  60

Val His Pro His Ser Met Leu Val Ile Thr Ile Asn Gly Thr Gly Met
65                  70                  75                  80

Ala Ile Glu Leu Thr Tyr Val Thr Leu Phe Leu Leu Tyr Ser Thr Gly
                85                  90                  95

Pro Ala Arg Arg Lys Val Val Leu Leu Leu Ala Ala Glu Val Ala Phe
            100                 105                 110

Val Cys Ala Val Ala Val Leu Val Leu Ser Leu Ala His Thr His Glu
        115                 120                 125

Arg Arg Ser Met Ile Val Gly Ile Leu Cys Val Leu Phe Gly Thr Gly
    130                 135                 140

Met Tyr Ala Ala Pro Leu Ser Val Met Lys Met Val Ile Gln Thr Lys
145                 150                 155                 160

Ser Val Glu Tyr Met Pro Leu Phe Leu Ser Leu Ala Ser Leu Val Asn
                165                 170                 175

Gly Ile Cys Trp Thr Ala Tyr Ala Leu Ile Lys Phe Asp Leu Tyr Ile
            180                 185                 190

Thr Ile Pro Asn Gly Leu Gly Val Leu Phe Ala Val Ala Gln Val Val
        195                 200                 205

Leu Tyr Ala Ile Tyr Tyr Lys Ser Thr Gln Glu Ile Ile Glu Ala Arg
```

```
                210                 215                 220
Arg Arg Lys Ala Asn Gln Val Ala Met Thr Glu Val Val Asp Asp
225                 230                 235                 240

Gly Lys Thr Asn Asn Ser His Ala Gly Ala Gly Leu Tyr
                245                 250

<210> SEQ ID NO 60
<211> LENGTH: 883
<212> TYPE: DNA
<213> ORGANISM: Gossypium hirsutum
<220> FEATURE:
<221> NAME/KEY: misc_feature
<222> LOCATION: (1)..(883)
<223> OTHER INFORMATION: Ceres CLONE ID no.1808334
<220> FEATURE:
<221> NAME/KEY: misc_feature
<222> LOCATION: (1)..(883)
<223> OTHER INFORMATION: Encodes the peptide sequence at SEQ ID NO:61

<400> SEQUENCE: 60
attgccagac cttgaaaaat cttacaattt tttttatata atttctgtta gaaaaaaacc      60
cagttcactt ttcagttctt ggtaccttgg ctgaccattt ttgtttgaat tgcaggttac     120
cagggtttag ccattgcttt tcatttgaag ctctcctccc cattgttttt aaggtcatat     180
atttattata tattatcagc acaaaaagaa aaaaatgggt ctctcaagtc ttccagctcc     240
atcagaagga gtgttatgta tactcttggt aaacacagct ttatctatat ctatagttaa     300
aggcataatc cgatcgatcc ttcacgttgt cggtatccat ctcccaccac catcatcgga     360
ttacactgaa aatctctcgg aatcattcga tttccacctt aatactcctg aaagttacat     420
tgaggaattc cggagtagga ccccaacaat tcatttcggt gctgttgtat gtagctgcaa     480
acggcctcag cacgactgtc aggtttgtct gactcagttt gagccaaaat ccgagattaa     540
ccacttgtcg tgtggccatc tctttcacaa ggtgtgtttg gaaaatggt tggattattg      600 gaatattaca tgccctcttt gcaggactcc cttgttgcct gaagaagaag cttcttgctt     660
tttgtaagaa gattattatc aagtatatta ttatgcagag ttgaggaatt cccgtgtaca     720
gcgcggtata taaagtata ctgttatctt tatcgagtgt gtcgttacc cgcaagtttg       780 taccttgctg tggtgatttg tgttatttga atcaatgcac atattgttgt ctgggttaat     840
gatatgttat tatatgcagt ctcaaaaaaa aaaaaaaaa aaa                         883

<210> SEQ ID NO 61
<211> LENGTH: 150
<212> TYPE: PRT
<213> ORGANISM: Gossypium hirsutum
<220> FEATURE:
<221> NAME/KEY: misc_feature
<222> LOCATION: (1)..(150)
<223> OTHER INFORMATION: Ceres CLONE ID no. 1808334
<220> FEATURE:
<221> NAME/KEY: misc_feature
<222> LOCATION: (95)..(136)
<223> OTHER INFORMATION: Pfam Name: zf-C3HC4
      Pfam Description: Zinc finger, C3HC4 type (RING finger)

<400> SEQUENCE: 61

Met Gly Leu Ser Ser Leu Pro Ala Pro Ser Glu Gly Val Leu Cys Ile
1               5                   10                  15

Leu Leu Val Asn Thr Ala Leu Ser Ile Ser Ile Val Lys Gly Ile Ile
                20                  25                  30

Arg Ser Ile Leu His Val Val Gly Ile His Leu Pro Pro Pro Ser Ser
            35                  40                  45
```

-continued

```
Asp Tyr Thr Glu Asn Leu Ser Glu Ser Phe Asp Phe His Leu Asn Thr
 50                  55                  60

Pro Glu Ser Tyr Ile Glu Glu Phe Arg Ser Arg Thr Pro Thr Ile His
 65                  70                  75                  80

Phe Gly Ala Val Val Cys Ser Cys Lys Arg Pro Gln His Asp Cys Gln
                 85                  90                  95

Val Cys Leu Thr Gln Phe Glu Pro Lys Ser Glu Ile Asn His Leu Ser
            100                 105                 110

Cys Gly His Leu Phe His Lys Val Cys Leu Glu Lys Trp Leu Asp Tyr
        115                 120                 125

Trp Asn Ile Thr Cys Pro Leu Cys Arg Thr Pro Leu Leu Pro Glu Glu
    130                 135                 140

Glu Ala Ser Cys Phe Leu
145                 150

<210> SEQ ID NO 62
<211> LENGTH: 1117
<212> TYPE: DNA
<213> ORGANISM: Panicum virgatum
<220> FEATURE:
<221> NAME/KEY: misc_feature
<222> LOCATION: (1)..(1117)
<223> OTHER INFORMATION: Ceres CLONE ID no.1822715
<220> FEATURE:
<221> NAME/KEY: misc_feature
<222> LOCATION: (1)..(1117)
<223> OTHER INFORMATION: Encodes the peptide sequence at SEQ ID NO:63

<400> SEQUENCE: 62
cttttccaac agcgacgcaa cgagctcgta acgcccgtac cctcgcacgc gcgcagagag      60
agagagagag agagagagag agagagcaag tgagcagaga agaagaggaa ggagcgagaa     120
gcctgggaag ggagagcgag cgcaaccgaa tcgatatgaa gccggagaag gcagcggtgg     180
ccgtggcagc cggcggcggc ggcgacgagt ggcggtgccg gaagcacccg gccgcgccga     240
gatccggcgg tggggtgtgc ccgtactgcc tccgcgaccg gctcctccgc ctgtgcccca     300
actgcgcacg cgtgcggccc tgcccctgcg ccgcgtcgtg cgcctccccg tcctcctcct     360
cggcgtccgg cgacgcggtg ggccgcgtgc acagcctcat cgagcgggag caccggatcg     420
cgcgctcgcg gtccgtggcc gcgggctcct ccgccgcgtt cgtcgccgcc gtgggtgccc     480
cctccgcggc ggggcccacc tccggggggcg gcaggcggaa ggcgcgcgtc tggggggtggc     540 cgccgttctg gaagcccgcg tcgcgggacg gggacgcggg gatggggggag gacgaggagg     600 aggggctggg cctgccgcgc tcgagctccg tgtccgcgac ggccgtggag accaagaccg     660
cggcggcggc ggcgcgcgcg aggtgggggt ggcacttccc gagcccgctg aaggcgttcc     720
ggcaccggag gtcgtcggcg agcgtggccg ggcgggcgtg agcgccaagg tacaccgccc     780
ccttctggag atggccggaa aagcgattcg cgggtggggg tcatgtggcc ggggatggtt     840
aattattaat tttaactgta taaggcggtg gattagagga ggagcgttgg atctcctttt     900 tctcctttg ttgtggcgtg ccgctaattc catgattaag ttagacgggg atgcgaaagc     960
ctgcgatctg ggcgggatgt gtgcatatgc tagtgggtga tctcctcatg gcttccttc    1020 acctttgta gtgtgcttgt acccgactct gtaacacacc aaattggata ttttaagctc    1080
tccaatttgt tctggctaaa aaaaaaaaaa aaaaaaa                             1117

<210> SEQ ID NO 63
<211> LENGTH: 201
<212> TYPE: PRT
<213> ORGANISM: Panicum virgatum
```

```
<220> FEATURE:
<221> NAME/KEY: misc_feature
<222> LOCATION: (1)..(201)
<223> OTHER INFORMATION: Ceres CLONE ID no. 1822715

<400> SEQUENCE: 63

Met Lys Pro Glu Lys Ala Ala Val Ala Val Ala Ala Gly Gly Gly
1               5                   10                  15

Asp Glu Trp Arg Cys Arg Lys His Pro Ala Ala Pro Arg Ser Gly Gly
            20                  25                  30

Gly Val Cys Pro Tyr Cys Leu Arg Asp Arg Leu Leu Arg Leu Cys Pro
            35                  40                  45

Asn Cys Ala Arg Val Arg Pro Cys Pro Cys Ala Ala Ser Cys Ala Ser
        50                  55                  60

Pro Ser Ser Ser Ser Ala Ser Gly Asp Ala Val Gly Arg Val His Ser
65                  70                  75                  80

Leu Ile Glu Arg Glu His Arg Ile Ala Arg Ser Arg Ser Val Ala Ala
                85                  90                  95

Gly Ser Ser Ala Ala Phe Val Ala Ala Val Gly Ala Pro Ser Ala Ala
            100                 105                 110

Gly Pro Thr Ser Gly Gly Gly Arg Arg Lys Ala Arg Val Trp Gly Trp
            115                 120                 125

Pro Pro Phe Trp Lys Pro Ala Ser Arg Asp Gly Asp Ala Gly Met Gly
        130                 135                 140

Glu Asp Glu Glu Gly Leu Gly Leu Pro Arg Ser Ser Ser Val Ser
145                 150                 155                 160

Ala Thr Ala Val Glu Thr Lys Thr Ala Ala Ala Ala Arg Ala Arg
                165                 170                 175

Trp Gly Trp His Phe Pro Ser Pro Leu Lys Ala Phe Arg His Arg Arg
            180                 185                 190

Ser Ser Ala Ser Val Ala Gly Arg Ala
            195                 200

<210> SEQ ID NO 64
<211> LENGTH: 1843
<212> TYPE: DNA
<213> ORGANISM: Panicum virgatum
<220> FEATURE:
<221> NAME/KEY: misc_feature
<222> LOCATION: (1)..(1843)
<223> OTHER INFORMATION: Ceres CLONE ID no.1827994
<220> FEATURE:
<221> NAME/KEY: misc_feature
<222> LOCATION: (1)..(1843)
<223> OTHER INFORMATION: Encodes the peptide sequence at SEQ ID NO:65

<400> SEQUENCE: 64
aaccgtcgcc tcgccattcc ccgcctgaat ccctaacgcc catggcctcc gtctccccg      60 ccgccgccgc agccgccgtc tccggccccc accacgcccg cctcctcctc ccctcctcat   120
tgcgccgcct cgcgcggccc cgcccgcgcc ctcgcccgcg actccgcctc gccgcctgcc   180
acgcggacac gctgctcccc tcctcctcct cctcatcgga ggtccgcgcg ccgccggccc   240
ccgcagtggg gccctccgcc gaatctgcca cggactgttt cgtcgactgg ctgcgcgcgc   300
gcgggttgac cccgggcaaa gtggatatcc gggagcggcc ggtgccctgc ctgcgcgagg   360
gcaaggaccc cccgctgcgc tacgtcgctg ccggcgacgc cctccaggcg ggggatgtgg   420
cgttcgaagt gccccatgtcg ctcgtcgtca gctggagcg ggtgctcggg acgaatcag    480 tagctgagtt gttgacgaac aacaagttgt ctgagttggc atgcttggct ttgtatctca   540
```

```
tgtatgagaa aaagcaagga aaggattcat attggtaccc ctacattaag gagcttgacc    600
gacaccgagg aagggggacaa ctagctgttg aatcaccact tttatggact gaaagtgaac    660
ttgattacct gactggaagc ccattaaagg atgaagttgt tgctagagat gaggcggtaa    720
ggagagagta taatgagctt gacacattgt ggttcatggc aggttcactg tttcagcaat    780 accctttga tatacctact gaggcttttc cgtttgagat attcaagcaa gcttttgttg    840
ccgtacagtc ttgtgtggtt catctgcaga aagttagttt agctcgaaga ttcgcgctag    900
ttcctttggg gccaccacta ttgacctaca agagcaactg caaagctatg ttgacagctg    960
atggtgattc tgttcggttg gtggtggatc gcccatataa agccggagaa ccaataatcg   1020
tctggtgtgg accacaaaca aactccaggc tggttctgaa ctatggtttt gttgatgagg   1080
acaatccctt tgatcggata gcaattgagg catccttaaa tacagaagat cctcaatacc   1140
aagaaaagag aatggttgct cagaggaaag gaaagcttgc tatccaaaat tttaatgtct   1200
atgtaggtaa agagaaagaa actgttgcag aaatactgcc ttacctgaga ttaggataca   1260
tttcagatcc ggatgaaatg cagtccatac tctcttctga aggagatact tgtccagtta   1320
gtccatgtac tgagcgagct gttcttgatc aacttgttgg ttacctggaa tctcgattgg   1380
ctggttatcc aacaactttg gatgaggatg aagttatgtt ggcagatggc aatttggaac   1440
caaagaagga agttgctaca aggcttgtaa ggttggagaa gaagatgctc catgcctgtc   1500
tccaggctgc taatgagttt ataaatgact tgcctgatca cacagtatca ccttgccctg   1560
ctccatatgc ccctgaactg aaatgagatg gtcatatcat caggactttc aagaattggg   1620 caaacacgcag aaaagcatcc tctatatgag atcattatat gttgcaaggg attcacaaat   1680
ctggccgttc aggtgcaatc gtgcaggcct cagcagatgt ggtagttagt tgcaatgcac   1740
agaagtgtgc gtgaatgttc ctttttgtt aatctagcag gttttgtatt cacgaagtag   1800
attctgtatc tctattttct gatgagcatg ggttcggagt gcc                    1843
```

<210> SEQ ID NO 65
<211> LENGTH: 514
<212> TYPE: PRT
<213> ORGANISM: Panicum virgatum
<220> FEATURE:
<221> NAME/KEY: misc_feature
<222> LOCATION: (1)..(514)
<223> OTHER INFORMATION: Ceres CLONE ID no. 1827994
<220> FEATURE:
<221> NAME/KEY: misc_feature
<222> LOCATION: (113)..(336)
<223> OTHER INFORMATION: Pfam Name: SET
      Pfam Description: SET domain

<400> SEQUENCE: 65

```
Met Ala Ser Val Ser Pro Ala Ala Ala Ala Ala Val Ser Gly Pro
1               5                  10                  15

His His Ala Arg Leu Leu Leu Pro Ser Ser Leu Arg Arg Leu Ala Arg
             20                  25                  30

Pro Arg Pro Arg Pro Arg Pro Arg Leu Arg Leu Ala Ala Cys His Ala
         35                  40                  45

Asp Thr Leu Leu Pro Ser Ser Ser Ser Ser Glu Val Arg Ala Pro
    50                  55                  60

Pro Ala Pro Ala Val Gly Pro Ser Ala Glu Ser Ala Thr Asp Cys Phe
65                  70                  75                  80

Val Asp Trp Leu Arg Ala Arg Gly Leu Thr Pro Gly Lys Val Asp Ile
                85                  90                  95

Arg Glu Arg Pro Val Pro Cys Leu Arg Glu Gly Lys Asp Pro Pro Leu
```

```
                    100                 105                 110
Arg Tyr Val Ala Ala Gly Asp Ala Leu Gln Ala Gly Asp Val Ala Phe
                115                 120                 125

Glu Val Pro Met Ser Leu Val Val Thr Leu Glu Arg Val Leu Gly Asp
            130                 135                 140

Glu Ser Val Ala Glu Leu Leu Thr Asn Asn Lys Leu Ser Glu Leu Ala
145                 150                 155                 160

Cys Leu Ala Leu Tyr Leu Met Tyr Glu Lys Lys Gln Gly Lys Asp Ser
                165                 170                 175

Tyr Trp Tyr Pro Tyr Ile Lys Glu Leu Asp Arg His Arg Gly Arg Gly
                180                 185                 190

Gln Leu Ala Val Glu Ser Pro Leu Leu Trp Thr Glu Ser Glu Leu Asp
                195                 200                 205

Tyr Leu Thr Gly Ser Pro Leu Lys Asp Glu Val Val Ala Arg Asp Glu
            210                 215                 220

Ala Val Arg Arg Glu Tyr Asn Glu Leu Asp Thr Leu Trp Phe Met Ala
225                 230                 235                 240

Gly Ser Leu Phe Gln Gln Tyr Pro Phe Asp Ile Pro Thr Glu Ala Phe
                245                 250                 255

Pro Phe Glu Ile Phe Lys Gln Ala Phe Val Ala Val Gln Ser Cys Val
                260                 265                 270

Val His Leu Gln Lys Val Ser Leu Ala Arg Arg Phe Ala Leu Val Pro
            275                 280                 285

Leu Gly Pro Pro Leu Leu Thr Tyr Lys Ser Asn Cys Lys Ala Met Leu
            290                 295                 300

Thr Ala Asp Gly Asp Ser Val Arg Leu Val Val Asp Arg Pro Tyr Lys
305                 310                 315                 320

Ala Gly Glu Pro Ile Ile Val Trp Cys Gly Pro Gln Thr Asn Ser Arg
                325                 330                 335

Leu Val Leu Asn Tyr Gly Phe Val Asp Glu Asn Pro Phe Asp Arg
                340                 345                 350

Ile Ala Ile Glu Ala Ser Leu Asn Thr Glu Asp Pro Gln Tyr Gln Glu
                355                 360                 365

Lys Arg Met Val Ala Gln Arg Lys Gly Lys Leu Ala Ile Gln Asn Phe
            370                 375                 380

Asn Val Tyr Val Gly Lys Glu Lys Glu Thr Val Ala Glu Ile Leu Pro
385                 390                 395                 400

Tyr Leu Arg Leu Gly Tyr Ile Ser Asp Pro Asp Glu Met Gln Ser Ile
                405                 410                 415

Leu Ser Ser Glu Gly Asp Thr Cys Pro Val Ser Pro Cys Thr Glu Arg
                420                 425                 430

Ala Val Leu Asp Gln Leu Val Gly Tyr Leu Glu Ser Arg Leu Ala Gly
                435                 440                 445

Tyr Pro Thr Thr Leu Asp Glu Asp Glu Val Met Leu Ala Asp Gly Asn
            450                 455                 460

Leu Glu Pro Lys Lys Glu Val Ala Thr Arg Leu Val Arg Leu Glu Lys
465                 470                 475                 480

Lys Met Leu His Ala Cys Leu Gln Ala Ala Asn Glu Phe Ile Asn Asp
                485                 490                 495

Leu Pro Asp His Thr Val Ser Pro Cys Pro Ala Pro Tyr Ala Pro Glu
                500                 505                 510

Leu Lys
```

<210> SEQ ID NO 66
<211> LENGTH: 1084
<212> TYPE: DNA
<213> ORGANISM: Gossypium hirsutum
<220> FEATURE:
<221> NAME/KEY: misc_feature
<222> LOCATION: (1)..(1084)
<223> OTHER INFORMATION: Ceres CLONE ID no.1837746
<220> FEATURE:
<221> NAME/KEY: misc_feature
<222> LOCATION: (1)..(1084)
<223> OTHER INFORMATION: Encodes the peptide sequence at SEQ ID NO:67

<400> SEQUENCE: 66

```
aaagccaaag aactctcctt atatctctct acccttttc tctcgcaaac tctaaaaaca      60
tcaaagagag cttaaaagca aaagaatcaa tggcagtcga agctcgtaat atgaatcttt    120
tccctcctca gttaatccct aatgcagatt ttatgaaagg tgatcaaggg agtggaaata    180
tacacaacac ccagatgcag caagaagttt cacagatttt ccctgcagtt tatcagtcgc    240
ttgtacgtga tccgatttca gccaaagctg atagtggggt tacttataat atgaatatcc    300
cagtttcggc cccaaggaaa aggcctaggg attcatattc atacacagtt gctcgaaaga    360
acgacttttg tggggtttct tctgttcttg acgatgatgc ttttcccag atccaacaac    420
aacaacaaca agaaatcgac cgtttcattg ctcaacatac agaaaaagtg aggttggaga    480
ttgaagaaag gaggaagagg caatcgagga tgttgattac agcgatccaa gaaggggtta    540
tgaagaaact gaaggaaaaa gatgaagaga tacaagaat ggggaaactg aactgggttc    600
ttcaagaaag agtgaaaagc ctgtatttag agaaccaact gtggagggac ttggcgcaaa    660
cgaacgaagc caccgccaat tccttacgca ccaatctaga acaagtcctt gcccacgtcg    720
gtgaggaacg tcacgccagc ggcggaggag cggccgcgtt ggccgacgac gcgggatcta    780
gctgtggaag cagcgatgaa gggtggcgca aggtggtgtt gccgcctact cagccacatg    840
atacgacggc agcggtggtt gggaacggta ataataatgg aaggaagtgt agaaagtgtg    900
gggagaaaga gtcaagtgtg ctgttgctgc catgcaggca tctctgtctc tgtacaatgt    960
gtgggtccac tctggtaggc acttgccctg tttgtgactc tgtcaccaat gccagtgttc   1020
atgttaacat gtcttgaaac aattttttt tcttttttag atattttagt gaaaacaaaa   1080
cagc                                                                1084
```

<210> SEQ ID NO 67
<211> LENGTH: 315
<212> TYPE: PRT
<213> ORGANISM: Gossypium hirsutum
<220> FEATURE:
<221> NAME/KEY: misc_feature
<222> LOCATION: (1)..(315)
<223> OTHER INFORMATION: Ceres CLONE ID no. 1837746

<400> SEQUENCE: 67

```
Met Ala Val Glu Ala Arg Asn Met Asn Leu Phe Pro Pro Gln Leu Ile
1               5                   10                  15

Pro Asn Ala Asp Phe Met Lys Gly Asp Gln Gly Ser Gly Asn Ile His
            20                  25                  30

Asn Thr Gln Met Gln Gln Glu Val Ser Gln Ile Phe Pro Ala Val Tyr
        35                  40                  45

Gln Ser Leu Val Arg Asp Pro Ile Ser Ala Lys Ala Asp Ser Gly Val
    50                  55                  60

Thr Tyr Asn Met Asn Ile Pro Val Ser Ala Pro Arg Lys Arg Pro Arg
65                  70                  75                  80
```

```
Asp Ser Tyr Ser Tyr Thr Val Ala Arg Lys Asn Asp Phe Cys Gly Val
            85                  90                  95

Ser Ser Val Leu Asp Asp Val Phe Ser Gln Ile Gln Gln Gln
            100                 105                 110

Gln Gln Glu Ile Asp Arg Phe Ile Ala Gln His Thr Glu Lys Val Arg
            115                 120                 125

Leu Glu Ile Glu Glu Arg Arg Lys Arg Gln Ser Arg Met Leu Ile Thr
        130                 135                 140

Ala Ile Gln Glu Gly Val Met Lys Lys Leu Lys Glu Lys Asp Glu Glu
145                 150                 155                 160

Ile Gln Arg Met Gly Lys Leu Asn Trp Val Leu Gln Glu Arg Val Lys
                165                 170                 175

Ser Leu Tyr Leu Glu Asn Gln Leu Trp Arg Asp Leu Ala Gln Thr Asn
            180                 185                 190

Glu Ala Thr Ala Asn Ser Leu Arg Thr Asn Leu Glu Gln Val Leu Ala
            195                 200                 205

His Val Gly Glu Glu Arg His Ala Ser Gly Gly Ala Ala Ala Leu
            210                 215                 220

Ala Asp Asp Ala Gly Ser Ser Cys Gly Ser Ser Asp Glu Gly Trp Arg
225                 230                 235                 240

Lys Val Val Leu Pro Pro Thr Gln Pro His Asp Thr Thr Ala Ala Val
                245                 250                 255

Val Gly Asn Gly Asn Asn Asn Gly Arg Lys Cys Arg Lys Cys Gly Glu
            260                 265                 270

Lys Glu Ser Ser Val Leu Leu Leu Pro Cys Arg His Leu Cys Leu Cys
            275                 280                 285

Thr Met Cys Gly Ser Thr Leu Val Gly Thr Cys Pro Val Cys Asp Ser
        290                 295                 300

Val Thr Asn Ala Ser Val His Val Asn Met Ser
305                 310                 315

<210> SEQ ID NO 68
<211> LENGTH: 1278
<212> TYPE: DNA
<213> ORGANISM: Gossypium hirsutum
<220> FEATURE:
<221> NAME/KEY: misc_feature
<222> LOCATION: (1)..(1278)
<223> OTHER INFORMATION: Ceres CLONE ID no.1855399
<220> FEATURE:
<221> NAME/KEY: misc_feature
<222> LOCATION: (1)..(1278)
<223> OTHER INFORMATION: Encodes the peptide sequence at SEQ ID NO:69

<400> SEQUENCE: 68
aaatctttcc cgtgaaagga tcccatggag cactacttct ttcaatgaac cctaaacacc      60
ctcaattatc atactcttat ttgactgacc taatcaaaca gaagcagcta ataagggttt     120
gtcaattgtg agtgactgat aaatagcttg gattttggaa tctctcccta cacttggatt     180
tcagataaaa acaaaatccc aggtgggaaa aattcatcac tgcccatcaa cagttcatca     240
ccaaaacccc aacagtttcc tcttcttttt ttccaagtca atggattctg cctccggagg     300
gagtgacaat agcatcaaag aggctatacc agcaacagct tcagccctgc tgtccgcggc     360
ttcacaacaa ggaggaggag gtggtagtga gtcgtctcct tccccagctc caccgagtag     420
gtacgagtca caaagcgtc gagactggaa cactttcttg cagtacttga ccaaccataa     480
acccccatta acactagctc gttgcagtgg cgcacacgta attgagttct tgaaatacct     540
tgaccagttc ggcaagacta aggttcacat aacggattgt ccctatttcg acatgtaaa     600
```

```
cccacctgct ccctgcgctt gcccactgaa gcaagcgtgg ggtagcctcg acgcgctgat    660
cggacggctc agagctgctt atgaagaaaa cggtggacgt ccagaatcca acccttttgg    720
cgcaagggct gtgaggattt atttgaggga agtgagagaa gggcaggcta agctagagg     780 gattccttat gagaagaaga agcgaaaaag gcccactgtc acaactacgg ctgtcggggt    840
caatgtgtcc aggacttcca ctcaaccagt tgatggcggt gggggtcgcg gcggcattgg    900
tggtggagat gatagtgttg gtgctaaaac tggggcaaat gttggtagtg ccaccgcagt    960
tgctgctgct accactaata gcgtatagtt ctttttccct attaacaaat tcttttcctc   1020 ttttttgcc tttaacagct gttttaaatg tgattacgag ttatatatat ctggtggttc    1080 tgtcggaaa ttggattgac atcccatgaa ccaaatttag aatttaggta gaattctagt    1140
tttaatctct ttcaatcaat ctctcctatt ttccccttc tctactttct tcatcatttc    1200
ttgctatgca tgtacttgaa aaggaatat aagaagtttt aatctttttt cccttctaa     1260 aaaaaaaaaa aaaaaaaa                                                 1278
```

```
<210> SEQ ID NO 69
<211> LENGTH: 235
<212> TYPE: PRT
<213> ORGANISM: Gossypium hirsutum
<220> FEATURE:
<221> NAME/KEY: misc_feature
<222> LOCATION: (1)..(235)
<223> OTHER INFORMATION: Ceres CLONE ID no. 1855399
<220> FEATURE:
<221> NAME/KEY: misc_feature
<222> LOCATION: (29)..(161)
<223> OTHER INFORMATION: Pfam Name: DUF640
      Pfam Description: Protein of unknown function (DUF640)

<400> SEQUENCE: 69

Met Asp Ser Ala Ser Gly Gly Ser Asp Asn Ser Ile Lys Glu Ala Ile
1               5                   10                  15

Pro Ala Thr Ala Ser Ala Leu Leu Ser Ala Ala Ser Gln Gln Gly Gly
            20                  25                  30

Gly Gly Gly Ser Glu Ser Ser Pro Ser Pro Ala Pro Pro Ser Arg Tyr
        35                  40                  45

Glu Ser Gln Lys Arg Arg Asp Trp Asn Thr Phe Leu Gln Tyr Leu Thr
    50                  55                  60

Asn His Lys Pro Pro Leu Thr Leu Ala Arg Cys Ser Gly Ala His Val
65                  70                  75                  80

Ile Glu Phe Leu Lys Tyr Leu Asp Gln Phe Gly Lys Thr Lys Val His
                85                  90                  95

Ile Thr Asp Cys Pro Tyr Phe Gly His Val Asn Pro Ala Pro Cys
            100                 105                 110

Ala Cys Pro Leu Lys Gln Ala Trp Gly Ser Leu Asp Ala Leu Ile Gly
        115                 120                 125

Arg Leu Arg Ala Ala Tyr Glu Glu Asn Gly Gly Arg Pro Glu Ser Asn
    130                 135                 140

Pro Phe Gly Ala Arg Ala Val Arg Ile Tyr Leu Arg Glu Val Arg Glu
145                 150                 155                 160

Gly Gln Ala Lys Ala Arg Gly Ile Pro Tyr Glu Lys Lys Arg Lys
                165                 170                 175

Arg Pro Thr Val Thr Thr Thr Ala Val Gly Val Asn Val Ser Arg Thr
            180                 185                 190

Ser Thr Gln Pro Val Asp Gly Gly Gly Arg Gly Ile Gly Gly
        195                 200                 205
```

```
Gly Asp Asp Ser Val Gly Ala Lys Thr Gly Ala Asn Val Gly Ser Ala
    210                 215                 220

Thr Ala Val Ala Ala Ala Thr Thr Asn Ser Val
225                 230                 235

<210> SEQ ID NO 70
<211> LENGTH: 1108
<212> TYPE: DNA
<213> ORGANISM: Gossypium hirsutum
<220> FEATURE:
<221> NAME/KEY: misc_feature
<222> LOCATION: (1)..(1108)
<223> OTHER INFORMATION: Ceres CLONE ID no.1919054
<220> FEATURE:
<221> NAME/KEY: misc_feature
<222> LOCATION: (1)..(1108)
<223> OTHER INFORMATION: Encodes the peptide sequence at SEQ ID NO:71

<400> SEQUENCE: 70
cccacagttc tagcagtaca gcacaaaaat aatcttatct aacaactact atttatgcaa      60
tttgttcact agctaattta ctccttcaca taatcctaca tttctaagca tcattgcatt     120
caaaaaaaca aaataaaggt ttcagtcttt tgtgtcctaa ttttctcgac ctactttctt     180
ctccaaagtt gcagtcaaaa tgttgagtac aaatgcgatt agaaccatcg ttgggatcat     240
cggaaatatc atctccttat tcctgtttct ctcgcccgtc cccacattta ttaaaatatt     300
taaattgaaa tccgtggaag agttcaagcc ggatccatat gtagcaacaa tcttgaactg     360
tgccatgtgg gtgttctatg gtctccccat tgtccatccc gacagtcttt taatcattac     420
catcaatggt gttggcctgg tgattgaggg cgtcttcgta accatcttct ttatcttctc     480
taacaacaag aagcgaaaga ggatttgctt ttatcttttg atcgaaatca tcttcatggc     540
agctgtagtt ttgattactt tacttgtgtt ccaaacaacc caaaaaaggt ccatgtttgt     600
tggaattttg gccattgtct tcaacattgg aatgtacact tcaccattga cagtcatgcg     660
tatggtgatt aagacaaaaa gcgtcaagta catgcccttc actctctccc tttttaactt     720
cttaaatgga gttgtttggg tgatttatgc attactcaaa tttgatatta acgtcttgat     780
tccgaatggc ttgggaaccc tgtcaggttt ggtgcagctt atactttatg catggttcta     840
tagaactacc aaatgggatg aagatgataa agcaccagct caacaagttc aactttccga     900
gatttgatga tgacgccatc aaattttatt tctctttatc ctcctttcaa gtggatttgt     960
cgttcttgtt tgtctatcat tcccaggttt ttagattttc gtagacaaaa aatctgtaca    1020
acaaatattt tcttgccagt atttcgattc cactttaatt gcagaaaatg tttggttccc    1080
gttcctacaa aaaaaaaaaa aaaaaaaa                                       1108

<210> SEQ ID NO 71
<211> LENGTH: 235
<212> TYPE: PRT
<213> ORGANISM: Gossypium hirsutum
<220> FEATURE:
<221> NAME/KEY: misc_feature
<222> LOCATION: (1)..(235)
<223> OTHER INFORMATION: Ceres CLONE ID no. 1919054
<220> FEATURE:
<221> NAME/KEY: misc_feature
<222> LOCATION: (132)..(218)
<223> OTHER INFORMATION: Pfam Name: MtN3_slv
    Pfam Description: MtN3/saliva family

<400> SEQUENCE: 71

Met Leu Ser Thr Asn Ala Ile Arg Thr Ile Val Gly Ile Ile Gly Asn
1               5                   10                  15
```

```
Ile Ile Ser Leu Phe Leu Phe Leu Ser Pro Val Pro Thr Phe Ile Lys
            20                  25                  30

Ile Phe Lys Leu Lys Ser Val Glu Glu Phe Lys Pro Asp Pro Tyr Val
        35                  40                  45

Ala Thr Ile Leu Asn Cys Ala Met Trp Val Phe Tyr Gly Leu Pro Ile
    50                  55                  60

Val His Pro Asp Ser Leu Leu Ile Ile Thr Ile Asn Gly Val Gly Leu
65                  70                  75                  80

Val Ile Glu Gly Val Phe Val Thr Ile Phe Phe Ile Phe Ser Asn Asn
                85                  90                  95

Lys Lys Arg Lys Arg Ile Cys Phe Tyr Leu Leu Ile Glu Ile Ile Phe
            100                 105                 110

Met Ala Ala Val Val Leu Ile Thr Leu Leu Val Phe Gln Thr Thr Gln
            115                 120                 125

Lys Arg Ser Met Phe Val Gly Ile Leu Ala Ile Val Phe Asn Ile Gly
        130                 135                 140

Met Tyr Thr Ser Pro Leu Thr Val Met Arg Met Val Ile Lys Thr Lys
145                 150                 155                 160

Ser Val Lys Tyr Met Pro Phe Thr Leu Ser Leu Phe Asn Phe Leu Asn
                165                 170                 175

Gly Val Val Trp Val Ile Tyr Ala Leu Leu Lys Phe Asp Ile Asn Val
            180                 185                 190

Leu Ile Pro Asn Gly Leu Gly Thr Leu Ser Gly Leu Val Gln Leu Ile
        195                 200                 205

Leu Tyr Ala Trp Phe Tyr Arg Thr Thr Lys Trp Asp Glu Asp Asp Lys
    210                 215                 220

Ala Pro Ala Gln Gln Val Gln Leu Ser Glu Ile
225                 230                 235

<210> SEQ ID NO 72
<211> LENGTH: 1014
<212> TYPE: DNA
<213> ORGANISM: Gossypium hirsutum
<220> FEATURE:
<221> NAME/KEY: misc_feature
<222> LOCATION: (1)..(1014)
<223> OTHER INFORMATION: Ceres CLONE ID no.1919714
<220> FEATURE:
<221> NAME/KEY: misc_feature
<222> LOCATION: (1)..(1014)
<223> OTHER INFORMATION: Encodes the peptide sequence at SEQ ID NO:73

<400> SEQUENCE: 72
gagcgcgttc cctcttctct agaaactgct gctgtttttt tttcatcctt ttaactcagt      60
ccctgaaaat tgagccgtta acgtcaaccc gattcaggcg gaaccgtttc ctcactcaaa     120
atcctcgcac aaactcagca gttaattaaa cacttcataa agttgagtcg ctttattagc     180
acagttgccg ttatagtgat aatcaaaggt gttgattctg taggaagaag gaaaaaagta     240
atggagaaat ctgttttttgt aaagatgta caacaactca atggaaatct ccaccattct     300
ttttcctctg tttctcaaag agatgtaact tacagctgtg gttcttgtgg gtatgagcta     360
aacctaagtt cctctagtag aaacaccgca acaatcggct ctaaatatgg aaaattgatt     420
aagcgaggga tgatatcatt cttcaatata gacgagacca gatttacgca ggtcgatgaa     480
ttccaatgca gaccctactt ttcgaagcac tcatggggtt tattccgcca tagaaccaaa     540
ttactttgtc gcaagtgtgg gaaccacatt ggcgatgctt atgatgataa atcttctggc     600
taccctcatg tcttagatgg ttctgattca tcctccggca ctgaaccttc taaccataga     660
```

-continued

```
aaatatgatg ttagaatccg tgccctacag ccttcgactg ctgaaggact cggctctcca      720 cttttttgcgt gatttcctgc agtgcatcat tgatggtctt cggttttgaat tatcaacgac    780 tgactgagcg ttttcgtatg ggattattgc tgtctattag ttggtttgag tcttccattt      840
tatgctgtct ttgctgtgtt tctgttaagt gtatatatga aaggtaagta atgtggagct      900
ttaaaatgag gttgagcaca gtaatgtcat tacccaaatt taagtgtaat atctgtttga      960
gttgaattaa atcaagtatt tttcttttgg ccttaaaaaa aaaaaaaaaa aaaa           1014
```

<210> SEQ ID NO 73
<211> LENGTH: 163
<212> TYPE: PRT
<213> ORGANISM: Gossypium hirsutum
<220> FEATURE:
<221> NAME/KEY: misc_feature
<222> LOCATION: (1)..(163)
<223> OTHER INFORMATION: Ceres CLONE ID no. 1919714

<400> SEQUENCE: 73

```
Met Glu Lys Ser Val Phe Val Lys Asp Val Gln Gln Leu Asn Gly Asn
1               5                  10                  15

Leu His His Ser Phe Ser Ser Val Ser Gln Arg Asp Val Thr Tyr Ser
            20                  25                  30

Cys Gly Ser Cys Gly Tyr Glu Leu Asn Leu Ser Ser Ser Arg Asn
        35                  40                  45

Thr Ala Thr Ile Gly Ser Lys Tyr Gly Lys Leu Ile Lys Arg Gly Met
    50                  55                  60

Ile Ser Phe Phe Asn Ile Asp Glu Thr Arg Phe Thr Gln Val Asp Glu
65                  70                  75                  80

Phe Gln Cys Arg Pro Tyr Phe Ser Lys His Ser Trp Gly Leu Phe Arg
                85                  90                  95

His Arg Thr Lys Leu Leu Cys Arg Lys Cys Gly Asn His Ile Gly Asp
            100                 105                 110

Ala Tyr Asp Asp Lys Ser Ser Gly Tyr Pro His Val Leu Asp Gly Ser
        115                 120                 125

Asp Ser Ser Ser Gly Thr Glu Pro Ser Asn His Arg Lys Tyr Asp Val
    130                 135                 140

Arg Ile Arg Ala Leu Gln Pro Ser Thr Ala Glu Gly Leu Gly Ser Pro
145                 150                 155                 160

Leu Phe Ala
```

<210> SEQ ID NO 74
<211> LENGTH: 2071
<212> TYPE: DNA
<213> ORGANISM: Gossypium hirsutum
<220> FEATURE:
<221> NAME/KEY: misc_feature
<222> LOCATION: (1)..(2071)
<223> OTHER INFORMATION: Ceres CLONE ID no.1920752
<220> FEATURE:
<221> NAME/KEY: misc_feature
<222> LOCATION: (1)..(2071)
<223> OTHER INFORMATION: Encodes the peptide sequence at SEQ ID NO:75

<400> SEQUENCE: 74

```
aacttgaaga gactcaaatc agagctctag ttgtgaagaa atataatcca ggtttgcttt       60
agtccacaag tagatgggcc tactcccttg aacatcttgc agatgggaga tgtcataact      120
atacttagca tagaacaact ttcttactaa atctctcttc tattttattt catttcttct      180
ctctgctact tttcatcctt tggtttcttg tataaatagc gtttccccctt tctttttttca    240
```

```
tgttgtttga tatagctttc taaggcaatc tttgggattt cccaaaccag gattttagtt    300
gtcttcacac tgaactttgc tattgttaag tctttttcat tttctttctg tagttttgtg    360
catcttgttt agttgtactg gaaagtggaa acggttttct tgggggtcat tttctcactc    420
gtattttgt tttattgcag caaatatttt atttgaatct cgagaactcc atggctatgg     480
taacattaac atcaaattac aacacaaacc tgtcgcaaac attgtccttt gaggaaaaaa    540
atagcagcct tcgtgatgtt tctttctcta ctttcttcga tggtgctgac gaaaactatg    600
aaagagaact ttcggcttca aaccgagagc tcagctccaa gacaaccaac accaaccaag    660
atgagcatca ttatttagga ctgaagaaag aagatggaga aattggagta tttggagctg    720
aaaaatactt caatggagga attgatttag aaagtccaag aataaacaaa atacatgcaa    780
aaacattgga atgcgttaaa gatggtagag tcagcataga gcctgtcaag cctgtaatat    840
atcagggaac tccaagtgtt cgatcagaat caagctggaa cagccgaagt gcattgctcc    900
gaagtactat gagaaatcct cctgggaaaa aacctcctaa agtgaatgga aagagttttc    960
tttcgggtct tgctggctgc aaatgttact gttctggtag aaattcagtt gagattgaag   1020
aagcacaagt tggtgaaata agtttcaaga gaccagctgc taatggagag ggcttgcaag   1080
gcaagccaaa taaaactgca tccagtaagg cgagcctaga ggttaataaa ccagtggcgg   1140
aaccctggac gaaggaagac attttttagtt tcccaactat gaattctaat aagggaattc   1200
gacctgttaa agtgtcactg caaggagatg tggatgaaat cggacggaaa tcattggagg   1260
ttttcggctc gccggcactt ggaaggagaa acaagtcttt gaacatcgag aggaggctgc   1320
aaatgttctc tctggattct aatcccaaag cagaaaaaat tgaaaatcct aaaggcaact   1380
acaacgatac agagagcgat gcaagttcag acttatttga gatagagagc ctcacaggaa   1440
aagtcaaccc atttcttgtc aaacaaattt ctgatgcggc gtctgggtgt gccaccccaa   1500
caacttgtta tgcaccaagt gaggccagca tagagtggag tgtggtcaca gcaagtgcag   1560
cagatttctc agtcatgtct gactatgaag agctaaggcc acctgtaact tttccaagcc   1620
caatgagaac atatccgaca cccaccaaaa ccaaaggttc taaaaacaag ggccgttcca   1680
gtggtctatt ggggtgtaac agccaaaaag ctgttgaagt tgctggagat acacacaaaa   1740
caaatgacaa ggcaggtttt gacccaagaa tgcgcagtgt gtctgattcc tacatacctg   1800
caacaagatt tggagctggt actaaacttg ctgcggcttt tcaacctact cattcagcag   1860
gagcttcaca tctcttgttt attcagtagc ttttaatagc tttccctgga ccttattttg   1920
tacaacttgt gatgggaaat ttcactacta taccttatgt ttcttttgta tccgtagtag   1980
tgttgaattc cgtaagtgat gctaatttt tagaaagtaa atccaaaaag ttcatggggg   2040
gtcatttgtt taaaaaaaaa aaaaaaaaa a                                  2071
```

<210> SEQ ID NO 75
<211> LENGTH: 472
<212> TYPE: PRT
<213> ORGANISM: Gossypium hirsutum
<220> FEATURE:
<221> NAME/KEY: misc_feature
<222> LOCATION: (1)..(472)
<223> OTHER INFORMATION: Ceres CLONE ID no. 1920752

<400> SEQUENCE: 75

Met Ala Met Val Thr Leu Thr Ser Asn Tyr Asn Thr Asn Leu Ser Gln
1               5                   10                  15

Thr Leu Ser Phe Glu Glu Lys Asn Ser Ser Leu Arg Asp Val Ser Phe
            20                  25                  30

```
Ser Thr Phe Phe Asp Gly Ala Asp Glu Asn Tyr Glu Arg Glu Leu Ser
         35                  40                  45

Ala Ser Asn Arg Glu Leu Ser Ser Lys Thr Thr Asn Thr Asn Gln Asp
 50                  55                  60

Glu His His Tyr Leu Gly Leu Lys Lys Glu Asp Gly Glu Ile Gly Val
 65                  70                  75                  80

Phe Gly Ala Glu Lys Tyr Phe Asn Gly Gly Ile Asp Leu Glu Ser Pro
                 85                  90                  95

Arg Ile Asn Lys Ile His Ala Lys Thr Leu Glu Cys Val Lys Asp Gly
             100                 105                 110

Arg Val Ser Ile Glu Pro Val Lys Pro Val Ile Tyr Gln Gly Thr Pro
         115                 120                 125

Ser Val Arg Ser Glu Ser Ser Trp Asn Ser Arg Ser Ala Leu Leu Arg
     130                 135                 140

Ser Thr Met Arg Asn Pro Pro Gly Lys Lys Pro Pro Lys Val Asn Gly
145                 150                 155                 160

Lys Ser Phe Leu Ser Gly Leu Ala Gly Cys Lys Cys Tyr Cys Ser Gly
                 165                 170                 175

Arg Asn Ser Val Glu Ile Glu Glu Ala Gln Val Gly Glu Ile Ser Phe
             180                 185                 190

Lys Arg Pro Ala Ala Asn Gly Glu Gly Leu Gln Gly Lys Pro Asn Lys
         195                 200                 205

Thr Ala Ser Ser Lys Ala Ser Leu Glu Val Asn Lys Pro Val Ala Glu
     210                 215                 220

Pro Trp Thr Lys Glu Asp Ile Phe Ser Phe Pro Thr Met Asn Ser Asn
225                 230                 235                 240

Lys Gly Ile Arg Pro Val Lys Val Ser Leu Gln Gly Asp Val Asp Glu
                 245                 250                 255

Ile Gly Arg Lys Ser Leu Glu Val Phe Gly Ser Pro Ala Leu Gly Arg
             260                 265                 270

Arg Asn Lys Ser Leu Asn Ile Glu Arg Arg Leu Gln Met Phe Ser Leu
         275                 280                 285

Asp Ser Asn Pro Lys Ala Glu Lys Ile Glu Asn Pro Lys Gly Asn Tyr
     290                 295                 300

Asn Asp Thr Glu Ser Asp Ala Ser Ser Asp Leu Phe Glu Ile Glu Ser
305                 310                 315                 320

Leu Thr Gly Lys Val Asn Pro Phe Leu Val Lys Gln Ile Ser Asp Ala
                 325                 330                 335

Ala Ser Gly Cys Ala Thr Pro Thr Thr Cys Tyr Ala Pro Ser Glu Ala
             340                 345                 350

Ser Ile Glu Trp Ser Val Val Thr Ala Ser Ala Asp Phe Ser Val
         355                 360                 365

Met Ser Asp Tyr Glu Glu Leu Arg Pro Pro Val Thr Phe Pro Ser Pro
     370                 375                 380

Met Arg Thr Tyr Pro Thr Pro Thr Lys Thr Lys Gly Ser Lys Asn Lys
385                 390                 395                 400

Gly Arg Ser Ser Gly Leu Leu Gly Cys Asn Ser Gln Lys Ala Val Glu
                 405                 410                 415

Val Ala Gly Asp Thr His Lys Thr Asn Asp Lys Ala Gly Phe Asp Pro
             420                 425                 430

Arg Met Arg Ser Val Ser Asp Ser Tyr Ile Pro Ala Thr Arg Phe Gly
         435                 440                 445

Ala Gly Thr Lys Leu Ala Ala Ala Phe Gln Pro Thr His Ser Ala Gly
```

```
                450                 455                 460
Ala Ser His Leu Leu Phe Ile Gln
465                 470

<210> SEQ ID NO 76
<211> LENGTH: 2216
<212> TYPE: DNA
<213> ORGANISM: Gossypium hirsutum
<220> FEATURE:
<221> NAME/KEY: misc_feature
<222> LOCATION: (1)..(2216)
<223> OTHER INFORMATION: Ceres CLONE ID no.1924114
<220> FEATURE:
<221> NAME/KEY: misc_feature
<222> LOCATION: (1)..(2216)
<223> OTHER INFORMATION: Encodes the peptide sequence at SEQ ID NO:77

<400> SEQUENCE: 76
gtgagcttag cggagaaaag agtcagaaaa atctgcaaca cagtttagtt tcaattatta     60
cagcaaaaac cagtcatctt cccattctcc acccctatta tcactaccac cacacttctc   120
tcatagtcat tcgccataaa agaaacagta acaaagattt tgttttttg agtttgagtg    180 tttgttttag tttgaaagtg agtgacagac attattagat tattgaaata tgtttatata   240
tatatatata tagtttctgt aataaataaa taaaaaaaaa gattcgtcaa agtgaaaaac   300
gtgcatcgat accccaaaaa tctcagttcc ttgaacgtat catactctgc taacttgcgc   360
cacttctctc tcttttctct gccattttaa tattttccca gtttcagaag attacaatca   420
tttcatcgtt taaattaatc aaataaagct ttttcacttt cactgttatt tagttttag    480 cttatagaga agttgtttgt tggttttttt tttcttttct tttgcttctt tttttagggc   540
tatggcggag ggttttgagc cctaccatgt cccacaacaa agcagaagag ataagctaag   600
aatcatgggt caaaatgaac caacaacggg tgttcctctt tcgggttgtt cgggtttact   660
ccctttttat gacccttctt tccttcttc cgatttgcta acttgcgccg ctgccgccgc   720
cggaagccat gaatatcacc accctcctcc gtcgggtaca aaagatggcg tgaacttcac   780
aggctttgtt ggtggggttt tcaactcttc tccttctttg gatcacttga acctagctc    840 cattcatgat gtggacaaca caacaacaa caaccagttt cttataccc cacaaaacct    900 gtcttatgat aataataacg gtggtggtgg gggtggtgaa gtggtggttt ataagcctga   960
acctttatct ctttcattat cttctcatta tacccaccaa aactctagta tctatactga  1020
tatggttcca gccatttta gtggtgctaa tggttcaaca tcgaactcag tcccactcgg   1080
tcctttcact ggctatgctt ccattttgaa aggttcaagg tttttaaggc ctgcacaaca   1140
gttattagaa gagctttgtg atgttggtaa gggaatttac actgaaaaag catctctcat  1200
ggagcttcct ccattgcaaa atccccacac taaccctctt gacggcggag atagcagcgg   1260
aagcggcggc ggaggtgatg gtcaaaggaa aaaatcaaca ctaatttcaa ttctcgacga   1320
ggtttacaag aggtacaagc aatactatca gcagatgcaa tccgttgtcg cttcgtttga   1380
atgtgtcgcc ggactaggga atgcagctcc atttgcaaac ttggctatga aagctatgtc   1440
taaacatttc aggtacttga gaacgcaat caccgaacag cttcagttta ctaataaagc    1500
tcatgctcag ataagcccc ggaaaaacga aggtccgagg ttcggaaatg gtgatggaag   1560 ctttttataac cgagctgttc aaaactccgg gttccttcaa aaccaaccag tttggcgtcc   1620
tcaacgaggc cttcccgaac gtgcagtgac cgtacttaga gcatggctat ttgaacactt   1680
tctacaccct tatccgaccg acacggacaa gctaatgttg gcgaaacaaa ccggtctttc   1740
acgtaaccag gtctcgaatt ggtttatcaa tgcaagagtt cggctttgga aaccaatggt   1800
```

-continued

```
ggaagaaata cacatgctcg aaacacggca aaaggacgag agaaatgcca acaagtcagg    1860
cgatgaaaac ccatcgacat cagcccaaag ggttgaagac aagacgccat caaagcgtac    1920
tagaaatgaa cttcccaatg tacctgtggg aaatgaacag ccaaacatgt caacctccta    1980
caacagcttt tctacccacc cgcatagcag cagtgtttcc ttaacactcg gtcttcatca    2040
gaacaacagt atcggattat cggagtcctt tcccataaac gcggctcaat gtttcggtct    2100
tggcatcgag ggaaacagtg agggatacgt tattggtggt cggcatttcg gaagggatgt    2160
tgtcggaggg cagcttttgc atgatttttgt gggttgaaaa aaaaaatgtt acaagc       2216
```

```
<210> SEQ ID NO 77
<211> LENGTH: 551
<212> TYPE: PRT
<213> ORGANISM: Gossypium hirsutum
<220> FEATURE:
<221> NAME/KEY: misc_feature
<222> LOCATION: (1)..(551)
<223> OTHER INFORMATION: Ceres CLONE ID no. 1924114
<220> FEATURE:
<221> NAME/KEY: misc_feature
<222> LOCATION: (253)..(288)
<223> OTHER INFORMATION: Pfam Name: Transposase_30
      Pfam Description: Bacillus transposase protein
<220> FEATURE:
<221> NAME/KEY: misc_feature
<222> LOCATION: (382)..(417)
<223> OTHER INFORMATION: Pfam Name: Homeobox
      Pfam Description: Homeobox domain

<400> SEQUENCE: 77

Met Ala Glu Gly Phe Glu Pro Tyr His Val Pro Gln Gln Ser Arg Arg
1               5                   10                  15

Asp Lys Leu Arg Ile Met Gly Gln Asn Glu Pro Thr Thr Gly Val Pro
            20                  25                  30

Leu Ser Gly Cys Ser Gly Leu Leu Pro Phe Tyr Asp Pro Ser Phe Leu
        35                  40                  45

Ser Ser Asp Leu Leu Thr Cys Ala Ala Ala Ala Gly Ser His Glu
    50                  55                  60

Tyr His His Pro Pro Pro Ser Gly Thr Lys Asp Gly Val Asn Phe Thr
65                  70                  75                  80

Gly Phe Val Gly Gly Val Phe Asn Ser Ser Pro Ser Leu Asp His Leu
                85                  90                  95

Asn Pro Ser Ser Ile His Asp Val Asp Asn Asn Asn Asn Asn Asn Gln
            100                 105                 110

Phe Leu Tyr Thr Pro Gln Asn Leu Ser Tyr Asp Asn Asn Gly Gly
        115                 120                 125

Gly Gly Gly Gly Glu Val Val Val Tyr Lys Pro Glu Pro Leu Ser Leu
    130                 135                 140

Ser Leu Ser Ser His Tyr Thr His Gln Asn Ser Ser Ile Tyr Thr Asp
145                 150                 155                 160

Met Val Pro Ala Ile Phe Ser Gly Ala Asn Gly Ser Thr Ser Asn Ser
                165                 170                 175

Val Pro Leu Gly Pro Phe Thr Gly Tyr Ala Ser Ile Leu Lys Gly Ser
            180                 185                 190

Arg Phe Leu Arg Pro Ala Gln Gln Leu Leu Glu Leu Cys Asp Val
        195                 200                 205

Gly Lys Gly Ile Tyr Thr Glu Lys Ala Ser Leu Met Glu Leu Pro Pro
    210                 215                 220

Leu Gln Asn Pro His Thr Asn Pro Leu Asp Gly Gly Asp Ser Ser Gly
```

```
                225                 230                 235                 240
Ser Gly Gly Gly Asp Gly Gln Arg Lys Lys Ser Thr Leu Ile Ser
                    245                 250                 255

Ile Leu Asp Glu Val Tyr Lys Arg Tyr Lys Gln Tyr Tyr Gln Gln Met
                260                 265                 270

Gln Ser Val Val Ala Ser Phe Glu Cys Val Ala Gly Leu Gly Asn Ala
            275                 280                 285

Ala Pro Phe Ala Asn Leu Ala Met Lys Ala Met Ser Lys His Phe Arg
        290                 295                 300

Tyr Leu Lys Asn Ala Ile Thr Glu Gln Leu Gln Phe Thr Asn Lys Ala
305                 310                 315                 320

His Ala Gln Ile Ser Pro Gly Lys Asn Glu Gly Pro Arg Phe Gly Asn
                325                 330                 335

Gly Asp Gly Ser Phe Tyr Asn Arg Ala Val Gln Asn Ser Gly Phe Leu
                340                 345                 350

Gln Asn Gln Pro Val Trp Arg Pro Gln Arg Gly Leu Pro Glu Arg Ala
                355                 360                 365

Val Thr Val Leu Arg Ala Trp Leu Phe Glu His Phe Leu His Pro Tyr
370                 375                 380

Pro Thr Asp Thr Asp Lys Leu Met Leu Ala Lys Gln Thr Gly Leu Ser
385                 390                 395                 400

Arg Asn Gln Val Ser Asn Trp Phe Ile Asn Ala Arg Val Arg Leu Trp
                405                 410                 415

Lys Pro Met Val Glu Glu Ile His Met Leu Glu Thr Arg Gln Lys Asp
                420                 425                 430

Glu Arg Asn Ala Asn Lys Ser Gly Asp Glu Asn Pro Ser Thr Ser Ala
            435                 440                 445

Gln Arg Val Glu Asp Lys Thr Pro Ser Lys Arg Thr Arg Asn Glu Leu
        450                 455                 460

Pro Asn Val Pro Val Gly Asn Glu Gln Pro Asn Met Ser Thr Ser Tyr
465                 470                 475                 480

Asn Ser Phe Ser Thr His Pro His Ser Ser Val Ser Leu Thr Leu
                485                 490                 495

Gly Leu His Gln Asn Asn Ser Ile Gly Leu Ser Glu Ser Phe Pro Ile
                500                 505                 510

Asn Ala Ala Gln Cys Phe Gly Leu Gly Ile Glu Gly Asn Ser Glu Gly
            515                 520                 525

Tyr Val Ile Gly Gly Arg His Phe Gly Arg Asp Val Val Gly Gly Gln
        530                 535                 540

Leu Leu His Asp Phe Val Gly
545                 550

<210> SEQ ID NO 78
<211> LENGTH: 1590
<212> TYPE: DNA
<213> ORGANISM: Gossypium hirsutum
<220> FEATURE:
<221> NAME/KEY: misc_feature
<222> LOCATION: (1)..(1590)
<223> OTHER INFORMATION: Ceres CLONE ID no.1942354
<220> FEATURE:
<221> NAME/KEY: misc_feature
<222> LOCATION: (1)..(1590)
<223> OTHER INFORMATION: Encodes the peptide sequence at SEQ ID NO:79

<400> SEQUENCE: 78
gttttggatc caaaaagcct ctccttctct cttcgattag atctagaaaa gagcgtcttc     60
```

```
tctcttcaaa ccctaatctg tgaatcgtcc ctctttaat tagcttttt ctttttcaaa      120
tatttttcgg ttttggcgg gataaattcg gggttttcat taatatcgcc caaagatttt      180
agagttaaaa attattaatt ttttttccgt ttcttgatcc gatcccgatc ttattcgagc      240
tagggttacg ttttccgtt tattgttgtt gttggtgaat caacagatgt ctcggtgttt      300
tccgtatcct ccaccggggt acgtaaagaa cggaatccgc gatgaggcac taattgaatc      360
gattaagatt aagagagaag aagagaaggc caagaaggaa aggaagaaag aaaagaagga      420
gaagaaagag aaaaaacggg agaagaaaga aagagataag tctcgggaca gtggtgaagc      480
tgaaagtaaa aagcgtggtc ataagaaaag gcataaagac gagaggagca aagaagatca      540
aaaaggagga gaccgtcaaa agaaaagaga gaatgaagtg gaatgttttg agaagagtac      600
gcttactgaa gaacatggtc aggcggttgg accacagaac tcttccgata gcacccttaa      660
cagcagtaaa agacagaagc tgagctcgcc tccagacagt gggcaaaatc ctggaagcat      720
tatccggatc cgattgcctt cccaaaggca taaagatcct gaagtgctac ccagcaagga      780
acagccttgc tctacctcag gaaacactga tgaggccttt gttcaacggg tgcatgagca      840
tgctcctaga ccaggcaaag aactggaaga acaaccttgg tcgacttcag atattaaacg      900
cccggagcta actttcaagc tcggcaaaga aaaagcttgc tcctcttctc gcacatcaga      960
aactcttgct cataatgcca aggtgccaac gctgtcaaac ttgtgtacca cttgccctac     1020
gaaattagct ttacaattca aaaccttgt ggaggattgg gttatgccta cactgcaaag     1080
cgagtcaacc agttctggcg atgatgactg gctggttcag aagaagcaaa acctcaacac     1140
tgaggttaaa acccacaaag atggaaatct taactctaac caaatgagct cggcaacttg     1200
gccacgtgct tgcttcttgc ccgaggccga tatatacgca ttaccattca cggtaccgtt     1260
ctgaactata ttttgcatag gagaaaaagg catgcaaagt gtgagaaact agaaaaaaaa     1320
tagtggttaa ttttagttca tggtgctgaa agtgtgaagg gtttgttgcc agcatttcag     1380
ctccttaatt tcgtttcaat gttgggaatt aggaccccca atttgaggag aggataaatt     1440
ttgtgcggcg accccttaga aaaagaaaa aaaagatggc tactgagggc ttttcttt       1500
taaaccatta ttggtgaaaa aagagaaaga ggttattgat gtattacaaa attcaattct     1560
ttctagtaat atgggtatcg ctctttgttc                                    1590
```

<210> SEQ ID NO 79
<211> LENGTH: 325
<212> TYPE: PRT
<213> ORGANISM: Gossypium hirsutum
<220> FEATURE:
<221> NAME/KEY: misc_feature
<222> LOCATION: (1)..(325)
<223> OTHER INFORMATION: Ceres CLONE ID no. 1942354

<400> SEQUENCE: 79

```
Met Ser Arg Cys Phe Pro Tyr Pro Pro Gly Tyr Val Lys Asn Gly
1               5                   10                  15

Ile Arg Asp Glu Ala Leu Ile Glu Ser Ile Lys Ile Lys Arg Glu Glu
            20                  25                  30

Glu Lys Ala Lys Lys Glu Arg Lys Glu Lys Lys Glu Lys Glu
        35                  40                  45

Lys Lys Arg Glu Lys Lys Glu Arg Asp Lys Ser Arg Asp Ser Gly Glu
    50                  55                  60

Ala Glu Ser Lys Lys Arg Gly His Lys Lys Arg His Lys Asp Glu Arg
65                  70                  75                  80

Ser Lys Glu Asp Gln Lys Gly Gly Asp Arg Gln Lys Lys Arg Glu Asn
```

```
                      85                  90                  95
Glu Val Glu Cys Phe Glu Lys Ser Thr Leu Thr Glu Glu His Gly Gln
                100                 105                 110
Ala Val Gly Pro Gln Asn Ser Ser Asp Ser Thr Leu Asn Ser Ser Lys
            115                 120                 125
Arg Gln Lys Leu Ser Ser Pro Pro Asp Ser Gly Gln Asn Pro Gly Ser
        130                 135                 140
Ile Ile Arg Ile Arg Leu Pro Ser Gln Arg His Lys Asp Pro Glu Val
145                 150                 155                 160
Leu Pro Ser Lys Glu Gln Pro Cys Ser Thr Ser Gly Asn Thr Asp Glu
                165                 170                 175
Ala Phe Val Gln Arg Val His Glu His Ala Pro Arg Pro Gly Lys Glu
            180                 185                 190
Leu Glu Glu Gln Pro Trp Ser Thr Ser Asp Ile Lys Arg Pro Glu Leu
        195                 200                 205
Thr Phe Lys Leu Gly Lys Glu Lys Ala Cys Ser Ser Arg Thr Ser
210                 215                 220
Glu Thr Leu Ala His Asn Ala Lys Val Pro Thr Leu Ser Asn Leu Cys
225                 230                 235                 240
Thr Thr Cys Pro Thr Lys Leu Ala Leu Gln Phe Lys Asn Leu Val Glu
                245                 250                 255
Asp Trp Val Met Pro Thr Leu Gln Ser Glu Ser Thr Ser Ser Gly Asp
            260                 265                 270
Asp Asp Trp Leu Val Gln Lys Lys Gln Asn Leu Asn Thr Glu Val Lys
        275                 280                 285
Thr His Lys Asp Gly Asn Leu Asn Ser Asn Gln Met Ser Ser Ala Thr
    290                 295                 300
Trp Pro Arg Ala Cys Phe Leu Pro Glu Ala Asp Ile Tyr Ala Leu Pro
305                 310                 315                 320
Phe Thr Val Pro Phe
            325

<210> SEQ ID NO 80
<211> LENGTH: 1160
<212> TYPE: DNA
<213> ORGANISM: Zea mays
<220> FEATURE:
<221> NAME/KEY: misc_feature
<222> LOCATION: (1)..(1160)
<223> OTHER INFORMATION: Ceres CLONE ID no.237610
<220> FEATURE:
<221> NAME/KEY: misc_feature
<222> LOCATION: (1)..(1160)
<223> OTHER INFORMATION: Encodes the peptide sequence at SEQ ID NO:81

<400> SEQUENCE: 80
agggactcgc ggttcgtggc ggccctggcc agagtctgcg cccgctcctg cccccgcccc      60
gggccaggcc accctcgcct cctcgcgcct ataaagtgcg ggcgtacggc gtacccgatt     120
gccccaagcc gcaacctcaa ccaccttccc aaatctcagt agtcgcctct cgtcgtcttc     180
gtctagcccg gcccgttcca aaacctccgt agccgccgcc gccaccccgg cgaccgaaga     240
tgatctcccc ggacgcagcc cgcaacgtag tcggcatcat cggcaatgtc atctccttcg     300
gcctcttcct gtcccccagtg ctgacgttct ggcggatcta caaggccaag gacgtggagg     360
agttcaagcc ggacccttac ctggcgacgc tgctcaactg catgctctgg gtgttctatg     420
gcatccccgt cgtccacccc aacagcattc tcgtcgtcac catcaacggc atcggcctcg     480
tcatcgaggc cgtctaccte actatcttct tcctctattc cgacagccag aagcgcaaga     540
```

```
aggcgttcgc gatcctggcc gtggagattc tgttcatggt cgccgtggtg ctcggtgtga    600
tcctcggcgc gcacactcac gagaaacgtt ccatgatcgt cggcatcctc tgcgtcatct    660
tcggctcgat gatgtacgcc tcaccactca ctatcatgag tcgagtgatc aagaccaaga    720
gcgttgagta catgcccttc ctcctgtcgc tggtgagctt cctcaacggc tgctgctgga    780
cggcctacgc gctcatccgc ttcgacctct acgtcacgat cccgaacgcc ctgggcgcat    840
tcttcggcct cgtccagctg atcctctact tctgctacta caagtcgacc cccaagaagg    900
agaagaacgt ggagctgccc accgtctcca gcaacgtcgg cggcggcaac gtcaccgtca    960
gcgttgagcg atagatgatg tagctgccgc cgcccgtcga gaacgaactc gacgagacgt   1020
gctttaccca caagtagttt tggccttgtc taattgctct tctcggatga tcgtttaagt   1080
gagtgttagt tagttttgcc ctgcgtgtga tgtcaggaac aattaatata tccatgtggc   1140
tgtgtttgcc attctagatg                                               1160
```

```
<210> SEQ ID NO 81
<211> LENGTH: 244
<212> TYPE: PRT
<213> ORGANISM: Zea mays
<220> FEATURE:
<221> NAME/KEY: misc_feature
<222> LOCATION: (1)..(244)
<223> OTHER INFORMATION: Ceres CLONE ID no. 237610
<220> FEATURE:
<221> NAME/KEY: misc_feature
<222> LOCATION: (132)..(218)
<223> OTHER INFORMATION: Pfam Name: MtN3_slv
      Pfam Description: MtN3/saliva family

<400> SEQUENCE: 81

Met Ile Ser Pro Asp Ala Ala Arg Asn Val Val Gly Ile Ile Gly Asn
1               5                   10                  15

Val Ile Ser Phe Gly Leu Phe Leu Ser Pro Val Leu Thr Phe Trp Arg
            20                  25                  30

Ile Tyr Lys Ala Lys Asp Val Glu Glu Phe Lys Pro Asp Pro Tyr Leu
        35                  40                  45

Ala Thr Leu Leu Asn Cys Met Leu Trp Val Phe Tyr Gly Ile Pro Val
    50                  55                  60

Val His Pro Asn Ser Ile Leu Val Val Thr Ile Asn Gly Ile Gly Leu
65                  70                  75                  80

Val Ile Glu Ala Val Tyr Leu Thr Ile Phe Phe Leu Tyr Ser Asp Ser
                85                  90                  95

Gln Lys Arg Lys Lys Ala Phe Ala Ile Leu Ala Val Glu Ile Leu Phe
            100                 105                 110

Met Val Ala Val Val Leu Gly Val Ile Leu Gly Ala His Thr His Glu
        115                 120                 125

Lys Arg Ser Met Ile Val Gly Ile Leu Cys Val Ile Phe Gly Ser Met
    130                 135                 140

Met Tyr Ala Ser Pro Leu Thr Ile Met Ser Arg Val Ile Lys Thr Lys
145                 150                 155                 160

Ser Val Glu Tyr Met Pro Phe Leu Leu Ser Leu Val Ser Phe Leu Asn
                165                 170                 175

Gly Cys Cys Trp Thr Ala Tyr Ala Leu Ile Arg Phe Asp Leu Tyr Val
            180                 185                 190

Thr Ile Pro Asn Ala Leu Gly Ala Phe Phe Gly Leu Val Gln Leu Ile
        195                 200                 205

Leu Tyr Phe Cys Tyr Tyr Lys Ser Thr Pro Lys Lys Glu Lys Asn Val
```

```
          210                 215                 220
Glu Leu Pro Thr Val Ser Ser Asn Val Gly Gly Gly Asn Val Thr Val
225                 230                 235                 240

Ser Val Glu Arg

<210> SEQ ID NO 82
<211> LENGTH: 1185
<212> TYPE: DNA
<213> ORGANISM: Glycine max
<220> FEATURE:
<221> NAME/KEY: misc_feature
<222> LOCATION: (1)..(1185)
<223> OTHER INFORMATION: Ceres CLONE ID no.471026
<220> FEATURE:
<221> NAME/KEY: misc_feature
<222> LOCATION: (1)..(1185)
<223> OTHER INFORMATION: Encodes the peptide sequence at SEQ ID NO:83

<400> SEQUENCE: 82
attcattcag cctccctaat acttagccac atctattgca tgctctctcc cctcatctcc      60
ttcttattct ctgcaatata tcatagtgcc aaactctcat ctttctctct ctctctcaca     120
cacacaatat aagtccaccc taaacaatca ccatggcagt tgaagctagt tacatgaatc     180
tcttgccttc tcagttactc actaacagag aactcatcaa atccaatcaa cagctacagc     240
atcaattaaa ctctgattac atgtacaaca ctactaccca gatggattct tcttcagctt     300
tgcctcaacc agcaacaatg cctgaatcac tcttgtcctt ctaccaatcc aacttttgtg     360
atccaaacaa ggcagatagt ggtctcacct accatattcc tctccagaga aagcgttcaa     420
gagatttcac caccgaatta acctctctcc cagctcacca gaagaacaaa atctcctctg     480
atccttcctt tctcaaccaa gagattctct accaatttca gaaccaacaa tcggaaattg     540
atcgagtcct tgcccatcat actgagaaag tgagaatgga gctggaggaa caaaaaatga     600
ggcaatcaag gatgtttgtg agcgcaatcc aagaagcaat ggcgaagaag ctgaaggaaa     660
aagaccaaga gattcagaga tggggaagc tgaattgggc ccttcaagaa gagtcaaaa     720 gcttgtgcat ggagaaccaa atttggaggg aattggcaca acaaacgaa tccacagcca     780 actacctacg aagcaatttg gaacaagtgc tggcacatgt cggcgaggaa cgcgccaccg     840
tggccgatga tgctcaatct agctgtggca gcaatgatgc ggcggaggcc ggaaacgaca     900
ctgcggcgtc cgcggcggcg accggtcgtg gtaggttgtg taagaactgt gggctgaggg     960
agtcagtggt gctgttgttg ccatgcaggc atctttgcct ttgcacaatg tgtgggtcca    1020
cagtaaggaa ttgtcctatt tgtgactctg acatggatgc tagcgtgcat gtcaatctct    1080
cttagtacaa ctttttttct tttttctttt tacataattt tcattgtaga gtttagaaca    1140
acagaaacta gaaaaaaat agtttatctt gtcaaaaga cagtt                     1185

<210> SEQ ID NO 83
<211> LENGTH: 310
<212> TYPE: PRT
<213> ORGANISM: Glycine max
<220> FEATURE:
<221> NAME/KEY: misc_feature
<222> LOCATION: (1)..(310)
<223> OTHER INFORMATION: Ceres CLONE ID no. 471026

<400> SEQUENCE: 83

Met Ala Val Glu Ala Ser Tyr Met Asn Leu Leu Pro Ser Gln Leu Leu
1               5                   10                  15

Thr Asn Arg Glu Leu Ile Lys Ser Asn Gln Gln Leu Gln His Gln Leu
            20                  25                  30
```

Asn Ser Asp Tyr Met Tyr Asn Thr Thr Thr Gln Met Asp Ser Ser Ser
            35                  40                  45

Ala Leu Pro Gln Pro Ala Thr Met Pro Glu Ser Leu Leu Ser Phe Tyr
 50                  55                  60

Gln Ser Asn Phe Cys Asp Pro Asn Lys Ala Asp Ser Gly Leu Thr Tyr
 65                  70                  75                  80

His Ile Pro Leu Gln Arg Lys Arg Ser Arg Asp Phe Thr Thr Glu Leu
                85                  90                  95

Thr Ser Leu Pro Ala His Gln Lys Asn Lys Ile Ser Ser Asp Pro Ser
            100                 105                 110

Phe Leu Asn Gln Glu Ile Leu Tyr Gln Phe Gln Asn Gln Gln Ser Glu
            115                 120                 125

Ile Asp Arg Val Leu Ala His His Thr Glu Lys Val Arg Met Glu Leu
            130                 135                 140

Glu Glu Gln Lys Met Arg Gln Ser Arg Met Phe Val Ser Ala Ile Gln
145                 150                 155                 160

Glu Ala Met Ala Lys Lys Leu Lys Glu Lys Asp Gln Glu Ile Gln Arg
                165                 170                 175

Met Gly Lys Leu Asn Trp Ala Leu Gln Glu Arg Val Lys Ser Leu Cys
            180                 185                 190

Met Glu Asn Gln Ile Trp Arg Glu Leu Ala Gln Thr Asn Glu Ser Thr
            195                 200                 205

Ala Asn Tyr Leu Arg Ser Asn Leu Glu Gln Val Leu Ala His Val Gly
            210                 215                 220

Glu Glu Arg Ala Thr Val Ala Asp Asp Ala Gln Ser Ser Cys Gly Ser
225                 230                 235                 240

Asn Asp Ala Ala Glu Ala Gly Asn Asp Thr Ala Ser Ala Ala Ala
                245                 250                 255

Thr Gly Arg Gly Arg Leu Cys Lys Asn Cys Gly Leu Arg Glu Ser Val
                260                 265                 270

Val Leu Leu Leu Pro Cys Arg His Leu Cys Leu Cys Thr Met Cys Gly
            275                 280                 285

Ser Thr Val Arg Asn Cys Pro Ile Cys Asp Ser Asp Met Asp Ala Ser
            290                 295                 300

Val His Val Asn Leu Ser
305                 310

<210> SEQ ID NO 84
<211> LENGTH: 1225
<212> TYPE: DNA
<213> ORGANISM: Glycine max
<220> FEATURE:
<221> NAME/KEY: misc_feature
<222> LOCATION: (1)..(1225)
<223> OTHER INFORMATION: Ceres CLONE ID no.473509
<220> FEATURE:
<221> NAME/KEY: misc_feature
<222> LOCATION: (1)..(1225)
<223> OTHER INFORMATION: Encodes the peptide sequence at SEQ ID NO:85

<400> SEQUENCE: 84
gccttcgttt tcaggtttct tcttttggtc atctaggaat tttgtgttta tgttcaaaat    60
tgctagatcg tgtgttgggg ttggggtggt gttctgtgga catgtcagat attaagaag    120 aaaccaacag agtttccatt ctcggtatct cttctctgat caggttgaca acttgacata    180
gcaatcctgc tttcttggtt ccccatttcc atgtttgtgg attcttcctg attcaaaggc    240
aatccattgt gtcttcttag ctcagttttg agcttcaaaa gttacaactt gcaacacaaa    300

```
tttttatctg taactttggt aatcctaaag gactcagcat tgatcaaaat gggcctttca    360
agtctcccag caccatctga aggagtatta tgtgtccttc tggtgaacac tgtattgtca    420
atttcaatat tcaaaggcat tgttaggaca atcctacaca ttgttggcat ccatctttca    480
tcatcatcct ccacttcacc ctcttcaccg gatccctcgc taaccgcacc tgagtcattt    540
gaattccatc ttagtccctc tgagagttac attgaagagt tcagaagccg acgccaaca     600 cttcggttcg acagtgtgtg ctgctgtaaa caacctgagc atgactgctc tgtatgcctc    660
actcagtttg aaccggaatc ggagataaac cgcttatcgt gcggccatct cttccacaaa    720
gtgtgcttag agaagtggct ggactactgg aacattacat gccctctttg caggactccc    780
ttgatgcctg aagatgacac vccttgcttt cagtaagcaa aaacaaggga gcatggcaat    840
aagagagagt ttcatgtaca gtgtagtgta catattcttg agggttttttg atgttcatgc   900 atctgagttc tgccacctt ataagttttt aacctttttc cttttatggt ctgagtttgt     960
ggaggatttt gttttccct ttttctgtct gtgctcttta gcacacatga ggggtatact     1020
ttttgcttgc atgttatgtt tgttcacaat gcccacctgg tttagacctc cttaaattct    1080
atatttgggc attttgatcc taatttggaa gcatggattg tagaatccat ttgttttgcc    1140
tttcaaactc tcatcaccat gtgtatatat agtgtatgtg tgtaaatagc tgtggtcggc    1200
aataaaattc agtcatcact aaacg                                          1225
```

<210> SEQ ID NO 85
<211> LENGTH: 155
<212> TYPE: PRT
<213> ORGANISM: Glycine max
<220> FEATURE:
<221> NAME/KEY: misc_feature
<222> LOCATION: (1)..(155)
<223> OTHER INFORMATION: Ceres CLONE ID no. 473509
<220> FEATURE:
<221> NAME/KEY: misc_feature
<222> LOCATION: (100)..(141)
<223> OTHER INFORMATION: Pfam Name: zf-C3HC4
    Pfam Description: Zinc finger, C3HC4 type (RING finger)

<400> SEQUENCE: 85

Met Gly Leu Ser Ser Leu Pro Ala Pro Ser Glu Gly Val Leu Cys Val
1               5                   10                  15

Leu Leu Val Asn Thr Val Leu Ser Ile Ser Ile Phe Lys Gly Ile Val
            20                  25                  30

Arg Thr Ile Leu His Ile Val Gly Ile His Leu Ser Ser Ser Ser
        35                  40                  45

Thr Ser Pro Ser Ser Pro Asp Pro Ser Leu Thr Ala Pro Glu Ser Phe
    50                  55                  60

Glu Phe His Leu Ser Pro Ser Glu Ser Tyr Ile Glu Glu Phe Arg Ser
65              70                  75                  80

Arg Thr Pro Thr Leu Arg Phe Asp Ser Val Cys Cys Cys Lys Gln Pro
            85                  90                  95

Glu His Asp Cys Ser Val Cys Leu Thr Gln Phe Glu Pro Glu Ser Glu
            100                 105                 110

Ile Asn Arg Leu Ser Cys Gly His Leu Phe His Lys Val Cys Leu Glu
        115                 120                 125

Lys Trp Leu Asp Tyr Trp Asn Ile Thr Cys Pro Leu Cys Arg Thr Pro
130                 135                 140

Leu Met Pro Glu Asp Asp Thr Pro Cys Phe Gln
145                 150                 155

<210> SEQ ID NO 86
<211> LENGTH: 1860
<212> TYPE: DNA
<213> ORGANISM: Glycine max
<220> FEATURE:
<221> NAME/KEY: misc_feature
<222> LOCATION: (1)..(1860)
<223> OTHER INFORMATION: Ceres CLONE ID no.479625
<220> FEATURE:
<221> NAME/KEY: misc_feature
<222> LOCATION: (1)..(1860)
<223> OTHER INFORMATION: Encodes the peptide sequence at SEQ ID NO:87

<400> SEQUENCE: 86

```
aacttgttgc accgtaactg aaaattgaaa ccctctttcg caaaatttcc caatttcgcg      60
aaaccctaac tagccctatg gaactctctc gtctcttcgt ttccgacacg tgcttcttct     120
cccctccgat tcgctgctcc ccttcgccgg cgctgtccac gtttttcgcc gtcaagaacc     180
gccggagcag gaggaggagc agcttctgtt ccgcctccaa tcccgacacc ttggtcgccg     240
gcggtgccgc cgtcgtcgct ggggccggcg agaagcacga ggaggacttg aagtcttgga     300
tgcacaaaca cggcctccct ccctgcaagg ttgtgctgaa ggataaacct tgccccaatg     360
attctcataa acctatacat tacgtcgcag caagtcaaga tcttcaggtt ggcgatgttg     420
cattctccgt tcctaattcc ttggtggtta cgctggagag ggtgctggga aacgagactg     480
ttgctgagct attgactaca aataaattgt ccgaattggc gtgcttggca ttgtatctga     540
tgtatgagaa aaagcagggg aagaaatctt tctggtatcc gtacatcagg agcttgatc      600
gccaacgagg taggggccaa ctgtctgtgg aatcacctct tctatggtta aaatctgagc     660
tggattacct gtcaggaagt ccaattaagg atgaagttat tcaaagggaa gaagcaataa     720
gaaaagagta taatgaactt gacacagtct ggtttatggc aggttctcta tttcagcaat     780
atccatatga cattcctact gaggcctttt catttgagat tttcaaacaa gcctttgctg     840
ctattcagtc ttgtgtggtg catttacaga agttagttt agctcggaga tttgctttag      900
ttccccctggg acctccttta ctgtcctacc aaagcaactg caaggcaatg ctaactgctg     960
ttgatggcgc tgttgagctt gcagttgatc gcccgtataa agccggggac ccaattgttg    1020
tgtggtgtgg ccctcaacct aactcaaagt tgcttataaa ctatggtttt gttgatgaaa    1080
ataattccaa tgatcgtctt atagttgagg cagctttaaa tactgaagat ccacaatatc    1140
aagataaaag aatggtggct caaagaaatg gaaagttatc agttcaagtt tttcatgtat    1200
atgctgggaa ggaaagggaa gctgtcttag atatgcttcg ttatatgcgt ttgggctatg    1260
tttcagatcc ttctgagatg gaatctgtca tctcctctca aggtccagtt tgtcctgtaa    1320
gcccttgtat ggaacgggct gcgttggatc agttggctga ttatttcaag gcacggctgg    1380
ctggctaccc tacaacattg gctgaagatg aatctatgct gacagatgat aatctgaatc    1440
caaagaagcg agttgctacc caatatgtta ggctggaaaa gaaaatgctc catgcctgtt    1500
tgcaggcaac caccgacttc attaaccagc ttccagacca cactatatct ccatgccccg    1560
ctccctatgc acctttattg aaatgaaagg aactggaaat gtatgtagtc tgaactgtac    1620
aaatatggat ttgatgaacc aggtcagtca aattatatat tcttgatatg catccaatta    1680
gaaatcccct gaattaaggt aatttgtggt ttatcctctt cagctttggt ttatatgtga    1740
atgtaggact ttaggattgg ataaagatac tcaattcttt aaacttctca ctgtgtgaaa    1800
aacacccttt gttagcaaac cattaaatgt cagctgagtt gtaagacaat aatttctttg    1860
```

<210> SEQ ID NO 87

-continued

```
<211> LENGTH: 502
<212> TYPE: PRT
<213> ORGANISM: Glycine max
<220> FEATURE:
<221> NAME/KEY: misc_feature
<222> LOCATION: (1)..(502)
<223> OTHER INFORMATION: Ceres CLONE ID no. 479625
<220> FEATURE:
<221> NAME/KEY: misc_feature
<222> LOCATION: (69)..(324)
<223> OTHER INFORMATION: Pfam Name: SET
      Pfam Description: SET domain

<400> SEQUENCE: 87

Met Glu Leu Ser Arg Leu Phe Val Ser Asp Thr Cys Phe Phe Ser Pro
1               5                   10                  15

Pro Ile Arg Cys Ser Pro Ser Pro Ala Leu Ser Thr Phe Phe Ala Val
            20                  25                  30

Lys Asn Arg Arg Ser Arg Arg Ser Ser Phe Cys Ser Ala Ser Asn
        35                  40                  45

Pro Asp Thr Leu Val Ala Gly Ala Ala Val Val Ala Gly Ala Gly
    50                  55                  60

Glu Lys His Glu Glu Asp Leu Lys Ser Trp Met His Lys His Gly Leu
65                  70                  75                  80

Pro Pro Cys Lys Val Val Leu Lys Asp Lys Pro Cys Pro Asn Asp Ser
                85                  90                  95

His Lys Pro Ile His Tyr Val Ala Ala Ser Gln Asp Leu Gln Val Gly
            100                 105                 110

Asp Val Ala Phe Ser Val Pro Asn Ser Leu Val Val Thr Leu Glu Arg
        115                 120                 125

Val Leu Gly Asn Glu Thr Val Ala Glu Leu Leu Thr Thr Asn Lys Leu
    130                 135                 140

Ser Glu Leu Ala Cys Leu Ala Leu Tyr Leu Met Tyr Glu Lys Lys Gln
145                 150                 155                 160

Gly Lys Lys Ser Phe Trp Tyr Pro Tyr Ile Arg Glu Leu Asp Arg Gln
                165                 170                 175

Arg Gly Arg Gly Gln Leu Ser Val Glu Ser Pro Leu Leu Trp Leu Lys
            180                 185                 190

Ser Glu Leu Asp Tyr Leu Ser Gly Ser Pro Ile Lys Asp Glu Val Ile
        195                 200                 205

Gln Arg Glu Glu Ala Ile Arg Lys Glu Tyr Asn Glu Leu Asp Thr Val
    210                 215                 220

Trp Phe Met Ala Gly Ser Leu Phe Gln Gln Tyr Pro Tyr Asp Ile Pro
225                 230                 235                 240

Thr Glu Ala Phe Ser Phe Glu Ile Phe Lys Gln Ala Phe Ala Ala Ile
                245                 250                 255

Gln Ser Cys Val Val His Leu Gln Lys Val Ser Leu Ala Arg Arg Phe
            260                 265                 270

Ala Leu Val Pro Leu Gly Pro Pro Leu Leu Ser Tyr Gln Ser Asn Cys
        275                 280                 285

Lys Ala Met Leu Thr Ala Val Asp Gly Ala Val Glu Leu Ala Val Asp
    290                 295                 300

Arg Pro Tyr Lys Ala Gly Asp Pro Ile Val Val Trp Cys Gly Pro Gln
305                 310                 315                 320

Pro Asn Ser Lys Leu Leu Ile Asn Tyr Gly Phe Val Asp Glu Asn Asn
                325                 330                 335

Ser Asn Asp Arg Leu Ile Val Glu Ala Ala Leu Asn Thr Glu Asp Pro
            340                 345                 350
```

```
Gln Tyr Gln Asp Lys Arg Met Val Ala Gln Arg Asn Gly Lys Leu Ser
            355                 360                 365

Val Gln Val Phe His Val Tyr Ala Gly Lys Glu Arg Glu Ala Val Leu
370                 375                 380

Asp Met Leu Arg Tyr Met Arg Leu Gly Tyr Val Ser Asp Pro Ser Glu
385                 390                 395                 400

Met Glu Ser Val Ile Ser Ser Gln Gly Pro Val Cys Pro Val Ser Pro
            405                 410                 415

Cys Met Glu Arg Ala Ala Leu Asp Gln Leu Ala Asp Tyr Phe Lys Ala
            420                 425                 430

Arg Leu Ala Gly Tyr Pro Thr Thr Leu Ala Glu Asp Glu Ser Met Leu
            435                 440                 445

Thr Asp Asp Asn Leu Asn Pro Lys Lys Arg Val Ala Thr Gln Tyr Val
            450                 455                 460

Arg Leu Glu Lys Lys Met Leu His Ala Cys Leu Gln Ala Thr Asp
465                 470                 475                 480

Phe Ile Asn Gln Leu Pro Asp His Thr Ile Ser Pro Cys Pro Ala Pro
            485                 490                 495

Tyr Ala Pro Leu Leu Lys
            500

<210> SEQ ID NO 88
<211> LENGTH: 1740
<212> TYPE: DNA
<213> ORGANISM: Glycine max
<220> FEATURE:
<221> NAME/KEY: misc_feature
<222> LOCATION: (1)..(1740)
<223> OTHER INFORMATION: Ceres CLONE ID no.519689
<220> FEATURE:
<221> NAME/KEY: misc_feature
<222> LOCATION: (1)..(1740)
<223> OTHER INFORMATION: Encodes the peptide sequence at SEQ ID NO:89

<400> SEQUENCE: 88
gttatgtgag tgcggcaata gtggaatagc ggtagagtgt gcgatcgaga aagcagaaag      60
cagaaagatg gggttggaat cggtgggaga tttagcgatt aacgtgattc tgaaaaaatt     120
aggagcccaa gacattgcga gagtggcgtg tgtgagcaaa aggttcagtt cttccgcttc     180
cgatgacact cttttggatca atctctgctt caatgaactc gctttgacac aacccctcga     240
tcatctcgga aaccctctct cttccttcaa ggaatgctat ctagcatgga gaggagcttt     300
tgttatgtac ccttggtctc ttgttaagcg tgtaaaaagg tgctgggata gaataaaaac     360
ctggttgacc aataattttc ctgaagcgga ggccactctt tgtaaaggtg caactgaagc     420
tgacattcag gagttggaga atgtattaaa ggtgaaattg cctcttccta caaggatcct     480
ttatcgcttt cacaatgggc aagaatttgc aaaggcagat ccagaaacta gtacatttgg     540
cagatctttg ggtctaattg gtggctactc cttctatggt catttggtga atgtttatct     600
attacctata tgtcagataa tcctagaaac tcagcaaact aggcgtcgct tgagcttttt     660
aagaagatca aagtatgttc ttgtggctgc ttcatccaca tacagtagaa agttgttttt     720
cctcaactgt accaatggtc aactatatgt cgggaccagg tctcctctta ccgaaagaga     780
cataatccct tgtgtacctc atgacctgat tagtttacat caggaattga atagttcaga     840
gcaacaagat gccatgctac tgtggttaga agaacatggt cgccgtttag aacacggctt     900
tatcaaactt catgatgaag gaaatggcaa aagcattaat cttttcccag aagaacccca     960
tatttgttca acggctgtta ctaatggtgt gaaggttcgc gcttctgcac tggttatccc    1020
```

```
tgagttgatg gatcttcaag atgaccttgg agagtactta tttgcttatt caatccgctt    1080
gtcccttgaa cctcaaggat gcattattaa tggaatgtcc ttcagctctt gccagctcca    1140
ttggaggcac tggatcatcc gtgctaatga tattgttata tctgatgtca gtggaaaagc    1200
tgttatagga cagtttccac ttttgcgtcc gggtgctcaa gaatttgttt atcagagttg    1260
cacgcctcta ccaacaccat caggttctat tgaaggttct tttacattta tacccggcag    1320
attggcagac ccaaaaggag acccttttct agctacagtg gctcgtttcc cgctccagct    1380
gccagactat atattctgat tttgattctg gatgggattg aagtatctct aatggcaatt    1440
gcagctctca gatattgttt gggtgtatta tgtccctttc gggagaggtt tttaagttgg    1500
acctgcacaa tttccctatc tataagagaa gcaaagtatg tacaatattt gatctctatc    1560
ataagagaag caaagtagat acaatatttg ttaggggtgt tcatggtttg attaggttgg    1620 atttttttgtt aaaaaatcat ccaaatcaaa cttaaaaaac ttgtgatttg gttcgattca    1680
gttttcattt aaaataaaat tcaaatcaga ccaagttaat agaaaaaaaa aaaaaaaaa     1740
```

<210> SEQ ID NO 89
<211> LENGTH: 443
<212> TYPE: PRT
<213> ORGANISM: Glycine max
<220> FEATURE:
<221> NAME/KEY: misc_feature
<222> LOCATION: (1)..(443)
<223> OTHER INFORMATION: Ceres CLONE ID no. 519689
<220> FEATURE:
<221> NAME/KEY: misc_feature
<222> LOCATION: (3)..(48)
<223> OTHER INFORMATION: Pfam Name: F-box
    Pfam Description: F-box domain
<220> FEATURE:
<221> NAME/KEY: misc_feature
<222> LOCATION: (302)..(439)
<223> OTHER INFORMATION: Pfam Name: DUF525
    Pfam Description: Protein of unknown function (DUF525)

<400> SEQUENCE: 89

Met Gly Leu Glu Ser Val Gly Asp Leu Ala Ile Asn Val Ile Leu Lys
 1               5                  10                  15

Lys Leu Gly Ala Gln Asp Ile Ala Arg Val Ala Cys Val Ser Lys Arg
             20                  25                  30

Phe Ser Ser Ser Ala Ser Asp Asp Thr Leu Trp Ile Asn Leu Cys Phe
         35                  40                  45

Asn Glu Leu Ala Leu Thr Gln Pro Leu Asp His Leu Gly Asn Pro Leu
     50                  55                  60

Ser Ser Phe Lys Glu Cys Tyr Leu Ala Trp Arg Gly Ala Phe Val Met
 65                  70                  75                  80

Tyr Pro Trp Ser Leu Val Lys Arg Val Lys Arg Cys Trp Asp Arg Ile
                 85                  90                  95

Lys Thr Trp Leu Thr Asn Asn Phe Pro Glu Ala Glu Ala Thr Leu Cys
            100                 105                 110

Lys Gly Ala Thr Glu Ala Asp Ile Gln Glu Leu Glu Asn Val Leu Lys
        115                 120                 125

Val Lys Leu Pro Leu Pro Thr Arg Ile Leu Tyr Arg Phe His Asn Gly
    130                 135                 140

Gln Glu Phe Ala Lys Ala Asp Pro Glu Thr Ser Thr Phe Gly Arg Ser
145                 150                 155                 160

Leu Gly Leu Ile Gly Gly Tyr Ser Phe Tyr Gly His Leu Val Asn Val
                165                 170                 175

```
Tyr Leu Leu Pro Ile Cys Gln Ile Ile Leu Glu Thr Gln Gln Thr Arg
                180                 185                 190

Arg Arg Leu Ser Phe Leu Arg Ser Lys Tyr Val Leu Val Ala Ala
        195                 200                 205

Ser Ser Thr Tyr Ser Arg Lys Leu Phe Phe Leu Asn Cys Thr Asn Gly
    210                 215                 220

Gln Leu Tyr Val Gly Thr Arg Ser Pro Leu Thr Glu Arg Asp Ile Ile
225                 230                 235                 240

Pro Cys Val Pro His Asp Leu Ile Ser Leu His Gln Glu Leu Asn Ser
                245                 250                 255

Ser Glu Gln Gln Asp Ala Met Leu Leu Trp Leu Glu Glu His Gly Arg
    260                 265                 270

Arg Leu Glu His Gly Phe Ile Lys Leu His Asp Glu Gly Asn Gly Lys
        275                 280                 285

Ser Ile Asn Leu Phe Pro Glu Glu Pro His Ile Cys Ser Thr Ala Val
    290                 295                 300

Thr Asn Gly Val Lys Val Arg Ala Ser Ala Leu Val Ile Pro Glu Leu
305                 310                 315                 320

Met Asp Leu Gln Asp Asp Leu Gly Glu Tyr Leu Phe Ala Tyr Ser Ile
                325                 330                 335

Arg Leu Ser Leu Glu Pro Gln Gly Cys Ile Ile Asn Gly Met Ser Phe
        340                 345                 350

Ser Ser Cys Gln Leu His Trp Arg His Trp Ile Ile Arg Ala Asn Asp
    355                 360                 365

Ile Val Ile Ser Asp Val Ser Gly Lys Ala Val Ile Gly Gln Phe Pro
370                 375                 380

Leu Leu Arg Pro Gly Ala Gln Glu Phe Val Tyr Gln Ser Cys Thr Pro
385                 390                 395                 400

Leu Pro Thr Pro Ser Gly Ser Ile Glu Gly Ser Phe Thr Phe Ile Pro
                405                 410                 415

Gly Arg Leu Ala Asp Pro Lys Gly Asp Pro Phe Leu Ala Thr Val Ala
        420                 425                 430

Arg Phe Pro Leu Gln Leu Pro Asp Tyr Ile Phe
    435                 440
```

<210> SEQ ID NO 90
<211> LENGTH: 848
<212> TYPE: DNA
<213> ORGANISM: Glycine max
<220> FEATURE:
<221> NAME/KEY: misc_feature
<222> LOCATION: (1)..(848)
<223> OTHER INFORMATION: Ceres CLONE ID no.662149
<220> FEATURE:
<221> NAME/KEY: misc_feature
<222> LOCATION: (1)..(848)
<223> OTHER INFORMATION: Encodes the peptide sequence at SEQ ID NO:91

<400> SEQUENCE: 90

```
aaaaacatat aacctatttc accaatccaa cagggtggtt gtgattttg ttgttgttgt      60
tgttgttagt gatcatcatg gacgctgcat caggggcagc gctgcggcg ttggcggctc     120
cccaatcaga gggatcaccg gctgcgccga ccgctacga gtcgcagaag cgacgcgact     180
ggaacacgtt cttgcagtac ctgaggaacc acaagccacc attgacgctg gcgcggtgca    240
gtggcgcgca cgtgatcgag tttttgaagt acctcgacca gttcgggaag actaaggtac    300
acatcttggg gtgcccgtat ttcggacacc ccaacccacc tgccccttgt gcctgtcctc    360
ttaaacaggc ttggggcagt ctggacgccc taattggacg actcagggcg gccttcgaag    420
```

-continued

```
aaaatggagg ccgtcctgag tctaatccat ttgcaactag ggctgtccga atttacctca    480
gagagataag agaaggtcag gccaaggcaa gaggaatccc ctacgagaag aagaaacgca    540
agagaactat tgtcaccact actgtcaccg ccgcagccac cgttatgtct accataacgg    600
gtagtagtcc taataatact attacaaacg gtgctggtag tagcactggt aacactacta    660
acggagctgg tgttagtgaa ccttctgctg ctgctactgc tacacctaat gttactactg    720
ctgctgccgt atagtataat tttaataatt ttgatcattt tttcctattt tctgctacta    780
tctactatct atctttattt ttaaggaaat taattgtggt tatggcttat gcaaaaaaaa    840
aaaaaaaa                                                             848
```

<210> SEQ ID NO 91
<211> LENGTH: 218
<212> TYPE: PRT
<213> ORGANISM: Glycine max
<220> FEATURE:
<221> NAME/KEY: misc_feature
<222> LOCATION: (1)..(218)
<223> OTHER INFORMATION: Ceres CLONE ID no. 662149
<220> FEATURE:
<221> NAME/KEY: misc_feature
<222> LOCATION: (8)..(140)
<223> OTHER INFORMATION: Pfam Name: DUF640
      Pfam Description: Protein of unknown function (DUF640)

<400> SEQUENCE: 91

Met Asp Ala Ala Ser Gly Ala Ala Pro Ala Ala Leu Ala Ala Pro Gln
1               5                   10                  15

Ser Glu Gly Ser Pro Ala Ala Pro Ser Arg Tyr Glu Ser Gln Lys Arg
            20                  25                  30

Arg Asp Trp Asn Thr Phe Leu Gln Tyr Leu Arg Asn His Lys Pro Pro
        35                  40                  45

Leu Thr Leu Ala Arg Cys Ser Gly Ala His Val Ile Glu Phe Leu Lys
    50                  55                  60

Tyr Leu Asp Gln Phe Gly Lys Thr Lys Val His Ile Leu Gly Cys Pro
65                  70                  75                  80

Tyr Phe Gly His Pro Asn Pro Pro Ala Pro Cys Ala Cys Pro Leu Lys
                85                  90                  95

Gln Ala Trp Gly Ser Leu Asp Ala Leu Ile Gly Arg Leu Arg Ala Ala
            100                 105                 110

Phe Glu Glu Asn Gly Gly Arg Pro Gly Ser Asn Pro Phe Ala Thr Arg
        115                 120                 125

Ala Val Arg Ile Tyr Leu Arg Glu Ile Arg Glu Gly Gln Ala Lys Ala
    130                 135                 140

Arg Gly Ile Pro Tyr Glu Lys Lys Lys Arg Lys Arg Thr Ile Val Thr
145                 150                 155                 160

Thr Thr Val Thr Ala Ala Ala Thr Val Met Ser Thr Ile Thr Gly Ser
                165                 170                 175

Ser Pro Asn Asn Thr Ile Thr Asn Gly Ala Gly Ser Ser Thr Gly Asn
            180                 185                 190

Thr Thr Asn Gly Ala Gly Val Ser Glu Pro Ser Ala Ala Ala Thr Ala
        195                 200                 205

Thr Pro Asn Val Thr Thr Ala Ala Ala Val
    210                 215

<210> SEQ ID NO 92
<211> LENGTH: 848
<212> TYPE: DNA

```
<213> ORGANISM: Glycine max
<220> FEATURE:
<221> NAME/KEY: misc_feature
<222> LOCATION: (1)..(848)
<223> OTHER INFORMATION: Ceres CLONE ID no.675127
<220> FEATURE:
<221> NAME/KEY: misc_feature
<222> LOCATION: (1)..(848)
<223> OTHER INFORMATION: Encodes the peptide sequence at SEQ ID NO:93

<400> SEQUENCE: 92
aacatcatca tcatcatcat cttgctacat tcattctcac aacaacaaca atgggcaaac      60
ccgctagttc ttcctcttcc tctattagca gcactaccaa ccgccgcctc ctcatttcaa     120
ccgcatcttc tctcactcaa caacttccta ctgatctcag gcttggactc ggcatttctg     180
ccactcaaca tgttgcttct tctatttcaa ggggccaatg caacaaccca ccatcctt      240
ttgtgaacaa taattattca caagctgctg cttctgctga agtgaatgat tgcagcaacg     300
atcatagcag cttctttgtg aaggtgtaca tggaagggat tccaatcgga agaaagctca     360
atatactagc tcatggaggc tactatgaat tagtcaggac tcttgaacac atgtttgaca     420
ctaccattct ttggggaaca gagatgaatg gggtgcaacc agagagatgc catgtgctaa     480
cttatgaaga tgaagaaggg gatttggtca tggttggaga tgtcccttgg gagatgttct     540
tatccgacgg kaaagaggtk gaagatcaca agggtagaca cattcgggtg ttagttaagt     600
gaggaacatg acactgcctc ttccttccac cagtgattaa tttcaagttt tgtcctctag     660
agtgagactc tactgttgtc gctgattaga aaacttagaa aatcttaatt tacttagtga     720
agtatgcaca gatagatgta tatgcatagc tcactctgct cttctttgga gattaatgga     780
aaagaatagt gttgtatatt agttctcacc cattctgggc taccggcttt atttctttc    840
cagaactc                                                             848

<210> SEQ ID NO 93
<211> LENGTH: 180
<212> TYPE: PRT
<213> ORGANISM: Glycine max
<220> FEATURE:
<221> NAME/KEY: misc_feature
<222> LOCATION: (1)..(180)
<223> OTHER INFORMATION: Ceres CLONE ID no. 675127
<220> FEATURE:
<221> NAME/KEY: misc_feature
<222> LOCATION: (34)..(175)
<223> OTHER INFORMATION: Pfam Name: AUX_IAA
      Pfam Description: AUX/IAA family

<400> SEQUENCE: 93

Met Gly Lys Pro Ala Ser Ser Ser Ser Ser Ile Ser Ser Thr Thr
1               5                   10                  15

Asn Arg Arg Leu Leu Ile Ser Thr Ala Ser Ser Leu Thr Gln Gln Leu
                20                  25                  30

Pro Thr Asp Leu Arg Leu Gly Leu Gly Ile Ser Ala Thr Gln His Val
            35                  40                  45

Ala Ser Ser Ile Ser Arg Gly Gln Trp Gln Gln Pro His His Pro Phe
        50                  55                  60

Val Asn Asn Asn Tyr Ser Gln Ala Ala Ala Ser Ala Glu Val Asn Asp
65                  70                  75                  80

Cys Ser Asn Asp His Ser Ser Phe Phe Val Lys Val Tyr Met Glu Gly
                85                  90                  95

Ile Pro Ile Gly Arg Lys Leu Asn Ile Leu Ala His Gly Gly Tyr Tyr
            100                 105                 110
```

```
Glu Leu Val Arg Thr Leu Glu His Met Phe Asp Thr Thr Ile Leu Trp
        115                 120                 125

Gly Thr Glu Met Asn Gly Val Gln Pro Glu Arg Cys His Val Leu Thr
    130                 135                 140

Tyr Glu Asp Glu Glu Gly Asp Leu Val Met Val Gly Asp Val Pro Trp
145                 150                 155                 160

Glu Met Phe Leu Ser Thr Val Lys Arg Leu Lys Ile Thr Arg Val Asp
            165                 170                 175

Thr Phe Gly Cys
        180

<210> SEQ ID NO 94
<211> LENGTH: 1409
<212> TYPE: DNA
<213> ORGANISM: Triticum aestivum
<220> FEATURE:
<221> NAME/KEY: misc_feature
<222> LOCATION: (1)..(1409)
<223> OTHER INFORMATION: Ceres CLONE ID no.885628
<220> FEATURE:
<221> NAME/KEY: misc_feature
<222> LOCATION: (1)..(1409)
<223> OTHER INFORMATION: Encodes the peptide sequence at SEQ ID NO:95

<400> SEQUENCE: 94
gttttctttg ccaccctgcc cgcccgtccc tcgccgatcg atgaccgcac ctcccaccac      60
atctgactaa ctccggccag ggacgcatcg ccttgcctgt atatatagga gcgagcggac     120
gacccgcgcg ccccatcaat cgccatggct gtggacctgc aacgccttcg ccacatgtta     180
ctcaccaccg gcgacggcgg cggtcaccac cagctctact ccgccgctgc tatgccagcg     240
agtgggcctt gttatggcgc tgcggtgtcg tgcgagcggg gcaccagcc gtacgcggac      300 ctcttcacgc tgccgccgcc gccgacgatg acttcggccc cgtatcagtg ttcagagttc     360
ttggcgatgg acgcggttga tctggctaag aagggcggca accccgacgg tgttcaggaa     420
atgatcacca agaagcggag gcgcgaggag cggtcgtcga tgcttagcgc ggccgacgct     480
cttgcggccc acgcgcagca gcagaccatc gacgtccacc gcatcctgct caaacatgcg     540
caaaagatgt ggactactct ggcggagcag aggcagagcc acgaggct catcgtgtgg       600 accgtggagg ccagggcggc gaagcggctc aaggccaagg atgaggacat tgagcggatc     660
aggagcatga actgggcgct cgaggagcgt cttcggaacc tcctcatgga ggctcagatg     720
tggcgcgatg tcgcgcagtc ccatgaggcc acgccaacg tgctccgcgg cgacctacag      780
cgggcgctcg actcccaggc ggttcgtggc ggtggaagcg acgacggtca ggaggacgac     840
gccgagtcgt gctgctgggg agagaagcag gtgcctttgt gcgcggagga ggaggtgggc     900
acgccggtag tggaggagcg tcacgcgaca ggagcaggaa ggtgcaaggg gtgccgcgag     960
ggcgcggccg ttgtgctgct gctgccgtgc aggcacctct gcgtgtgcgc gccgtgcgcg    1020
gccgcggcgc aggcgtgccc ggcgtgcgga agcgccaaga atggcatcgt ctgcatcaac    1080
ttttcgtgat gcgggaggaa tagtttttaga gtagacatt tgttttccttc tgaaacttac    1140 tagagtcgac ttttgttttgt attctttttgt tcacttttttc tattgttgtt gaccgaaagc    1200
ggctcctctg ccatgcgccg tgtgaggttg ggctgctgac atgtgggcca ggtttttcaac    1260 gggtccacat gtcaatggta gaacgatagg gtgccgaagg ttagagtatc ctcctacttg    1320
tgttgacggg atgataaata ggaggatggt tggatcacat agatatgaga ggacttgtat    1380 ccccttttg tttaaaaaaa aaaaaaaaa                                       1409
```

```
<210> SEQ ID NO 95
<211> LENGTH: 314
<212> TYPE: PRT
<213> ORGANISM: Triticum aestivum
<220> FEATURE:
<221> NAME/KEY: misc_feature
<222> LOCATION: (1)..(314)
<223> OTHER INFORMATION: Ceres CLONE ID no. 885628

<400> SEQUENCE: 95

Met Ala Val Asp Leu Gln Arg Leu Arg His Met Leu Leu Thr Thr Gly
1               5                   10                  15

Asp Gly Gly His His Gln Leu Tyr Ser Ala Ala Met Pro Ala
            20                  25                  30

Ser Gly Pro Cys Tyr Gly Ala Ala Val Ser Cys Glu Arg Gly His Gln
            35                  40                  45

Pro Tyr Ala Asp Leu Phe Thr Leu Pro Pro Pro Thr Met Thr Ser
    50                  55                  60

Ala Pro Tyr Gln Cys Ser Glu Phe Leu Ala Met Asp Ala Val Asp Leu
65              70                  75                  80

Ala Lys Lys Gly Gly Asn Pro Asp Gly Val Gln Glu Met Ile Thr Lys
                85                  90                  95

Lys Arg Arg Arg Glu Glu Arg Ser Ser Met Leu Ser Ala Ala Asp Ala
            100                 105                 110

Leu Ala Ala His Ala Gln Gln Thr Ile Asp Val His Arg Ile Leu
            115                 120                 125

Leu Lys His Ala Gln Lys Met Trp Thr Thr Leu Ala Glu Gln Arg Gln
        130                 135                 140

Ser His Thr Arg Leu Ile Val Trp Thr Val Glu Ala Arg Ala Ala Lys
145                 150                 155                 160

Arg Leu Lys Ala Lys Asp Glu Asp Ile Glu Arg Ile Arg Ser Met Asn
                165                 170                 175

Trp Ala Leu Glu Glu Arg Leu Arg Asn Leu Leu Met Gly Ala Gln Met
            180                 185                 190

Trp Arg Asp Val Ala Gln Ser His Glu Ala Thr Ala Asn Val Leu Arg
        195                 200                 205

Gly Asp Leu Gln Arg Ala Leu Asp Ser Gln Ala Val Arg Gly Gly Gly
    210                 215                 220

Ser Asp Asp Gly Gln Glu Asp Asp Ala Glu Ser Cys Cys Trp Gly Glu
225                 230                 235                 240

Lys Gln Val Pro Leu Cys Ala Glu Glu Val Gly Thr Pro Val Val
                245                 250                 255

Glu Glu Arg His Ala Thr Gly Ala Gly Arg Cys Lys Gly Cys Arg Glu
            260                 265                 270

Gly Ala Ala Val Val Leu Leu Leu Pro Cys Arg His Leu Cys Val Cys
        275                 280                 285

Ala Pro Cys Ala Ala Ala Gln Ala Cys Pro Ala Cys Gly Ser Ala
    290                 295                 300

Lys Asn Gly Ile Val Cys Ile Asn Phe Ser
305                 310

<210> SEQ ID NO 96
<211> LENGTH: 916
<212> TYPE: DNA
<213> ORGANISM: Brassica napus
<220> FEATURE:
<221> NAME/KEY: misc_feature
<222> LOCATION: (1)..(916)
<223> OTHER INFORMATION: Ceres CLONE ID no.964932
```

```
<220> FEATURE:
<221> NAME/KEY: misc_feature
<222> LOCATION: (1)..(916)
<223> OTHER INFORMATION: Encodes the peptide sequence at SEQ ID NO:97

<400> SEQUENCE: 96
acgatacccc ctcctctcct ccttttcct ctccaccatc ttcccttatc aactcaagac     60
ccataaagtt caagactcaa gactcataaa gctcctctca tattcatcat aacctaaaac    120
caaaacctca aagagttaat aaaacctaaa ttatacatca gatcttgata tcatggatcc    180
tatccacggc tttatgagca catcaaacat ctcacacaac acaaaccttta tgatcgccgc    240 cgcagcagcc accactacca ctacctcctc ctcctcgtct cctctggcg gctccgcgac     300 aaaccaactg agtaggtacg agaatcagaa gagaagagac tggaacactt tcggacaata    360
tctacgcaac caccgtccac cactttctct ctcccgttgc agtggtgctc atgttcttga    420
gttcctcagg tacctcgacc aattcggcaa gaccaaggtt cacatgcaaa tatgtccttt    480
ctttggacac ccaaacccac cagcaccatg tacctgccca ctcagacaag cgtggggcag    540
cctcgacgca ctcattggcc ggcttcgagc tgcttttgaa gagaacggtg gttcaccaga    600
gacgaaccct tttggtgcac gagctgttcg actctaccta agggaagttc gtgattcgca    660
ggctaaagcg cgtgggatca gctatgaaaa gaagaagcgg aagcgacctc ctcaggcgcc    720
actaccaccg cctcatcagc cggtgatttc gaatagtcct aatttgcaat aagtcatatc    780
agtaagatat gtttcagtca actacgtttc cttacaactt tatatagtat ttgtcaatga    840
cgaacatgca ggagttgtct aaaaagctgc atgcccttct tctttatttg gccagctaag    900
aaaaaaaaaa aaaaaa                                                    916

<210> SEQ ID NO 97
<211> LENGTH: 199
<212> TYPE: PRT
<213> ORGANISM: Brassica napus
<220> FEATURE:
<221> NAME/KEY: misc_feature
<222> LOCATION: (1)..(199)
<223> OTHER INFORMATION: Ceres CLONE ID no. 964932
<220> FEATURE:
<221> NAME/KEY: misc_feature
<222> LOCATION: (30)..(162)
<223> OTHER INFORMATION: Pfam Name: DUF640
      Pfam Description: Protein of unknown function (DUF640)

<400> SEQUENCE: 97
```

Met Asp Pro Ile His Gly Phe Met Ser Thr Ser Asn Ile Ser His Asn
1               5                   10                  15

Thr Asn Leu Met Ile Ala Ala Ala Ala Thr Thr Thr Thr Thr Thr Ser
            20                  25                  30

Ser Ser Ser Ser Ser Gly Gly Ser Ala Thr Asn Gln Leu Ser Arg
        35                  40                  45

Tyr Glu Asn Gln Lys Arg Arg Asp Trp Asn Thr Phe Gly Gln Tyr Leu
    50                  55                  60

Arg Asn His Arg Pro Leu Ser Leu Ser Arg Cys Ser Gly Ala His
65                  70                  75                  80

Val Leu Glu Phe Leu Arg Tyr Leu Asp Gln Phe Gly Lys Thr Lys Val
                85                  90                  95

His Met Gln Ile Cys Pro Phe Phe Gly His Pro Asn Pro Ala Pro
                100                 105                 110

Cys Thr Cys Pro Leu Arg Gln Ala Trp Gly Ser Leu Asp Ala Leu Ile
            115                 120                 125

| Gly | Arg | Leu | Arg | Ala | Ala | Phe | Glu | Glu | Asn | Gly | Gly | Ser | Pro | Glu | Thr |
|-----|-----|-----|-----|-----|-----|-----|-----|-----|-----|-----|-----|-----|-----|-----|-----|
| 130 |     |     |     |     | 135 |     |     |     |     | 140 |     |     |     |     |     |

| Asn | Pro | Phe | Gly | Ala | Arg | Ala | Val | Arg | Leu | Tyr | Leu | Arg | Glu | Val | Arg |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

| Asp | Ser | Gln | Ala | Lys | Ala | Arg | Gly | Ile | Ser | Tyr | Glu | Lys | Lys | Lys | Arg |
|-----|-----|-----|-----|-----|-----|-----|-----|-----|-----|-----|-----|-----|-----|-----|-----|
|     |     |     |     | 165 |     |     |     |     | 170 |     |     |     |     | 175 |     |

| Lys | Arg | Pro | Pro | Gln | Ala | Pro | Leu | Pro | Pro | His | Gln | Pro | Val | Ile |
|-----|-----|-----|-----|-----|-----|-----|-----|-----|-----|-----|-----|-----|-----|-----|
|     |     |     | 180 |     |     |     |     | 185 |     |     |     |     | 190 |     |

| Ser | Asn | Ser | Pro | Asn | Leu | Gln |
|-----|-----|-----|-----|-----|-----|-----|
|     |     | 195 |     |     |     |     |

<210> SEQ ID NO 98
<211> LENGTH: 1905
<212> TYPE: DNA
<213> ORGANISM: Arabidopsis thaliana
<220> FEATURE:
<221> NAME/KEY: misc_feature
<222> LOCATION: (1)..(1905)
<223> OTHER INFORMATION: Ceres CLONE ID no.101035
<220> FEATURE:
<221> NAME/KEY: misc_feature
<222> LOCATION: (1)..(1905)
<223> OTHER INFORMATION: Encodes the peptide sequence at SEQ ID NO:99

<400> SEQUENCE: 98

| acactgttac | tctctctctc | tcttcttctt | cttcttcttc | ttctgcatct | catcgacatc | 60 |
| atcctttccc | atggctgatg | catacgagcc | ttatcatgtt | cttcaacaaa | gccggcgaga | 120 |
| caaacttcgt | attccatctc | tcgattccca | cttccacttt | caccctcctc | ctcctccttc | 180 |
| ctccggcggc | ggaggtggcg | tctttcctct | cgctgattcc | gatttcctcg | cagccggtgg | 240 |
| ctttcactcc | aacaacaaca | acaaccacat | atctaaccct | agctacagta | aatttcatgg | 300 |
| atttctcggt | ggcccttctt | cttcttcatc | caccgcagtc | gccgtcgccg | gagatcattc | 360 |
| ctttaacgcc | ggacttttctt | ccggagacgt | tcttgtcttc | aaacccgagc | tctatctct | 420 |
| atctttgtcc | tctcacccta | gactcgctta | cgatctagtc | gttcccggtg | ttgttaactc | 480 |
| cggattctgt | agatctgccg | gtgaagccaa | cgccgccgcc | gtcaccatcg | cgtctagaag | 540 |
| ctctggtcct | ctcggaccct | tcacgggcta | cgcgtcgatt | cttaaaggat | caaggttctt | 600 |
| gaaaccagca | cagatgcttc | ttgatgagtt | ttgtaatgtg | ggtcgtggga | tttacaccga | 660 |
| caaagtcatc | gacgacgatg | attcttctct | gcttttttgat | ccgacggttg | agaatctctg | 720 |
| cggtgtttct | gatggcggcg | gaggagataa | tggaaagaaa | aaatcaaaac | tcatctccat | 780 |
| gctcgacgag | gtttacaaga | ggtataagca | atactatgag | cagctacaag | ctgtgatggg | 840 |
| atcattcgaa | tgcgttgcag | gtctcgggca | cgctgctccg | tacgctaact | tagccttgaa | 900 |
| agcgttgtct | aagcatttca | gtgtttgaa | gaatgctata | acggaccagc | ttcaattcag | 960 |
| ccacaacaac | aagatccaac | aacaacaaca | atgtggtcat | ccgatgaact | ctgagaataa | 1020 |
| gactgattct | ttaagatttg | gaggaagtga | tagttctaga | ggcttatgtt | ctgctggtca | 1080 |
| aagacatgga | tttcctgatc | atcatgctcc | tgtttggaga | ccgcaccgtg | gcctacccga | 1140 |
| acgtgctgtt | actgttctaa | gggcttggct | cttcgatcat | ttcttgcatc | cttatccaac | 1200 |
| agatacagac | aaactcatgc | tggctaagca | gacaggtctc | tccagaaatc | aggtatcgaa | 1260 |
| ttggttcata | aacgcaagag | ttagggtttg | gaagccgatg | gtggaagaga | ttcacatgct | 1320 |
| ggagactcga | caatctcaga | gatcttcttc | ttcctcttgg | agagacgaac | gtactagcac | 1380 |
| caccgtcttc | cctgacaaca | acaacaacaa | cccatcttcg | tcctcggcac | agcaaagacc | 1440 |
| taacaactca | tctccgccta | gacgggcacg | aaacgacgac | gttcatggca | caaacaacaa | 1500 |

```
caacagctat gtaaacagtg ggagcggcgg cggtagtgcg gttggtttct cgtatggaat    1560
tgggtcgtcg aatgtgccgg tgatgaatag cagcacaaac ggaggagtgt ctttgacgtt    1620
agggcttcat catcagattg ggttaccgga gccttttccg atgacaactg ctcagaggtt    1680
tgggcttgat ggtggtagtg gcgatggtgg tggtgggtat gaagggcaaa atcgtcagtt    1740
tgggagagat tttattggtg gtagtaatca tcagtttcta catgattttg taggttgaga    1800
ttatttgtgt ggaaaggaaa aaatatgttt gacgtttggg tatgtataag aagatatggg    1860
ggaattgaaa tgcatatgat gtgtatatta gaatgtttct tcttc                    1905
```

```
<210> SEQ ID NO 99
<211> LENGTH: 575
<212> TYPE: PRT
<213> ORGANISM: Arabidopsis thaliana
<220> FEATURE:
<221> NAME/KEY: misc_feature
<222> LOCATION: (1)..(575)
<223> OTHER INFORMATION: Ceres CLONE ID no. 101035
<220> FEATURE:
<221> NAME/KEY: misc_feature
<222> LOCATION: (169)..(292)
<223> OTHER INFORMATION: Pfam Name: POX
      Pfam Description: Associated with HOX
<220> FEATURE:
<221> NAME/KEY: misc_feature
<222> LOCATION: (350)..(408)
<223> OTHER INFORMATION: Pfam Name: Homeobox
      Pfam Description: Homeobox domain

<400> SEQUENCE: 99

Met Ala Asp Ala Tyr Glu Pro Tyr His Val Leu Gln Gln Ser Arg Arg
1               5                   10                  15

Asp Lys Leu Arg Ile Pro Ser Leu Asp Ser His Phe His Phe His Pro
            20                  25                  30

Pro Pro Pro Pro Ser Ser Gly Gly Gly Gly Val Phe Pro Leu Ala
        35                  40                  45

Asp Ser Asp Phe Leu Ala Ala Gly Gly Phe His Ser Asn Asn Asn Asn
    50                  55                  60

Asn His Ile Ser Asn Pro Ser Tyr Ser Asn Phe Met Gly Phe Leu Gly
65                  70                  75                  80

Gly Pro Ser Ser Ser Ser Thr Ala Val Ala Val Ala Gly Asp His
                85                  90                  95

Ser Phe Asn Ala Gly Leu Ser Ser Gly Asp Val Leu Val Phe Lys Pro
            100                 105                 110

Glu Pro Leu Ser Leu Ser Leu Ser Ser His Pro Arg Leu Ala Tyr Asp
        115                 120                 125

Leu Val Val Pro Gly Val Val Asn Ser Gly Phe Cys Arg Ser Ala Gly
    130                 135                 140

Glu Ala Asn Ala Ala Val Thr Ile Ala Ser Arg Ser Ser Gly Pro
145                 150                 155                 160

Leu Gly Pro Phe Thr Gly Tyr Ala Ser Ile Leu Lys Gly Ser Arg Phe
                165                 170                 175

Leu Lys Pro Ala Gln Met Leu Leu Asp Glu Phe Cys Asn Val Gly Arg
            180                 185                 190

Gly Ile Tyr Thr Asp Lys Val Ile Asp Asp Ser Ser Leu Leu
        195                 200                 205

Phe Asp Pro Thr Val Glu Asn Leu Cys Gly Val Ser Asp Gly Gly Gly
    210                 215                 220

Gly Asp Asn Gly Lys Lys Lys Ser Lys Leu Ile Ser Met Leu Asp Glu
```

```
                225                 230                 235                 240
Val Tyr Lys Arg Tyr Lys Gln Tyr Tyr Glu Gln Leu Gln Ala Val Met
                245                 250                 255

Gly Ser Phe Glu Cys Val Ala Gly Leu Gly His Ala Ala Pro Tyr Ala
                260                 265                 270

Asn Leu Ala Leu Lys Ala Leu Ser Lys His Phe Lys Cys Leu Lys Asn
                275                 280                 285

Ala Ile Thr Asp Gln Leu Gln Phe Ser His Asn Asn Lys Ile Gln Gln
                290                 295                 300

Gln Gln Gln Cys Gly His Pro Met Asn Ser Glu Asn Lys Thr Asp Ser
305                 310                 315                 320

Leu Arg Phe Gly Gly Ser Asp Ser Ser Arg Gly Leu Cys Ser Ala Gly
                325                 330                 335

Gln Arg His Gly Phe Pro Asp His His Ala Pro Val Trp Arg Pro His
                340                 345                 350

Arg Gly Leu Pro Glu Arg Ala Val Thr Val Leu Arg Ala Trp Leu Phe
                355                 360                 365

Asp His Phe Leu His Pro Tyr Pro Thr Asp Thr Asp Lys Leu Met Leu
                370                 375                 380

Ala Lys Gln Thr Gly Leu Ser Arg Asn Gln Val Ser Asn Trp Phe Ile
385                 390                 395                 400

Asn Ala Arg Val Arg Val Trp Lys Pro Met Val Glu Glu Ile His Met
                405                 410                 415

Leu Glu Thr Arg Gln Ser Gln Arg Ser Ser Ser Ser Trp Arg Asp
                420                 425                 430

Glu Arg Thr Ser Thr Thr Val Phe Pro Asp Asn Asn Asn Asn Pro
                435                 440                 445

Ser Ser Ser Ala Gln Gln Arg Pro Asn Asn Ser Ser Pro Pro Arg
450                 455                 460

Arg Ala Arg Asn Asp Asp Val His Gly Thr Asn Asn Asn Asn Ser Tyr
465                 470                 475                 480

Val Asn Ser Gly Ser Gly Gly Ser Ala Val Gly Phe Ser Tyr Gly
                485                 490                 495

Ile Gly Ser Ser Asn Val Pro Val Met Asn Ser Ser Thr Asn Gly Gly
                500                 505                 510

Val Ser Leu Thr Leu Gly Leu His His Gln Ile Gly Leu Pro Glu Pro
                515                 520                 525

Phe Pro Met Thr Thr Ala Gln Arg Phe Gly Leu Asp Gly Gly Ser Gly
                530                 535                 540

Asp Gly Gly Gly Gly Tyr Glu Gly Gln Asn Arg Gln Phe Gly Arg Asp
545                 550                 555                 560

Phe Ile Gly Gly Ser Asn His Gln Phe Leu His Asp Phe Val Gly
                565                 570                 575

<210> SEQ ID NO 100
<211> LENGTH: 1942
<212> TYPE: DNA
<213> ORGANISM: Arabidopsis thaliana
<220> FEATURE:
<221> NAME/KEY: misc_feature
<222> LOCATION: (1)..(1942)
<223> OTHER INFORMATION: Ceres CLONE ID no.41610
<220> FEATURE:
<221> NAME/KEY: misc_feature
<222> LOCATION: (1)..(1942)
<223> OTHER INFORMATION: Encodes the peptide sequence at SEQ ID NO:101

<400> SEQUENCE: 100
```

```
aaaacgcaaa agaagaacgg agcaaaatct tcagaatcgt cgccggagaa tctttacgtt      60
tcgacataat cggaattttg gaattgataa ttccgatgga aggggttatc acatgtttcc     120
atacgaaatg cgtctctctt ccaattcgtt ctttcccact ttctagggtt tcttcacttc     180
ctcggtggag gaacaataaa ttgatctctt catcgcgatc ggttcatcta agaagcttgt     240
gcgtttcggc ttcgagctca gatactttag tcgcgggcgg ttcaccaaag gaagacgaga     300
ggcagagcaa agtatcgagc aagaaggaag gagatgactc cgaggatttg aagttttgga     360
tggataagaa tgggttgcca ccttgcaagg ttattctcaa ggagaaacca gctcatgatc     420
agaagcataa acctatacat tatgttgctg ctagtgagga tcttcagaag ggtgatgtgg     480
cgttttcagt tcctgattct ctggtggtca ctctggaaag agttttggga aacgagacta     540
ttgctgaact gttgacgacg aacaaattat ccgaactggc ttgtctagct ttgtatttga     600
tgtatgagaa gaaacaagga aagaaatcag tatggtatcc ctatataaga gaacttgatc     660
gtcaaagagg aagaggtcag ttagatgcgg aatcccsttt gctgtggtca gaggctgagt     720
tagattacct aactggtagt cctaccaagg ccgaagttct tgagagggct gaagggatca     780
aaagagaata caatgagctt gacactgtct ggttcatggc tggatctttg tttcagcaat     840
acccatttga cataccaact gaagcttttt catttgagat tttcaaacag gcatttgttg     900
ccattcagtc atgtgtggtg catttacaaa atgtcggttt ggctcgtcgg tttgctttgg     960
ttcctcttgg tcctcccttg ttggcctatt gttccaactg caaggcaatg cttactgctg    1020
ttgatggtgc tgttgaactc gtggtagata ggccatataa ggccggggat cctatagttg    1080
tctggtgtgg gccacaacca aatgcgaaat tgcttctgaa ctatggattt gttgatgagg    1140 ataacccctta tgatagagta atagttgagg cagcgttcaa cactgaggat ccccaatacc    1200
aggacaagag aatggttgct caaaggaacg gaaaattatc ccaacaagta tttcaggttc    1260
gtgtgggaaa agaaagagaa gctgttcaag acatgcttcc ctacctgcgg ttgggttaca    1320
tgtctgatcc ttctgaaatg cagtcagtaa tttcatccca aggtccagtt tgtccgatga    1380
gcccttgtat ggaaagagca gtactagatc agcttgctaa ttacttcatg agacggttat    1440
ctggctaccc tactactccg aaagaagatg atgcattgtt ggcagatcct agtttgagtc    1500
ctaggaagcg agttgcaacc cggcttgtcc aactggagaa gaaaatacta gttgcatgcc    1560
ttacgacaac agttgatctt ttaaatcagt tgcccgatac agccatctct ccatgcccag    1620
caccatatgc tccttccttg aaataaaaag gttcgtgttg tagctgcaat tgtgtgggaca    1680 tggcaggagt aattttttggt cgtgtccttg atcattacaa tctgaggtcg cttaactacg    1740
gtagataagg gtgtactagg agcgttatct gccgcttgac acgcaaatgt ttcagcatat    1800
gattgtcctt tttttcttac aacaatgaag ccttaagtcg cattgttcaa agtgtacata    1860
catgaatgaa ccttcttgtt cttccccaac tccctctgta atgttttatc tctgttttag    1920
aaatttagaa tttatcattt ct                                             1942
```

```
<210> SEQ ID NO 101
<211> LENGTH: 516
<212> TYPE: PRT
<213> ORGANISM: Arabidopsis thaliana
<220> FEATURE:
<221> NAME/KEY: misc_feature
<222> LOCATION: (1)..(516)
<223> OTHER INFORMATION: Ceres CLONE ID no. 41610
<220> FEATURE:
<221> NAME/KEY: misc_feature
<222> LOCATION: (83)..(338)
<223> OTHER INFORMATION: Pfam Name: SET
```

Pfam Description: SET domain

<400> SEQUENCE: 101

| Met | Glu | Gly | Val | Ile | Thr | Cys | Phe | His | Thr | Lys | Cys | Val | Ser | Leu | Pro |
|---|---|---|---|---|---|---|---|---|---|---|---|---|---|---|---|
| 1 | | | | 5 | | | | | 10 | | | | | 15 | |

Ile Arg Ser Phe Pro Leu Ser Arg Val Ser Ser Leu Pro Arg Trp Arg
                  20                  25                  30

Asn Asn Lys Leu Ile Ser Ser Ser Arg Ser Val His Leu Arg Ser Leu
                  35                  40                  45

Cys Val Ser Ala Ser Ser Ser Asp Thr Leu Val Ala Gly Gly Ser Pro
                  50                  55                  60

Lys Glu Asp Glu Arg Gln Ser Lys Val Ser Ser Lys Lys Glu Gly Asp
65                  70                  75                  80

Asp Ser Glu Asp Leu Lys Phe Trp Met Asp Lys Asn Gly Leu Pro Pro
                  85                  90                  95

Cys Lys Val Ile Leu Lys Glu Lys Pro Ala His Asp Gln Lys His Lys
                  100               105             110

Pro Ile His Tyr Val Ala Ala Ser Glu Asp Leu Gln Lys Gly Asp Val
                  115               120             125

Ala Phe Ser Val Pro Asp Ser Leu Val Val Thr Leu Glu Arg Val Leu
                  130               135             140

Gly Asn Glu Thr Ile Ala Glu Leu Leu Thr Thr Asn Lys Leu Ser Glu
145                150               155             160

Leu Ala Cys Leu Ala Leu Tyr Leu Met Tyr Glu Lys Lys Gln Gly Lys
                  165               170             175

Lys Ser Val Trp Tyr Pro Tyr Ile Arg Glu Leu Asp Arg Gln Arg Gly
                  180               185             190

Arg Gly Gln Leu Asp Ala Glu Ser Pro Leu Leu Trp Ser Glu Ala Glu
                  195               200             205

Leu Asp Tyr Leu Thr Gly Ser Pro Thr Lys Ala Glu Val Leu Glu Arg
                  210               215             220

Ala Glu Gly Ile Lys Arg Glu Tyr Asn Glu Leu Asp Thr Val Trp Phe
225                230               235             240

Met Ala Gly Ser Leu Phe Gln Gln Tyr Pro Phe Asp Ile Pro Thr Glu
                  245               250             255

Ala Phe Ser Phe Glu Ile Phe Lys Gln Ala Phe Val Ala Ile Gln Ser
                  260               265             270

Cys Val Val His Leu Gln Asn Val Gly Leu Ala Arg Arg Phe Ala Leu
                  275               280             285

Val Pro Leu Gly Pro Pro Leu Leu Ala Tyr Cys Ser Asn Cys Lys Ala
                  290               295             300

Met Leu Thr Ala Val Asp Gly Ala Val Glu Leu Val Asp Arg Pro
305                310               315             320

Tyr Lys Ala Gly Asp Pro Ile Val Val Trp Cys Gly Pro Gln Pro Asn
                  325               330             335

Ala Lys Leu Leu Leu Asn Tyr Gly Phe Val Asp Glu Asp Asn Pro Tyr
                  340               345             350

Asp Arg Val Ile Val Glu Ala Ala Phe Asn Thr Glu Asp Pro Gln Tyr
                  355               360             365

Gln Asp Lys Arg Met Val Ala Gln Arg Asn Gly Lys Leu Ser Gln Gln
                  370               375             380

Val Phe Gln Val Arg Val Gly Lys Glu Arg Glu Ala Val Gln Asp Met
385                390               395             400

Leu Pro Tyr Leu Arg Leu Gly Tyr Met Ser Asp Pro Ser Glu Met Gln

```
                   405                 410                 415
Ser Val Ile Ser Ser Gln Gly Pro Val Cys Pro Met Ser Pro Cys Met
            420                 425                 430

Glu Arg Ala Val Leu Asp Gln Leu Ala Asn Tyr Phe Met Arg Arg Leu
        435                 440                 445

Ser Gly Tyr Pro Thr Thr Pro Lys Glu Asp Asp Ala Leu Leu Ala Asp
    450                 455                 460

Pro Ser Leu Ser Pro Arg Lys Arg Val Ala Thr Arg Leu Val Gln Leu
465                 470                 475                 480

Glu Lys Lys Ile Leu Val Ala Cys Leu Thr Thr Thr Val Asp Leu Leu
                485                 490                 495

Asn Gln Leu Pro Asp Thr Ala Ile Ser Pro Cys Pro Ala Pro Tyr Ala
            500                 505                 510

Pro Ser Leu Lys
        515

<210> SEQ ID NO 102
<211> LENGTH: 1670
<212> TYPE: DNA
<213> ORGANISM: Arabidopsis thaliana
<220> FEATURE:
<221> NAME/KEY: misc_feature
<222> LOCATION: (1)..(1670)
<223> OTHER INFORMATION: Ceres CLONE ID no.110454
<220> FEATURE:
<221> NAME/KEY: misc_feature
<222> LOCATION: (1)..(1670)
<223> OTHER INFORMATION: Encodes the peptide sequence at SEQ ID NO:103

<400> SEQUENCE: 102
aaaaaggatc aaacatagta tagcttggac tcttttttgcc gtctatgatc tctctcaatc    60
tctcatctta gctttctttc tctctctctt tgtgtcttca tttgtttatc tcatcaatgg   120
attcaaattt tcattactcg atagatctta acgaagatca aaaccatcac gaacaaccct   180
ttttctatcc tcttggatcc tcttcctcgc ttcatcatca tcatcatcat catcatcatc   240
aagtcccttc taattcttca tcttcttctt cgtccatttc atcgctctcc tcttacctcc   300
ctttcttgat caactctcaa gaagatcaac atgttgccta caacaacact tatcacgctg   360
atcatctcca tctttctcaa cccctcaagg ccaagatgtt tgtggctaac ggtggatcat   420
catcatgcga tcacatggtg ccaaagaagg agacaagact gaaactaacg ataaggaaaa   480
aagatcacga agaccaaccc catcctcttc atcaaaaccc gacaaaaccc gattcagact   540
ccgacaagtg gttgatgtcc ccaaagatgc ggttgatcaa gaaacaatc accaacaata   600 aacagctcac tgatcagact aataataata tcataaaga aagtgatcac taccctttga   660
atcataagac taatttcgac gaggatcacc atgaagatct taatttcaag aacgtcttga   720
ccaggaagac cacggccgcg accaccgaga tcgctacaa taatcaac gagaacggtt   780 atagtaataa caatggcgtg attagggttt gttcggattg taacaccacc aagactcctc   840
tttggcgaag tggacctcga ggtcccaagt ctctttgtaa cgcatgtggt atacggcaaa   900
gaaaggcaag gcgagccgct atggccgcgg ccgctgcagc cggcgaccaa gaggtggcgg   960
tagcgccccg agtgcaacaa ttaccgctga aaagaagtt gcaaataaa aaaaagaga   1020 tcaaacggag gggaaaaata caatcactct cctccaatgg tggccaaggc caaaagtgc   1080 aagatcaaag aggaagagga gaaggaaatg gaagcggaaa cggttgccgg agattcagag   1140
atcagcaaat ctacaacttc ttctaattct tcgatttcgt caaacaaatt ttgcttcgat   1200
gatttgacaa taatgttgag caaaagctca gcttatcaac aagtgttccc acaagatgag   1260
```

```
aaggaggctg ctgttttgct catggctctg tcgtatggaa tggttcacgg ttgatcagat    1320
catcacaata tcctcattac aaaaaggttt attttaatag taatatatag attatagtaa    1380
tcataataat gattgattgt taaatcttgg agtgattagt ttagtttttg cagttggtct    1440
aatatcagga gtcaaaacat tttataataa gagtgtgtga gagtttaata tgataattaa    1500
tagctctata tatgtttatg gagattttgg ttttgagttt gttgtgtttt tgttttccga    1560
tggaacgaac attagtcacc cgataatgtg ggtaattctt gttcatttac aagtttata     1620 gtactgtatt gtgtaacgag gttggagaaa taatataatc aattaagggt               1670
```

<210> SEQ ID NO 103
<211> LENGTH: 349
<212> TYPE: PRT
<213> ORGANISM: Arabidopsis thaliana
<220> FEATURE:
<221> NAME/KEY: misc_feature
<222> LOCATION: (1)..(349)
<223> OTHER INFORMATION: Ceres CLONE ID no. 110454
<220> FEATURE:
<221> NAME/KEY: misc_feature
<222> LOCATION: (232)..(267)
<223> OTHER INFORMATION: Pfam Name: GATA
     Pfam Description: GATA zinc finger

<400> SEQUENCE: 103

Met Asp Ser Asn Phe His Tyr Ser Ile Asp Leu Asn Glu Asp Gln Asn
1               5                   10                  15

His His Glu Gln Pro Phe Phe Tyr Pro Leu Gly Ser Ser Ser Ser Leu
            20                  25                  30

His His His His His His His His Gln Val Pro Ser Asn Ser Ser
        35                  40                  45

Ser Ser Ser Ser Ser Ile Ser Ser Leu Ser Ser Tyr Leu Pro Phe Leu
    50                  55                  60

Ile Asn Ser Gln Glu Asp Gln His Val Ala Tyr Asn Asn Thr Tyr His
65                  70                  75                  80

Ala Asp His Leu His Leu Ser Gln Pro Leu Lys Ala Lys Met Phe Val
                85                  90                  95

Ala Asn Gly Gly Ser Ser Ser Cys Asp His Met Val Pro Lys Lys Glu
            100                 105                 110

Thr Arg Leu Lys Leu Thr Ile Arg Lys Lys Asp His Glu Asp Gln Pro
        115                 120                 125

His Pro Leu His Gln Asn Pro Thr Lys Pro Asp Ser Asp Ser Asp Lys
    130                 135                 140

Trp Leu Met Ser Pro Lys Met Arg Leu Ile Lys Lys Thr Ile Thr Asn
145                 150                 155                 160

Asn Lys Gln Leu Thr Asp Gln Thr Asn Asn Asn His Lys Glu Ser
                165                 170                 175

Asp His Tyr Pro Leu Asn His Lys Thr Asn Phe Asp Glu Asp His His
            180                 185                 190

Glu Asp Leu Asn Phe Lys Asn Val Leu Thr Arg Lys Thr Thr Ala Ala
        195                 200                 205

Thr Thr Glu Asn Arg Tyr Asn Thr Ile Asn Glu Asn Gly Tyr Ser Asn
    210                 215                 220

Asn Asn Gly Val Ile Arg Val Cys Ser Asp Cys Asn Thr Thr Lys Thr
225                 230                 235                 240

Pro Leu Trp Arg Ser Gly Pro Arg Gly Pro Lys Ser Leu Cys Asn Ala
                245                 250                 255

```
Cys Gly Ile Arg Gln Arg Lys Ala Arg Arg Ala Ala Met Ala Ala Ala
            260                 265                 270

Ala Ala Ala Gly Asp Gln Glu Val Ala Val Ala Pro Arg Val Gln Gln
        275                 280                 285

Leu Pro Leu Lys Lys Lys Leu Gln Asn Lys Lys Glu Ile Lys Arg
290                 295                 300

Arg Gly Lys Ile Gln Ser Leu Ser Ser Asn Gly Gln Gly Gln Lys
305                 310                 315                 320

Val Gln Asp Gln Arg Gly Arg Gly Glu Gly Asn Gly Ser Gly Asn Gly
                325                 330                 335

Cys Arg Arg Phe Arg Asp Gln Gln Ile Tyr Asn Phe Phe
            340                 345

<210> SEQ ID NO 104
<211> LENGTH: 1011
<212> TYPE: DNA
<213> ORGANISM: Arabidopsis thaliana
<220> FEATURE:
<221> NAME/KEY: misc_feature
<222> LOCATION: (1)..(1011)
<223> OTHER INFORMATION: Ceres CLONE ID no.11922
<220> FEATURE:
<221> NAME/KEY: misc_feature
<222> LOCATION: (1)..(1011)
<223> OTHER INFORMATION: Encodes the peptide sequence at SEQ ID NO:105

<400> SEQUENCE: 104
aattaggttt tcttctacac ttgttcttct tcatttgctc tcttcttcat caatctctct      60 cttttttgtaa acggcgattt taaaatggtt gatgcaaaac aagttcgttt catcatcgga    120
gttatcggaa atgttatctc ctttggtctc tttgccgcac cagcgaagac tttctggagg    180
atcttcaaga agaaatcagt ggaagagttt tcgtatgtgc cgtacgtagc aacggtgatg    240
aattgtatgt tgtgggtgtt ttacggtctc cctgtggttc acaaagacag tattctagtt    300
tcaaccatta atggtgttgg gttagttatc gaacttttct acgttggtgt ctacttgatg    360
tactgtggtc acaagaagaa ccatcgaagg aacattttgg gattcttagc tcttgaagtt    420
attttggtgg tggctatcat tcttattacg ctctttgcgc ttaagggtga ttttgttaag    480
caaacatttg ttggtgtgat ttgcgatgtc ttcaacattg ctatgtatgg agctccttca    540
ttggccatta ttaaagtggt aaaaacaaag agtgttgaat acatgccatt cttgttgtct    600
ttggtctgtt tcgttaatgc tggaatttgg actacttact cgctcatctt caagatcgat    660
tactacgtcc tcgcaagtaa tgggattgga acctttttgg cactttctca gttgatagtg    720
tacttcatgt actataagtc aactccaaag gagaagacgg tgaagccatc agaagttgag    780
atttctgcta cggagagggt ttagaagaat tgtgctttgg attctatctt cttacgtaca    840
ttttacatac acaatttgtg tgtatgttta ggcttttggg tttttatgtt tggtagaatt    900
ttccaatcgt ttagtttctg gatttggagg attcgtcttg gttcattttc ttaatacatt    960
tttatggtgt gaaacgcttt gacggaaatc atcaagtttt ggatttattc t             1011

<210> SEQ ID NO 105
<211> LENGTH: 239
<212> TYPE: PRT
<213> ORGANISM: Arabidopsis thaliana
<220> FEATURE:
<221> NAME/KEY: misc_feature
<222> LOCATION: (1)..(239)
<223> OTHER INFORMATION: Ceres CLONE ID no. 11922
<220> FEATURE:
<221> NAME/KEY: misc_feature
<222> LOCATION: (134)..(221)
```

<223> OTHER INFORMATION: Pfam Name: MtN3_slv
      Pfam Description: MtN3/saliva family

<400> SEQUENCE: 105

```
Met Val Asp Ala Lys Gln Val Arg Phe Ile Ile Gly Val Ile Gly Asn
1               5                   10                  15

Val Ile Ser Phe Gly Leu Phe Ala Ala Pro Ala Lys Thr Phe Trp Arg
            20                  25                  30

Ile Phe Lys Lys Lys Ser Val Glu Phe Ser Tyr Val Pro Tyr Val
        35                  40                  45

Ala Thr Val Met Asn Cys Met Leu Trp Val Phe Tyr Gly Leu Pro Val
    50                  55                  60

Val His Lys Asp Ser Ile Leu Val Ser Thr Ile Asn Gly Val Gly Leu
65                  70                  75                  80

Val Ile Glu Leu Phe Tyr Val Gly Val Tyr Leu Met Tyr Cys Gly His
                85                  90                  95

Lys Lys Asn His Arg Arg Asn Ile Leu Gly Phe Leu Ala Leu Glu Val
            100                 105                 110

Ile Leu Val Val Ala Ile Ile Leu Ile Thr Leu Phe Ala Leu Lys Gly
        115                 120                 125

Asp Phe Val Lys Gln Thr Phe Val Gly Val Ile Cys Asp Val Phe Asn
    130                 135                 140

Ile Ala Met Tyr Gly Ala Pro Ser Leu Ala Ile Ile Lys Val Val Lys
145                 150                 155                 160

Thr Lys Ser Val Glu Tyr Met Pro Phe Leu Leu Ser Leu Val Cys Phe
                165                 170                 175

Val Asn Ala Gly Ile Trp Thr Thr Tyr Ser Leu Ile Phe Lys Ile Asp
            180                 185                 190

Tyr Tyr Val Leu Ala Ser Asn Gly Ile Gly Thr Phe Leu Ala Leu Ser
        195                 200                 205

Gln Leu Ile Val Tyr Phe Met Tyr Tyr Lys Ser Thr Pro Lys Glu Lys
    210                 215                 220

Thr Val Lys Pro Ser Glu Val Glu Ile Ser Ala Thr Glu Arg Val
225                 230                 235
```

<210> SEQ ID NO 106
<211> LENGTH: 815
<212> TYPE: DNA
<213> ORGANISM: Arabidopsis thaliana
<220> FEATURE:
<221> NAME/KEY: misc_feature
<222> LOCATION: (1)..(815)
<223> OTHER INFORMATION: Ceres CLONE ID no.28780
<220> FEATURE:
<221> NAME/KEY: misc_feature
<222> LOCATION: (1)..(815)
<223> OTHER INFORMATION: Encodes the peptide sequence at SEQ ID NO:107

<400> SEQUENCE: 106

```
aactactaaa cactaaatta tcaatccgct ctcttctcaa aaaaaaaaaa tcgactctaa     60
aatcaaactc tctcaaagct ccccaaaaaa accctagttc tgaatggaat cggcggattc    120
cggacgatcc gatccggtaa aaggagacga cccgggtcca tctttcgtct cttcaccacc    180
agctacacct agcaggtatg agtcacagaa gcgacgcgac tggaacacgt tcttgcagta    240
cctcaagaac cacaagccgc tctctcgcgt tgtcacggtgt agcggagcgc atgtgatcga    300
gtttctcaag tacctcgacc agttcggtaa gaccaaagtc cacgtggcgg cttgtcctta    360
cttcggccat cagcaacctc cgtctccttg ctcatgccct ctcaagcaag cttggggatc    420
```

```
tctcgatgct tgatcggac ggttgagagc tgcctacgag gagaacggtg gacggccgga    480 ttctaaccccg ttcgccgcac gtgcggttcg gatttacttg agggaagtca gagagagtca    540
ggcaaaggct cgtgggattc cttacgagaa aaagaaacgg aaacggccgc caactgtcac    600
caccgttaga gttgacgtcg cttcttcgag acaaagtgac ggagaccctt gtaacgtcgg    660
tgctccatct gttgccgagg ccgtaccgcc ttagatcgaa ttatatataa tattatagtt    720
ttcttgatta atgatatata tatacttatc tctatgtatg tatggaactc acttcatctt    780
ttgttcctta gtacctaatt attaaatttt gttcc                               815
```

```
<210> SEQ ID NO 107
<211> LENGTH: 196
<212> TYPE: PRT
<213> ORGANISM: Arabidopsis thaliana
<220> FEATURE:
<221> NAME/KEY: misc_feature
<222> LOCATION: (1)..(196)
<223> OTHER INFORMATION: Ceres CLONE ID no. 28780
<220> FEATURE:
<221> NAME/KEY: misc_feature
<222> LOCATION: (13)..(145)
<223> OTHER INFORMATION: Pfam Name: DUF640
      Pfam Description: Protein of unknown function (DUF640)

<400> SEQUENCE: 107
```

Met Glu Ser Ala Asp Ser Gly Arg Ser Asp Pro Val Lys Gly Asp Asp
1               5                   10                  15

Pro Gly Pro Ser Phe Val Ser Pro Pro Ala Thr Pro Ser Arg Tyr
            20                  25                  30

Glu Ser Gln Lys Arg Arg Asp Trp Asn Thr Phe Leu Gln Tyr Leu Lys
        35                  40                  45

Asn His Lys Pro Pro Leu Ala Leu Ser Arg Cys Ser Gly Ala His Val
    50                  55                  60

Ile Glu Phe Leu Lys Tyr Leu Asp Gln Phe Gly Lys Thr Lys Val His
65                  70                  75                  80

Val Ala Ala Cys Pro Tyr Phe Gly His Gln Gln Pro Pro Ser Pro Cys
                85                  90                  95

Ser Cys Pro Leu Lys Gln Ala Trp Gly Ser Leu Asp Ala Leu Ile Gly
            100                 105                 110

Arg Leu Arg Ala Ala Tyr Glu Glu Asn Gly Gly Arg Pro Asp Ser Asn
        115                 120                 125

Pro Phe Ala Ala Arg Ala Val Arg Ile Tyr Leu Arg Glu Val Arg Glu
    130                 135                 140

Ser Gln Ala Lys Ala Arg Gly Ile Pro Tyr Glu Lys Lys Arg Lys
145                 150                 155                 160

Arg Pro Pro Thr Val Thr Thr Val Arg Val Asp Val Ala Ser Ser Arg
                165                 170                 175

Gln Ser Asp Gly Asp Pro Cys Asn Val Gly Ala Pro Ser Val Ala Glu
            180                 185                 190

Ala Val Pro Pro
        195

```
<210> SEQ ID NO 108
<211> LENGTH: 1702
<212> TYPE: DNA
<213> ORGANISM: Arabidopsis thaliana
<220> FEATURE:
<221> NAME/KEY: misc_feature
<222> LOCATION: (1)..(1702)
<223> OTHER INFORMATION: Ceres ANNOT ID no. 542218
<220> FEATURE:
```

```
<221> NAME/KEY: misc_feature
<222> LOCATION: (1)..(1702)
<223> OTHER INFORMATION: Encodes the peptide sequence at SEQ ID NO:109

<400> SEQUENCE: 108
```

| | | | | | |
|---|---|---|---|---|---|
| atgggtctag | aggatgctgg | agatttggtt | ctccacatcg | tcttatccaa | aatcggccct | 60 |
| gaaaacaccg | cgagagtggc | ttgtgtcagt | aaacgcctta | aggtctccgc | ctccgaggaa | 120 |
| tctctctggt | ctatcttctg | ctccaatgat | cttaatatct | ctactcctct | cgatccccat | 180 |
| ggagatcctg | ctccttcctt | caaggtcaat | ttcactcttt | tcttcttttc | acattttcta | 240 |
| gggttttgat | tgtttagcgc | cttagaattt | gacctgaatt | tgagactacc | ttaaagtaaa | 300 |
| gattttctc | ttaattcatc | agagagcata | tcaattgtgg | agggagtcat | ttagaatgta | 360 |
| tccttggaat | ctggttaaaa | gagttagact | ttgttgggac | aacctcaaac | aatggttgac | 420 |
| cttaaacttc | cctgaagcaa | aggcaacact | gaggaaaggt | gtcacagaag | atgatcttca | 480 |
| agaattcgag | acttctctca | aagtgaaact | tcctttgccc | acaaggcttc | tctaccgttt | 540 |
| cgttgatggt | caagagcttt | cttcccccaa | tgggcttgat | ggctctttgg | ggcttatagg | 600 |
| tggctattcc | gcttattctc | atgacgttaa | tgtctacttg | ctacctctta | aggaagtgat | 660 |
| gagggagaca | aaggaaagtt | tcatgcgcga | cctcggtttc | tcgagtagat | tagaccttat | 720 |
| tgttatggct | gcatccgtag | ttgccagtct | gaaaatattt | ttattagact | gcacaaccgg | 780 |
| acagcttttt | actgggacaa | gtaaccgcca | attgcttcct | tgtgtacccg | atgctttggt | 840 |
| tagatcggtt | catgatacca | acggcgatca | gcaacaggat | gccatgctgc | tttggttgga | 900 |
| agaacatggc | cggcggttac | aaaccggcac | tataaatgtc | cgtcaacaga | acaatgtcaa | 960 |
| gagtatcagt | ttgttcccgg | agattcctcc | cttgtgttct | gtctccgtaa | ctaatggtgt | 1020 |
| gcaggtaaag | caatgtgtta | ttcagttta | ttgatattca | ggtttgtgga | ttgtgggttg | 1080 |
| aaaagcttgt | tcatgaataa | tgcaggtacg | tgcttcgtct | gttttatcc | cggaaatatc | 1140 |
| gaaccttcgg | gatcagccac | cggcatactg | gtatgcatat | tcaatccgga | tgtctctcat | 1200 |
| gccagaagga | tgcatcttga | atgggacaca | tcatagctct | tgccaactgt | attggagaca | 1260 |
| ttgggttatc | cgagctgata | atgaagtgat | agataatgtt | aatggagaag | ctgtcatagg | 1320 |
| aaaggtgtag | ttttgctttt | agttcaagat | aacaacaatt | tgtttgttga | aggaccaaca | 1380 |
| gtcgtttcc | gttttgtgat | atgaactctg | ttttgttata | tttgtagtac | ccgctcttac | 1440 |
| aagccgggga | ggaagagttt | gtgtatgaga | gttgttccag | ttttccgaca | actgctggat | 1500 |
| ccattgatgg | ctctttcacc | tttgtacctg | gaaggtatat | gatgatgtga | agaatcttag | 1560 |
| accacatgtc | ttgtagtttt | gaaactaaac | tggaatcttg | accttatgat | tatttttct | 1620 |
| tagtttgaga | gatccaaaag | ggagtcaatt | cgaagtcaaa | gtcgtagagt | ttcctctgga | 1680 |
| gttaccggac | tacatcttct | ga | | | | 1702 |

```
<210> SEQ ID NO 109
<211> LENGTH: 436
<212> TYPE: PRT
<213> ORGANISM: Arabidopsis thaliana
<220> FEATURE:
<221> NAME/KEY: misc_feature
<222> LOCATION: (1)..(436)
<223> OTHER INFORMATION: Ceres ANNOT ID no. 542218
<220> FEATURE:
<221> NAME/KEY: misc_feature
<222> LOCATION: (295)..(432)
<223> OTHER INFORMATION: Pfam Name: DUF525
      Pfam Description: Protein of unknown function (DUF525)

<400> SEQUENCE: 109
```

```
Met Gly Leu Glu Asp Ala Gly Asp Leu Val Leu His Ile Val Leu Ser
1               5                   10                  15

Lys Ile Gly Pro Glu Asn Thr Ala Arg Val Ala Cys Val Ser Lys Arg
            20                  25                  30

Leu Lys Val Ser Ala Ser Glu Ser Leu Trp Ser Ile Phe Cys Ser
        35                  40                  45

Asn Asp Leu Asn Ile Ser Thr Pro Leu Asp Pro His Gly Asp Pro Ala
50                      55                  60

Pro Ser Phe Lys Arg Ala Tyr Gln Leu Trp Arg Glu Ser Phe Arg Met
65                  70                  75                  80

Tyr Pro Trp Asn Leu Val Lys Arg Val Arg Leu Cys Trp Asp Asn Leu
                85                  90                  95

Lys Gln Trp Leu Thr Leu Asn Phe Pro Glu Ala Lys Ala Thr Leu Arg
            100                 105                 110

Lys Gly Val Thr Glu Asp Asp Leu Gln Glu Phe Glu Thr Ser Leu Lys
            115                 120                 125

Val Lys Leu Pro Leu Pro Thr Arg Leu Leu Tyr Arg Phe Val Asp Gly
    130                 135                 140

Gln Glu Leu Ser Ser Pro Asn Gly Leu Asp Gly Ser Leu Gly Leu Ile
145                 150                 155                 160

Gly Gly Tyr Ser Ala Tyr Ser His Asp Val Asn Val Tyr Leu Leu Pro
                165                 170                 175

Leu Lys Glu Val Met Arg Glu Thr Lys Glu Ser Phe Met Arg Asp Leu
            180                 185                 190

Gly Phe Ser Ser Arg Leu Asp Leu Ile Val Met Ala Ala Ser Val Val
        195                 200                 205

Ala Ser Leu Lys Ile Phe Leu Leu Asp Cys Thr Thr Gly Gln Leu Phe
    210                 215                 220

Thr Gly Thr Ser Asn Arg Gln Leu Leu Pro Cys Val Pro Asp Ala Leu
225                 230                 235                 240

Val Arg Ser Val His Asp Thr Asn Gly Asp Gln Gln Asp Ala Met
            245                 250                 255

Leu Leu Trp Leu Glu Glu His Gly Arg Arg Leu Gln Thr Gly Thr Ile
        260                 265                 270

Asn Val Arg Gln Gln Asn Asn Val Lys Ser Ile Ser Leu Phe Pro Glu
    275                 280                 285

Ile Pro Pro Leu Cys Ser Val Ser Val Thr Asn Gly Val Gln Val Arg
    290                 295                 300

Ala Ser Ser Val Phe Ile Pro Glu Ile Ser Asn Leu Arg Asp Gln Pro
305                 310                 315                 320

Pro Ala Tyr Trp Tyr Ala Tyr Ser Ile Arg Met Ser Leu Met Pro Glu
                325                 330                 335

Gly Cys Ile Leu Asn Gly Thr His His Ser Ser Cys Gln Leu Tyr Trp
            340                 345                 350

Arg His Trp Val Ile Arg Ala Asp Asn Glu Val Ile Asp Asn Val Asn
        355                 360                 365

Gly Glu Ala Val Ile Gly Lys Tyr Pro Leu Leu Gln Ala Gly Glu Glu
    370                 375                 380

Glu Phe Val Tyr Glu Ser Cys Ser Ser Phe Pro Thr Thr Ala Gly Ser
385                 390                 395                 400

Ile Asp Gly Ser Phe Thr Phe Val Pro Gly Ser Leu Arg Asp Pro Lys
                405                 410                 415

Gly Ser Gln Phe Glu Val Lys Val Val Glu Phe Pro Leu Glu Leu Pro
```

Asp Tyr Ile Phe
    435

<210> SEQ ID NO 110
<211> LENGTH: 2009
<212> TYPE: DNA
<213> ORGANISM: Arabidopsis thaliana
<220> FEATURE:
<221> NAME/KEY: misc_feature
<222> LOCATION: (1)..(2009)
<223> OTHER INFORMATION: Ceres ANNOT ID no. 508164
<220> FEATURE:
<221> NAME/KEY: misc_feature
<222> LOCATION: (1)..(2009)
<223> OTHER INFORMATION: Encodes the peptide sequence at SEQ ID NO:111

<400> SEQUENCE: 110

| | | | | | | |
|---|---|---|---|---|---|---|
| atggacaaca | acaacaacaa | caacactttt | agttctctgg | ataatgtcat | gactaaccaa | 60 |
| aatcctcttc | tcatggattt | tataccttca | agagaagatt | caacttcatt | ctcaacaatg | 120 |
| cttccatgga | ataccatcag | atcagatcct | ctacaaatgg | gtggctttga | tattttcaat | 180 |
| tctatgctga | ctaacaaata | cttatcatct | tctccacggt | ctatcgatgt | tcaagataac | 240 |
| cgcaatgttg | agttcatggc | tcctcctcct | catcctcctc | cacttcatcc | tttggatcat | 300 |
| ttaagacact | atgatgattc | ctcaaacaac | atgtggggtt | ttgaagcaaa | tagtgagttt | 360 |
| caggcatttt | caggtgtagt | tggtccaagt | gaaccaatga | tgtctacatt | cggtgaagaa | 420 |
| gatttcccgt | ttctaatttc | gaataaaaga | acaatgagc | tttcattgag | tcttgcatca | 480 |
| gatgtttctg | atgaatgctc | ggagataagt | ctttgtgcag | ctacaagatt | agcctcagag | 540 |
| caagcttctt | gcagcagcaa | agacatttct | aataacgttg | ttactcaagg | tttctctcaa | 600 |
| cttatatttg | gctcaaaata | ccttcactct | gttcaagaaa | tactatctca | tttcgccgca | 660 |
| tactcgctcg | attattcatc | tcgaggaacc | gagtcaggag | ctgctagttc | agcctttact | 720 |
| tcacgttttg | agaatataac | tgagtttctt | gatggtgatt | ctaataactc | ggaggcgggt | 780 |
| ttcggatcta | catttcaaag | gagagcatta | gaagcaaaga | aaacccatct | cttggatctt | 840 |
| cttcaaatgg | tatgtaatat | attcattcac | tttttttgca | taagttaaaa | aaatggtttg | 900 |
| atatatatga | tgaagtttta | tgagttgata | tttctcttca | ggtggatgat | cgatatagtc | 960 |
| attgcgtaga | tgagattcat | acggttatat | cagcgttcca | tgctgcaacc | gagttagatc | 1020 |
| cacagttaca | cacccggttt | gccctccaaa | ccgtttcctt | cttatacaag | aacctgagag | 1080 |
| agagaatctg | caagaagata | atctctatgg | gatctgtatt | ggagagaggc | aaagacaaga | 1140 |
| ctcaagaaac | ctctatgttc | caccagcatt | gccttcttca | gcagctgaaa | cgaaagaacc | 1200 |
| atcagatttg | gagacctcaa | cgaggtttgc | ctgagaaatc | tgtttcggtt | ctacggaatt | 1260 |
| ggatgttcca | aaacttcctt | cacccgtaac | aatccttact | cttcttaact | atctacttta | 1320 |
| tgatgatgac | attgttaact | cgattttata | agcaaagtta | tgtttatttt | aatgcagtta | 1380 |
| cccgaaagat | tcggagaaac | atcttctagc | tatacgaagt | ggcttgacaa | gaagtcaggt | 1440 |
| aatgtctcat | gtttgttttc | ttatgcaatg | actcattgat | aacaagcttt | gttttcttat | 1500 |
| gcaatgactc | attgataaga | tctttgtttt | cttatgcaat | gacttattga | taacatcttt | 1560 |
| gctcacaatg | atagcaaata | tggtattcaa | atgagtaata | tatatcttga | catactagtc | 1620 |
| atgtctgaaa | accggtatt | ggttatttta | agatgagatt | agggctagga | aaaaatcaag | 1680 |
| cttttctctt | gaactacaaa | tgagactaga | ttatgtattc | ttgaattcac | aataatgtta | 1740 |
| ctcaagtcct | aggattgtag | tcgcacatat | gttttgttac | tgaagtaagt | taaagcgggc | 1800 |

-continued

```
aaatgatata gagtgtgtct ctttgttgtg tgtgattaaa ggtatcaaac tggtttataa      1860
atgcgcgggt taggctatgg aagccgatga tagaagagat gtatgcggaa atgaacaaga      1920
ggaagctcaa taacagtcac attcaaccca acggaccaac tcttcgaatg ccaaaatctg      1980
ttatgatgag ccaagcaatg cataaataa                                       2009
```

```
<210> SEQ ID NO 111
<211> LENGTH: 473
<212> TYPE: PRT
<213> ORGANISM: Arabidopsis thaliana
<220> FEATURE:
<221> NAME/KEY: misc_feature
<222> LOCATION: (1)..(473)
<223> OTHER INFORMATION: Ceres ANNOT ID no. 508164
<220> FEATURE:
<221> NAME/KEY: misc_feature
<222> LOCATION: (200)..(334)
<223> OTHER INFORMATION: Pfam Name: POX
      Pfam Description: Associated with HOX
<220> FEATURE:
<221> NAME/KEY: misc_feature
<222> LOCATION: (374)..(432)
<223> OTHER INFORMATION: Pfam Name: Homeobox
      Pfam Description: Homeobox domain

<400> SEQUENCE: 111
```

Met Asp Asn Asn Asn Asn Asn Thr Phe Ser Ser Leu Asp Asn Val
1               5                   10                  15

Met Thr Asn Gln Asn Pro Leu Leu Met Asp Phe Ile Pro Ser Arg Glu
                20                  25                  30

Asp Ser Thr Ser Phe Ser Thr Met Leu Pro Trp Asn Thr Ile Arg Ser
            35                  40                  45

Asp Pro Leu Gln Met Gly Gly Phe Asp Ile Phe Asn Ser Met Leu Thr
        50                  55                  60

Asn Lys Tyr Leu Ser Ser Ser Pro Arg Ser Ile Asp Val Gln Asp Asn
65                  70                  75                  80

Arg Asn Val Glu Phe Met Ala Pro Pro His Pro Pro Leu His
                85                  90                  95

Pro Leu Asp His Leu Arg His Tyr Asp Asp Ser Ser Asn Asn Met Trp
                100                 105                 110

Gly Phe Glu Ala Asn Ser Glu Phe Gln Ala Phe Ser Gly Val Val Gly
            115                 120                 125

Pro Ser Glu Pro Met Met Ser Thr Phe Gly Glu Glu Asp Phe Pro Phe
        130                 135                 140

Leu Ile Ser Asn Lys Arg Asn Asn Glu Leu Ser Leu Ser Leu Ala Ser
145                 150                 155                 160

Asp Val Ser Asp Glu Cys Ser Glu Ile Ser Leu Cys Ala Ala Thr Arg
                165                 170                 175

Leu Ala Ser Glu Gln Ala Ser Cys Ser Ser Lys Asp Ile Ser Asn Asn
            180                 185                 190

Val Val Thr Gln Gly Phe Ser Gln Leu Ile Phe Gly Ser Lys Tyr Leu
        195                 200                 205

His Ser Val Gln Glu Ile Leu Ser His Phe Ala Ala Tyr Ser Leu Asp
    210                 215                 220

Tyr Ser Ser Arg Gly Thr Glu Ser Gly Ala Ala Ser Ala Phe Thr
225                 230                 235                 240

Ser Arg Phe Glu Asn Ile Thr Glu Phe Leu Asp Gly Asp Ser Asn Asn
                245                 250                 255

Ser Glu Ala Gly Phe Gly Ser Thr Phe Gln Arg Arg Ala Leu Glu Ala

```
                    260                 265                 270
Lys Lys Thr His Leu Leu Asp Leu Leu Gln Met Val Asp Asp Arg Tyr
                275                 280                 285

Ser His Cys Val Asp Glu Ile His Thr Val Ile Ser Ala Phe His Ala
                290                 295                 300

Ala Thr Glu Leu Asp Pro Gln Leu His Thr Arg Phe Ala Leu Gln Thr
305                 310                 315                 320

Val Ser Phe Leu Tyr Lys Asn Leu Arg Glu Arg Ile Cys Lys Lys Ile
                325                 330                 335

Ile Ser Met Gly Ser Val Leu Glu Arg Gly Lys Asp Lys Thr Gln Glu
                340                 345                 350

Thr Ser Met Phe His Gln His Cys Leu Leu Gln Gln Leu Lys Arg Lys
                355                 360                 365

Asn His Gln Ile Trp Arg Pro Gln Arg Gly Leu Pro Glu Lys Ser Val
                370                 375                 380

Ser Val Leu Arg Asn Trp Met Phe Gln Asn Phe Leu His Pro Tyr Pro
385                 390                 395                 400

Lys Asp Ser Glu Lys His Leu Leu Ala Ile Arg Ser Gly Leu Thr Arg
                405                 410                 415

Ser Gln Val Ser Asn Trp Phe Ile Asn Ala Arg Val Arg Leu Trp Lys
                420                 425                 430

Pro Met Ile Glu Glu Met Tyr Ala Glu Met Asn Lys Arg Lys Leu Asn
                435                 440                 445

Asn Ser His Ile Gln Pro Asn Gly Pro Thr Leu Arg Met Pro Lys Ser
                450                 455                 460

Val Met Met Ser Gln Ala Met His Lys
465                 470

<210> SEQ ID NO 112
<211> LENGTH: 799
<212> TYPE: DNA
<213> ORGANISM: Arabidopsis thaliana
<220> FEATURE:
<221> NAME/KEY: misc_feature
<222> LOCATION: (1)..(799)
<223> OTHER INFORMATION: Ceres ANNOT ID no. 1271642
<220> FEATURE:
<221> NAME/KEY: misc_feature
<222> LOCATION: (1)..(799)
<223> OTHER INFORMATION: Encodes the peptide sequence at SEQ ID NO:112

<400> SEQUENCE: 112
ctctgaatct tcaaaacgca aaaacatgga cgaagatggt ttttcacaat gttcaaaaca    60
cttttcaaaa cgcggttatt ttagcggtgg gggcgtttgt ccatttttgtc tccacgaacg   120 tctctcttct ctttgtccag attgtgctca cgatcttcct tgttcgtgta gctcacgcgc   180
cgccgtatct ttctctcctt cgtcttcttc gtcttcctcg tcgttctcta tcttcgccgg   240
agatatcagt tttaatatat ccggcgttgg atcggtgggc cgagtcgcga gtttgattga   300
atgtgaaccg gcgtttcgga gatcgaaatc tatggcgatc ccgattaaac cggattcggt   360
tattgattcc ggtttggatc atggtaggag taagaaaacg tcgtcgtttt ggagaatttt   420
tatgggaaac agaggagata ctaaaccggc tattatgaag aaatcaagat ccgttgcggt   480
cgccggagaa tttggatttt ctccggttcc ggttccggcg accggaaagg gtaaaggctg   540
gaattttccg agtccgatca aggttttccg gcaatctcga gtctcgaaga tgatatttca   600
acaacggtct ccattgtata gaggttgaga ttattatttt tttgttaagg cttttttttt   660
ttggttttgc aaattattag tttgatcatt tacatgtttt tttaaagtt cttgtattag   720
```

```
aaaagggaac aacaatatta gtttcttgaa attcttttt aattgttgtt tataatttgt    780
aatatagata tgtgattca                                                799
```

<210> SEQ ID NO 113
<211> LENGTH: 200
<212> TYPE: PRT
<213> ORGANISM: Arabidopsis thaliana
<220> FEATURE:
<221> NAME/KEY: misc_feature
<222> LOCATION: (1)..(200)
<223> OTHER INFORMATION: Ceres ANNOT ID no. 1271642

<400> SEQUENCE: 113

```
Met Asp Glu Asp Gly Phe Ser Gln Cys Ser Lys His Phe Ser Lys Arg
1               5                   10                  15

Gly Tyr Phe Ser Gly Gly Gly Val Cys Pro Phe Cys Leu His Glu Arg
            20                  25                  30

Leu Ser Ser Leu Cys Pro Asp Cys Ala His Asp Leu Pro Cys Ser Cys
        35                  40                  45

Ser Ser Arg Ala Ala Val Ser Phe Ser Pro Ser Ser Ser Ser Ser Ser
50                  55                  60

Ser Ser Phe Ser Ile Phe Ala Gly Asp Ile Ser Phe Asn Ile Ser Gly
65                  70                  75                  80

Val Gly Ser Val Gly Arg Val Ala Ser Leu Ile Glu Cys Glu Pro Ala
                85                  90                  95

Phe Arg Arg Ser Lys Ser Met Ala Ile Pro Ile Lys Pro Asp Ser Val
            100                 105                 110

Ile Asp Ser Gly Leu Asp His Gly Arg Ser Lys Lys Thr Ser Ser Phe
        115                 120                 125

Trp Arg Ile Phe Met Gly Asn Arg Gly Asp Thr Lys Pro Ala Ile Met
130                 135                 140

Lys Lys Ser Arg Ser Val Ala Val Ala Gly Glu Phe Gly Phe Ser Pro
145                 150                 155                 160

Val Pro Val Pro Ala Thr Gly Lys Gly Lys Gly Trp Asn Phe Pro Ser
                165                 170                 175

Pro Ile Lys Val Phe Arg Gln Ser Arg Val Ser Lys Met Ile Phe Gln
            180                 185                 190

Gln Arg Ser Pro Leu Tyr Arg Gly
        195                 200
```

<210> SEQ ID NO 114
<211> LENGTH: 405
<212> TYPE: DNA
<213> ORGANISM: Arabidopsis thaliana
<220> FEATURE:
<221> NAME/KEY: misc_feature
<222> LOCATION: (1)..(405)
<223> OTHER INFORMATION: Ceres ANNOT ID no. 1270068
<220> FEATURE:
<221> NAME/KEY: misc_feature
<222> LOCATION: (1)..(405)
<223> OTHER INFORMATION: Encodes the peptide sequence at SEQ ID NO:115

<400> SEQUENCE: 114

```
atggctgaca ctggtgaggt tcaatttatg aagcctttca tctcagaaaa gtcatctaaa    60
tcattggaaa tcccttggg attcaacgaa tacttcccag caccatttcc aataactgtg    120
gacctcctgg actatagtgg gagatcttgg acgttaggaa tgaagaaaag aggagagaaa    180
gtgtttctta cagttggttg ggagaatttt gtaaaagata caatctcga agatggcaag    240
```

```
tatttgcagt tcatctatga ccgcgacagg acctttatg ttatcatata tggtcataac    300
atgtgtagcg aatatagaga cttccctcaa gtcgcagtag aggttgatga ctatgaaaac    360
ggtgaagaag aagaagacgg cgacgatcaa gacaaacatc agtaa                    405
```

```
<210> SEQ ID NO 115
<211> LENGTH: 134
<212> TYPE: PRT
<213> ORGANISM: Arabidopsis thaliana
<220> FEATURE:
<221> NAME/KEY: misc_feature
<222> LOCATION: (1)..(134)
<223> OTHER INFORMATION: Ceres ANNOT ID no. 1270068
<220> FEATURE:
<221> NAME/KEY: misc_feature
<222> LOCATION: (8)..(102)
<223> OTHER INFORMATION: Pfam Name: B3
      Pfam Description: B3 DNA binding domain

<400> SEQUENCE: 115

Met Ala Asp Thr Gly Glu Val Gln Phe Met Lys Pro Phe Ile Ser Glu
 1               5                  10                  15

Lys Ser Ser Lys Ser Leu Glu Ile Pro Leu Gly Phe Asn Glu Tyr Phe
            20                  25                  30

Pro Ala Pro Phe Pro Ile Thr Val Asp Leu Leu Asp Tyr Ser Gly Arg
        35                  40                  45

Ser Trp Thr Val Arg Met Lys Lys Arg Gly Glu Lys Val Phe Leu Thr
    50                  55                  60

Val Gly Trp Glu Asn Phe Val Lys Asp Asn Asn Leu Glu Asp Gly Lys
65                  70                  75                  80

Tyr Leu Gln Phe Ile Tyr Asp Arg Asp Arg Thr Phe Tyr Val Ile Ile
                85                  90                  95

Tyr Gly His Asn Met Cys Ser Glu Tyr Arg Asp Phe Pro Gln Val Ala
            100                 105                 110

Val Glu Val Asp Asp Tyr Glu Asn Gly Glu Glu Glu Asp Gly Asp
        115                 120                 125

Asp Gln Asp Lys His Gln
        130
```

```
<210> SEQ ID NO 116
<211> LENGTH: 1320
<212> TYPE: DNA
<213> ORGANISM: Arabidopsis thaliana
<220> FEATURE:
<221> NAME/KEY: misc_feature
<222> LOCATION: (1)..(1320)
<223> OTHER INFORMATION: Ceres ANNOT ID no. 550552
<220> FEATURE:
<221> NAME/KEY: misc_feature
<222> LOCATION: (1)..(1320)
<223> OTHER INFORMATION: Encodes the peptide sequence at SEQ ID NO:117

<400> SEQUENCE: 116
atggtgacac taacaccatc ttctgctagt accccaaaaa catcttttga tttcatgaag    60
aataacaaca gtcacagcag tctctatgtt tcttcttctt cttacttgag cagcaaggaa   120
gatgctcttg tcacgaccaa gaagctcatg gaaccaagca aaacactaaa catgagcatt   180
aatccaaaac aagaggagtt tggtgatgag aagaaaatgg tgaagaaagc tcctgaagat   240
ccagagattg gtgtgtttgg agctgagaag tacttcaatg agacatggga ttcagaccaa   300
ggttctagtg ttctgtctct gacaaaccca gaagttgaga gaaccgtcgt cgactcgaag   360
cagagcgcga agaaatctac tggtactccg agtgtccggt ctgaatcaag ctggaatagt   420
```

| | | |
|---|---|---|
| cagagcgtgt tgcttcagaa caaactggtg aatagctgca acagttcctt caaggaaaag | 480 |
| aagaacagta atggtcagat tcaaaaggtg accaataata agaagagttt tctcgcaaat | 540 |
| ttggggtgta aatgcgcatg ctctgatggg gattctgtag atgtcgagga gaaaacctcg | 600 |
| gtcaagagaa gcgctgatcc gaatatctct gttatcacaa tgagatcttc tgcggatatg | 660 |
| aacacagaac tgatcaagat tcagaagcaa gaggagttat cacagaggaa gtctcttgaa | 720 |
| gttttggat ctccagtggc tattgagaag aagagtagtg ttgttcagaa gaaactacca | 780 |
| ttgcctccat ggaaatcgag aacagaggag gacgacacaa agagtgaagg gagtgattca | 840 |
| agctcggatc ttttcgagat agagggtctt acagggaacc ctaaacctt tcttacgagg | 900 |
| caaggaagtg atccagcttc acctacgtgt tatgcgccaa gtgaagtaag cgtagagtgg | 960 |
| agcatagtga cagcaagtgc agcagatttc tctgttatgt cagaatgtgc aacaagtcct | 1020 |
| gtaagaagaa accgacctac tcagattcct cgaatcccta ttaccgctaa atcagcaccg | 1080 |
| cagagacgga aatcgagtag cagcagcgga gggaatggtt tcttgatgag ctgcaagagt | 1140 |
| cataaatctg ttatggtttc tggtgattta dacagaagaa gcagcatgaa caagacacaa | 1200 |
| ccgagttacg ttcctagatt cccaatggag actactaaac ctaagagttt cgaaacacga | 1260 |
| agaaggatca gcaacagctc gatttctcac acacaatcat ctcttcttta tagtcagtga | 1320 |

<210> SEQ ID NO 117
<211> LENGTH: 439
<212> TYPE: PRT
<213> ORGANISM: Arabidopsis thaliana
<220> FEATURE:
<221> NAME/KEY: misc_feature
<222> LOCATION: (1)..(439)
<223> OTHER INFORMATION: Ceres ANNOT ID no. 550552

<400> SEQUENCE: 117

```
Met Val Thr Leu Thr Pro Ser Ser Ala Ser Thr Pro Lys Thr Ser Phe
1               5                   10                  15

Asp Phe Met Lys Asn Asn Ser His Ser Ser Leu Tyr Val Ser Ser
            20                  25                  30

Ser Ser Tyr Leu Ser Ser Lys Glu Asp Ala Leu Val Thr Thr Lys Lys
        35                  40                  45

Leu Met Glu Pro Ser Lys Thr Leu Asn Met Ser Ile Asn Pro Lys Gln
    50                  55                  60

Glu Glu Phe Gly Asp Glu Lys Lys Met Val Lys Ala Pro Glu Asp
65              70                  75                  80

Pro Glu Ile Gly Val Phe Gly Ala Glu Lys Tyr Phe Asn Gly Asp Met
                85                  90                  95

Asp Ser Asp Gln Gly Ser Ser Val Leu Ser Leu Thr Asn Pro Glu Val
            100                 105                 110

Glu Arg Thr Val Val Asp Ser Lys Gln Ser Ala Lys Lys Ser Thr Gly
        115                 120                 125

Thr Pro Ser Val Arg Ser Glu Ser Ser Trp Asn Ser Gln Ser Val Leu
    130                 135                 140

Leu Gln Asn Lys Leu Val Asn Ser Cys Asn Ser Phe Lys Glu Lys
145                 150                 155                 160

Lys Asn Ser Asn Gly Gln Ile Gln Lys Val Thr Asn Asn Lys Ser
                165                 170                 175

Phe Leu Ala Asn Leu Gly Cys Lys Cys Ala Cys Ser Asp Gly Asp Ser
            180                 185                 190

Val Asp Val Glu Glu Lys Thr Ser Val Lys Arg Ser Ala Asp Pro Asn
        195                 200                 205
```

```
Ile Ser Val Ile Thr Met Arg Ser Ser Ala Asp Met Asn Thr Glu Leu
    210                 215                 220
Ile Lys Ile Gln Lys Gln Glu Glu Leu Ser Gln Arg Lys Ser Leu Glu
225                 230                 235                 240
Val Phe Gly Ser Pro Val Ala Ile Glu Lys Lys Ser Val Val Gln
                245                 250                 255
Lys Lys Leu Pro Leu Pro Pro Trp Lys Ser Arg Thr Glu Glu Asp Asp
            260                 265                 270
Thr Lys Ser Glu Gly Ser Asp Ser Ser Asp Leu Phe Glu Ile Glu
            275                 280                 285
Gly Leu Thr Gly Asn Pro Lys Pro Phe Leu Thr Arg Gln Gly Ser Asp
    290                 295                 300
Pro Ala Ser Pro Thr Cys Tyr Ala Pro Ser Glu Val Ser Val Glu Trp
305                 310                 315                 320
Ser Ile Val Thr Ala Ser Ala Ala Asp Phe Ser Val Met Ser Glu Cys
                325                 330                 335
Ala Thr Ser Pro Val Arg Arg Asn Arg Pro Thr Gln Ile Pro Arg Ile
            340                 345                 350
Pro Ile Thr Ala Lys Ser Ala Pro Gln Arg Arg Lys Ser Ser Ser Ser
    355                 360                 365
Ser Gly Gly Asn Gly Phe Leu Met Ser Cys Lys Ser His Lys Ser Val
370                 375                 380
Met Val Ser Gly Asp Leu Asp Arg Arg Ser Ser Met Asn Lys Thr Gln
385                 390                 395                 400
Pro Ser Tyr Val Pro Arg Phe Pro Met Glu Thr Thr Lys Pro Lys Ser
                405                 410                 415
Phe Glu Thr Arg Arg Arg Ile Ser Asn Ser Ser Ile Ser His Thr Gln
            420                 425                 430
Ser Ser Leu Leu Tyr Ser Gln
        435

<210> SEQ ID NO 118
<211> LENGTH: 1520
<212> TYPE: DNA
<213> ORGANISM: Arabidopsis thaliana
<220> FEATURE:
<221> NAME/KEY: misc_feature
<222> LOCATION: (1)..(1520)
<223> OTHER INFORMATION: Ceres ANNOT ID no. 1319615
<220> FEATURE:
<221> NAME/KEY: misc_feature
<222> LOCATION: (1)..(1520)
<223> OTHER INFORMATION: Encodes the peptide sequence at SEQ ID NO:119

<400> SEQUENCE: 118
accgactata tatatatata tatgctgctc ttcattaacc ccaagaaaga aaaccaaagt      60
gtgaagtccg aatctctctg attctacaat tcacaaaaac cggaaaaaaa aaagacaag     120 taaagaaagc tttgttcagt ttacttcaat ggaagcaaaa cccttagcat catcatcatc    180
tgaaccaaac atgatttctc catcatcaaa cattaaacca aaattaaaag atgaagatta    240
tatggagctg gtgtgtgaaa atgggcagat tcttgcaaag attcgaagac caagaacaa    300 cggttctttt caaagcaac gtaggcaatc tctcctggat ttgtatgaga ccgagtacag    360
cgagggtttc aagaaaaaca tcaagattct tggagacaca caagttgttc cggtgagtca    420
gtctaagcca aacaagata aagaaaccaa tgaacaaatg aacaacaata agaagaagct    480
aaagtcctcc aaaatcgaat ttgagagaaa tgtttcgaaa agcaacaaat gtgttgaatc    540
```

-continued

| | |
|---|---|
| atcaacatta attgatgttt ctgctaaagg tccaaagaat gttgaagtta ctacagctcc | 600 |
| tcctgatgag caatctgcag ctgttggtag atccacggaa ttgtattttg cttcttcatc | 660 |
| gaagttttct cgaggaactt cgagagatct aagttgttgt tctttaaaga ggaagtatgg | 720 |
| agatattgaa gaagaagaat caacctattt aagtaataat tcagatgatg aatcagatga | 780 |
| tgcgaagaca caagttcatg cgagaacaag aaagccggtg actaaaagaa aacgaagcac | 840 |
| agaagtccat aagttatatg aaagaaaacg aagagatgaa ttcaacaaga aaatgcgtgc | 900 |
| tttgcaggac ctactaccaa attgttacaa ggatgataag gcttcattgt tggatgaggc | 960 |
| tatcaaatat atgcggaccc ttcaacttca agttcagatg atgagtatgg gaatggatt | 1020 |
| aataagacca cctacgatgt tgccaatggg tcattactct cccatgggtc taggaatgca | 1080 |
| tatgggtgca gcagcaacac caacatcaat accgcaattc ctgcctatga atgttcaagc | 1140 |
| aaccggtttt ccggggatga acaatgcacc accacaaatg ctaagctttc ttaatcaccc | 1200 |
| aagtggacta attccaaaca ctcctatctt ttctccattg gaaaattgct ctcagccatt | 1260 |
| cgtggtgcct tcgtgtgttt ctcagactca ggctacttct tttactcaat tcccaaagtc | 1320 |
| tgcgtccgcc tcaaacttag aagatgcaat gcaatataga ggaagcaacg gtttagtta | 1380 |
| ttatcgctcg ccaaactaat gatttgtaga aagttgatgt tttctccaac taactaactt | 1440 |
| taagcaaaaa aaaatgatcg tctactctgt gttgttagtc tatgggcttt tgggccttga | 1500 |
| ttcttggaac gatttgaact | 1520 |

<210> SEQ ID NO 119
<211> LENGTH: 416
<212> TYPE: PRT
<213> ORGANISM: Arabidopsis thaliana
<220> FEATURE:
<221> NAME/KEY: misc_feature
<222> LOCATION: (1)..(416)
<223> OTHER INFORMATION: Ceres ANNOT ID no. 1319615
<220> FEATURE:
<221> NAME/KEY: misc_feature
<222> LOCATION: (230)..(279)
<223> OTHER INFORMATION: Pfam Name: HLH
    Pfam Description: Helix-loop-helix DNA-binding domain

<400> SEQUENCE: 119

Met Glu Ala Lys Pro Leu Ala Ser Ser Ser Glu Pro Asn Met Ile
1               5                   10                  15

Ser Pro Ser Ser Asn Ile Lys Pro Lys Leu Lys Asp Glu Asp Tyr Met
            20                  25                  30

Glu Leu Val Cys Glu Asn Gly Gln Ile Leu Ala Lys Ile Arg Arg Pro
        35                  40                  45

Lys Asn Asn Gly Ser Phe Gln Lys Gln Arg Arg Gln Ser Leu Leu Asp
    50                  55                  60

Leu Tyr Glu Thr Glu Tyr Ser Glu Gly Phe Lys Lys Asn Ile Lys Ile
65                  70                  75                  80

Leu Gly Asp Thr Gln Val Val Pro Val Ser Gln Ser Lys Pro Gln Gln
            85                  90                  95

Asp Lys Glu Thr Asn Glu Gln Met Asn Asn Lys Lys Lys Leu Lys
            100                 105                 110

Ser Ser Lys Ile Glu Phe Glu Arg Asn Val Ser Lys Ser Asn Lys Cys
        115                 120                 125

Val Glu Ser Ser Thr Leu Ile Asp Val Ser Ala Lys Gly Pro Lys Asn
    130                 135                 140

Val Glu Val Thr Thr Ala Pro Pro Asp Glu Gln Ser Ala Ala Val Gly
145                 150                 155                 160

```
Arg Ser Thr Glu Leu Tyr Phe Ala Ser Ser Lys Phe Ser Arg Gly
            165                 170                 175

Thr Ser Arg Asp Leu Ser Cys Cys Ser Leu Lys Arg Lys Tyr Gly Asp
        180                 185                 190

Ile Glu Glu Glu Ser Thr Tyr Leu Ser Asn Asn Ser Asp Asp Glu
            195                 200                 205

Ser Asp Asp Ala Lys Thr Gln Val His Ala Arg Thr Arg Lys Pro Val
210                 215                 220

Thr Lys Arg Lys Arg Ser Thr Glu Val His Lys Leu Tyr Glu Arg Lys
225                 230                 235                 240

Arg Arg Asp Glu Phe Asn Lys Lys Met Arg Ala Leu Gln Asp Leu Leu
            245                 250                 255

Pro Asn Cys Tyr Lys Asp Asp Lys Ala Ser Leu Leu Asp Glu Ala Ile
            260                 265                 270

Lys Tyr Met Arg Thr Leu Gln Leu Gln Val Gln Met Met Ser Met Gly
            275                 280                 285

Asn Gly Leu Ile Arg Pro Pro Thr Met Leu Pro Met Gly His Tyr Ser
    290                 295                 300

Pro Met Gly Leu Gly Met His Met Gly Ala Ala Thr Pro Thr Ser
305                 310                 315                 320

Ile Pro Gln Phe Leu Pro Met Asn Val Gln Ala Thr Gly Phe Pro Gly
            325                 330                 335

Met Asn Asn Ala Pro Pro Gln Met Leu Ser Phe Leu Asn His Pro Ser
            340                 345                 350

Gly Leu Ile Pro Asn Thr Pro Ile Phe Ser Pro Leu Glu Asn Cys Ser
            355                 360                 365

Gln Pro Phe Val Val Pro Ser Cys Val Ser Gln Thr Gly Ala Thr Ser
            370                 375                 380

Phe Thr Gln Phe Pro Lys Ser Ala Ser Ala Ser Asn Leu Glu Asp Ala
385                 390                 395                 400

Met Gln Tyr Arg Gly Ser Asn Gly Phe Ser Tyr Tyr Arg Ser Pro Asn
            405                 410                 415

<210> SEQ ID NO 120
<211> LENGTH: 1500
<212> TYPE: DNA
<213> ORGANISM: Arabidopsis thaliana
<220> FEATURE:
<221> NAME/KEY: misc_feature
<222> LOCATION: (1)..(1500)
<223> OTHER INFORMATION: Promoter Construct YP2622
<220> FEATURE:
<221> NAME/KEY: misc_feature
<222> LOCATION: (1)..(1500)
<223> OTHER INFORMATION: 1.5 KB version of promoter construct PR0924
<220> FEATURE:
<221> NAME/KEY: misc_feature
<222> LOCATION: (1186)..(1191)
<223> OTHER INFORMATION: Motif Name: -10PEHVPSBD
<220> FEATURE:
<221> NAME/KEY: misc_feature
<222> LOCATION: (358)..(362)
<223> OTHER INFORMATION: Motif Name: ASF1MOTIFCAMV
<220> FEATURE:
<221> NAME/KEY: misc_feature
<222> LOCATION: (646)..(651)
<223> OTHER INFORMATION: Motif Name: IBOX
<220> FEATURE:
<221> NAME/KEY: misc_feature
<222> LOCATION: (1018)..(1023)
<223> OTHER INFORMATION: Motif Name: IBOX
<220> FEATURE:
<221> NAME/KEY: misc_feature
```

```
<222> LOCATION: (89)..(94)
<223> OTHER INFORMATION: Motif Name: GT1CORE
<220> FEATURE:
<221> NAME/KEY: misc_feature
<222> LOCATION: (1243)..(1248)
<223> OTHER INFORMATION: Motif Name: GT1CORE
<220> FEATURE:
<221> NAME/KEY: misc_feature
<222> LOCATION: (217)..(222)
<223> OTHER INFORMATION: Motif Name: REALPHALGLHCB21
<220> FEATURE:
<221> NAME/KEY: misc_feature
<222> LOCATION: (283)..(288)
<223> OTHER INFORMATION: Motif Name: REALPHALGLHCB21
<220> FEATURE:
<221> NAME/KEY: misc_feature
<222> LOCATION: (1377)..(1383)
<223> OTHER INFORMATION: Motif Name: TATA-box
<220> FEATURE:
<221> NAME/KEY: misc_feature
<222> LOCATION: (1409)..(1409)
<223> OTHER INFORMATION: transcription start site
<220> FEATURE:
<221> NAME/KEY: misc_feature
<222> LOCATION: (1409)..(1500)
<223> OTHER INFORMATION: 5' untranslated region

<400> SEQUENCE: 120
tcttccccac aaaattgcaa ctgatgaagt caatacttgt atagtgagtc aagctataaa      60
tgtctagtga tagttttgtc tcttaaaagg ttaacaaaag ttatgacaag ctgaaaaatc     120
agagtttgct aggagtatta cttacagtta tcagtttaag tatcacattt atagtattgt     180
atacaatgat tcttaaattc caccttttcc gtgcgaaacc aaattttcta ttggaaacat     240
agaatgtaaa caaaatatg ggacgttgtc cgttccaaca ttaaccaaac ttgtctatta     300
ctaatattcg tgttggtttg atgttggatg tctaaattcg ttgaatcatg tgtctcttga     360
cgaaatatgc atcttcttat ttcttagtat agatgcactt tatcattctt ttagtacatg     420
cttaattttt ttttttaaaa tatgttgatt gtcatattgc caaagtatg aattaaagac     480 gcacatctaa cacaagttag cagccgtaaa tccttccata aatttatttt gcaagttttg     540
ctcattatat aatgagcgga atttatgata taatcgtttg taataatgtt atgttttgat     600
caaaatttga aattaaaagt aggtgagaac ttgttataca gtgtagataa ggtggatctt     660
gaatataaaa ataaaattta taagatgtat ttaaagcaga aaagcataaa actttagata     720
aaataatgta aaaatgtgtt agcatcaatg ttgggatatt ggccgacccg aacttaatca     780
atgtcggaag ccattacttc tctcccaaaa gaccttttc cttcggagaa ctaggaactt     840
cctcactacc tttcgcttaa cgtgaaagcc ataaatttca tatattcata aaaatcagaa     900
aatctaaaac tgtttagtat cacctgtttt tggtatagac tattggtttt gtgttacttc     960
ctaaactata tgatttcgta cttcattgga tcttatagag atgaatattc gtaaaaagat    1020
aagttatctg gtgaaacgtt acttcagtca tgttgggtct agatttacat actactatga    1080
aacattttaa gataataatt atcctagcca actatatgtt ctatattatg ggccaagaag    1140
atatagaact aaaagttcag aatttaacga tataaattac tagtatattc taatacttga    1200
atgattactg ttttagttgt ttagaataaa tagtagcgtg ttggttaaga taccatctat    1260
ccacatctat atttgtgtgg gttacataaa atgtacataa tattatatac atatatatgt    1320 atattttga taaagccata tattactcct tgacctctgc ccccatttcc ttttactata    1380
aataggaata ctcatgatcc tctaattcag caatcaacac caacgaacac aacctttccc    1440
aaagccaata ataaaagaac aaaagctttt agtttcatca aagacgaagc tgccttagaa    1500
```

```
<210> SEQ ID NO 121
<211> LENGTH: 2000
<212> TYPE: DNA
<213> ORGANISM: Arabidopsis thaliana
<220> FEATURE:
<221> NAME/KEY: misc_feature
<222> LOCATION: (1)..(2000)
<223> OTHER INFORMATION: Promoter Construct YP2623
<220> FEATURE:
<221> NAME/KEY: misc_feature
<222> LOCATION: (1)..(2000)
<223> OTHER INFORMATION: 2 KB version of promoter construct PR0924
<220> FEATURE:
<221> NAME/KEY: misc_feature
<222> LOCATION: (1686)..(1691)
<223> OTHER INFORMATION: Motif Name: -10PEHVPSBD
<220> FEATURE:
<221> NAME/KEY: misc_feature
<222> LOCATION: (858)..(862)
<223> OTHER INFORMATION: Motif Name: ASF1MOTIFCAMV
<220> FEATURE:
<221> NAME/KEY: misc_feature
<222> LOCATION: (1146)..(1151)
<223> OTHER INFORMATION: Motif Name: IBOX
<220> FEATURE:
<221> NAME/KEY: misc_feature
<222> LOCATION: (1518)..(1523)
<223> OTHER INFORMATION: Motif Name: IBOX
<220> FEATURE:
<221> NAME/KEY: misc_feature
<222> LOCATION: (589)..(594)
<223> OTHER INFORMATION: Motif Name: GT1CORE
<220> FEATURE:
<221> NAME/KEY: misc_feature
<222> LOCATION: (1743)..(1748)
<223> OTHER INFORMATION: Motif Name: GT1CORE
<220> FEATURE:
<221> NAME/KEY: misc_feature
<222> LOCATION: (717)..(722)
<223> OTHER INFORMATION: Motif Name: REALPHALGLHCB21
<220> FEATURE:
<221> NAME/KEY: misc_feature
<222> LOCATION: (783)..(788)
<223> OTHER INFORMATION: Motif Name: REALPHALGLHCB21
<220> FEATURE:
<221> NAME/KEY: misc_feature
<222> LOCATION: (1877)..(1883)
<223> OTHER INFORMATION: Motif Name: TATA-box
<220> FEATURE:
<221> NAME/KEY: misc_feature
<222> LOCATION: (1909)..(1909)
<223> OTHER INFORMATION: transcription start site
<220> FEATURE:
<221> NAME/KEY: misc_feature
<222> LOCATION: (1909)..(2000)
<223> OTHER INFORMATION: 5' untranslated region

<400> SEQUENCE: 121
taaatggaaa caaaacatat gtcaatgtca agcatacagc taaaatatca ttatctaata      60
ttaagagtaa aacaagataa ttaaaaattg aaacaacacc atattttat agctttactt     120 atcgtatttt tctagtcttc atggtaattg tgttgcttta ttttgtttat aaatgaattt     180
ggttcgacca gatagtctaa tatcagtttt taaacactgg ttttaataaa atcatatgtc     240
ggcaattcaa cctgttacgt tgtatgattg tatcctagtc aaatagggga ggagtacta     300 gtcgtttcaa ttagtttacg taatcaatcc aaagaaacta taagctataa agatcctcaa     360
tttgttggtt acaataaaaa caacagttgt caaaatttat gtttataaaa agtaataact     420
atgttccttc ccatatagag caaagtacct caggataggc aaaccgtact taatagccct     480
tattcataat ttgatccaac tcttccccac aaaattgcaa ctgatgaagt caatacttgt     540
atagtgagtc aagctataaa tgtctagtga gtagttttgtc tcttaaaagg ttaacaaaag     600
ttatgacaag ctgaaaaatc agagtttgct aggagtatta cttacagtta tcagtttaag     660
```

```
tatcacattt atagtattgt atacaatgat tcttaaattc cacctttcc gtgcgaaacc      720 aaattttcta ttggaaacat agaatgtaaa caaaaatatg ggacgttgtc cgttccaaca      780
ttaaccaaac ttgtctatta ctaatattcg tgttggtttg atgttggatg tctaaattcg      840
ttgaatcatg tgtctcttga cgaaatatgc atcttcttat ttcttagtat agatgcactt      900
tatcattctt ttagtacatg cttaattttt ttttttaaaa tatgttgatt gtcatattgc      960
caaaagtatg aattaaagac gcacatctaa cacaagttag cagccgtaaa tccttccata     1020
aatttatttt gcaagttttg ctcattatat aatgagcgga atttatgata taatcgtttg     1080
taataatgtt atgttttgat caaaatttga aattaaaagt aggtgagaac ttgttataca     1140
gtgtagataa ggtggatctt gaatataaaa ataaaattta taagatgtat ttaaagcaga     1200
aaagcataaa actttagata aaataatgta aaaatgtgtt agcatcaatg ttgggatatt     1260
ggccgacccg aacttaatca atgtcggaag ccattacttc tctcccaaaa gacctttttc     1320
cttcggagaa ctaggaactt cctcactacc tttcgcttaa cgtgaaagcc ataaatttca     1380
tatattcata aaaatcagaa aatctaaaac tgtttagtat cacctgtttt tggtatagac     1440
tattggtttt gtgttacttc ctaaactata tgatttcgta cttcattgga tcttatagag     1500
atgaatattc gtaaaaagat aagttatctg gtgaaacgtt acttcagtca tgttgggtct     1560
agatttacat actactatga aacattttaa gataataatt atcctagcca actatatgtt     1620
ctatattatg ggccaagaag atatagaact aaaagttcag aatttaacga tataaattac     1680
tagtatattc taatacttga atgattactg ttttagttgt ttagaataaa tagtagcgtg     1740
ttggttaaga taccatctat ccacatctat atttgtgtgg gttacataaa atgtacataa     1800
tattatatac atatatatgt atattttttga taaagccata tattactcct tgacctctgc     1860
ccccatttcc ttttactata aataggaata ctcatgatcc tctaattcag caatcaacac     1920
caacgaacac aaccttttcc aaagccaata ataaaagaac aaaagctttt agtttcatca     1980
aagacgaagc tgccttagaa                                                 2000
```

```
<210> SEQ ID NO 122
<211> LENGTH: 2995
<212> TYPE: DNA
<213> ORGANISM: Arabidopsis thaliana
<220> FEATURE:
<221> NAME/KEY: misc_feature
<222> LOCATION: (1)..(2995)
<223> OTHER INFORMATION: 2995 bp version of promoter construct PR0924

<400> SEQUENCE: 122
```

```
taacgagtta acatgttgcc agtttgaatc aagaagcttg gatgatgaat gaatggatcg       60
gtttgtggta caattcttaa aattgtagta gaggagacag agaaaaaaca tgataagact      120
ttggtattta caacttgacg gagacaagac agtaagccaa atctgtcaca aaaacactca      180
aactcttttc tcagtgtttt gagtttaaag agagacttat tcacttcccc tttcgtaaca      240
cttatttgtc tcccaaccaa acagtttctg tcctttccct tgtcctccca cgtgcatctt      300
tatatctcat gacttttcgt ttctagatct tgaataatgt cttagtggat taggtttgtt      360
gtcggtaaat taggtgaccg ttttttttctt atatttggaa gatcgcggga tgaagcagat      420
actgagtttc agggcataca cacctaattt gaaaatcatt gttagtccaa tttcactta      480 atcttgttta caaaaaaatt gatctgaaaa tgttgatggg ataagtaaaa atgtaagttt      540
tgctagtagt catgatataa aatagcaaa accagatcaa ttttgagcaa aaggaagaaa      600
caaaaaacag atcgatccca cgagcaagac taagtgtaaa gtggttccca caagagccat      660
```

```
atggatatgg tccttcaact tttaaagccc attacttcag tggtcgaccc gacattacgc    720
cacgagtagt cacgcacgca cgactccgtt cacgtgacat tcacgttgat atttccccct    780
ctactctctt ctgcttggtt gatctaaaaa acatgaagag accaacctaa tttcatatta    840
atatatgata tagacttcat actcaacagt cactttcgta atccaaatcc atatcttacg    900
aaattagttc ttaataaagg ttgtggatta agttataata ttgtgttaag agttaagaca    960
cagcatataa ccttgtacca acagtgcttt attcttaaat ggaaacaaaa catatgtcaa   1020
tgtcaagcat acagctaaaa tatcattatc taatattaag agtaaaacaa gataattaaa   1080
aattgaaaca acaccatatt tttatagctt tacttatcgt attttttctag tcttcatggt   1140
aattgtgttg ctttattttg tttataaatg aatttggttc gaccagatag tctaatatca   1200
gttttttaaac actggtttta ataaaatcat atgtcggcaa ttcaacctgt tacgttgtat   1260
gattgtatcc tagtcaaata ggggaggagg tactagtcgt ttcaattagt ttacgtaatc   1320
aatccaaaga aactataagc tataaagatc ctcaatttgt tggttacaat aaaaacaaca   1380
gttgtcaaaa tttatgttta taaaaagtaa taactatgtt ccttcccata tagagcaaag   1440
tacctcagga taggcaaacc gtacttaata gcccttattc ataatttgat ccaactcttc   1500
cccacaaaat tgcaactgat gaagtcaata cttgtatagt gagtcaagct ataaatgtct   1560
agtgatagtt ttgtctctta aaaggttaac aaaagttatg acaagctgaa aaatcagagt   1620
ttgctaggag tattacttac agttatcagt ttaagtatca catttatagt attgtataca   1680
atgattctta aattccacct tttccgtgcg aaaccaaatt ttctattgga aacatagaat   1740
gtaaacaaaa atatgggacg ttgtccgttc caacattaac caaacttgtc tattactaat   1800
attcgtgttg gtttgatgtt ggatgtctaa attcgttgaa tcatgtgtct cttgacgaaa   1860
tatgcatctt cttatttctt agtatagatg cactttatca ttctttttagt acatgcttaa   1920
tttttttttt taaaatatgt tgattgtcat attgccaaaa gtatgaatta agacgcaca    1980
tctaacacaa gttagcagcc gtaaatcctt ccataaattt attttgcaag ttttgctcat   2040
tatataatga gcggaatttta tgatataatc gtttgtaata atgttatgtt ttgatcaaaa   2100
tttgaaatta aaagtaggtg agaacttgtt atacagtgta gataaggtgg atcttgaata   2160
taaaaataaa atttataaga tgtatttaaa gcagaaaagc ataaaacttt agataaaata   2220
atgtaaaaat gtgttagcat caatgttggg atattggccg acccgaactt aatcaatgtc   2280
ggaagccatt acttctctcc caaaagacct ttttccttcg gagaactagg aacttcctca   2340
ctacctttcg cttaacgtga aagccataaa tttcatatat tcataaaaat cagaaaatct   2400
aaaactgttt agtatcacct gttttttggta tagactattg gttttgtgtt acttcctaaa   2460
ctatatgatt tcgtacttca ttggatctta tagagatgaa tattcgtaaa aagataagtt   2520
atctggtgaa acgttacttc agtcatgttg ggtctagatt tacatactac tatgaaacat   2580
tttaagataa taattatcct agccaactat atgttctata ttatgggcca agaagatata   2640
gaactaaaag ttcagaattt aacgatataa attactagta tattctaata cttgaatgat   2700
tactgtttta gttgtttaga ataaatagta gcgtgttggt taagatacca tctatccaca   2760
tctatatttg tgtgggttac ataaaatgta cataatatta tatacatata tatgtatatt   2820
tttgataaag ccatatatta ctccttgacc tctgccccca tttccttta ctataaatag    2880
gaatactcat gatcctctaa ttcagcaatc aacaccaacg aacacaacct tttccaaagc   2940
caataataaa agaacaaaag cttttagttt catcaaagac gaagctgcct tagaa        2995
```

```
<210> SEQ ID NO 123
<211> LENGTH: 2985
<212> TYPE: DNA
<213> ORGANISM: Arabidopsis thaliana
<220> FEATURE:
<221> NAME/KEY: misc_feature
<222> LOCATION: (1)..(2985)
<223> OTHER INFORMATION: 2985 bp version of promoter construct PR0924

<400> SEQUENCE: 123
acatgttgcc agtttgaatc aagaagcttg gatgatgaat gaatggatcg gtttgtggta      60
caattcttaa aattgtagta gaggagacag agaaaaaaca tgataagact ttggtattta     120
caacttgacg gagacaagac agtaagccaa atctgtcaca aaaacactca aactcttttc     180
tcagtgtttt gagtttaaag agagacttat tcacttcccc tttcgtaaca cttatttgtc     240
tcccaaccaa acagtttctg tcctttccct tgtcctccca cgtgcatctt tatatctcat     300
gacttttcgt ttctagatct tgaataatgt cttagtggat taggtttgtt gtcggtaaat     360
taggtgaccg ttttttttctt atatttggaa gatcgcggga tgaagcagat actgagtttc     420
agggcataca cacctaattt gaaaatcatt gttagtccaa tttcacttta atcttgttta     480
caaaaaaatt gatctgaaaa tgttgatggg ataagtaaaa atgtaagttt tgctagtagt     540
catgatataa taatagcaaa accagatcaa ttttgagcaa aaggaagaaa caaaaaacag     600
atcgatccca cgagcaagac taagtgtaaa gtggttccca caagagccat atggatatgg     660
tccttcaact tttaaagccc attacttcag tggtcgaccc gacattacgc cacgagtagt     720
cacgcacgca cgactccgtt cacgtgacat tcacgttgat atttccccct ctactctctt     780
ctgcttggtt gatctaaaaa acatgaagag accaacctaa tttcatatta atatatgata     840
tagacttcat actcaacagt cactttcgta atccaaatcc atatcttacg aaattagttc     900
ttaataaagg ttgtggatta agttataata ttgtgttaag agttaagaca cagcatataa     960
ccttgtacca acagtgcttt attcttaaat ggaaacaaaa catatgtcaa tgtcaagcat    1020
acagctaaaa tatcattatc taatattaag agtaaaacaa gataattaaa aattgaaaca    1080
acaccatatt tttatagctt tacttatcgt atttttctag tcttcatggt aattgtgttg    1140
ctttattttg tttataaatg aatttggttc gaccagatag tctaatatca gttttttaaac    1200 actggtttta ataaaatcat atgtcggcaa ttcaacctgt tacgttgtat gattgtatcc    1260
tagtcaaata ggggaggagg tactagtcgt ttcaattagt ttacgtaatc aatccaaaga    1320
aactataagc tataaagatc ctcaatttgt tggttacaat aaaaacaaca gttgtcaaaa    1380
tttatgttta taaaaagtaa taactatgtt ccttcccata tagagcaaag tacctcagga    1440
taggcaaacc gtacttaata gcccttattc ataatttgat ccaactcttc cccacaaaat    1500
tgcaactgat gaagtcaata cttgtatagt gagtcaagct ataaatgtct agtgatagtt    1560
ttgtctctta aaaggttaac aaaagttatg acaagctgaa aaatcagagt ttgctaggag    1620
tattacttac agtatcagt ttaagtatca catttatagt attgtataca atgattctta     1680
aattccacct tttccgtgcg aaaccaaatt ttctattgga acatagaat gtaaacaaaa     1740 atatgggacg ttgtccgttc caacattaac caaacttgtc tattactaat attcgtgttg    1800
gtttgatgtt ggatgtctaa attcgttgaa tcatgtgtct cttgacgaaa tatgcatctt    1860
cttatttctt agtatagatg cacttttatca ttctttagt acatgcttaa tttttttttt    1920
taaaatatgt tgattgtcat attgccaaaa gtatgaatta aagacgcaca tctaacacaa    1980
gttagcagcc gtaaatcctt ccataaaattt attttgcaag ttttgctcat tatataatga    2040
gcggaattta tgatataatc gtttgtaata atgttatgtt ttgatcaaaa tttgaaatta    2100
```

| | |
|---|---|
| aaagtaggtg agaacttgtt atacagtgta gataaggtgg atcttgaata taaaaataaa | 2160 |
| atttataaga tgtatttaaa gcagaaaagc ataaaacttt agataaaata atgtaaaaat | 2220 |
| gtgttagcat caatgttggg atattggccg acccgaactt aatcaatgtc ggaagccatt | 2280 |
| acttctctcc caaaagacct ttttccttcg gagaactagg aacttcctca ctacctttcg | 2340 |
| cttaacgtga aagccataaa tttcatatat tcataaaaat cagaaaatct aaaactgttt | 2400 |
| agtatcacct gttttggta tagactattg gttttgtgtt acttcctaaa ctatatgatt | 2460 |
| tcgtacttca ttggatctta tagagatgaa tattcgtaaa aagataagtt atctggtgaa | 2520 |
| acgttacttc agtcatgttg ggtctagatt tacatactac tatgaaacat tttaagataa | 2580 |
| taattatcct agccaactat atgttctata ttatgggcca agaagatata gaactaaaag | 2640 |
| ttcagaattt aacgatataa attactagta tattctaata cttgaatgat tactgtttta | 2700 |
| gttgtttaga ataaatagta gcgtgttggt taagatacca tctatccaca tctatatttg | 2760 |
| tgtgggttac ataaaatgta cataatatta tatacatata tatgtatatt tttgataaag | 2820 |
| ccatatatta ctccttgacc tctgccccca tttccttta ctataaatag gaatactcat | 2880 |
| gatcctctaa ttcagcaatc aacaccaacg aacacaacct tttccaaagc caataataaa | 2940 |
| agaacaaaag cttttagttt catcaaagac gaagctgcct tagaa | 2985 |

<210> SEQ ID NO 124
<211> LENGTH: 2975
<212> TYPE: DNA
<213> ORGANISM: Arabidopsis thaliana
<220> FEATURE:
<221> NAME/KEY: misc_feature
<222> LOCATION: (1)..(2975)
<223> OTHER INFORMATION: 2975 bp version of promoter construct PR0924

<400> SEQUENCE: 124

| | |
|---|---|
| agtttgaatc aagaagcttg gatgatgaat gaatggatcg gtttgtggta caattcttaa | 60 |
| aattgtagta gaggagacag agaaaaaaca tgataagact ttggtattta caacttgacg | 120 |
| gagacaagac agtaagccaa atctgtcaca aaaacactca aactcttttc tcagtgtttt | 180 |
| gagtttaaag agagacttat tcacttcccc tttcgtaaca cttatttgtc tcccaaccaa | 240 |
| acagtttctg tccttccct tgtcctccca cgtgcatctt tatatctcat gacttttcgt | 300 |
| ttctagatct tgaataatgt cttagtggat taggtttgtt gtcggtaaat taggtgaccg | 360 |
| ttttttcttt atatttggaa gatcgcggga tgaagcagat actgagtttc agggcataca | 420 |
| cacctaattt gaaaatcatt gttagtccaa tttcacttta atcttgttta caaaaaaatt | 480 |
| gatctgaaaa tgttgatggg ataagtaaaa atgtaagttt tgctagtagt catgatataa | 540 |
| taatagcaaa accagatcaa ttttgagcaa aaggaagaaa caaaaaacag atcgatccca | 600 |
| cgagcaagac taagtgtaaa gtggttccca caagagccat atggatatgg tccttcaact | 660 |
| tttaaagccc attacttcag tggtcgaccc gacattacgc cacgagtagt cacgcacgca | 720 |
| cgactccgtt cacgtgacat tcacgttgat atttccccct ctactctctt ctgcttggtt | 780 |
| gatctaaaaa acatgaagag accaacctaa tttcatatta atatatgata tagacttcat | 840 |
| actcaacagt cactttcgta atccaaatcc atatcttacg aaattagttc ttaataaagg | 900 |
| ttgtggatta agttataata ttgtgttaag agttaagaca cagcatataa ccttgtacca | 960 |
| acagtgcttt attcttaaat ggaaacaaaa catatgtcaa tgtcaagcat acagctaaaa | 1020 |
| tatcattatc taatattaag agtaaaacaa gataattaaa aattgaaaca acaccatatt | 1080 |
| tttatagctt tacttatcgt attttttctag tcttcatggt aattgtgttg ctttattttg | 1140 |

```
tttataaatg aatttggttc gaccagatag tctaatatca gttttaaac actggttta      1200 ataaaatcat atgtcggcaa ttcaacctgt tacgttgtat gattgtatcc tagtcaaata    1260
ggggaggagg tactagtcgt ttcaattagt ttacgtaatc aatccaaaga aactataagc    1320
tataaagatc ctcaatttgt tggttacaat aaaaacaaca gttgtcaaaa tttatgttta    1380
taaaaagtaa taactatgtt ccttcccata tagagcaaag tacctcagga taggcaaacc    1440
gtacttaata gcccttattc ataatttgat ccaactcttc cccacaaaat tgcaactgat    1500
gaagtcaata cttgtatagt gagtcaagct ataaatgtct agtgatagtt ttgtctctta    1560
aaaggttaac aaaagttatg acaagctgaa aaatcagagt ttgctaggag tattacttac    1620
agttatcagt ttaagtatca catttatagt attgtataca atgattctta aattccacct    1680
tttccgtgcg aaaccaaatt ttctattgga aacatagaat gtaaacaaaa atatgggacg    1740
ttgtccgttc caacattaac caaacttgtc tattactaat attcgtgttg gtttgatgtt    1800
ggatgtctaa attcgttgaa tcatgtgtct cttgacgaaa tatgcatctt cttatttctt    1860
agtatagatg cactttatca ttcttttagt acatgcttaa tttttttttt taaaatatgt    1920
tgattgtcat attgccaaaa gtatgaatta agacgcaca tctaacacaa gttagcagcc     1980
gtaaatcctt ccataaattt attttgcaag ttttgctcat tatataatga gcggaattta    2040
tgatataatc gtttgtaata atgttatgtt ttgatcaaaa tttgaaatta aaagtaggtg    2100
agaacttgtt atacagtgta gataaggtgg atcttgaata taaaaataaa atttataaga   2160
tgtatttaaa gcagaaaagc ataaaacttt agataaaata atgtaaaaat gtgttagcat   2220
caatgttggg atattggccg acccgaactt aatcaatgtc ggaagccatt acttctctcc    2280
caaaagacct ttttccttcg gagaactagg aacttcctca ctaccttcg cttaacgtga     2340 aagccataaa tttcatatat tcataaaaat cagaaaatct aaaactgttt agtatcacct    2400 gttttggta tagactattg gttttgtgtt acttcctaaa ctatatgatt tcgtacttca     2460
ttggatctta tagagatgaa tattcgtaaa aagataagtt atctggtgaa acgttacttc    2520
agtcatgttg ggtctagatt tacatactac tatgaaacat tttaagataa taattatcct    2580
agccaactat atgttctata ttatgggcca agaagatata gaactaaaag ttcagaattt    2640
aacgatataa attactagta tattctaata cttgaatgat tactgttta gttgtttaga     2700 ataaatagta gcgtgttggt taagatacca tctatccaca tctatatttg tgtgggttac    2760
ataaaatgta cataatatta tatacatata tatgtatatt tttgataaag ccatatatta    2820
ctccttgacc tctgcccca tttccttta ctataaatag gaatactcat gatcctctaa      2880
ttcagcaatc aacaccaacg aacacaacct tttccaaagc caataataaa agaacaaaag    2940
cttttagttt catcaaagac gaagctgcct tagaa                               2975
```

```
<210> SEQ ID NO 125
<211> LENGTH: 3000
<212> TYPE: DNA
<213> ORGANISM: Populus balsamifera subsp. trichocarp
<220> FEATURE:
<221> NAME/KEY: misc_feature
<223> OTHER INFORMATION: Promoter of Ceres ANNOT ID no. 1455585
<220> FEATURE:
<221> NAME/KEY: misc_feature
<222> LOCATION: (737)..(742)
<223> OTHER INFORMATION: Motif Name: -10PEHVPSBD
<220> FEATURE:
<221> NAME/KEY: misc_feature
<222> LOCATION: (1825)..(1829)
<223> OTHER INFORMATION: Motif Name: ASF1MOTIFCAMV
<220> FEATURE:
```

```
<221> NAME/KEY: misc_feature
<222> LOCATION: (2681)..(2865)
<223> OTHER INFORMATION: Motif Name: ASF1MOTIFCAMV
<220> FEATURE:
<221> NAME/KEY: misc_feature
<222> LOCATION: (2843)..(2849)
<223> OTHER INFORMATION: Motif Name: BOXCPSAS1
<220> FEATURE:
<221> NAME/KEY: misc_feature
<222> LOCATION: (215)..(219)
<223> OTHER INFORMATION: Motif Name: IBOXCORE
<220> FEATURE:
<221> NAME/KEY: misc_feature
<222> LOCATION: (515)..(519)
<223> OTHER INFORMATION: Motif Name: IBOXCORE
<220> FEATURE:
<221> NAME/KEY: misc_feature
<222> LOCATION: (523)..(527)
<223> OTHER INFORMATION: Motif Name: IBOXCORE
<220> FEATURE:
<221> NAME/KEY: misc_feature
<222> LOCATION: (840)..(844)
<223> OTHER INFORMATION: Motif Name: IBOXCORE
<220> FEATURE:
<221> NAME/KEY: misc_feature
<222> LOCATION: (1425)..(1430)
<223> OTHER INFORMATION: Motif Name: CACGTGMOTIF
<220> FEATURE:
<221> NAME/KEY: misc_feature
<222> LOCATION: (2225)..(2230)
<223> OTHER INFORMATION: Motif Name: GT1CORE
<220> FEATURE:
<221> NAME/KEY: misc_feature
<222> LOCATION: (2394)..(2399)
<223> OTHER INFORMATION: Motif Name: GT1CORE
<220> FEATURE:
<221> NAME/KEY: misc_feature
<222> LOCATION: (2593)..(2598)
<223> OTHER INFORMATION: Motif Name:REALPHALGLHCB21
<220> FEATURE:
<221> NAME/KEY: misc_feature
<222> LOCATION: (2853)..(2858)
<223> OTHER INFORMATION: Motif Name: TATA-box
<220> FEATURE:
<221> NAME/KEY: misc_feature
<222> LOCATION: (2902)..(2902)
<223> OTHER INFORMATION: transcription start site
<220> FEATURE:
<221> NAME/KEY: misc_feature
<222> LOCATION: (2902)..(3000)
<223> OTHER INFORMATION: 5' untranslated region

<400> SEQUENCE: 125
tccattagta aatacaccaa ggatggatgt tagcatatta gcataattgg caaaaaaaaa      60
aaaaaaagac ttatttcgag gactgttttt ttttttttt  catttgatat ttaaaagcat     120
ggggtatccg cacaatatgc tgctgctatt agatggtaat cttaaatggt aatttcatga     180
attaagatat cttaaactgg agtgagttgg tttagataaa aagaatatgt tatttgtaaa     240
gtccgtcttg gtgttgattt agtttaaagt ttaagttgta aatttccctg agttaatttt     300 atttttatttt taaaatactt aaaataatat caaatacaaa gttttttcat taaccctagc    360
caaacttata gttcgcggtt catcaagttg actctacaag ccaagccgaa tcttaccact     420
atttttttat ttatttgaat tcagaactca aatcatatta tagagaaaaa aaataatgaa     480
ttttctaatt ctagcatgga catgtttctg atgggataat aagataaatt tagtttttaat    540 aagtagaaat tgaaagagga agggagtttc cagcacaatg aaaattgcta atcttgcact     600
acatgcacgt acgtttgctt aatatatgtt tcaaactctc ataggtacgt gtgatcacac     660
gactccctcc attttatttc ctttcctttc aactgtagat gtggaatgtg atgcaaacta     720
atggctaaat tagggatatt cttgtttgaa attgtaaaac cattgttttg acagacttgg     780
```

```
caatgtccat atgggtttac ttacctcgtc tatgtatggc taaacataca aagcctagag    840
ataaaattct ttgttttgt taggcaaaag catggagtta gtgtcagata tttgactatg     900
gaattggtat gctatcaaat ccttcaacaa acccaacaaa aaacgaagat ctttcggaga    960
agtgactgca agtgacaacg attactgacc ataaagtccc aattaaccat gtggggtggc   1020
ttgatttgtg aaggttagct tagccttagct tccgccataa tttcttgcca ccccacctgc  1080
agctgtaact cttgcctcg tcccatagta cagtttttca tctctaggaa ctaatcgaat   1140
ccatcattgt caaaatccat ccatgccagc aaactgtacc atagtttgga cttgtgagga   1200
gaaagctaaa tgagcaacaa acgctatgta caatttgttt gcaactttga gtacacacac   1260
ctgtaattgg gttccaccac cacacgagca tgatccaagc acattaattg attggactgg   1320
tcataaaaga attaacccta gctggttttg atggtgtcaa tccacactag ccagtactgt   1380
agactattgg ggcatgctag catgctcgtg accatgctgg ccatcacgtg aacttcacat   1440 ggtataccttt ctctgtgttc aaaacatcaa agacgaacta cttcatgggg gaatattgga  1500 accccacccct gcccttctat ggtgaccaat taccaaagaa acatgcacca aaccctatat  1560
tatattagtg gggtaccgtg ctttgtctag ctagctagat cactctcctc tctctctcta   1620
gcattattga ccttagcaat gtagaactaa actccgacaa aaagaatcct tattattgta   1680
ataggaaagt agaagagagt gttatggttt tagtatcatc ataatcaaga aaatcaagag   1740
aatgttttct aactagtagt agaactaccc cccattatta tggaggttct tgaatgatag   1800
agagttcatg catcatgata tgtttgacga acttcttgcc gacatgctgg acatgtatat   1860
tgatgaaatc atgtgcacaa tcctacaaaa tatatatatt ctgtatgtta caagaggcaa   1920
atgccacttg tcaatgatca taaatgatgg agtttttgt ttacttaaca ccaatttgta    1980
gtaaggtaaa gacatatgta tatgcaaatt gcacttccgt gcgttactac aaacaattcg   2040 attctttaa ttagttagtt ataatttcac taaaacataa tgccttttg ttaaatatat     2100 tttcttatta cttagagtg tttttataaa aacattttta ttttttttt ttttattagc    2160 atattaaaat cattcaaaaa catttatttt gatattttc agaagaaaat caatttaaaa    2220
agcaggttaa aacataaaaa caagtgttat ttaagtaatt ttgagattaa atatctataa   2280
aaaactagaa tattttgaat tcatacatac ttttattcga acccaaagac taattaactc   2340
tctacgagga aaatggtaac attttttactc acaaagttga aatggacctt ggtggttaag  2400
gtcaatccag tcaagaaaag ctcatgcttg cccaagttgc atggtgtaat ttgctttcaa   2460
tctaatacta tataaatcaa taaactgtcc tcataccata cagaagcctg ttgtatttc    2520 cagaaatcat cagactatgc tgtactaact aaaagtcata ttgatttaga ctgtcagtgg   2580
gtcatgtacc ataaccaaat ttaagaaagg ggggcctcga gttgttgaac gtatggacac   2640
aagagaacaa gctggggttc agacttgaga gttaagacga tgacgagagc tccccgggct   2700
aactggtcct agcacgttag tgcaccctttt ccttacctgt cgtatcaatg ctaggctttt   2760
gcccgaccta acttccatgt tgtccctgac tcactctctc ttacaggaca agatggccaa   2820
cttcgtatgc ctttaattct ctctcccact tgtatatata tacatgtttc acactttcaa   2880
gcaagaagta tccatcagcc aactcacccc gtttcttgct tctgttcata ttttattact   2940
actaccttaa agcattttgt gctaccttgc ttgcttgtta atcaatatct agagggtatc   3000
```